US 6,331,553 B1

(12) United States Patent
Esaki et al.

(10) Patent No.: US 6,331,553 B1
(45) Date of Patent: Dec. 18, 2001

(54) AROMATIC AMINE DERIVATIVES HAVING NOS INHIBITING ACTION

(75) Inventors: Toru Esaki; Toshihiko Makino; Yoshikazu Nishimura; Toshiaki Nagafuji, all of Shizuoka-ken (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/331,733

(22) PCT Filed: Dec. 24, 1997

(86) PCT No.: PCT/JP97/04762

§ 371 Date: Jun. 24, 1999

§ 102(e) Date: Jun. 24, 1999

(87) PCT Pub. No.: WO98/28257

PCT Pub. Date: Jul. 2, 1998

(30) Foreign Application Priority Data

Dec. 24, 1996  (JP) .................................... 8-359791

(51) Int. Cl.$^7$ .......................... C07D 213/02; A61K 31/44

(52) U.S. Cl. .......................... 514/352; 514/272; 514/370; 514/377; 514/658; 544/330; 546/304; 564/433; 548/190; 548/234

(58) Field of Search .......................... 546/304; 514/352, 514/370, 377, 272, 658; 564/433; 544/330; 548/190, 234

(56) References Cited

FOREIGN PATENT DOCUMENTS

| 6192080 | 7/1994 | (JP) . |
| 9505363 | 2/1995 | (WO) . |
| 9509619 | 4/1995 | (WO) . |

OTHER PUBLICATIONS

International Search Report for PCT/JP97/04762, 1998.*
Matsui et al., "Participation of nitric oxide in pathogenetics mechanism underlying brain damage" *JIKKEN IGAKU*, vol. 11, pp. 2457–2462, (1995).
Matsui et al., "Increase notric oxide production mediates ischemic brain damage", *JIKKEN IGAKU*, vol. 13 pp. 1011–1019, (1995).
Nathan, "Nitric oxide as a secretory product of mammalian cells", *FASEB J.*, vol. 6, pp. 3051–3064, (1992).
Nagafuji et al., "Nitric Oxide Synthase in Cerebral Ischemia", *Molecular and Chemical Neuropathology*, vol. 26 pp. 107–157, (1995).
Siesjo, "Cell Damage in the Brain: A Speculative Synthesis", *Journal of Cerebral Blood Flow and Metabolism* vol. 1, pp. 155–185, (1981).
Siesjo, "Cerebral circulation and metabolism", *J. Neurosurg*, vol. 60, pp. 883–908, (1984).

Choi, "Calcium–mediated neurotoxicity:relationship to specific channel types and role in ischemic damage" *Tins*, vol. 11, No. 10, pp. 465–469, (1988).
Siesjo et al., "Calcium Fluxes, Calcium Antagonists, and Calcium–Related Pathology in Brain Ischemia, Hypoglycemia, and Spreading Depression: A Unifying Hypothesis", *Journal of Cerebral Blood Flow and Metabolism* vol. 9, pp. 127–140, (1989).
Dawson et al., "A Novel Neuronal Messenger Molecule in Brain: The Free Radical, Nitric Oxide", *Annals of Neurology*, vol. 32, No. 3, pp. 297–311, (1992).
Zhang et al., "Upregulation of neuronal nitric oxide synthase and mRNA, and selective sparing of nitric oxide synthase-containing neurons after focal cerebral ischemia in rat", *Brain Res.*, vol. 645, pp. 85–95, (1994).
Carreau et al., "Neuroprotective efficacy of N– nitro–L–arginie after focal cerebral ischemia in the mouse and inhibition of cortical nitric oxide synthase", *European Journal of Pharmacology*, vol. 256, pp. 241–249 (1994).
Huang et al., "Effect of Cerebral Ischemia in Mice Deficient in Neuronal Nitric Oxide Synthase", *Science* vol. 265, pp. 1883–1885, (1994).
Moncada et al., Nitric Oxide:Physiology, Pathophysiology, and Pharmacology, *Pharmacological Reviews*, vol. 43 pp. 109–142, (1991).
Huang et al., "Enlarged Infarcts in Endothelial Nitric Oxide Synthase Knockout Mice Are Attenuated by Nitro–L–Arginine", *Journal of Cerebral Blood Flow Meta olism*, vol. 16, pp. 981–987, (1996).
Nagafuji et al., "Blockade of nitric oxide formation by N–nitro–L–argine mitigates ischemic brain edema and subsequent cerebral infarction in rats", vol. 147, pp. 159–162, (1992).
Nagafuji et al., "A narow therapeutical window of a nitric oxide synthase inhibitor against transient ischemic brain injury", *European Journal of Pharmacology*, vol. 248, pp. 325–328, (1993).

(List continued on next page.)

Primary Examiner—Zinna Northington Davis
(74) *Attorney, Agent, or Firm*—Browdy and Neimark

(57) ABSTRACT

Compounds represented by the general formula (1):

$$R_1\!\!\diagdown\!\!N\!\!-\!\!(CH_2)_n\!\!-\!\!\underset{R_4}{\overset{R_3}{C}}\!\!-\!\!(CH_2)_m\!\!-\!\!\underset{X_3\ \ X_4}{\overset{X_1\ \ X_2}{\diagup\diagdown}}\!\!\underset{R_5}{\overset{}{N}}\!\!-\!\!A \qquad (1)$$

(where $R_1$ and $R_2$ are typically a hydrogen atom; $R_3$ and $R_4$ are typically a hydrogen atom or a lower alkyl group; $R_5$ is typically a hydrogen atom; $X_1$, $X_2$, $X_3$ and $X_4$ are typically a hydrogen atom or a lower alkoxy group; A is typically an optionally substituted pyridine ring; m and n are each 0 or 1) have an NOS inhibiting activity and are useful as therapeutics of cerebrovascular diseases and other pharmaceuticals.

43 Claims, No Drawings

OTHER PUBLICATIONS

Iadecola et al., "Nitric Oxide Synthase Inhibition and Cerebrovascular Regulation", *Journal of Cerebral Blood Flow and Metabolism,* vol. 14, pp. 175–192, (1994).

Nagafuji et al., "The neuroprotective effect of a potent and selective inhibitor of type I NOS (L–MIN) in a model of focal cerebral ischaemia", *Neuroreport,* vol. 6, pp. 1541–1545, (1995).

Nowicki et al., "Nitric oxide mediates neuronal death after focal cerebral ischemia in the mouse", *European Journal of Pharmacology,* vol. 204, pp. 339–340, (1991).

Dawson et al., "Nitric oxide mediated glutamate neurotoxicity in primary cortical cultures", *Proc. Natl. Acad Sci.,* vol. 88, pp. 6368–6371, (1991).

Iadecola et al., "Marked Induction of Calcium–Independent Nitric Oxide Synthase Activity After Focal Cerebral Ischemia", *Journal of Cerebral Blood Flow and Metabolism,* vol. 15, pp. 52–59, (1995).

Iadecola et al., "Inducible Nitric Oxide Synthase Gene Expression in Brain Following Cerebral Ischemia" *Journal of Cerebral Blood Flow and Metabolism,* vol. 15, pp. 378–384, (1995).

Cury et al., "Cold–induced Brain Edema in Mice", *The Journal of Biological Chemistry,* vol. 268, No. 21 pp. 15394–15398, (1993).

MacKenzie et al., "Effect of 7–nitro indazole on quinolinic acid–induced striatal toxicity in the rat" *Neuroreport,* vol. 6, No. 13, pp. 1789–1794, (1995).

Mesenge et al., "Reduction of the Neurological Deficit in Mice with Traumatic Brain injury by Nitric Oxide Synthase Inhibitors", *Journal of Neurotrauma,* vol. 13, No. 1, pp. 11–17, (1996).

Wallis et al., "Traumatic neuroprotection with inhibitors of nitric oxide and ADP–ribosylation" *Brain Research,* vol. 710, pp. 169–177, (1996).

Moore et al., "L–N–nitro arginine methyl ester exhibits antinociceptive activity in the mouse", *Br. J. Pharm.* vol. 102, pp. 198–202, (1991).

Olesen et al., "Nitric oxide is a key molecule in migrain and other vascular headaches", *Trends Pharm.* vol. 15, pp. 149–153, (1994).

Youdim et al., "The Neurotoxicity of Iron and Nitric $O_{xide}$", *Advances in Neurology,* vol. 60, pp. 259–266 (1993).

Schulz et al., "Inhibition of Neuronal Nitric Oxide Synthase by 7–Nitroindazole $Prot_{ec}ts$ Against MPTP–Induced Neurotoxicity in Mice", *Journal of Neurochemistry,* vol. 64, pp. 936–939, (1995).

Haniraye et al., "Inhibition of neuronal nitric oxide synthase prevents MPIP–indiced parkinsonism in baboons" *Nature Medicine,* vol. 2, No. 9, pp. 1017–1021, (1996).

Hu et al., "Amyloid 25–35 activates nitric oxide synthase in a neuronal clone", *NeuroReport,* vol. 4, No. 6 pp. 760–762, (1993).

Meda et al., "Activation of microglial cells by –amyloid proteins and interferon", *Nature,* vol. 374, pp. 647–650, (1995).

Monnet et al., "Blockade of Nitric Oxide $_{s}$ynthesis Inhibits Hippocampal Hyperemia in Kainic Acid–Induced Seizures", *Journal of Cerebral Blood Flow and Metabolism,* vol. 14, pp. 581–590, (1994).

Kolesnikov et al., "N– Nitro–L–arginine prevents morphine tolerance", *European Journal of Pharmacology* vol. 221, pp. 399–400, (1992).

Cappendijk et al., "Inhibitory effect of nitric oxide (N0) synthase inhibitors on naloxone–precipitated withdrawal syndrome in morphine–dependent mice", *Neuroscience Letters,* vol. 162, pp. 97–100, (1993).

Kilbourn et al., "Overproduction of Nitric Oxide in Cytokine–Mediated and Septic Shock", *Journal of the Cancer Institute,* vol. 84, No. 11, pp. 827–831, (1992).

Cobb et al., "Nitric oxide as a target for therapy in septic shock", *Critical Care Medicine,* vol. 21, No. 9 pp. 1261–1263, (1993).

Lorenie et al., "L–arginine pathway in the spesis syndrome", *Critical Care Medicine,* vol. 21, No. 9, pp. 1287–1295, (1993).

Farrell et al., "Increased concentrations of nitrite in synovial fluid and serum sample suggest increased nitric oxide synthesis in rheumatic diseases", *Annals of the Rheumatic Diseases,* vol. 51, pp. 1219–1222, (1992).

Matsuzake et al., "Generation of the topa quinone cofactor in bacterial monoamine oxidase by cupric ion–dependent autooxidation of a specific tyrosyl residue", *FEBS Letters,* vol. 351, pp. 360–364, (1994).

Ialenti et al., "Modulation of Adjuvant arthritis by endogenous nitric oxide", *Br. J. Pharmacol.,* vol. 110 pp. 701–706, (1993).

Zembowicz et al., "Induction of nitric oxide synthase $_{acti}$vity by toxic shock syndrome toxin 1 in a macrophage–monocyte cell line", *Proc. Natl. Acad.,* vol. 89, pp. 2051–2055, (1992).

Koprowski et al., "In vivo expression of inducible nitric oxide synthase in $experime_{nt}$ally induced neurologic diseases", *Proc. Natl. Acad.,* vol. 90, pp. 3024–3027, (1993).

Kolb et al., Suppression of low Dose streptozotocin induced diabetes in mice by administration of a nitric oxide synthase inhibitor:, *Life Science,* vol. 49, pp. PL–213–PL–217, (1991).

Lambert et al., "Characterization of cell selectivity of two novel inhibitors of nitric oxide synthesis" *European Journal of Pharmacology,* vol. 216, pp. 131–134, (1992).

Furfine et al., "Selective Inhibition of Constitutive Nitric Oxide Synthase by L–N –Nitroarginine" *Biochemistry,* vol. 32, pp. 8512–8517, (1993).

Narayanan et al., "Synthesis of L–Thioci$_{tr}$ulline, L–Homothiocitrulline, and S–Methyl–L–thiocitrulline: A new Class of Protein Nitric Oxide Synthase Inhibitors", *J. Med. Chem.,* vol. 37, pp. 885–887, (1994).

Furfine et al., "Potent and Selective Inhibition of Human Nitric Oxide Synthases", *The Journal of Biological Chemistry,* vol. 269, pp. 26677–26683, (1994).

Narayanan et al., "S–Alkyl–L–thiocitrullines", *The Journal of Biological Chemistry,* vol. 270, No. 19, pp. 11103–11110, (1995).

Zhang et al., "ARL 17477, a Potent and Selective Neuronal NOS Inhibitor Decreases Infarct Volume After Transient Middle Cerbral Artery Occlusion in Rats", *Journal of Cerebral Blood Flow and Metabolism,* vol. 16 pp. 599–604, (1996).

McCall et al., "Indentification of N–iminoethyl–L–amithine as an irreversible inhibitor of nitric oxide synthase in phagocytic cells", *Br. J. Pharm.,* vol. 102, pp. 234–238, (1991).

Griffiths et al., "Aminoguanidine selectively inhibits inducible nitric oxide synthase", *Br. J. Pharm.* vol. 110, pp. 963–968, (1993).

Hasan et al., "Inhibition of nitric oxide formation by guanidines", *European Journal of Pharm.,* vol. 249 pp. 101–106, (1993).

Dressman et al., "Solid Phase Synthesis of Hydantions Using a Carbamate Linker and a Novel Cyclization/Cleavage Step", *Tetrahedron Letters,* vol. 37, No. 7, pp. 937–940, (1996).

\* cited by examiner

AROMATIC AMINE DERIVATIVES HAVING NOS INHIBITING ACTION

CROSS REFERENCE TO RELATED APPLICATION

The present application is the national stage under 35 U.S.C. 371 of PCT/JP97/04762, filed Dec. 24, 1997.

TECHNICAL FIELD

This invention relates to N-substituted aniline derivatives, more particularly to compounds represented by the general formula (I) that have a nitric oxide synthase (NOS) inhibiting action to suppress the production of nitric oxide (NO) and thereby prove effective against disorders and diseases in which excessive NO or NO metabolites are supposedly involved, namely, cerebrovascular diseases [cerebral hemorrhage, subarachnoid hemorrhage, cerebral infarction (atherothrombotic infarction, lacunar infarction and cardiogenic embolism), transient ischemic attack and cerebral edema], traumatic brain injury, spinal injury, pains [headache (migraine, tension headache, cluster headache and chronic paroxysmal headache)], Parkinson's disease, Alzheimer's disease, seizure, morphine tolerance or dependence, septic shock, chronic rheumatoid arthritis, osteoarthritis, viral or nonviral infections and diabetes mellitus. The invention also relates to possible tautomers, stereoisomers and optically active forms of said compounds, as well as pharmaceutically acceptable salts thereof. The invention further relates to preventives and therapeutics that contain said compounds, derivatives or pharmaceutically acceptable salts as active ingredients.

BACKGROUND ART

The number of deaths from cerebrovascular diseases in Japan had increased until 1970 when it began to decline mostly due to the improvement in their acute-phase therapy. Nevertheless, cerebrovascular diseases remain the second leading cause of death among adult diseases, next only to cancers. As for the incidence of cerebrovascular diseases, many statistical surveys indicate that it is generally constant and in view of the fact that the number of elderly persons will increase at an uncomparably faster speed in Japan than any other country in the world, the number of patients suffering from cerebrovascular diseases is estimated to increase rather than decrease in the future. The declining mortality and the growing population of aged people combine to increase the cases of cerebrovascular diseases in the chronic phase and this has presented with a national problem not only from the aspects of individual patients and society at large but also from the viewpoint of medical economics since patients with chronic cerebrovascular disease are inevitably involved in long-term care. In cerebral infarction that accounts for most cases of cerebrovascular diseases, cerebral arteries are occluded and blood deficit starting at the blocked site extends to the peripheral site, causing an ischemic state. The symptoms of cerebral infarction in the chronic phase are in almost all cases derived from the loss of neurons and it would be extremely difficult to develop medications or established therapeutic methods for achieving complete recovery from those symptoms. Therefore, it is no exaggeration that the improvement in the performance of treatments for cerebral infarction depends on how patients in an acute phase can be treated with a specific view to protecting neurons and how far their symptoms can be ameliorated in the acute phase. However, most of the medications currently in clinical use are antiplatelet drugs, anticoagulants and thrombolytics and none of these have a direct nerve protecting action (see Kazuo MINEMATSU et al., "MEDICINA", published by Igaku Shoin, 32, 1995 and Hidehiro MIZUSAWA et al., published by Nankodo, "Naika" 79, 1997). Therefore, it is desired to develop a drug that provides an effective therapy for cerebrovascular diseases, in particular cerebral infarction, by working in an entirely novel and different mechanism of action from the conventional medications.

A presently dominant theory based on genetic DNA analyses holds that NOS exists in at least three isoforms, namely, calcium-dependent nNOS (type 1) which is present constitutively in neurons, calcium-dependent eNOS (type 3) which is present constitutively in vascular endothelial cells, and apparently calcium-independent iNOS (type 2) which is induced and synthesized by stimulation with cytokines and/or lipopolysaccharides (LPS) in macrophages and many other cells (Nathan et al., FASEB J. 16, 3051–3064, 1992; Nagafuji et al., Mol. Chem. Neuropathol. 26, 107–157, 1995).

A mechanism that has been proposed as being most probable for explaining the brain tissue damage which accompanies cerebral ischemia is a pathway comprising the sequence of elevation in the extracellular glutamic acid level, hyperactivation of glutamic acid receptors on the post-synapses, elevation in the intracellular calcium level and activation of calcium-dependent enzymes (Siesjö, J. Cereb. Blood Flow Metab. 1, 155–185, 1981; Siesjö, J. Neurosurg. 60, 883–908, 1984; Choi, Trends Neurosci. 11, 465–469, 1988; Siesjö and Bengstsson, J. Cereb. Blood Flow Metab. 9, 127–140, 1989). As already mentioned, nNOS is calcium-dependent, so the inhibition of hyperactivation of this type of NOS isoforms would contribute to the neuro-protective effects of NOS inhibitors (Dawson et al., Annals Neurol. 32, 297–311, 1992).

As a matter of fact, the mRNA level of nNOS and the number of nNOS containing neurons start to increase early after focal cerebral ischemia in rats and their temporal alterations coincide with the development of infarction (Zhang et al., Brain Res. 654, 85–95, 1994). In addition, in a mouse model of focal cerebral ischemia, the percent inhibition of nNOS activity and the percent reduction of infarct volume correlate to each other at least in a dose range of $N^G$-nitro-L-arginine (L-NA) that produces a recognizable infarct volume reductive action (Carreau et al., Eur. J. Pharmacol. 256, 241–249, 1994). Further in addition, it has been reported that in nNOS knockout mice, the infarct volume observed after focal cerebral ischemia is significantly smaller than that in the control (Huang et al., Science 265, 1883–1885, 1994).

Referring now to NO, it is at least one of the essences of endothelium-derived relaxing factor (EDRF) and, hence, is believed to take part in the adjustment of the tension of blood vessels and the blood flow (Moncade et al., Pharmacol. Rev. 43, 109–142, 1991). As a matter of fact, it was reported that when rats were administered high doses of L-NA, the cerebral blood flow was found to decrease in a dose-dependent manner as the blood pressure increased (Toru MATSUI et al., Jikken Igaku, 11, 55–60, 1993). The brain has a mechanism by which the cerebral blood flow is maintained at a constant level notwithstanding the variations of blood pressure over a specified range (which is commonly referred to as "autoregulation mechanism") ("NOSOTCHU JIKKEN HANDBOOK", complied by Keiji SANO, published by IPC, 247–249, 1990). The report of Matsui et al. suggests the failure of this "autoregulation mechanism" to operate. Therefore, if eNOS is particularly inhibited beyond a certain limit in an episode of brain ischemia, the cerebral blood flow will decrease and the blood pressure will increase, thereby aggravating the dynamics of microcirculation, possibly leading to an expansion of the ischemic lesion. It was also reported that in eNOS knockout mice, the infarct observed after focal cerebral ischemia was larger than that in the control but could be reduced significantly by administration of L-NA (Huang et al., J. Cereb. Blood Flow Metab. 16, 981–987, 1996). These reports show that eNOS-derived NO probably works protectively on the brain tissue through the intermediary of a vasodilating action, a platelet aggregation suppressing action and so forth.

The present inventors previously found that L-NA, already known to be a NOS inhibitor, possessed ameliorative effects on the brain edema and cerebral infarction following phenomena that developed after experimental cerebral ischemia (Nagafuji et al., Neurosci. Lett. 147, 159–162, 1992; Japanese Patent Public Disclosure No. 192080/1994), as well as necrotic neuronal cell death (Nagafuji et al., Eur. J. Pharmacol. Env. Tox. 248, 325–328, 1993). On the other hand, relatively high doses of NOS inhibitors have been reported to be entirely ineffective against ischemic brain damage and sometimes aggravating it (Idadecola et al., J. Cereb. Blood Flow Metab. 14, 175–192, 1994; Toshiaki NAGAFUJI and Toru MATSUI, Jikken Igaku, 13, 127–135, 1995; Nagafuji et al., Mol. Chem. Neuropathol. 26, 107–157, 1995). It should, however, be stressed that as a matter of fact, all papers that reported the changes of NO or NO-related metabolites in the brain and blood in permanent or temporary cerebral ischemic models agreed in their results to show the increase in the levels of those substances (Toshiaki NAGAFUJI and Toru MATSUI, Jikken Igaku, 13, 127–135, 1995; Nagafuji et al., Mol. Chem. Neuropathol. 26, 107–157, 1995).

One of the reasons for explaining the fact that conflicting reports have been made about the effectiveness of NOS inhibitors in cerebral ischemic models would be the low selectivity of the employed NOS inhibitors for nNOS. As a matter of fact, no existing NOS inhibitors including L-NA and $N^G$-nitro-L-arginine methyl ester (L-NAME) have a highly selective inhibitory effect on a specific NOS isoform (Nagafuji et al. Neuroreport 6, 1541–1545, 1995; Nagafuji et al. Mol. Chem. Neuropathol. 26, 107–157, 1995). Therefore, it may well be concluded that desirable therapeutics of ischemic cerebrovascular diseases should have a selective inhibitory effect on nNOS (Nowicki et al., Eur. J. Pharmacol. 204, 339–340, 1991; Dawson et al., Proc. Natl. Acad. Sci. USA 88, 6368–6371, 1991; Iadecola et al., J. Cereb. Blood Flow Metab. 15, 52–59, 1995; Iadecola et al., J. Cereb. Blood Flow Metab. 15, 378–384, 1995; Toshiaki NAGAFUJI and Toru MATSUI, Jikken Igaku 13, 127–135, 1995; Nagafuji et al., Mol. Chem. Neuropathol. 26, 107–157, 1995).

It has also been suggested that nNOS inhibitors have the potential for use as therapeutics of traumatic brain injuries (Oury et al., J. Biol. Chem. 268, 15394–15398, 1993; MacKenzie et al., Neuroreport 6, 1789–1794, 1995; Mesenge et al., J. Neurotrauma. 13, 11–16, 1996; Wallis et al., Brain Res., 710, 169–177, 1996), headache and other pains (Moore et al., Br. J. Pharmacol. 102, 198–202, 1991; Olesen., Trends Pharmacol. 15, 149–153, 1994), Parkinson's disease (Youdim et al., Advances Neurol. 60, 259–266, 1993; Schulz et al., J. Neurochem. 64, 936–939, 1995; Hantraye et al., Nature Medicine 2, 1017–1021, 1996), Alzheimer's disease (Hu and EI-FaKahany, Neuroreport 4, 760–762, 1993 Meda et al., Nature 374, 647–650, 1995), seizure (Rigaud-Monnet et al., J. Cereb. Blood Flow Metab. 14, 581–590, 1994), and morphine tolerance and dependence (Kolesnikov et al., Eur. J. Pharmacol. 221, 399–400, 1992; Cappendijk et al., Neurosci. Lett. 162, 97–100, 1993).

Upon stimulation by certain kinds of cytokines and/or LPS, iNOS is induced in immunocytes such as macrophages and glial cells and other cells, and the resulting large amount of NO will dilate blood vessels to cause a fatal drop in blood pressure. Therefore, it is speculated that an iNOS inhibitor may be effective against septic shocks (Kilbourn and Griffith, J. Natl. Cancer Inst. 84, 827–831, 1992; Cobb et al., Crit. Care Med. 21, 1261–1263, 1993; Lorente et al., Crit. Care Med. 21, 1287–1295, 1993). Further, it has been suggested that iNOS inhibitors are useful as therapeutics of chronic rheumatoid arthritis and osteoarthritis (Farrell et al., Ann, Rheum. Dis. 51, 1219–1222, 1992; Hauselmann et al., FEBS Lett. 352, 361–364, 1994; Islante et al., Br. J. Pharmacol. 110, 701–706, 1993), viral or nonviral infections (Zembvitz and Vane, Proc. Natl. Acad. Sci. USA 89, 2051–2055, 1992; Koprowski et al., Proc. Natl. Acad. Sci. USA 90, 3024–3027, 1993) and diabetes mellitus (Kolb et al., Life Sci. PL213–PL217, 1991).

The NOS inhibitors so far reported to have a certain degree of selectivity for nNOS are $N^G$-cyclopropyl-L-arginine (L-CPA)(Lamberte et al., Eur. J. Pharmacol. 216, 131–134, 1992), L-NA (Furfine et al., Biochem. 32, 8512–8517, 1993), S-methyl-L-thiocitrulline (L-MIN) (Narayanan and Griffith, J. Med. Chem. 37, 885–887, 1994; Furfine et al., J. Biol. Chem. 37, 885–887, 1994; Furfine et al. J. Biol. Chem. 269, 26677–26683, 1994; WO95/09619; Narayanan et al., J. Biol. Chem. 270, 11103–11110, 1995; Nagafuji et al., Neuroreport 6, 1541–1545, 1995), S-ethyl-L-thiocitrulline (L-EIN) (Furfine et al., J. Biol. Chem. 269, 26677–26683, 1994; WO95/09619; Narayanan et al., J. Biol. Chem. 270, 11103–11110, 1995), and ARL 17477 (Gentile et al., WO95/05363; Zhang et al., J. Cereb. Blood Flow Metab., 16, 599–604, 1996).

In addition, the inhibitors that have been reported to have a certain degree of selectivity for iNOS are $N^G$-iminoethyl-L-ornithine (L-NIO) (McCall et al., Br. J. Pharmacol. 102, 234–238, 1991) and aminoguanidine (AG) (Griffith et al., Br. J. Pharmacol. 110, 963–968, 1993; Hasan et al. Eur. J. Pharmacol. 249, 101–106, 1993).

DISCLOSURE OF INVENTION

An object of the present invention is to provide novel compounds that have an inhibitory effect on calcium-dependent nNOS which is present constitutively in the brain, particularly in neurons or an inducible and apparently calcium-independent iNOS and which are useful as therapeutics of cerebrovascular diseases [cerebral hemorrhage, subarachnoid hemorrhage, cerebral infarction (atherothrombotic infarction, lacunar infarction and cardiogenic embolism), transient ischemic attack and cerebral edema], traumatic brain injury, spinal injury, pains [headache (migraine, tension headache, cluster headache and chronic paroxysmal headache)], Parkinson's disease, Alzheimer's disease, seizure, morphine tolerance or dependence, septic shock, chronic rheumatoid arthritis, osteoarthritis, viral or nonviral infections and diabetes mellitus.

As a result of the intensive studies made in order to attain the stated object, the present inventors found that aromatic amine derivatives represented by the general formula (I), or possible tautomers, stereoisomers and optically active forms of said compounds, as well as pharmaceutically acceptable salts thereof have an inhibitory action on type 1 NOS and so forth, thereby exhibiting marked effectiveness as therapeutics of cerebrovascular diseases (especially as therapeutics of occlusive cerebrovascular diseases):

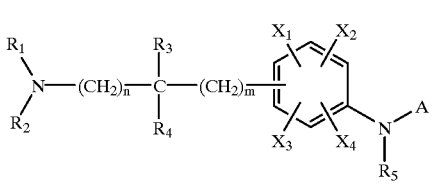

(1)

(where $R_1$ and $R_2$ which may be the same or different are each a hydrogen atom, an optionally substituted lower alkyl group, an acyl group or a lower alkoxycarbonyl group, or $R_1$ and $R_2$ may combine together to form a 3- to 8-membered ring;

$R_3$ and $R_4$ which may be the same or different are each a hydrogen atom, an optionally substituted lower alkyl group, or $R_3$ and $R_4$ may combine together to form a monocyclic or fused ring having 3–10 carbon atoms;

$R_5$ is a hydrogen atom, a lower alkyl group, an acyl group or a lower alkoxycarbonyl group;

$X_1$, $X_2$, $X_3$, and $X_4$, which may be the same or different are each a hydrogen atom, a halogen atom, a nitro group, a cyano group, a hydroxyl group, an optionally substituted lower alkyl group, a lower alkenyl group, a lower alkynyl group, an optionally substituted lower alkoxy group, an optionally substituted lower alkylthio group, a phenyl group optionally substituted by a halogen atom and/or a lower alkyl group, $NX_5X_6$ or $C(=O)X_7$;

where $X_5$ and $X_6$ which may be the same or different are each a hydrogen atom, an optionally substituted lower alkyl group, an acyl group, an optionally substituted lower alkoxycarbonyl group, or $X_5$ and $X_6$ may combine together to form a 3- to 8-membered ring;

$X_7$ is a hydrogen atom, a hydroxyl group, an optionally substituted lower alkyl group, an optionally substituted lower alkoxy group, or $NX_8X_9$;

where $X_8$ and $X_9$ which may be the same or different are each a hydrogen atom, an optionally substituted lower alkyl group, or $x_8$ and $X_9$ may combine together to form a 3- to 8-membered ring;

A is an optionally substituted benzene ring or a 5- or 6-membered aromatic hetero ring which is optionally substituted and which contains at least one nitrogen atom as a hetero atom;

n and m are each an integer of 0 or 1).

The present invention has been accomplished on the basis of this finding.

The present invention also provides a process for producing a compound of the general formula (1) which is represented by the reaction pathway (A):

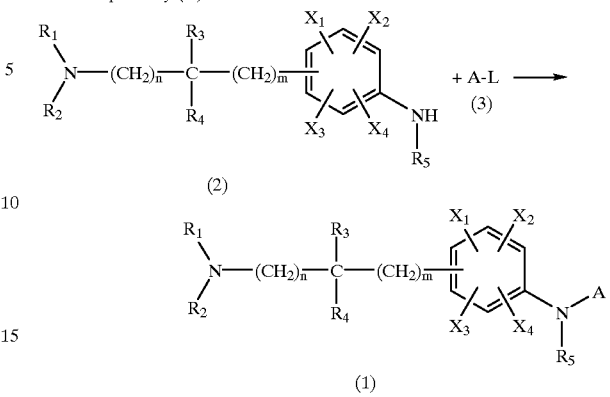

namely, a process in which a substituted aniline represented by the general formula (2) (where $R_1$, $R_2$, $R_3$, $R_4$, $X_1$, $X_2$, $X_3$, $X_4$, n and m have the same meanings as defined above; $R_5$ is a hydrogen atom or an optionally substituted lower alkyl group) is reacted with a compound represented by the general formula (3) (where A has the same meaning as defined above; L is a leaving group) to produce a compound represented by the general formula (1).

The present invention further provides a process for producing a compound of the general formula (1) which is represented by the reaction pathway (B):

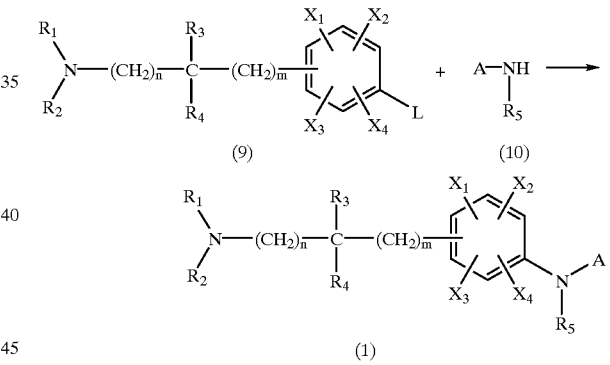

namely, a process in which a substituted benzene represented by the general formula (9) (where $R_1$, $R_2$, $R_3$, $R_4$, $X_1$, $X_2$, $X_3$, $X_4$, L, n and m have the same meanings as defined above) is reacted with a compound represented by the general formula (10) (where A and $R_5$ have the same meanings as defined above) to produce a compound represented by the general formula (1).

BEST MODE FOR CARRYING OUT THE INVENTION

In the present invention, the 5- or 6-membered aromatic hetero ring as an example of A which contains at least one nitrogen atom as a hetero atom may be exemplified by a pyrrole ring, a pyrrole-1-oxide ring, a pyrazole ring, a pyrazole-1-oxide ring, a pyrazole-2-oxide ring, a pyrazole-1,2-dioxide ring, an imidazole ring, an imidazole-1-oxide ring, an imidazole-3-oxide ring, an imidazole-1,3-dioxide ring, an isoxazole ring, an isoxazole-2-oxide ring, an oxazole ring, an oxazole-3-oxide ring, an isothiazole ring, an isothiazole-1-oxide ring, an isothiazole1,1-dioxide ring, an isothiazole-1,2-dioxide ring, an isothiazole-2-oxide ring, a thiazole ring, a thiazole-1-oxide ring, a thiazole-1,1-dioxide ring, a thiazole-3-oxide ring, a pyridine ring, a pyridine-N-oxide ring, a pyridazine ring, a pyridazine-1-oxide ring, a pyridazine-1,2-dioxide ring, a pyrimidine ring, a pyrimidine-1-oxide ring, a pyrimidine-1,3-dioxide ring, a pyrazine ring, a pyrazine-1-oxide ring or a pyrazine-1,4-dioxide ring or the like;

the substituent in A is a hydroxyl group, a halogen atom, a nitro group, a cyano group, a trifluoromethyl group, a lower alkoxy group, a lower alkyl group, a lower alkylthio group, $NX_{10}X_{11}$ or $C(=O)X_{12}$;

where $X_{10}$ and $X_{11}$ which may be the same or different are each a hydrogen atom, an optionally substituted lower alkyl group, an acyl group, an optionally substituted lower alkoxycarbonyl group, or $X_{10}$ and $X_{11}$ may combine together to form a 3- to 8-membered ring;

$X_{12}$ is a hydrogen atom, a hydroxyl group, an optionally substituted lower alkyl group, an optionally substituted lower alkoxy group or $NX_{13}X_{14}$;

where $X_{13}$ and $X_{14}$ which may be the same or different are each a hydrogen atom, an optionally substituted lower alkyl group, or $X_{13}$ and $X_{14}$ may combine together to form a 3- to 8-membered ring;

the lower alkyl group is a straight-chained alkyl group having 1–6 carbon atoms, or a branched or cyclic alkyl group having 3–8 carbon atoms and may be exemplified by a methyl group, an ethyl group, an n-propyl group, an n-butyl group, an n-pentyl group, an n-hexyl group, an i-propyl group, an i-butyl group, a sec-butyl group, a t-butyl group, an i-pentyl group, a neopentyl group, a t-pentyl group, an i-hexyl group, a cyclopropyl group, a cyclobutyl group, a cyclopentyl group, a cyclohexyl group, a cycloheptyl group or a cyclooctyl group or the like;

the lower alkenyl group is a straight-chained alkenyl group having 2–6 carbon atoms or a branched alkenyl group having 3–6 carbon atoms and may be exemplified by a vinyl group, an allyl group, a 1-butenyl group, a 1-pentenyl group, a 1-hexenyl group, a 2-butenyl group, a 2-pentenyl group, a 2-hexenyl group, an isopropenyl group, a 2-butenyl group or a 1-methyl-1-propenyl group or the like;

the lower alkynyl group is a straight-chained alkynyl group having 2–6 carbon atoms or a branched alkynyl group having 3–6 carbon atoms and may be exemplified by an ethynyl group, a 1-propynyl group, a 1-butynyl group, a 1-pentynyl group, a 1-hexynyl group, a 2-propynyl group, a 2-butynyl group, a 2-pentynyl group, a 2-hexynyl group, a 1-methyl-2-propynyl group, a 3-methyl-1-butynyl group or a 1-ethyl-2-propynyl group or the like;

the lower alkoxy group is a straight-chained alkoxy group having 1–6 carbon atoms or a branched or cyclic alkoxy group having 3–8 carbon atoms and may be exemplified by a methoxy group, an ethoxy group, an n-propoxy group, an n-butoxy group, an n-pentoxy group, an n-hexoxy group, an i-propoxy group, an i-butoxy group, a sec-butoxy group, a t-butoxy group, an i-pentoxy group, a neopentoxy group, a t-pentoxy group, an i-hexoxy group, a cyclopropoxy group, a cyclobutoxy group, a cyclopentoxy group, a cyclohexoxy group, a cycloheptoxy group or a cyclooctoxy group or the like;

the lower alkylthio group is a straight-chained alkylthio group having 1–6 carbon atoms or a branched or cyclic alkylthio group having 3–8 carbon atoms and may be exemplified by a methylthio group, an ethylthio group, an n-propylthio group, an n-butylthio group, an n-pentylthio group, an n-hexylthio group, an i-propylthio group, an i-butylthio group, a sec-butylthio group, a t-butylthio group, an i-pentylthio group, a neopentylthio group, a t-pentylthio group, an i-hexylthio group, a cyclopropylthio group, a cyclobutylthio group, a cyclopentylthio group, a cyclohexylthio group, a cycloheptylthio group or a cyclooctylthio group or the like;

the acyl group is not only a formyl group but also an alkylcarbonyl group the alkyl portion of which is a lower alkyl group, as well as an arylcarbonyl group and may be exemplified by an acetyl group, a propionyl group, a butyryl group, a valeryl group, an isobutyryl group, an isovaleryl group, a pivaloyl group, a benzoyl group, a phthaloyl group or a toluoyl group or the like;

the lower alkoxycarbonyl group is an alkoxycarbonyl group the alkyl portion of which is a lower alkyl group and may be exemplified by a methoxycarbonyl group, an ethoxycarbonyl group, an n-propoxycarbonyl group, an n-butoxycarbonyl group, an n-pentoxycarbonyl group, an n-hexoxycarbonyl group, an i-propoxycarbonyl group, an i-butoxycarbonyl group, a sec-butoxycarbonyl group, a t-butoxycarbonyl group, an i-pentoxycarbonyl group, a neopentoxycarbonyl group, a t-pentoxycarbonyl group, an i-hexoxycarbonyl group, a cyclopropoxycarbonyl group, a cyclobutoxycarbonyl group, a cyclopentoxycarbonyl group, a cyclohexoxycarbonyl group, a cycloheptoxycarbonyl group, or a cyclooctoxycarbonyl group or the like;

the halogen atom is a fluorine atom, a chlorine atom, a bromine atom or an iodine atom;

the leaving group is a halogen atom, a trifluoromethanesulfonyloxy group, a p-toluenesulfonyloxy group or a methanesulfonyloxy group;

the substituent in the case where $R_1$, $R_2$, $R_3$, $R_4$, $X_1$, $X_2$, $X_3$, $X_4$, $X_5$, $X_6$, $X_7$, $X_8$, $X_9$, $X_{10}$, $X_{11}$, $X_{12}$, $X_{13}$, or $X_{14}$ is a optionally substituted lower alkyl group, an optionally substituted lower alkoxy group, an optionally substituted lower alkylthio group or an optionally substituted lower alkoxycarbonyl group may be exemplified by a halogen atom, a phenyl group optionally substituted by a halogen atom or a lower alkyl group or a cyclic alkyl group having 3–8 carbon atoms;

the ring as the 3- to 8-membered ring optionally formed by $R_1$ and $R_2$ taken together, the ring as the 3- to 8-membered ring optionally formed by $X_5$ and $X_6$ taken together, the ring as the 3- to 8-membered ring optionally formed by $X_8$ and $X_9$ taken together, the ring as the 3- to 8-membered ring optionally formed by $X_{10}$ and $X_{11}$ taken together, and the ring as the 3- to 8-membered ring optionally formed by $X_{13}$ and $X_{14}$ taken together are each a hetero ring containing at least one nitrogen atom as a hetero atom and may be exemplified by a pyrrole ring, a pyrazole ring, an imidazole ring, a triazole ring, an aziridine ring, an azetidine ring, a pyrrolidine ring, a piperidine ring, a piperazine ring, a morpholine ring, a thiomorpholine ring, an azepane ring or an azocane ring or the like;

the ring as the monocyclic or fused ring having 3–10 carbon atoms that is optionally formed by $R_3$ and $R_4$ taken together may be exemplified by a cyclopropane ring, a cyclobutane ring, a cyclopentane ring, a cyclohexane ring, a cycloheptane ring, a cyclooctane ring, an indane ring or a tetralin ring or the like;

$NX_5X_6$, $NX_8X_9$, $NX_{10}X_{11}$, and $NX_{13}X_{14}$ may be exemplified by an amino group, a methylamino group, a benzylamino group, an ethylamino group, a dimethylamino group, an ethylmethylamino group, a pyrrolidine-1-yl group, a piperidine-1-yl group, a morpholine-4-yl group, an acetamido group, a benzamido group, an N-methylacetamide group, a benzamido group, a tert-butoxycarbonylamino group, an N-methyl-t-butoxycarbonylamino group, a pyrrole-1-yl group, a pyrazole-1-yl group, an imidazole-1-yl group, a triazole-1-yl group, an aziridine-1-yl group, an azetidine-1-yl group, a pyrrolidine-1-yl group, a piperidine-1-yl group, a piperazine-1-yl group, a morpholine-4-yl group or a thiomorpholine-4-yl group or the like;

$C(=O)X_7$ may be exemplified by a formyl group, a carboxyl group, an acetyl group, a propionyl group, a cyclobutyryl group, a methoxycarbonyl group, an ethoxycarbonyl group, a t-butoxycarbonyl group, a carbamoyl group, an N-methylcarbamoyl group, an N-ethylcarbamoyl group, an N,N-dimethylcarbamoyl group, an N-ethyl-N-methylcarbamoyl group, a pyrrolidinecarbonyl group, a piperidinecarbonyl group or a morpholinecarbonyl group or the like;

$R_1$ and $R_2$ are preferably a hydrogen atom;

$R_3$ and $R_4$ are preferably a hydrogen atom, a lower alkyl group having 1–3 carbon atoms or a monocyclic ring having 3–5 carbon atoms, with a hydrogen atom, a methyl group, an ethyl group or a cyclobutyl group being particularly preferred;

$R_5$ is preferably a hydrogen atom;

$X_1$, $X_2$, $X_3$, and $X_4$ are preferably a hydrogen atom, a halogen atom, a lower alkyl group having 1–3 carbon atoms or a lower alkoxy group having 1–3 carbon atoms, with a hydrogen atom, a fluorine atom, a chlorine atom, a methyl group, an ethyl group, a methoxy group, an ethyoxy group or an n-propoxy group being particularly preferred;

A is preferably an optionally substituted benzene or pyridine ring, and more preferred is a benzene or pyridine ring that is substituted by a nitro group, a lower alkyl group having 1–3 carbon atoms, a lower alkoxy group having 1–3 carbon atoms or a lower alkylthio group having 1–3 carbon atoms, with a 6-methoxy-3-nitrobenzene-2-yl group, a 6-methyl-3-nitropyridine-2-yl group, a 6-methoxy-3-nitropyridine-2-yl group or a 4-methylpyridine-2-yl group being particularly preferred;

m and n are such that if they are both zero, the substituents other than $X_1$, $X_2$, $X_3$, and $X_4$ are preferably meta-substituted on the benzene nucleus whereas if m+n=1, the substituents other than $X_1$, $X_2$, $X_3$, and $X_4$ are preferably ortho- or para-substituted on the benzene nucleus.

Preferred compounds represented by the general formula (1) are 2-(3-aminomethylphenylamino)-6-methoxy-3-nitropyridine, 2-(3-aminomethylphenylamino)-6-methyl-3-nitropyridine, 2-(3-aminomethylphenylamino)-3-ethyl-3-nitropyridine, 2-(3-aminomethylphenylamino)-6-ethoxy-3-nitropyridine, 2-(3-aminomethylphenylamino)-6-methylthio-3-nitropyridine, 2-(3-aminomethylphenylamino)-6-methyl-3-nitrobenzene, 2-(3-aminomethylphenylamino)-6-methoxy-3-nitrobenzene, 2-(3-aminomethyl-2-methylphenylamino)-6-methoxy-3-nitropyridine, 2-(4-aminoethylphenylamino)-6-methoxy-3-nitropyridine, 2-(3-(1-amino-1-methylethyl)phenylamino)-6-methoxy-3-nitropyridine, 2-(3-aminomethyl-2-methoxyphenylamino)-6-methoxy-3-nitropyridine, 2-(3-aminomethyl-4-chlorophenylamino)-6-methoxy-3-nitropyridine, 2-(3-aminomethyl-4-fluorophenylamino)-6-methoxy-3-nitropyridine, 2-(3-aminomethyl-2-ethoxyphenylamino)-6-methoxy-3-nitropyridine, 2-(3-aminomethyl-2-chlorophenylamino)-6-methoxy-3-nitropyridine, 2-(3-aminomethylphenylamino)-4-methylpyridine, 2-(3-(1-amino-1-methylethyl)phenylamino)-4-methylpyridine, 2-(3-aminomethyl-2-methylphenylamino)-4-methylpyridine, 2-(3-aminomethyl-4-ethylphenylamino)-4-methylpyridine, 2-(3-aminomethyl-4-ethoxyphenylamino)-4-methylpyridine, 2-(2-aminoethylphenylamino)-4-methylpyridine, 2-(3-aminomethyl-2-chlorophenylamino)-4-methylpyridine, 2-(3-(1-amino-cyclobutyl)phenylamino)-4-methylpyridine, 2-(4-aminoethylphenylamino)-4-methylpyridine, 2-(3-aminomethyl-2-ethoxyphenylamino)-4-methylpyridine, 2-(3-aminomethyl-4-chlorophenylamino)-4-methylpyridine, 2-(3-aminomethyl-2-(n-propoxy)phenylamino)-4-methylpyridine, 2-(3-aminomethyl-4-chloro-2-ethoxyphenylamino)-4-methylpyridine, 2-(3-aminomethyl-2-ethoxy-4-methylphenylamino)-4-methylpyridine, 2-(3-aminomethyl-2-methoxyphenylamino)-4-methylpyridine and 2-(3-aminomethyl-2-(i-propoxy)phenylamino)-4-methylpyridine.

In addition to the compounds represented by the general formula (1), the present invention also encompasses their possible tautomers, stereoisomers, optionally active forms and mixtures thereof.

The compounds of the invention which are represented by the general formula (1) may typically be synthesized by the following schemes:

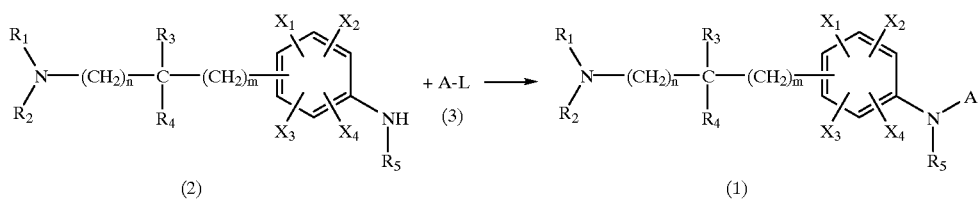

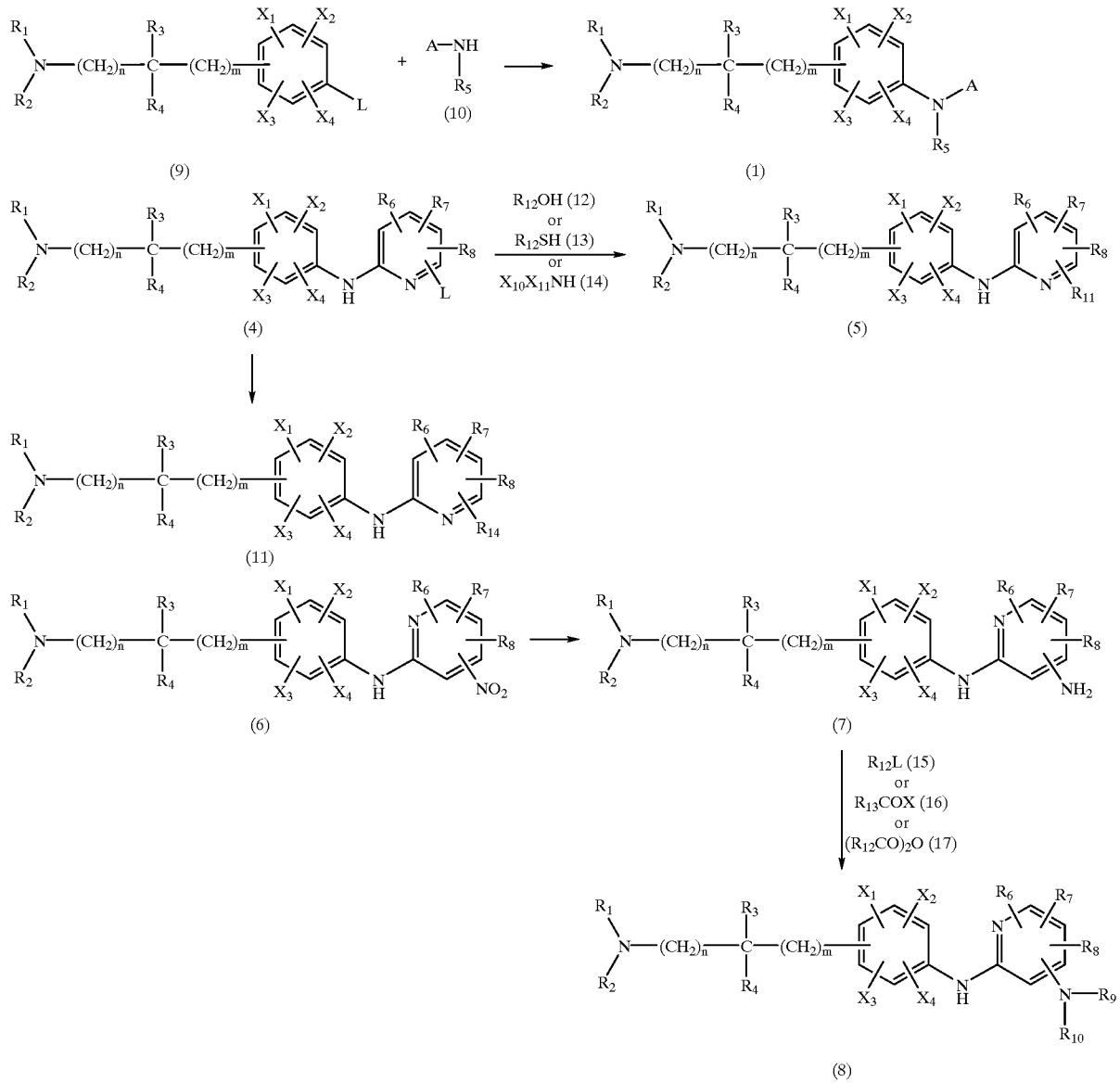

The compound represented by the general formula (1) can be synthesized by reacting a compound of the general formula (2), used as a starting material, with a compound of the general formula (3).

In the general formulas (1), (2) and (3), $R_1$, $R_2$, $R_3$, $R_4$, $R_5$, $X_1$, $X_2$, $X_3$, $X_4$, $X_5$, $X_6$, $X_7$, $X_8$, $X_9$, A, L, n and m each have the same meanings as defined above.

Stated more specifically, the compound represented by the general formula (1) can be synthesized by reacting the compound of the general formula (2) with the compound of the general formula (3) in the presence of a base such as potassium carbonate, triethylamine, diisopropylethylamine, potassium t-butoxide or sodium t-butoxide, with a metal catalyst such as copper, palladium or nickel and a ligand such as diphenylphophinoethane, diphenylphosphinopropane, diphenylphosphinoferrocene or 2,2'-bis(diphenylphosphino)-1,1'-binaphthyl being added as required, in a solvent inert to the reaction as exemplified by an alcohol such as methanol, ethanol or i-propanol or dimethylformamide, tetrahydrofuran, acetonitrile, toluene or 1,4-dioxane, at a temperature between room temperature and the boiling point of the reaction mixture. Preferably synthesis can be made by performing the reaction in the presence of triethylamine or diisopropylethylamine in dimethylformamide at 60° C. or by performing the reaction in the presence of potassium carbonate, potassium t-butoxide or sodium t-butoxide, with a palladium catalyst and a ligand diphenylphosphinoferrocene or 2,2'-bis(diphenylphosphino)-1,1'-binaphthyl added, in acetonitrile or toluene at a temperature between 80° C. and the boiling point of the reaction mixture.

The compound represented by the general formula (1) can also be synthesized by reacting a compound of the general formula (9), used as a starting material, with a compound of the general formula (10).

In the general formulas (1), (9) and (10), $R_1$, $R_2$, $R_3$, $R_4$, $X_1$, $X_2$, $X_3$, $X_4$, $R_5$, A, L, m and n each have the same meanings as defined above.

Stated more specifically, the compound represented by the general formula (1) can be synthesized by reacting the compound of the general formula (9) with the compound of the general formula (10) in the presence of a base such as potassium carbonate, triethylamine, potassium t-butoxide or sodium t-butoxide, preferably in the presence of potassium t-butoxide, with a metal catalyst such as copper, palladium or nickel and a ligand such as diphenylphosphinoethane, diphenylphosphinopropane, diphenylphosphinoferrocene or 2,2'-bis(diphenylphosphino)-1,1'-binaphthyl being added as required, preferably a palladium catalyst and a ligand diphenylphosphinoferrocene being added, in a solvent inert to the reaction as exemplified by an alcohol such as methanol, ethanol or i-propanol or dimethylformamide, tetrahydrofuran, acetonitrile, toluene or dioxane, preferably in toluene, at a temperature between room temperature and the boiling point of the reaction mixture, preferably at 80° C.

Among the compounds represented by the general formula (1), one which is represented by the general formula (5) where A is an optionally substituted pyridine ring and one of the substituents present is a lower alkoxy group, a lower alkylthio group or $NX_{10}X_{11}$ can also be synthesized starting with a compound of the general formula (4) with the leaving group attached.

In the general formulas (4), (5), (12), (13) and (14), $R_1$, $R_2$, $R_3$, $R_4$, $X_1$, $X_2$, $X_3$, $X_4$, L, m and n each has the same meanings as defined above;

$R_6$ is an electron withdrawing group such as a nitro group, a cyano group, a trifluoromethyl group or $C(=O)X_7$;

$R_7$ and $R_8$ are each a hydrogen atom, a halogen atom, a nitro group, a cyano group, a trifluoromethyl group, a hydroxyl group, a lower alkoxy group, a lower alkyl group, a lower alkylthio group, $NX_5X_6$ or $C(=O)X_7$;

where $X_5$, $X_6$, and $X_7$ each has the same meanings as defined above;

$R_{11}$ is a lower alkoxy group, a lower alkylthio group or $NX_{10}X_{11}$;

$R_{12}$ and $X_1$ are each a lower alkyl group;

$X_{11}$ is a hydrogen atom or a lower alkyl group.

Stated more specifically, the compound represented by the general formula (5) can also be synthesized from the compound of the formula (4) by desirably reacting it with a corresponding compound of the general formula (12), (13) or (14) in the presence of a base such as triethylamine or sodium hydride in a solvent inert to the reaction such as dimethylformamide, tetrahydrofuran or acetonitrile at a temperature between room temperature and the boiling point of the reaction mixture.

Among the compounds represented by the general formula (1), one which is represented by the general formula (11) where A is an optionally substituted pyridine ring and one of the substituents present is a lower alkyl group can also be synthesized by decarboxylation a compound obtained by performing a nucleophilic substitution on a lower alkyl dicarbonate corresponding to a compound of the general formula (4) with the leaving group attached.

In the general formulas (4) and (11), $R_1$, $R_2$, $R_3$, $R_4$, $R_6$, $R_7$, $R_8$, $X_1$, $X_2$, $X_3$, $X_4$, m and n each have the same meanings as defined above; and $R_{14}$ is a lower alkyl group.

Stated more specifically, the compound represented by the general formula (11) can also be synthesized from the compound of the general formula (4) by desirably reacting it with a corresponding lower alkyl dicarbonate in the presence of a base such as sodium hydride in a solvent inert to the reaction as exemplified by dimethylformamide, tetrahydrofuran or acetonitrile, preferably in dimethylformamide, at a temperature between room temperature and the boiling point of the reaction mixture, preferably at room temperature and thereafter subjecting the product to reaction in aqueous sulfuric acid at the boiling point of the reaction mixture.

Examples of the lower alkyl dicarbonate include dimethyl malonate, diethyl malonate, diethyl methylmalonate, diethyl ethylmalonate, diethyl n-propylmalonate, diethyl i-propylmalonate, diethyl n-butylmalonate, diethyl i-butylmalonate, diethyl t-butylmalonate, diethyl n-pentylmalonate and so forth.

Among the compounds represented by the general formula (1), one which is represented by the general formula (7) here A is an optionally substituted pyridine ring and one of the substituents present is an amino group can also be synthesized by reducing the nitro group in the corresponding general formula (6).

In the general formulas (6) and (7), $R_1$, $R_2$, $R_3$, $R_4$, m and n each have the same meanings as defined above;

$R_6$, $R_7$, and $R_8$ are each a hydrogen atom, a halogen atom, a trifluoromethyl group, a hydroxyl group, a lower alkyl group, a lower alkoxy group, a lower alkylthio group, $NX_5X_6$ or $COX_7$;

where $X_5$, $X_6$, and $X_7$ each have the same meanings as defined above;

$X_1$, $X_2$, $X_3$, and $X_4$ are each a hydrogen atom, a halogen atom, a phenyl group optionally substituted with a halogen atom and/or a lower alkyl group, a hydroxyl group, an optionally substituted lower alkyl group, an optionally substituted lower alkoxy group, $NX_5X_6$ or $COX_7$;

where $X_5$, $X_6$, and $X_7$, each have the same meanings as defined above.

Stated more specifically, the compound represented by the general formula (7) can also be synthesized by subjecting the compound of the general formula (6) to catalytic reduction in a solvent inert to the reaction as exemplified by ethanol, methanol, ethyl acetate, acetic acid or 1,4-dioxane, preferably in ethanol or methanol, in a hydrogen atmosphere at a temperature between room temperature and the boiling point of the reaction mixture, preferably at room temperature, with palladium-carbon, Raney nickel or platinum oxide used as a catalyst, or by performing reduction using nickel (II) chloride or sodium borohydride, so as to reduce the nitro group.

Among the compounds represented by the general formula (1), one which is represented by the general formula (8) where A is an optionally substituted pyridine ring and one of the substituents present is $NR_9R_{10}$, can also be synthesized with a compound of the general formula (7) used as a starting material.

In the general formulas (7), (8), (15), (16) and (17), $R_1$, $R_2$, $R_3$, $R_4$, $R_6$, $R_7$, $R_8$, $R_{12}$, $X_1$, $X_2$, $X_3$, $X_4$, L, m and n each have the same meanings as defined above;

$R_9$ is a hydrogen atom or a lower alkyl group;

$R_{10}$ is a lower alkyl group, an acyl group or a lower alkoxycarbonyl group;

$R_{13}$ is a lower alkyl group optionally substituted by a phenyl group; and

X is a halogen atom.

Stated more specifically, the compound represented by the general formula (8) can also be synthesized from the compound of the general formula (7) by desirably reacting it with a corresponding compound of the general formula (15), (16) or (17) in the presence of a base such as triethylamine or potassium carbonate in a solvent inert to the reaction at a temperature between room temperature and the boiling point of the reaction mixture, preferably at room temperature.

If in the process of synthesizing the compounds represented by the above formulas (1), (5), (7), (8) and (11), a protective group is necessary for the primary or secondary amino group, they are first protected either with a suitable resin or with one of the appropriate protective groups described in Green and Wuts, "PROTECTIVE GROUPS IN ORGANIC SYNTHESIS", 2nd Edition, John Wiley & Sons Inc., p. 309, 1991, and thereafter the respective reactions are performed. If necessary, the protected groups may be subjected to a deprotecting reaction. Examples of the amino protecting group include a t-butoxycarbonyl group, a trifluoroacetyl group and so forth.

The amino protecting reaction such as t-butoxycarbonylation may be performed by reacting the respective compound with di-t-butyl dicarbonate in a solvent inert to the reaction as exemplified by an alcohol such as methanol, ethanol or i-propanol or methylene dichloride, dimethyl-formamide or 1,4-dioxane in the presence of an organic base such as triethylamine or 4-dimethylamiopyridine at a temperature between 0° C. and room temperature.

The amino protecting reaction may also be performed with a Wang resin by reacting the respective compound with a 4-nitrophenyloxycarbonyl-Wang resin (Tetrahedron Lett., 37, 937–940 (1996)) in a solvent inert to the reaction as exemplified by methylene chloride, dimethylformamide or 1,4-dioxane in the presence of an organic base such as 4-methylmorpholine, triethylamine or 4-dimethylaminopyridine at a temperature between 0° C. and room temperature.

If the protecting group is a t-butoxycarbonyl group or the Wang resin mentioned above, a reaction for deprotecting the amino group is preferably performed in a solvent inert to the reaction as exemplified by methanol, ethanol, 1,4-dioxane or methylene chloride or without using any solvent at all, with the aid of a deprotecting agent such as trifluoroacetic acid, hydrochloric acid, sulfuric acid or methanesulfonic acid at a temperature between 0° C. and room temperature, with the use of anhydrous conditions, room temperature and trifluoroacetic acid being particularly preferred.

If the compounds of the invention which are represented by the general formula (1) have asymmetric carbons in their structure, the pure forms of their stereoisomers and optically active forms can be obtained by known techniques in the art, such as chromatography on optical isomer separating columns and fractional crystallization.

Pharmaceutically acceptable salts of the compounds of the invention which are represented by the general formula (1) may be of any types as long as they are pharmaceutically acceptable salts and typical examples include salts with inorganic acids such as hydrochloric acid, sulfuric acid, nitric acid, hydrobrobromic acid and hydroiodic acid, salts with organic acids such as formic acid, acetic acid, oxalic acid and tartaric acid, salts with alkali metals such as sodium and potassium, and salts with alkaline earth metals such as calcium and magnesium.

The compounds of the invention or salts thereof may be formulated with suitable excipients, adjuvants, lubricants, antiseptics, disintegrators, buffering agents, binders, stabilizers, wetting agents, emulsifiers, coloring agents, flavoring agents, fragrances, etc. to form tablets, granules, subtilized granules, powders, capsules, syrups, elixirs, suspensions, emulsions, injections, etc. for oral or parenteral administration. When the cerebrovascular diseases to be treated are in a hyperacute phase (immediately after the stroke), an acute phase (from the stroke to 2 or 3 days later) or in a subacute phase (2 or 3 days up to 2 weeks after the stroke), administration is effected primarily by intramuscular or intravenous injection. In addition, oral administration may be performed in a chronic phase (the third week after stroke and onward) if the patient admits ingestion.

The compounds of the invention or salts thereof may be administered in doses that vary with the physical constitution of the patient, his or her age, physical condition, the severity of the disease, the time of lapse after the onset of the disease and other factors; typical daily doses range from 0.5 to 5 mg/body for oral administration and from 1 to 10 mg/body for parenteral administration. It should generally be noted that even if the same dose is administered, the plasma concentration may sometimes vary considerably between patients; hence, an optimal dose of the drug should ideally be determined for each patient on the basis of a monitored plasma concentration of the drug.

If the compounds of the invention or salts thereof are to be formulated as preparations for internal application, lactose, sucrose, sorbitol, mannitol, starches such as potato starch or corn starch, starch derivatives and common additives such as cellulose derivatives or gelatin are suitably used as vehicles, with lubricants such as magnesium stearate, carbowaxes and polyethylene glycol being optionally added concurrently; the resulting mixtures may be formulated in the usual manner into granules, tablets, capsules or other forms suitable for internal application.

If the compounds of the invention or salts thereof are to be formulated as aqueous preparations, effective amounts of the principal ingredients may be dissolved in distilled water for injection, with antioxidants, stabilizers, dissolution aids, buffering agents, preservatives, etc. added as required and, after complete solutions are formed, they are filtered, filled into ampules and sealed in the usual manner and sterilized by a suitable medium such as high-pressure vapor or dry heat so as to prepare injections.

If the compounds of the invention or salts thereof are to be formulated as lyophilized preparations, aqueous solutions having the principal ingredients dissolved in distilled water for injection may be freeze-dried in the usual manner; depending on the need, excipients that provide for easy lyophilization, such as sugars (e.g. lactose, maltose and sucrose), sugar alcohols (e.g. mannitol and inositol), glycine and the like, may be added before freeze-drying is performed in the usual manner to make the intended preparations.

EXAMPLES

Lists of the compounds prepared in the Examples of the invention are given in Tables 1–37 below.

TABLE 1

Structure (1):
$R_1R_2N-(CH_2)_m-C(R_3)(R_4)-(CH_2)_n-$ attached to benzene ring with $X_1, X_2, X_3, X_4$ positions, Y, Z, and $N(A)(R_5)$ group, with $R_6$ substituent.

A = (2): pyridine-type ring with $R_7, R_8, R_9$
A = (3): ring with W, U, $R_7, R_8, R_9$
A = (4): ring with W, U, $R_7, R_8, R_9$
A = (5): pyrrole-type with T, $R_7, R_8, R_9$
A = (6): pyrrole-type with T, $R_7, R_8, R_9$
A = (7): pyrrole-type with T, $R_7, R_8$

| Ex. No. | A | Y | Z | $R_6$ | Substitution position of A | $R_7$ *1 | $R_8$ *1 | $R_9$ *1 | $X_1$ *2 | $X_2$ *2 | $X_3$ *2 | $X_4$ *2 | Substitution position of W* | $R_1$ | $R_2$ | n | $R_3$ | $R_4$ | m | $R_5$ | salt |
|---|---|---|---|---|---|---|---|---|---|---|---|---|---|---|---|---|---|---|---|---|---|
| 1 | (2) | $CR_6$ | N | $NO_2$ | 2 | 4-H | 5-H | 6-H | 2-H | 4-H | 5-H | 6-H | 3 | $CO_2{}^tBu$ | $CO_2{}^tBu$ | 0 | H | H | 0 | H | HCl |
| 2 | (2) | $CR_6$ | N | $NO_2$ | 2 | 4-H | 5-H | 6-H | 2-H | 4-H | 5-H | 6-H | 3 | H | H | 0 | H | H | 0 | H | |
| 3 | (2) | $CR_6$ | N | $NO_2$ | 2 | 4-H | 5-H | 6-H | 2-H | 4-H | 5-H | 6-H | 3 | $CO_2{}^tBu$ | $CO_2{}^tBu$ | 0 | H | H | 0 | H | 2HCl |
| 4 | (2) | $CR_6$ | N | $NO_2$ | 2 | 4-H | 5-H | 6-H | 2-H | 4-H | 5-H | 6-H | 3 | H | H | 0 | H | H | 0 | H | |
| 5 | (2) | $CR_6$ | N | NHMe | 2 | 4-H | 5-H | 6-H | 2-H | 4-H | 5-H | 6-H | 3 | $CO_2{}^tBu$ | $CO_2{}^tBu$ | 0 | H | H | 0 | H | |
| 6 | (2) | $CR_6$ | N | NHMe | 2 | 4-H | 5-H | 6-H | 2-H | 4-H | 5-H | 6-H | 3 | H | H | 0 | H | H | 0 | H | 2HCl |
| 7 | (2) | $CR_6$ | N | NHEt | 2 | 4-H | 5-H | 6-H | 2-H | 4-H | 5-H | 6-H | 3 | $CO_2{}^tBu$ | $CO_2{}^tBu$ | 0 | H | H | 0 | H | |
| 8 | (2) | $CR_6$ | N | NHEt | 2 | 4-H | 5-H | 6-H | 2-H | 4-H | 5-H | 6-H | 3 | H | H | 0 | H | H | 0 | H | 2HCl |
| 9 | (2) | $CR_6$ | N | H | 2 | 4-H | 5-$NO_2$ | 6-H | 2-H | 4-H | 5-H | 6-H | 3 | $CO_2{}^tBu$ | $CO_2{}^tBu$ | 0 | H | H | 0 | H | HCl |
| 10 | (2) | $CR_6$ | N | H | 2 | 4-H | 5-$NO_2$ | 6-H | 2-H | 4-H | 5-H | 6-H | 3 | H | H | 0 | H | H | 0 | H | 2HCl |
| 11 | (2) | $CR_6$ | N | H | 2 | 4-H | 5-$NH_2$ | 6-H | 2-H | 4-H | 5-H | 6-H | 3 | $CO_2{}^tBu$ | $CO_2{}^tBu$ | 0 | H | H | 0 | H | HCl |
| 12 | (2) | $CR_6$ | N | H | 2 | 4-H | 5-H | 6-H | 2-H | 4-H | 5-H | 6-H | 3 | H | H | 0 | H | H | 0 | H | |
| 13 | (2) | $CR_6$ | N | $NO_2$ | 2 | 4-Me | 5-H | 6-H | 2-H | 4-H | 5-H | 6-H | 3 | $CO_2{}^tBu$ | $CO_2{}^tBu$ | 0 | H | H | 0 | H | |
| 14 | (2) | $CR_6$ | N | $NO_2$ | 2 | 4-Me | 5-H | 6-H | 2-H | 4-H | 5-H | 6-H | 3 | H | H | 0 | H | H | 0 | H | |
| 15 | (2) | $CR_6$ | N | $NO_2$ | 2 | 4-Me | 5-H | 6-H | 2-H | 4-H | 5-H | 6-H | 3 | $CO_2{}^tBu$ | $CO_2{}^tBu$ | 0 | H | H | 0 | H | |

*1: Numerals represent substitution positions in the structural formulas of (2)–(7) employed.
*2: Numerals represent substitution positions on the benzene ring.

*: W = 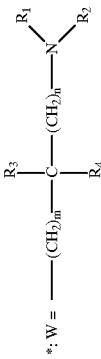

TABLE 2

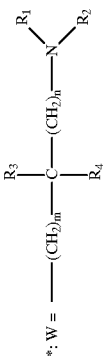

| Ex. No. | A | Y | Z | R₆ | Substitution position of A | R₇*¹ | R₈*¹ | R₉*¹ | X₁*² | X₂*² | X₃*² | X₄*² | Substitution position of W* | R₁ | R₂ | n | R₃ | R₄ | m | R₅ | salt |
|---|---|---|---|---|---|---|---|---|---|---|---|---|---|---|---|---|---|---|---|---|---|
| 16 | (2) | CR₆ | N | NH₂ | 2 | 4-Me | 5-H | 6-H | 2-H | 4-H | 5-H | 6-H | 3 | H | H | 0 | H | H | 0 | H | 2HCl |
| 17 | (2) | CR₆ | N | NO₂ | 2 | 4-H | 5-H | 6-OMe | 2-H | 4-H | 5-H | 6-H | 3 | CO₂ᵗBu | CO₂ᵗBu | 0 | H | H | 0 | H | HCl |
| 18 | (2) | CR₆ | N | NH₂ | 2 | 4-H | 5-H | 6-OMe | 2-H | 4-H | 5-H | 6-H | 3 | H | H | 0 | H | H | 0 | H | 2HCl |
| 19 | (2) | CR₆ | N | NH₂ | 2 | 4-H | 5-H | 6-OMe | 2-H | 4-H | 5-H | 6-H | 3 | H | H | 0 | H | H | 0 | H | 2HCl |
| 20 | (2) | CR₆ | N | NO₂ | 2 | 4-H | 5-H | 6-OMe | 2-H | 4-OMe | 5-H | 6-H | 3 | CO₂ᵗBu | CO₂ᵗBu | 0 | H | H | 0 | H | HCl |
| 21 | (2) | CR₆ | N | NO₂ | 2 | 4-H | 5-H | 6-OMe | 2-H | 4-OMe | 5-H | 6-H | 3 | H | H | 0 | H | H | 0 | H | HCl |
| 22 | (2) | CR₆ | N | NO₂ | 2 | 4-H | 5-H | 6-OMe | 2-H | 4-Et | 5-H | 6-H | 3 | CO₂ᵗBu | CO₂ᵗBu | 0 | H | H | 0 | H | HCl |
| 23 | (2) | CR₆ | N | NO₂ | 2 | 4-H | 5-H | 6-OMe | 2-H | 4-Et | 5-H | 6-H | 3 | H | H | 0 | H | H | 0 | H | HCl |
| 24 | (2) | CR₆ | N | NO₂ | 2 | 4-H | 5-H | 6-OMe | 2-H | 4-Et | 5-H | 6-H | 3 | CO₂ᵗBu | H | 0 | indan-2-yl | H | 0 | H | HCl |
| 25 | (2) | CR₆ | N | NO₂ | 2 | 4-H | 5-H | 6-OMe | 2-H | 4-H | 5-H | 6-H | 3 | H | H | 0 | indan-2-yl | H | 0 | H | HCl |
| 26 | (2) | CR₆ | N | NO₂ | 2 | 4-H | 5-H | 6-OMe | 2-H | 4-H | 5-H | 6-H | 3 | CO₂ᵗBu | CO₂ᵗBu | 0 | H | H | 0 | H | HCl |
| 27 | (2) | CR₆ | N | NO₂ | 2 | 4-H | 5-H | 6-Cl | 2-H | 4-H | 5-H | 6-H | 3 | H | H | 0 | H | H | 0 | H | HCl |
| 28 | (2) | CR₆ | N | NO₂ | 2 | 4-H | 5-H | 6-Cl | 2-H | 4-H | 5-H | 6-H | 3 | CO₂ᵗBu | CO₂ᵗBu | 0 | H | H | 0 | H | HCl |
| 29 | (2) | CR₆ | N | NO₂ | 2 | 4-H | 5-H | 6-NHMe | 2-H | 4-H | 5-H | 6-H | 3 | H | H | 0 | H | H | 0 | H | HCl |
| 30 | (2) | CR₆ | N | NO₂ | 2 | 4-H | 5-H | 6-NHMe | 2-H | 4-H | 5-H | 6-H | 3 | CO₂ᵗBu | CO₂ᵗBu | 0 | H | H | 0 | H | HCl |

*¹: Numerals represent substitution positions in the structural formulas of (2)–(7) employed.
*²: Numerals represent substitution positions on the benzene ring.

*: W =

TABLE 3

Structural formulas (1)-(7) with substituents as described.

| Ex. No. | A | Y | Z | R_6 | Substitution position of A | R_7 *1 | R_8 *1 | R_9 *1 | X_1 *2 | X_2 *2 | X_3 *2 | X_4 *2 | Substitution position of W * | R_1 | R_2 | n | R_3 | R_4 | m | R_5 | salt |
|---|---|---|---|---|---|---|---|---|---|---|---|---|---|---|---|---|---|---|---|---|---|
| 31 | (2) | CR_6 | N | NO_2 | 2 | 4-H | 5-H | 6-NHEt | 2-H | 4-H | 5-H | 6-H | 3 | CO_2^tBu | CO_2^tBu | 0 | H | H | 0 | H | HCl |
| 32 | (2) | CR_6 | N | NO_2 | 2 | 4-H | 5-H | 6-NHEt | 2-H | 4-H | 5-H | 6-H | 3 | H | H | 0 | H | H | 0 | H | HCl |
| 33 | (2) | CR_6 | N | NO_2 | 2 | 4-H | 5-H | 6-NH^nPr | 2-H | 4-H | 5-H | 6-H | 3 | CO_2^tBu | CO_2^tBu | 0 | H | H | 0 | H | HCl |
| 34 | (2) | CR_6 | N | NO_2 | 2 | 4-H | 5-H | 6-NH^nPr | 2-H | 4-H | 5-H | 6-H | 3 | H | H | 0 | H | H | 0 | H | HCl |
| 35 | (2) | CR_6 | N | NO_2 | 2 | 4-H | 5-H | 6-NMe_2 | 2-H | 4-H | 5-H | 6-H | 3 | CO_2^tBu | CO_2^tBu | 0 | H | H | 0 | H | HCl |
| 36 | (2) | CR_6 | N | NO_2 | 2 | 4-H | 5-H | 6-NMe_2 | 2-H | 4-H | 5-H | 6-H | 3 | H | H | 0 | H | H | 0 | H | HCl |
| 37 | (2) | CR_6 | N | CO_2H | 2 | 4-H | 5-H | 6-Cl | 2-H | 4-H | 5-H | 6-H | 3 | CO_2^tBu | CO_2^tBu | 0 | H | H | 0 | H | HCl |
| 38 | (2) | CR_6 | N | CO_2H | 2 | 4-H | 5-H | 6-Cl | 2-H | 4-H | 5-H | 6-H | 3 | H | H | 0 | H | H | 0 | H | 2HCl |
| 39 | (2) | CR_6 | N | H | 2 | 4-H | 5-H | 6-OMe | 2-H | 4-H | 5-H | 6-H | 3 | CO_2^tBu | CO_2^tBu | 0 | H | H | 0 | H | HCl |
| 40 | (2) | CR_6 | N | H | 2 | 4-H | 5-H | 6-OMe | 2-H | 4-H | 5-H | 6-H | 3 | H | H | 0 | H | H | 0 | H | 2HCl |
| 41 | (2) | CR_6 | N | CF_3 | 2 | 4-H | 5-H | 6-H | 2-H | 4-H | 5-H | 6-H | 3 | CO_2^tBu | CO_2^tBu | 0 | H | H | 0 | H | HCl |
| 42 | (2) | CR_6 | N | CF_3 | 2 | 4-H | 5-H | 6-H | 2-H | 4-H | 5-H | 6-H | 3 | H | H | 0 | H | H | 0 | H | 2HCl |
| 43 | (2) | CR_6 | N | CO_2Me | 2 | 4-H | 5-H | 6-OMe | 2-H | 4-H | 5-H | 6-H | 3 | CO_2^tBu | CO_2^tBu | 0 | H | H | 0 | H | HCl |
| 44 | (2) | CR_6 | N | CO_2Me | 2 | 4-H | 5-H | 6-OMe | 2-H | 4-H | 5-H | 6-H | 3 | H | H | 0 | H | H | 0 | H | HCl |
| 45 | (2) | CR_6 | N | CO_2H | 2 | 4-H | 5-H | 6-OMe | 2-H | 4-H | 5-H | 6-H | 3 | H | H | 0 | H | H | 0 | H | HCl |

*1: Numerals represent substitution positions in the structural formulas of (2)-(7) employed.
*2: Numerals represent substitution positions on the benzene ring.

*: W = 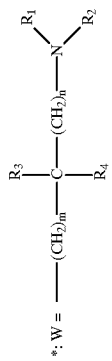

TABLE 4

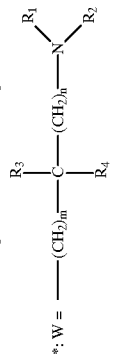

| Ex. No. | A | Y | Z | R_6 | Substitution position of A | R_7*1 | R_8*1 | R_9*1 | X_1*2 | X_2*2 | X_3*2 | X_4*2 | Substitution position of W* | R_1 | R_2 | n | R_3 | R_4 | m | R_5 | salt |
|---|---|---|---|---|---|---|---|---|---|---|---|---|---|---|---|---|---|---|---|---|---|
| 46 | (2) | CR_6 | N | H | 2 | 4-OBn | 5-H | 6-H | 2-H | 4-H | 5-H | 6-H | 3 | Ac | H | 0 | H | H | 0 | H | HCl |
| 47 | (2) | CR_6 | N | H | 2 | 4-OBn | 5-H | 6-H | 2-H | 4-H | 5-H | 6-H | 3 | H | H | 0 | H | H | 0 | H | 2HCl |
| 48 | (2) | CR_6 | N | H | 2 | 4-H | 5-H | 6-H | 2-H | 4-cyclobutyl | 5-H | 6-H | 3 | Bz | H | 0 | H | H | 0 | H | HCl |
| 49 | (2) | CR_6 | N | H | 2 | 4-H | 5-H | 6-H | 2-H | 4-cyclopentyl | 5-H | 6-H | 3 | H | H | 0 | H | H | 0 | H | HCl |
| 50 | (2) | CR_6 | N | H | 2 | 4-H | 5-H | 6-H | 2-H | 4-piperidino | 5-H | 6-H | 3 | H | H | 0 | H | H | 0 | H | 2HCl |
| 51 | (2) | CR_6 | N | H | 2 | 4-H | 5-H | 6-H | 2-H | 4-O(CH_2)_2Ph | 5-H | 6-H | 3 | H | H | 0 | H | H | 0 | H | 2HCl |
| 52 | (2) | CR_6 | N | NO_2 | 2 | 4-H | 5-H | 6-Me | 2-H | 4-H | 5-H | 6-H | 3 | H | H | 0 | H | H | 0 | H | HCl |
| 53 | (2) | CR_6 | N | NO_2 | 2 | 4-H | 5-H | 6-Et | 2-H | 4-H | 5-H | 6-H | 3 | H | H | 0 | H | H | 0 | H | HCl |
| 54 | (2) | CR_6 | N | NO_2 | 2 | 4-H | 5-H | 6-nPr | 2-H | 4-H | 5-H | 6-H | 3 | Bn | H | 0 | H | H | 0 | H | HCl |
| 55 | (2) | CR_6 | N | NO_2 | 2 | 4-H | 5-H | 6-iPr | 2-H | 4-H | 5-H | 6-H | 3 | H | H | 0 | H | H | 0 | H | HCl |
| 56 | (2) | CR_6 | N | NO_2 | 2 | 4-H | 5-H | 6-OH | 2-H | 4-H | 5-H | 6-H | 3 | H | H | 0 | H | H | 0 | H | HCl |
| 57 | (2) | CR_6 | N | NO_2 | 2 | 4-H | 5-H | 6-OEt | 2-H | 4-H | 5-H | 6-H | 3 | H | CH_2CH_2Ph | 0 | H | H | 0 | H | HCl |
| 58 | (2) | CR_6 | N | NO_2 | 2 | 4-H | 5-H | 6-OnPr | 2-H | 4-H | 5-H | 6-H | 3 | CH_2CH_2Cl | H | 0 | H | H | 0 | H | HCl |
| 59 | (2) | CR_6 | N | NO_2 | 2 | 4-H | 5-H | 6-OiPr | 2-H | 4-H | 5-H | 6-H | 3 | H | H | 0 | H | H | 0 | H | HCl |
| 60 | (2) | CR_6 | N | NO_2 | 2 | 4-H | 5-H | 6-SH | 2-H | 4-H | 5-H | 6-H | 3 | CH_2CH_2Cl | CH_2CH_2Cl | 0 | H | H | 0 | H | HCl |

*1: Numerals represent substitution positions in the structural formulas of (2)–(7) employed.
*2: Numerals represent substitution positions on the benzene ring.

*: W =

TABLE 5

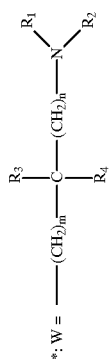

| Ex. No. | A | Y | Z | R_6 | Substitution position of A | R_7 *1 | R_8 *1 | R_9 *1 | X_1 *2 | X_2 *2 | X_3 *2 | X_4 *2 | Substitution position of W* | R_1 | R_2 | n | R_3 | R_4 | m | R_5 | salt |
|---|---|---|---|---|---|---|---|---|---|---|---|---|---|---|---|---|---|---|---|---|---|
| 61 | (2) | CR_6 | N | NO_2 | 2 | 4-H | 5-H | 6-SMe | 2-H | 4-H | 5-H | 6-H | 3 | H | H | 0 | H | H | 0 | H | HCl |
| 62 | (2) | CR_6 | N | NO_2 | 2 | 4-H | 5-H | 6-SEt | 2-H | 4-H | 5-H | 6-H | 3 | H | H | 0 | H | H | 0 | H | HCl |
| 63 | (2) | CR_6 | N | NO_2 | 2 | 4-H | 5-H | 6-S^nPr | 2-H | 4-H | 5-H | 6-H | 3 | H | H | 0 | H | H | 0 | Me | HCl |
| 64 | (2) | CR_6 | N | NO_2 | 2 | 4-H | 5-H | 6-S^iPr | 2-H | 4-H | 5-H | 6-H | 3 | H | H | 0 | H | H | 0 | Et | HCl |
| 65 | (2) | CR_6 | N | H | 2 | 4-NO_2 | 5-H | 6-OMe | 2-H | 4-H | 5-H | 6-H | 3 | H | H | 0 | H | H | 0 | H | HCl |
| 66 | (2) | CR_6 | N | H | 2 | 4-NO_2 | 5-H | 6-Et | 2-H | 4-H | 5-NHAc | 6-H | 3 | H | H | 0 | H | H | 0 | H | HCl |
| 67 | (2) | CR_6 | N | H | 2 | 4-H | 5-NO_2 | 6-OMe | 2-H | 4-NHBn | 5-H | 6-H | 3 | H | H | 0 | H | H | 0 | H | HCl |
| 68 | (2) | CR_6 | N | CO_2H | 2 | 4-H | 5-NO_2 | 6-Et | 2-H | 4-NO_2 | 5-H | 6-H | 3 | H | H | 0 | H | H | 0 | H | HCl |
| 69 | (2) | CR_6 | N | CO_2H | 2 | 4-H | 5-H | 6-OMe | 2-H | 4-H | 5-NO_2 | 6-H | 3 | H | H | 0 | H | H | 0 | ^nPr | HCl |
| 70 | (2) | CR_6 | N | CO_2Me | 2 | 4-H | 5-H | 6-Et | 2-H | 4-H | 5-H | 6-H | 3 | H | H | 0 | H | H | 0 | Ac | HCl |
| 71 | (2) | CR_6 | N | CO_2Me | 2 | 4-H | 5-H | 6-OMe | 2-H | 4-H | 5-H | 6-H | 3 | H | H | 0 | H | H | 0 | Bn | HCl |
| 72 | (2) | CR_6 | N | CONH_2 | 2 | 4-H | 5-H | 6-Et | 2-H | 4-F | 5-H | 6-H | 3 | H | H | 0 | H | H | 0 | H | HCl |
| 73 | (2) | CR_6 | N | CONH_2 | 2 | 4-H | 5-H | 6-OMe | 2-H | 4-H | 5-Br | 6-H | 3 | H | H | 0 | H | H | 0 | H | 2HCl |
| 74 | (2) | CR_6 | N | CONH_2 | 2 | 4-H | 5-H | 6-Et | 2-H | 4-H | 5-H | 6-H | 3 | H | H | 0 | H | H | 0 | H | 2HCl |
| 75 | (2) | CR_6 | N | CF_3 | 2 | 4-H | 5-H | 6-OMe | 2-H | 4-CH_2Br | 5-H | 6-H | 3 | H | H | 0 | H | H | 0 | H | 2HCl |

*1: Numerals represent substitution positions in the structural formulas of (2)–(7) employed.
*2: Numerals represent substitution positions on the benzene ring.

TABLE 6

| Ex. No. | A | Y | Z | R$_6$ | Substitution position of A | R$_7$*[1] | R$_8$*[1] | R$_9$*[1] | X$_1$*[2] | X$_2$*[2] | X$_3$*[2] | X$_4$*[2] | R$_1$ | R$_2$ | Substitution position of W* | R$_3$ | n | R$_4$ | R$_5$ | salt |
|---|---|---|---|---|---|---|---|---|---|---|---|---|---|---|---|---|---|---|---|---|
| 76 | (2) | CR$_6$ | N | CF$_3$ | 2 | 4-H | 5-H | 6-Et | 2-H | 4-H | 5-H | 6-H | H | H | 3 | H | 0 | H | H | 2HCl |
| 77 | (2) | CR$_6$ | N | NO$_2$ | 2 | 4-H | 5-H | 6-OMe | 2-H | 4-Me | 5-H | 6-H | H | H | 3 | H | 0 | H | H | HCl |
| 78 | (2) | CR$_6$ | N | NO$_2$ | 2 | 4-H | 5-H | 6-H | 2-H | 4-$^n$Pr | 5-H | 6-H | H | H | 3 | H | 0 | H | H | HCl |
| 79 | (2) | CR$_6$ | N | NO$_2$ | 2 | 4-H | 5-H | 6-H | 2-H | 4-NHMe | 5-H | 6-H | H | H | 3 | H | 0 | H | H | 2HCl |
| 80 | (2) | CR$_6$ | N | NO$_2$ | 2 | 4-H | 5-H | 6-H | 2-H | 4-NHEt | 5-H | 6-H | H | H | 3 | H | 0 | H | H | 2HCl |
| 81 | (2) | CR$_6$ | N | NO$_2$ | 2 | 4-H | 5-H | 6-H | 2-H | 4-NMe$_2$ | 5-H | 6-H | H | H | 3 | H | 0 | H | H | 2HCl |
| 82 | (2) | CR$_6$ | N | NO$_2$ | 2 | 4-H | 5-H | 6-H | 2-H | 4-pyrrolidin-1-yl | 5-H | 6-H | H | H | 3 | H | 0 | H | H | 2HCl |
| 83 | (2) | CR$_6$ | N | NO$_2$ | 2 | 4-H | 5-H | 6-H | 2-H | 4-OH | 5-H | 6-H | H | H | 3 | H | 0 | H | H | HCl |
| 84 | (2) | CR$_6$ | N | NO$_2$ | 2 | 4-H | 5-H | 6-H | 2-H | 4-OEt | 5-H | 6-H | H | H | 3 | H | 0 | H | H | HCl |
| 85 | (2) | CR$_6$ | N | NO$_2$ | 2 | 4-H | 5-H | 6-H | 2-H | 4-H | 5-Me | 6-H | H | H | 3 | H | 0 | H | H | HCl |
| 86 | (2) | CR$_6$ | N | NO$_2$ | 2 | 4-H | 5-H | 6-H | 2-F | 4-H | 5-Et | 6-H | H | H | 3 | CH$_2$CH$_2$OH | 0 | CH$_2$CH$_2$OH | H | HCl |
| 87 | (2) | CR$_6$ | N | NO$_2$ | 2 | 4-H | 5-H | 6-H | 2-Cl | 4-H | 5-H | 6-H | H | H | 3 | H | 0 | H | H | HCl |
| 88 | (2) | CR$_6$ | N | NO$_2$ | 2 | 4-H | 5-H | 6-H | 2-Me | 4-H | 5-H | 6-H | H | H | 3 | H | 0 | H | H | HCl |
| 89 | (2) | CR$_6$ | N | NO$_2$ | 2 | 4-H | 5-H | 6-H | 2-OH | 4-H | 5-H | 6-H | H | H | 3 | H | 0 | H | H | HCl |
| 90 | (2) | CR$_6$ | N | NO$_2$ | 2 | 4-H | 5-H | 6-H | 2-OMe | 4-H | 5-H | 6-H | H | H | 3 | H | 0 | H | H | HCl |

*[1]: Numerals represent substitution positions in the structural formulas of (2)–(7) employed.
*[2]: Numerals represent substitution positions on the benzene ring.

*: W = 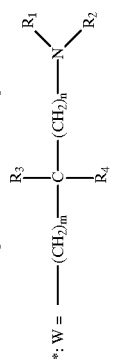

TABLE 7

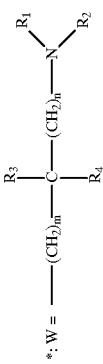

| Ex. No. | A | Y | Z | $R_6$ | Substitution position of A | $R_7$ *1 | $R_8$ *1 | $R_9$ *1 | $X_1$ *2 | $X_2$ *2 | $X_3$ *2 | $X_4$ *2 | Substitution position of W* | $R_1$ | $R_2$ | n | $R_3$ | $R_4$ | m | $R_5$ | salt |
|---|---|---|---|---|---|---|---|---|---|---|---|---|---|---|---|---|---|---|---|---|---|
| 91 | (2) | $CR_6$ | N | $NO_2$ | 2 | 4-H | 5-H | 6-OMe | 2-H | 4-H | 5-H | 6-H | 3 | H | H | 0 | Me | H | 0 | H | HCl |
| 92 | (2) | $CR_6$ | N | $NO_2$ | 2 | 4-H | 5-H | 6-OMe | 2-H | 4-CN | 5-H | 6-H | 3 | H | H | 0 | Et | H | 0 | H | HCl |
| 93 | (2) | $CR_6$ | N | $NO_2$ | 2 | 4-H | 5-H | 6-OMe | 2-H | 4-CN | 5-H | 6-H | 3 | H | H | 0 | nPr | H | 0 | H | HCl |
| 94 | (2) | $CR_6$ | N | $NO_2$ | 2 | 4-H | 5-H | 6-cyclobutylthio | 2-H | 4-H | 5-H | 6-H | 3 | H | H | 0 | Me | Me | 0 | H | HCl |
| 95 | (2) | $CR_6$ | N | $NO_2$ | 2 | 4-H | 5-H | 6-cyclopentylthio | 2-H | 4-H | 5-H | 6-H | 3 | H | H | 0 | —$(CH_2)_2$— | | 0 | H | HCl |
| 96 | (2) | $CR_6$ | N | $NO_2$ | 2 | 4-H | 5-H | 6-cyclohexylthio | 2-H | 4-H | 5-H | 6-H | 3 | H | H | 0 | —$(CH_2)_3$— | | 0 | H | HCl |
| 97 | (2) | $CR_6$ | N | $NO_2$ | 2 | 4-H | 5-H | 6-OMe | 2-H | 4-H | 5-H | 6-H | 3 | H | H | 0 | —$(CH_2)_4$— | | 0 | H | HCl |
| 98 | (2) | $CR_6$ | N | $NO_2$ | 2 | 4-H | 5-H | 6-OMe | 2-H | 4-H | 5-H | 6-H | 3 | Me | H | 0 | H | H | 0 | H | HCl |
| 99 | (2) | $CR_6$ | N | $NO_2$ | 2 | 4-H | 5-H | 6-OMe | 2-H | 4-H | 5-H | 6-H | 3 | Et | H | 0 | H | H | 0 | H | HCl |
| 100 | (2) | $CR_6$ | N | $NO_2$ | 2 | 4-H | 5-H | 6-OMe | 2-OMe | 4-H | 5-H | 6-H | 3 | Me | Me | 0 | H | H | 0 | H | HCl |
| 101 | (2) | $CR_6$ | N | $NO_2$ | 2 | 4-H | 5-H | 6-OMe | 2-OMe | 4-H | 5-H | 6-H | 3 | —$(CH_2)_3$— | | 0 | H | H | 0 | H | HCl |
| 102 | (2) | $CR_6$ | N | $NO_2$ | 2 | 4-H | 5-H | 6-OMe | 2-H | 4-H | 5-H | 6-H | 3 | —$(CH_2)_4$— | | 0 | H | H | 0 | H | HCl |
| 103 | (2) | $CR_6$ | N | $NO_2$ | 2 | 4-H | 5-H | 6-OMe | 2-H | 4-H | 5-H | 6-H | 3 | —$(CH_2)_5$— | | 0 | H | H | 0 | H | HCl |
| 104 | (2) | $CR_6$ | N | $NO_2$ | 2 | 4-H | 5-H | 6-H | 2-H | 4-H | 5-H | 6-H | 3 | H | H | 0 | $CH_2OH$ | H | 0 | H | HCl |
| 105 | (2) | $CR_6$ | N | $NO_2$ | 2 | 4-H | 5-H | 6-H | 2-H | 4-H | 5-H | 6-H | 3 | H | H | 0 | $CH_2CH_2OH$ | H | 0 | H | HCl |

*1: Numerals represent substitution positions in the structural formulas of (2)–(7) employed.
*2: Numerals represent substitution positions on the benzene ring.

*: W =

TABLE 8

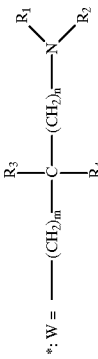

| Ex. No. | A | Y | Z | R6 | Substitution position of A | R7*1 | R8*1 | R9*1 | X1*2 | X2*2 | X3*2 | X4*2 | Substitution position of W* | R1 | R2 | n | R3 | R4 | (6) | (5) | m | R5 | salt |
|---|---|---|---|---|---|---|---|---|---|---|---|---|---|---|---|---|---|---|---|---|---|---|---|
| 106 | (2) | CR6 | N | H | 2 | 4-OMe | 5-H | 6-NO2 | 2-H | 4-Ph | 5-H | 6-H | 3 | H | H | 0 | H | H | H | H | 0 | H | HCl |
| 107 | (2) | CR6 | N | OH | 2 | 4-H | 5-H | 6-OMe | 2-H | 4-H | 5-H | 6-H | 3 | H | H | 0 | H | H | H | H | 0 | H | 2HCl |
| 108 | (2) | CR6 | N | CHO | 2 | 4-H | 5-H | 6-OMe | 2-H | 4-H | 5-H | 6-H | 3 | H | H | 0 | H | H | H | H | 0 | H | HCl |
| 109 | (2) | CR6 | N | CO2H | 4 | 2-H | 5-H | 6-Et | 2-H | 4-H | 5-H | 6-H | 3 | H | H | 0 | H | H | H | H | 0 | H | HCl |
| 110 | (2) | CR6 | N | CONH2 | 4 | 2-H | 5-H | 6-OMe | 2-H | 4-H | 5-H | 6-H | 3 | H | H | 0 | H | H | H | H | 0 | H | 2HCl |
| 111 | (2) | CR6 | N | CO2Me | 4 | 2-H | 5-H | 6-Et | 2-Me | 4-H | 5-Me | 6-Me | 3 | H | H | 0 | H | H | H | H | 0 | H | HCl |
| 112 | (2) | CR6 | N | CN | 4 | 2-H | 5-H | 6-H | 2-H | 4-Me | 5-H | 6-H | 3 | H | H | 0 | H | H | H | H | 0 | H | 2HCl |
| 113 | (2) | CR6 | N | CF3 | 5 | 2-Me | 5-OEt | 6-H | 2-H | 4-H | 5-Br | 6-H | 3 | H | H | 0 | H | H | H | H | 0 | H | HCl |
| 114 | (2) | CR6 | N | NO2 | 4 | 2-H | 4-NO2 | 6-H | 2-H | 4-H | 5-H | 6-H | 3 | H | H | 0 | H | H | H | H | 0 | H | HCl |
| 115 | (2) | CR6 | N | H | 5 | 2-H | 5-H | 6-OMe | 2-H | 4-H | 5-H | 6-H | 3 | H | H | 0 | H | H | H | H | 0 | H | 2HCl |
| 116 | (2) | CR6 | N | NO2 | 2 | 4-H | 5-H | 6-Me | 2-H | 4-H | 5-H | 6-H | 3 | H | H | 0 | H | H | H | H | 0 | H | HCl |
| 117 | (2) | CR6 | N | NO2 | 2 | 4-H | 5-H | 6-Et | 2-H | 4-H | 5-H | 6-H | 3 | H | H | 0 | H | H | H | H | 0 | Me | HCl |
| 118 | (2) | CR6 | N | NO2 | 2 | 4-H | 5-H | 6-OEt | 2-H | 4-H | 5-H | 6-H | 3 | H | H | 0 | H | H | H | H | 0 | Et | HCl |
| 119 | (2) | CR6 | N | NO2 | 2 | 4-H | 5-H | 6-H | 2-H | 4-H | 5-H | 6-H | 3 | H | H | 0 | H | H | H | H | 0 | nPr | HCl |
| 120 | (2) | CR6 | N | NO2 | 2 | 4-H | 5-H | 6-H | 2-H | 4-H | 5-H | 6-H | 3 | H | H | 0 | H | H | H | H | 0 | Ac | HCl |

*1: Numerals represent substitution positions in the structural formulas of (2)–(7) employed.
*2: Numerals represent substitution positions on the benzene ring.

TABLE 9

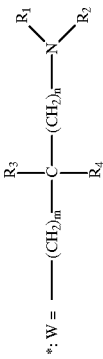

| Ex. No. | Y | Z | R6 | Substitution position of A | A | R7 [*1] | R8 [*1] | R9 [*1] | X1 [*2] | X2 [*2] | X3 [*2] | X4 [*2] | Substitution position of W [*] | R1 | R2 | n | R3 | R4 | m | R5 | salt |
|---|---|---|---|---|---|---|---|---|---|---|---|---|---|---|---|---|---|---|---|---|---|
| 121 | CR6 | N | NO2 | 2 | (2) | 4-H | 5-H | 6-SMe | 2-H | 4-H | 5-H | 6-H | | H | H | 0 | H | H | 0 | CO2Me | HCl |
| 122 | CR6 | N | NO2 | 2 | (2) | 4-H | 5-H | 6-SEt | 2-H | 4-H | 5-H | 6-H | | H | H | 0 | H | H | 0 | CO2Et | HCl |
| 123 | CR6 | N | NO2 | 2 | (2) | 4-H | 5-H | 6-OMe | 2-H | 4-H | 5-Ph | 6-H | | H | H | 0 | Me | Me | 0 | H | HCl |
| 124 | CR6 | N | NO2 | 2 | (2) | 4-H | 5-H | 6-OMe | 2-H | 4-CONH2 | 5-H | 6-H | | H | H | 0 | CH2OH | H | 0 | H | HCl |
| 125 | CR6 | N | NO2 | 2 | (2) | 4-H | 5-H | 6-OMe | 2-Me | 4-H | 5-H | 6-H | | H | H | 0 | CH2Br | H | 0 | H | HCl |
| 126 | CR6 | N | NO2 | 2 | (2) | 4-H | 5-H | 6-OMe | 2-Me | 4-H | 5-H | 6-H | | H | H | 0 | H | H | 0 | H | HCl |
| 127 | CR6 | N | NO2 | 2 | (2) | 4-H | 5-H | 6-OMe | 2-CH2OH | 4-H | 5-H | 6-H | | H | H | 0 | H | H | 0 | H | HCl |
| 128 | CR6 | N | CO2H | 2 | (2) | 4-H | 5-H | 6-OMe | 2-H | 4-H | 5-H | 6-H | | H | H | 0 | Bn | H | 0 | H | HCl |
| 129 | CR6 | N | CO2H | 2 | (2) | 4-H | 5-H | 6-Me | 2-Me | 4-H | 5-H | 6-H | | H | H | 0 | CH2CH2Ph | H | 0 | H | HCl |
| 130 | CR6 | N | CO2H | 2 | (2) | 4-H | 5-H | 6-Me | 2-H | 4-H | 5-H | 6-H | | H | H | 0 | CH2OH | H | O | H | HCl |
| 131 | CR6 | N | CO2Me | 2 | (2) | 4-H | 5-H | 6-Me | 2-H | 4-H | 5-H | 6-NO2 | | H | H | 0 | H | H | 0 | H | HCl |
| 132 | CR6 | N | CO2Me | 2 | (2) | 4-H | 5-H | 6-Me | 2-Cl | 4-OMe | 5-H | 6-H | | H | H | 0 | H | H | 0 | H | HCl |
| 133 | CR6 | N | CO2Me | 2 | (2) | 4-H | 5-H | 6-OMe | 2-H | 4-NHAC | 5-H | 6-H | | H | H | 0 | H | H | 0 | H | HCl |
| 134 | CR6 | N | CO2Me | 2 | (2) | 4-H | 5-H | 6-Et | 2-Me | 4-H | 5-H | 6-H | | H | H | 0 | H | H | 0 | H | HCl |
| 135 | CR6 | N | CO2Me | 2 | (2) | 4-H | 5-H | 6-Et | 2-H | 4-CONH2 | 5-H | 6-H | 2 | CH2CH2F | H | 0 | H | H | 0 | H | HCl |

[*1]: Numerals represent substitution positions in the structural formulas of (2)–(7) employed.
[*2]: Numerals represent substitution positions on the benzene ring.

*: W = —(CH2)n— with R1, R2 on N and R3, R4 on C, (CH2)m

TABLE 10

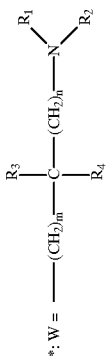

| Ex. No. | A | Y | Z | R₆ | Substitution position of A R₇*¹ | R₈*¹ | R₉*¹ | X₁*² | X₂*² | X₃*² | X₄*² | Substitution position of W* | R₁ | R₂ | n | R₃ | R₄ | m | R₅ | salt |
|---|---|---|---|---|---|---|---|---|---|---|---|---|---|---|---|---|---|---|---|---|
| 136 | (2) | N | CR₆ | H | 4 | 2-CONMe₂ | 5-H | 6-OMe | 3-H | 4-H | 5-H | 6-H | 2 | H | H | 1 | H | H | 0 | H | 2HCl |
| 137 | (2) | N | CR₆ | H | 4 | 2-CONHMe | 5-H | 6-Et | 3-H | 4-H | 5-H | 6-H | 2 | H | H | 1 | H | H | 0 | H | 2HCl |
| 138 | (2) | N | CR₆ | H | 4 | 2-NHAC | 5-H | 6-H | 3-H | 4-H | 5-H | 6-H | 2 | H | H | 1 | H | H | 0 | H | 2HCl |
| 139 | (2) | N | CR₆ | H | 4 | 2-NHCO₂Me | 5-H | 6-H | 3-H | 4-H | 5-H | 6-H | 2 | H | H | 1 | H | H | 0 | H | 2HCl |
| 140 | (2) | N | CR₆ | H | 4 | 2-NHBz | 5-H | 6-H | 3-H | 4-H | 5-H | 6-H | 2 | H | H | 1 | H | H | 0 | H | 2HCl |
| 141 | (2) | N | CR₆ | NO₂ | 5 | 2-H | 4-H | 6-F | 2-H | 3-H | 5-H | 6-H | 2 | H | H | 0 | H | H | 0 | H | HCl |
| 142 | (2) | N | CR₆ | NO₂ | 5 | 2-H | 4-H | 6-Br | 2-H | 3-H | 5-H | 6-H | 2 | H | H | 0 | H | H | 0 | H | HCl |
| 143 | (2) | N | CR₆ | NO₂ | 5 | 2-H | 4-H | 6-H | 2-CO₂H | 3-CO₂Me | 5-H | 6-H | 4 | H | H | 0 | H | H | 0 | H | HCl |
| 144 | (2) | N | CR₆ | NO₂ | 5 | 2-H | 4-H | 6-H | 2-H | 3-CONHMe | 5-H | 6-H | 4 | H | H | 0 | H | H | 1 | H | HCl |
| 145 | (2) | N | CR₆ | NO₂ | 5 | 2-H | 4-H | 6-H | 2-H | 3-H | 5-H | 6-H | 4 | H | H | 0 | H | H | 1 | H | HCl |
| 146 | (2) | N | CR₆ | H | 5 | 3-H | 4-H | 6-H | 2-H | 3-H | 5-CHO | 6-H | 4 | H | H | 0 | H | H | 1 | H | HCl |
| 147 | (2) | N | CR₆ | H | 2 | 3-H | 4-H | 6-OMe | 2-H | 4-H | 5-H | 6-H | 3 | H | H | 0 | H | H | 1 | CHO | HCl |
| 148 | (2) | N→O | CR₆ | H | 2 | 3-H | 4-H | 6-OMe | 2-H | 4-H | 5-H | 6-H | 3 | H | H | 0 | H | H | 0 | H | HCl |
| 149 | (2) | N→O | CR₆ | H | 2 | 3-H | 4-H | 6-Me | 2-H | 4-H | 5-H | 6-H | 3 | H | H | 0 | H | H | 0 | H | HCl |
| 150 | (2) | N→O | CR₆ | H | 2 | 3-H | 4-H | 6-Et | 2-H | 4-H | 5-H | 6-H | 3 | H | H | 0 | H | H | 0 | H | HCl |

*¹:Numerals represent substitution positions in the structural formulas of (2)–(7) employed.
*²:Numerals represent substitution positions on the benzene ring.

*: W = —(CH₂)ₘ—C(R₃)(R₄)—(CH₂)ₙ—N(R₁)(R₂)

TABLE 11

Structures (1)–(7):

(1): 
$$R_1R_2N-(CH_2)_n-C(R_3)(R_4)-\text{(benzene ring with } X_1, X_2, X_3, X_4\text{)}-(CH_2)_m-N(R_5)-A$$

(2) A = Z-containing 6-membered ring with $R_7, R_8, R_9$
(3) A = W,U-containing ring with $R_7, R_8, R_9$
(4) A = W,U-containing ring with $R_7, R_8, R_9$
(5) A = 5-membered ring with T, N-$R_9$, $R_7, R_8$
(6) A = 5-membered ring with T, N-$R_9$, $R_7, R_8$
(7) A = 5-membered ring with T, NH, $R_7, R_8$

| Ex. No. | A | Y | Z | $R_6$ | Substitution position of A | $R_7$[*1] | $R_8$[*1] | $R_9$[*1] | $X_1$[*2] | $X_2$[*2] | $X_3$[*2] | $X_4$[*2] | Substitution position of W[*] | $R_1$ | $R_2$ | n | $R_3$ | $R_4$ | m | $R_5$ | salt |
|---|---|---|---|---|---|---|---|---|---|---|---|---|---|---|---|---|---|---|---|---|---|
| 151 | (2) | $CR_6$ | CH | $NO_2$ | 2 | 4-H | 5-H | 6-Me | 2-H | 4-H | 5-H | 6-H | 3 | H | H | 0 | H | H | 0 | H | HCl |
| 152 | (2) | $CR_6$ | CH | $NO_2$ | 2 | 4-H | 5-H | 6-Et | 2-H | 4-H | 5-H | 6-H | 3 | H | H | 0 | H | H | 0 | H | HCl |
| 153 | (2) | $CR_6$ | CH | $NO_2$ | 2 | 4-H | 5-H | 6-OMe | 2-H | 4-H | 5-H | 6-H | 3 | H | H | 0 | H | H | 0 | H | HCl |
| 154 | (2) | $CR_6$ | CH | $NO_2$ | 2 | 4-H | 5-NHMe | 6-H | 2-H | 4-H | 5-H | 6-H | 3 | $CH_2CH_2F$ | H | 0 | H | H | 0 | H | 2HCl |
| 155 | (2) | $CR_6$ | CH | $NO_2$ | 2 | 4-H | 5-NMe$_2$ | 6-H | 2-H | 4-H | 5-H | 6-H | 3 | $CH_2CH_2Cl$ | $CH_2CH_2Cl$ | 0 | H | H | 0 | H | 2HCl |
| 156 | (2) | $CR_6$ | CH | $NO_2$ | 2 | 4-H | 5-NHEt | 6-H | 2-H | 4-H | 5-H | 6-H | 3 | $CH_2CH_2Br$ | $CH_2CH_2Br$ | 0 | H | H | 0 | H | 2HCl |
| 157 | (2) | $CR_6$ | CH | $NO_2$ | 2 | 4-SMe | 5-H | 6-H | 2-H | 4-H | 5-H | 6-H | 3 | H | H | 0 | H | H | 0 | H | HCl |
| 158 | (2) | $CR_6$ | CH | $NO_2$ | 2 | 4-SEt | 5-H | 6-H | 2-H | 4-H | 5-H | 6-H | 3 | H | H | 0 | H | H | 0 | H | HCl |
| 159 | (2) | $CR_6$ | CH | $NO_2$ | 2 | 4-S$^n$Pr | 5-H | 6-H | 2-H | 4-H | 5-H | 6-H | 3 | H | H | 0 | H | H | 0 | H | HCl |
| 160 | (2) | $CR_6$ | CH | $CO_2H$ | 2 | 4-H | 5-H | 6-Me | 2-Me | 4-H | 5-H | 6-H | 3 | H | H | 0 | —(CH$_2$)$_2$— | H | 0 | H | HCl |
| 161 | (2) | $CR_6$ | CH | $CO_2H$ | 2 | 4-H | 5-H | 6-$^n$Pr | 2-H | 4-Et | 5-$^n$Pr | 6-H | 3 | H | H | 0 | —(CH$_2$)$_3$— | H | 0 | H | HCl |
| 162 | (2) | $CR_6$ | CH | $CO_2H$ | 2 | 4-H | 5-H | 6-NH$^n$Pr | 2-H | 4-H | 5-H | 6-H | 3 | H | H | 0 | —(CH$_2$)$_4$— | H | 0 | H | 2HCl |
| 163 | (2) | $CR_6$ | CH | $CO_2H$ | 2 | 4-H | 5-H | 6-F | 2-NHBn | 4-H | 5-H | 6-H | 3 | H | H | 0 | H | H | 0 | H | HCl |
| 164 | (2) | $CR_6$ | CH | $CO_2H$ | 2 | 4-H | 5-H | 6-Cl | 2-H | 4-NHEt | 5-H | 6-H | 3 | H | H | 0 | H | H | 0 | H | 2HCl |
| 165 | (2) | $CR_6$ | CH | $CO_2H$ | 2 | 4-H | 5-H | 6-Br | 2-H | 4-H | 5-H | 6-SEt | 3 | H | H | 0 | H | H | 0 | H | HCl |

*[1]: Numerals represent substitution positions in the structural formulas of (2)–(7) employed.
*[2]: Numerals represent substitution positions on the benzene ring.

[*]: W =

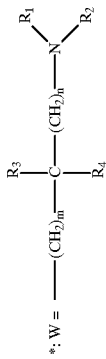

TABLE 12

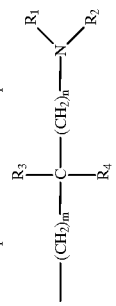

| Ex. No. | A | Y | Z | R₆ | Substitution position of A | R₇*¹ | R₈*¹ | R₉*¹ | X₁*² | X₂*² | X₃*² | X₄*² | Substitution position of W* | R₁ | R₂ | n | R₃ | R₄ | m | R₅ | salt |
|---|---|---|---|---|---|---|---|---|---|---|---|---|---|---|---|---|---|---|---|---|---|
| 166 | (2) | CR₆ | CH | CO₂Me | 2 | 4-H | 5-H | 6-Me | 2-H | 4-pyrrolidin-1-yl | 5-H | 6-H | 3 | H | H | 0 | H | H | 0 | H | 2HCl |
| 167 | (2) | CR₆ | CH | CO₂Me | 2 | 4-H | 5-H | 6-Et | 2-H | 4-pyrrolidin-1-yl | 5-H | 6-H | 3 | H | H | 0 | H | H | 0 | H | 2HCl |
| 168 | (2) | CR₆ | CH | CO₂Me | 2 | 4-H | 5-H | 6-OMe | 2-OMe | 4-H | 5-H | 6-H | 3 | H | H | 0 | H | H | 0 | H | HCl |
| 169 | (2) | CR₆ | CH | H | 2 | 4-H | 5-CONH₂ | 6-Me | 2-OEt | 4-H | 5-H | 6-H | 3 | Bn | H | 0 | H | H | 0 | H | HCl |
| 170 | (2) | CR₆ | CH | H | 2 | 4-H | 5-CONH₂ | 6-Me | 2-H | 4-OBn | 5-H | 6-H | 3 | CH₂CH₂Ph | H | 0 | H | H | 0 | H | HCl |
| 171 | (2) | CR₆ | CH | H | 2 | 4-H | 5-CONMe₂ | 6-Me | 2-F | 4-H | 5-H | 6-H | 3 | H | H | 0 | H | H | 0 | H | HCl |
| 172 | (2) | CR₆ | CH | H | 2 | 4-H | 5-CONMe₂ | 6-Et | 2-Cl | 4-H | 5-H | 6-H | 3 | Ac | H | 0 | H | H | 0 | H | HCl |
| 173 | (2) | CR₆ | CH | H | 2 | 4-NHAc | 5-H | 6-OMe | 2-Br | 4-H | 5-H | 6-H | 3 | H | H | 0 | H | H | 0 | H | HCl |
| 174 | (2) | CR₆ | CH | H | 2 | 4-NHAc | 5-H | 6-Me | 2-H | 4-H | 5-H | 6-H | 3 | H | H | 0 | H | H | 0 | H | HCl |
| 175 | (2) | CR₆ | CH | H | 2 | 4-NHAc | 5-H | 6-Me | 2-H | 4-H | 5-H | 6-H | 3 | H | H | 0 | Me | H | 0 | H | HCl |
| 176 | (2) | CR₆ | CH | H | 2 | 4-NHBn | 5-H | 6-Me | 2-H | 4-H | 5-H | 6-H | 3 | H | H | 0 | Me | Me | 0 | H | HCl |
| 177 | (2) | CR₆ | CH | H | 2 | 4-NHBn | 5-H | 6-Me | 2-H | 4-H | 5-H | 6-H | 3 | H | H | 0 | Me | Et | 0 | H | HCl |
| 178 | (2) | CR₆ | CH | H | 2 | 4-NHBz | 5-H | 6-Me | 2-H | 4-H | 5-H | 6-H | 3 | Bz | H | 0 | Bn | H | 0 | H | HCl |
| 179 | (2) | CR₆ | CH | CF₃ | 2 | 4-H | 5-H | 6-Me | 2-H | 4-H | 5-H | 6-H | 3 | H | H | 0 | CH₂OH | H | 0 | H | HCl |
| 180 | (2) | CR₆ | CH | CF₃ | 2 | 4-H | 5-H | 6-Me | 2-H | 4-H | 5-H | 6-H | 3 | H | H | 0 | H | H | 0 | H | HCl |

*¹:Numerals represent substitution positions in the structural formulas of (2)–(7) employed.
*²:Numerals represent substitution positions on the benzene ring.

TABLE 13

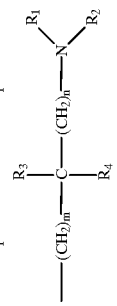

*1: Numerals represent substitution positions in the structural formulas of (2)–(7) employed.
*2: Numerals represent substitution positions on the benzene ring.

| Ex. No. | A | Y | Z | R₆ | Substitution position of A | R₇ *1 | R₈ *1 | R₉ *1 | X₁ *2 | X₂ *2 | X₃ *2 | X₄ *2 | Substitution position of W* | R₁ | R₂ | n | R₃ | R₄ | m | R₅ | salt |
|---|---|---|---|---|---|---|---|---|---|---|---|---|---|---|---|---|---|---|---|---|---|
| 181 | (2) | CR₆ | CH | CN | 2 | 4-H | 5-H | 6-cyclobutyl | 2-H | 4-OH | 5-H | 6-H | 3 | H | H | 0 | H | H | 0 | H | HCl |
| 182 | (2) | CR₆ | CH | CN | 2 | 4-H | 5-H | 6-cyclopentyl | 2-H | 4-H | 5-CN | 6-H | 3 | H | H | 0 | H | H | 0 | H | HCl |
| 183 | (2) | CR₆ | CH | OH | 2 | 4-H | 5-H | 6-cyclohexyl | 2-H | 4-H | 5-H | 6-H | 3 | H | H | 0 | CH₂CH₂OH | CH₂CH₂OH | 0 | H | HCl |
| 184 | (2) | CR₆ | CH | OH | 2 | 4-H | 5-H | 6-H | 2-H | 4-H | 5-H | 6-NO₂ | 3 | H | H | 0 | H | H | 0 | H | 2HCl |
| 185 | (2) | CR₆ | CH | OH | 2 | 4-H | 5-H | 6-H | 2-H | 4-H | 5-H | 6-OH | 3 | H | H | 0 | H | H | 0 | H | 2HCl |
| 186 | (2) | CR₆ | CH | NH₂ | 2 | 4-H | 5-NHCOMe | 6-H | 2-H | 4-CH₂Ph | 5-H | 6-H | 3 | H | H | 0 | H | H | 0 | H | 2HCl |
| 187 | (2) | CR₆ | CH | NH₂ | 2 | 4-H | 5-NHCO₂Me | 6-H | 2-H | 4-CH₂OH | 5-H | 6-H | 3 | H | H | 0 | H | H | 0 | H | 2HCl |
| 188 | (2) | CR₆ | CH | NH₂ | 2 | 4-H | 5-CHO | 6-H | 2-H | 4-H | 5-H | 6-H | 3 | H | H | 0 | H | H | 0 | H | 2HCl |
| 189 | (2) | CR₆ | CH | CHO | 2 | 4-H | 5-H | 6-H | 2-CH₂OH | 4-H | 5-H | 6-H | 3 | H | H | 0 | H | H | 0 | H | HCl |
| 190 | (2) | CR₆ | CMe | CHO | 2 | 4-H | 5-H | 6-cyclobutylthio | 2-H | 4-H | 5-H | 6-H | 3 | H | H | 0 | H | H | 0 | H | HCl |
| 191 | (2) | CR₆ | CH | CHO | 2 | 4-H | 5-H | 6-cyclopentylthio | 2-H | 4-H | 5-H | 6-H | 3 | H | H | 0 | H | H | 0 | H | HCl |
| 192 | (2) | CR₆ | CH | NO₂ | 2 | 4-H | 5-H | 6-cyclohexylthio | 2-H | 4-H | 5-H | 6-H | 3 | H | H | 0 | H | H | 0 | H | HCl |
| 193 | (2) | CR₆ | CH | NO₂ | 2 | 4-H | 5-H | 6-H | 2-OH | 4-H | 5-H | 6-H | 3 | H | H | 0 | H | H | 0 | H | HCl |
| 194 | (2) | CR₆ | CH | NO₂ | 2 | 4-H | 5-H | 6-H | 2-CN | 4-H | 5-H | 6-H | 3 | Me | H | 0 | H | H | 0 | H | HCl |
| 195 | (2) | CR₆ | CH | NO₂ | 2 | 4-H | 5-H | 6-H | 2-H | 4-H | 5-H | 6-NO₂ | 3 | Me | Me | 0 | H | H | 0 | H | HCl |

*: W =

TABLE 14

Structural formula (1):
$R_1R_2N-(CH_2)_m-C(R_3)(R_4)-(CH_2)_n$ attached to benzene ring with $X_1, X_2, X_3, X_4$ substituents, and $-N(A)(R_5)$ group with Y=Z framework including $CR_6$.

A = (2) through (7) represent various ring structures.

| Ex. No. | A | Y | Z | R$_6$ | Substitution position of A | R$_7$*[1] | R$_8$*[1] | R$_9$*[1] | $X_1$*[2] | $X_2$*[2] | $X_3$*[2] | $X_4$*[2] | Substitution position of W*  | R$_1$ | R$_2$ | R$_3$ | n | R$_4$ | m | R$_5$ | salt |
|---|---|---|---|---|---|---|---|---|---|---|---|---|---|---|---|---|---|---|---|---|---|
| 196 | (2) | CR$_6$ | CH | H | 2 | 4-H | 5-H | 6-Me | 2-H | 3-H | 4-H | 5-H | 3 | H | Me | Me | 0 | H | 0 | H | HCl |
| 197 | (2) | CR$_6$ | CH | H | 2 | 4-H | 5-H | 6-Me | 2-H | 3-H | 4-H | 5-H | 3 | Me | Me | H | 0 | H | 0 | H | HCl |
| 198 | (2) | CR$_6$ | CEt | H | 2 | 4-H | 5-H | 6-Me | 2-H | 3-H | 4-H | 5-H | 3 | H | H | H | 0 | H | 0 | H | HCl |
| 199 | (2) | CR$_6$ | CH | H | 2 | 4-H | 5-H | 6-Et | 2-H | 3-H | 4-H | 5-H | 3 | H | H | H | 0 | H | 0 | Ac | HCl |
| 200 | (2) | CR$_6$ | CH | H | 2 | 4-H | 5-H | 6-Et | 2-H | 3-H | 4-H | 5-H | 3 | H | H | H | 0 | H | 0 | Me | HCl |
| 201 | (2) | CR$_6$ | CH | H | 2 | 4-H | 5-H | 6-OMe | 2-H | 3-H | 4-H | 5-H | 3 | H | H | H | 0 | H | 0 | Ac | HCl |
| 202 | (2) | CR$_6$ | CH | H | 2 | 4-H | 5-H | 6-OMe | 2-H | 3-H | 4-H | 5-H | 3 | H | H | H | 0 | H | 0 | $^n$Pr | HCl |
| 203 | (2) | CR$_6$ | CH | NO$_2$ | 2 | 4-H | 5-H | 6-Me | 2-H | 3-H | 4-H | 5-H | 4 | H | H | H | 0 | H | 1 | CO$_2$Me | HCl |
| 204 | (2) | CR$_6$ | CH | NO$_2$ | 2 | 4-H | 5-H | 6-Me | 2-H | 3-H | 4-H | 5-H | 4 | H | H | H | 0 | H | 1 | CO$_2$Et | HCl |
| 205 | (2) | CR$_6$ | C$^n$Pr | NO$_2$ | 2 | 4-H | 5-H | 6-Me | 2-H | 3-H | 4-H | 5-H | 4 | H | H | CH$_2$OH | 0 | H | 1 | H | HCl |
| 206 | (2) | CR$_6$ | CH | NO$_2$ | 2 | 4-H | 5-H | 6-Me | 2-H | 3-H | 4-H | 5-H | 4 | H | H | CH$_2$Ph | 0 | H | 1 | H | HCl |
| 207 | (2) | CR$_6$ | CH | NO$_2$ | 2 | 4-H | 5-H | 6-OMe | 2-H | 3-H | 4-H | 5-H | 5 | H | H | H | 1 | H | 0 | H | HCl |
| 208 | (2) | CR$_6$ | CH | NO$_2$ | 2 | 4-H | 5-H | 6-OMe | 2-H | 3-H | 4-H | 5-H | 5 | H | H | CH$_2$CH$_2$Ph | 1 | H | 0 | H | HCl |
| 209 | (2) | CR$_6$ | CH | NO$_2$ | 2 | 4-H | 5-H | 6-OMe | 2-H | 3-H | 4-H | 5-H | 5 | H | H | CH$_2$Ph | 1 | H | 0 | H | HCl |
| 210 | (2) | CR$_6$ | CH | NO$_2$ | 2 | 4-H | 5-H | 6-OMe | 2-H | 3-H | 4-H | 5-H | 5 | H | H | CH$_2$Ph | 1 | H | 0 | H | HCl |

*[1]: Numerals represent substitution positions in the structural formulas of (2)–(7) employed.
*[2]: Numerals represent substitution positions on the benzene ring.

*: W = 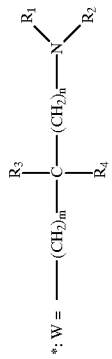

TABLE 15

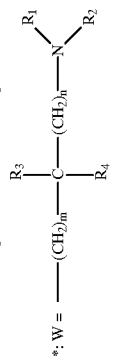

| Ex. No. | A | Y | Z | Substitution position of A | R₇*¹ | R₈*¹ | R₉*¹ | X₁*² | X₂*² | X₃*² | X₄*² | Substitution position of W* | R₁ | R₂ | n | R₃ | R₄ | m | R₅ | salt |
|---|---|---|---|---|---|---|---|---|---|---|---|---|---|---|---|---|---|---|---|---|
| 211 | (2) | N | N | 2 | 4-NO₂ | 5-H | 6-Me | 2-H | 4-H | 5-H | 6-H | 3 | H | H | 0 | H | H | 0 | H | HCl |
| 212 | (2) | N | N | 2 | 4-NO₂ | 5-H | 6-Et | 2-H | 4-H | 5-H | 6-H | 3 | H | H | 0 | H | H | 0 | H | HCl |
| 213 | (2) | N | N | 2 | 4-NO₂ | 5-H | 6-ⁿPr | 2-H | 4-H | 5-H | 6-H | 3 | H | H | 0 | H | H | 0 | H | HCl |
| 214 | (2) | N | N | 2 | 4-NO₂ | 5-H | 6-ⁱPr | 2-H | 4-H | 5-H | 6-H | 3 | H | H | 0 | H | H | 0 | H | HCl |
| 215 | (2) | N | N | 2 | 4-CO₂H | 5-H | 6-OMe | 2-H | 4-H | 5-H | 6-H | 3 | H | H | 0 | H | H | 0 | H | HCl |
| 216 | (2) | N | N | 2 | 4-CO₂H | 5-H | 6-OEt | 2-H | 4-H | 5-H | 6-H | 3 | H | H | 0 | H | H | 0 | H | HCl |
| 217 | (2) | N | N | 2 | 4-CO₂H | 5-H | 6-OⁿPr | 2-H | 4-H | 5-H | 6-H | 3 | H | H | 0 | H | H | 0 | H | HCl |
| 218 | (2) | N | N | 2 | 4-CO₂H | 5-H | 6-OⁱPr | 2-H | 4-H | 5-H | 6-H | 3 | H | H | 0 | H | H | 0 | H | HCl |
| 219 | (2) | N | N | 2 | 4-CO₂Me | 5-H | 6-NHMe | 2-H | 4-H | 5-H | 6-H | 3 | Bn | H | 0 | H | H | 0 | H | HCl |
| 220 | (2) | N | N | 2 | 4-CO₂Me | 5-H | 6-NMe₂ | 2-H | 4-H | 5-H | 6-H | 3 | CH₂CH₂Ph | H | 0 | H | H | 0 | H | HCl |
| 221 | (2) | N | N | 2 | 4-CO₂Et | 5-H | 6-NHEt | 2-H | 4-H | 5-H | 6-H | 3 | CH₂(CH₂)₂Ph | H | 0 | H | H | 0 | H | HCl |
| 222 | (2) | N | N | 2 | 4-CO₂Et | 5-H | 6-NHⁿPr | 2-H | 4-H | 5-H | 6-H | 3 | H | H | 0 | H | H | 0 | H | HCl |
| 223 | (2) | N | N | 2 | 4-CO₂Et | 5-H | 6-H | 2-Me | 4-H | 5-H | 6-H | 3 | H | H | 0 | H | H | 0 | H | HCl |
| 224 | (2) | N | N | 2 | 4-CO₂ⁿPr | 5-H | 6-H | 2-Et | 4-H | 5-H | 6-H | 3 | H | H | 0 | Bn | H | 0 | H | HCl |
| 225 | (2) | N | N | 2 | 4-CO₂ⁿPr | 5-H | 6-H | 2-ⁿPr | 4-H | 5-H | 6-H | 3 | H | H | 0 | CH₂CH₂Ph | H | 0 | H | HCl |

*¹:Numerals represent substitution positions in the structural formulas of (2)–(7) employed.
*²:Numerals represent substitution positions on the benzene ring.

TABLE 16

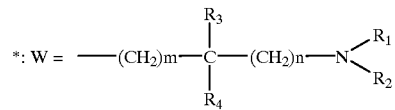

| Ex. No. | A | Y | Z | Substitution position of A | $R_7^{*1}$ | $R_8^{*1}$ | $R_9^{*1}$ | $X_1^{*2}$ | $X_2^{*2}$ | $X_3^{*2}$ | $X_4^{*2}$ |
|---|---|---|---|---|---|---|---|---|---|---|---|
| 226 | (2) | N | N | 4 | 2-$CF_3$ | 5-H | 6-H | 2-H | 4-OMe | 5-H | 6-H |
| 227 | (2) | N | N | 4 | 2-$CF_3$ | 5-H | 6-H | 2-H | 4-OEt | 5-H | 6-H |
| 228 | (2) | N | N | 4 | 2-$CF_3$ | 5-H | 6-H | 2-H | 4-$O^nPr$ | 5-H | 6-H |
| 229 | (2) | N | N | 4 | 2-H | 5-CN | 6-H | 2-H | 3-H | 5-NHMe | 6-H |
| 230 | (2) | N | N | 4 | 2-H | 5-CN | 6-H | 2-H | 3-H | 5-NHEt | 6-H |
| 231 | (2) | N | N | 4 | 2-H | 5-CN | 6-H | 2-H | 3-H | 5-$NH^nPr$ | 6-H |
| 232 | (2) | N | N | 4 | 2-H | 5-H | 6-$CONH_2$ | 2-H | 3-H | 5-H | 6-SMe |
| 233 | (2) | N | N | 4 | 2-H | 5-H | 6-$CONH_2$ | 2-H | 3-H | 5-H | 6-SEt |
| 234 | (2) | N | N | 4 | 2-H | 5-H | 6-$CONH_2$ | 2-H | 3-H | 5-H | 6-$S^nPr$ |
| 235 | (2) | N | N | 5 | 2-OMe | 4-H | 6-H | 3-H | 4-H | 5-H | 6-$NO_2$ |
| 236 | (2) | N | N | 5 | 2-OEt | 4-H | 6-H | 3-H | 4-H | 5-H | 6-$NO_2$ |
| 237 | (2) | N | N | 5 | 2-H | 4-cyclopropyl | 6-H | 3-H | 4-H | 5-H | 6-$NO_2$ |
| 238 | (2) | N | N | 5 | 2-H | 4-cyclobutyl | 6-H | 3-H | 4-H | 5-H | 6-$NO_2$ |
| 239 | (2) | N | N | 5 | 2-H | 4-cyclopentyl | 6-H | 3-H | 4-H | 5-H | 6-$CO_2H$ |
| 240 | (2) | N | N | 5 | 2-H | 4-cyclohexyl | 6-H | 3-H | 4-H | 5-H | 6-$CO_2H$ |

| Ex. No. | Substitution position of W* | $R_1$ | $R_2$ | n | $R_3$ | $R_4$ | m | $R_5$ | salt |
|---|---|---|---|---|---|---|---|---|---|
| 226 | 3 | H | H | 0 | H | H | 0 | H | 2HCl |
| 227 | 3 | H | H | 0 | H | H | 0 | H | 2HCl |
| 228 | 3 | H | H | 0 | H | H | 0 | H | 2HCl |
| 229 | 4 | Ac | H | 1 | H | H | 0 | H | HCl |
| 230 | 4 | Bz | H | 1 | H | H | 0 | H | HCl |
| 231 | 4 | $CO_2^tBu$ | H | 1 | H | H | 0 | H | |
| 232 | 4 | H | H | 1 | H | H | 0 | H | 2HCl |
| 233 | 4 | H | H | 1 | H | H | 0 | H | 2HCl |
| 234 | 4 | H | H | 1 | H | H | 0 | H | 2HCl |
| 235 | 2 | Me | H | 1 | H | H | 0 | H | 2HCl |
| 236 | 2 | Me | Me | 1 | H | H | 0 | H | 2HCl |
| 237 | 2 | Et | H | 1 | H | H | 0 | H | 2HCl |
| 238 | 2 | Et | Et | 1 | H | H | 0 | H | 2HCl |
| 239 | 2 | $CH_2CH_2Cl$ | $CH_2CH_2Cl$ | 1 | H | H | 0 | H | 2HCl |
| 240 | 2 | $CH_2CH_2Br$ | $CH_2CH_2Br$ | 1 | H | H | 0 | H | 2HCl |

*1 Numerals represent substitution positions in the structural formulas of (2)–(7) employed.
*2 Numerals represent substitution positions on the benzene ring.

*: W = —$(CH_2)_m$—C($R_3$)($R_4$)—$(CH_2)_n$—N($R_1$)($R_2$)

TABLE 17

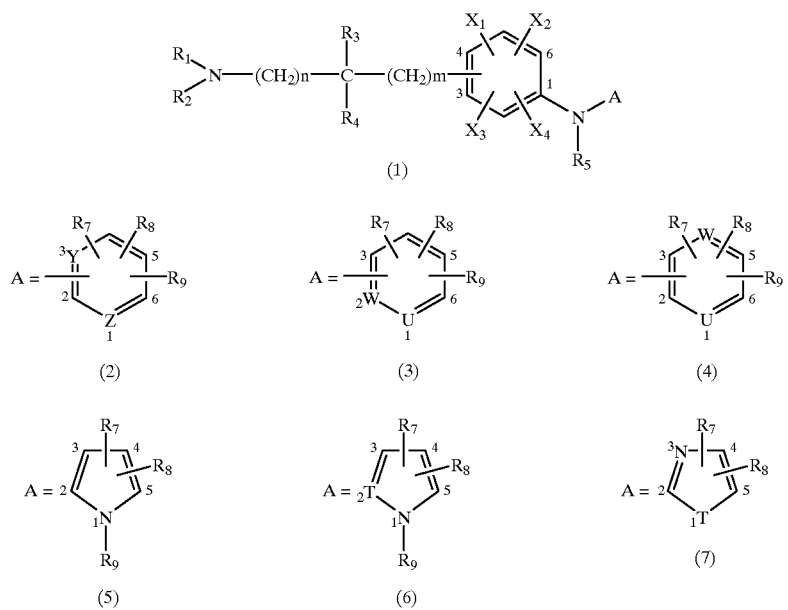

| Ex. No. | A | Y | Z | Substitution position of A | $R_7$[*1] | $R_8$[*1] | $R_9$[*1] | $X_1$[*2] | $X_2$[*2] | $X_3$[*2] | $X_4$[*2] |
|---|---|---|---|---|---|---|---|---|---|---|---|
| 241 | (2) | N | N | 2 | 4-CHO | 5-H | 6-H | 2-H | 4-NHAc | 5-H | 6-H |
| 242 | (2) | N | N | 2 | 4-CHO | 5-H | 6-H | 2-H | 4-NHBz | 5-H | 6-H |
| 243 | (2) | N | N | 2 | 4-$NH_2$ | 5-H | 6-H | 2-H | 4-H | 5-$CONH_2$ | 6-H |
| 244 | (2) | N | N | 2 | 4-$NH_2$ | 5-H | 6-H | 2-H | 4-H | 5-CONHMe | 6-H |
| 245 | (2) | N | N | 2 | 4-$NH_2$ | 5-H | 6-H | 2-H | 4-H | 5-CONHEt | 6-H |
| 246 | (2) | N | N | 2 | 4-H | 5-OH | 6-H | 2-H | 4-H | 5-H | 6-$CO_2$Me |
| 247 | (2) | N | N | 2 | 4-H | 5-OH | 6-H | 2-H | 4-H | 5-H | 6-$CO_2$Et |
| 248 | (2) | N | N | 2 | 4-H | 5-H | 6-pyrrolidin-1-yl | 2-H | 4-H | 5-H | 6-$CO_2^n$Pr |
| 249 | (2) | N | N | 2 | 4-H | 5-H | 6-piperidino | 2-H | 4-$CH_2$OH | 5-H | 6-H |
| 250 | (2) | N | N | 2 | 4-H | 5-H | 6-H | 2-H | 4-F | 5-H | 6-H |
| 251 | (2) | N | N | 2 | 4-H | 5-H | 6-H | 2-H | 4-Cl | 5-H | 6-H |
| 252 | (2) | N | N | 2 | 4-H | 5-H | 6-H | 2-H | 4-Br | 5-H | 6-H |
| 253 | (2) | N→O | N→O | 2 | 4-H | 5-H | 6-H | 2-H | 4-H | 5-$CH_2$Br | 6-H |
| 254 | (2) | N→O | N→O | 2 | 4-H | 5-H | 6-H | 2-H | 4-H | 5-CN | 6-H |
| 255 | (2) | N→O | N→O | 2 | 4-H | 5-H | 6-H | 2-H | 4-H | 5-$CF_3$ | 6-H |

| Ex. No. | Substitution position of W* | $R_1$ | $R_2$ | n | $R_3$ | $R_4$ | m | $R_5$ | salt |
|---|---|---|---|---|---|---|---|---|---|
| 241 | 3 | —$CH_2CH_2$— | | 0 | H | H | 0 | H | HCl |
| 242 | 3 | —$CH_2CH_2CH_2$— | | 0 | H | H | 0 | H | HCl |
| 243 | 3 | —$CH_2(CH_2)_2CH_2$— | | 0 | H | H | 0 | H | 2HCl |
| 244 | 3 | H | H | 0 | Me | H | 0 | Me | 2HCl |
| 245 | 3 | H | H | 0 | Me | Me | 0 | Et | 2HCl |
| 246 | 3 | H | H | 0 | Et | H | 0 | $^n$Pr | 2HCl |
| 247 | 3 | H | H | 0 | Et | Et | 0 | CHO | HCl |
| 248 | 3 | H | H | 0 | —$CH_2CH_2$— | | 0 | Ac | 2HCl |
| 249 | 3 | H | H | 0 | —$CH_2CH_2CH_2$— | | 0 | Bz | 2HCl |
| 250 | 3 | H | H | 0 | —$CH_2(CH_2)_2CH_2$— | | 0 | $CO_2$Et | HCl |
| 251 | 3 | H | H | 0 | H | H | 0 | $CO_2^n$Pr | HCl |
| 252 | 3 | H | H | 0 | H | H | 0 | $CO_2^t$Bu | HCl |
| 253 | 3 | H | H | 0 | $CH_2CH_2$F | $CH_2CH_2$F | 0 | H | HCl |
| 254 | 3 | H | H | 0 | $CH_2CH_2$Cl | $CH_2CH_2$Cl | 0 | H | HCl |
| 255 | 3 | H | H | 0 | $CH_2CH_2$Br | $CH_2CH_2$Br | 0 | H | HCl |

[*1]Numerals represent substitution positions in the structural formulas of (2)–(7) employed.
[*2]Numerals represent substitution positions on the benzene ring.

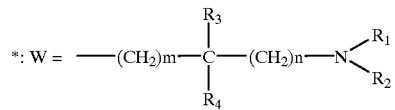

TABLE 18

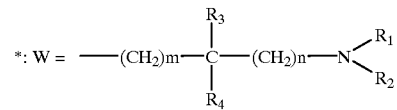

| Ex. No. | A | T | R$_6$ | Substitution position of A | R$_7$[*1] | R$_8$[*1] | R$_9$[*1] | X$_1$[*2] | X$_2$[*2] | X$_3$[*2] | X$_4$[*2] |
|---|---|---|---|---|---|---|---|---|---|---|---|
| 256 | (5) | CR$_6$ | NO$_2$ | 2 | 4-H | 5-Me | H | 2-H | 4-OMe | 5-H | 6-H |
| 257 | (5) | CR$_6$ | NO$_2$ | 2 | 4-H | 5-Et | H | 2-H | 4-OEt | 5-H | 6-H |
| 258 | (5) | CR$_6$ | NO$_2$ | 2 | 4-H | 5-$^n$Pr | Me | 2-H | 4-O$^n$Pr | 5-H | 6-H |
| 259 | (5) | CR$_6$ | NO$_2$ | 2 | 4-H | 5-$^i$Pr | H | 2-H | 4-O$^i$Pr | 5-H | 6-H |
| 260 | (5) | CR$_6$ | CO$_2$H | 2 | 4-H | 5-OMe | H | 2-Me | 4-H | 5-H | 6-H |
| 261 | (5) | CR$_6$ | CO$_2$H | 2 | 4-H | 5-OEt | H | 2-Et | 4-H | 5-H | 6-H |
| 262 | (5) | CR$_6$ | CO$_2$H | 2 | 4-H | 5-O$^n$Pr | Et | 2-$^n$Pr | 4-H | 5-H | 6-H |
| 263 | (5) | CR$_6$ | CO$_2$Me | 2 | 4-H | 5-SMe | H | 2-H | 4-H | 5-NO$_2$ | 6-H |
| 264 | (5) | CR$_6$ | CO$_2$Et | 2 | 4-H | 5-SEt | H | 2-H | 4-H | 5-NO$_2$ | 6-H |
| 265 | (5) | CR$_6$ | CO$_2$$^n$Pr | 2 | 4-H | 5-S$^n$Pr | $^n$Pr | 2-H | 4-H | 5-NO$_2$ | 6-H |
| 266 | (5) | CR$_6$ | CN | 2 | 4-H | 5-H | H | 2-H | 4-H | 5-H | 6-CO$_2$H |
| 267 | (5) | CR$_6$ | CN | 2 | 4-H | 5-H | H | 2-H | 4-H | 5-H | 6-CO$_2$Me |
| 268 | (5) | CR$_6$ | CN | 2 | 4-H | 5-H | H | 2-H | 4-H | 5-H | 6-CO$_2$Et |
| 269 | (5) | CR$_6$ | CF$_3$ | 2 | 4-H | 5-H | H | 2-H | 4-NH$_2$ | 5-H | 6-H |
| 270 | (5) | CR$_6$ | CF$_3$ | 2 | 4-H | 5-H | H | 2-H | 4-CONH$_2$ | 5-H | 6-H |

| Ex. No. | Substitution position of W* | R$_1$ | R$_2$ | n | R$_3$ | R$_4$ | m | R$_5$ | salt |
|---|---|---|---|---|---|---|---|---|---|
| 256 | 3 | Me | H | 0 | H | H | 0 | Me | HCl |
| 257 | 3 | H | H | 0 | Me | H | 0 | H | HCl |
| 258 | 3 | H | H | 0 | H | H | 0 | Et | HCl |
| 259 | 3 | H | H | 0 | H | H | 0 | H | HCl |
| 260 | 3 | Et | H | 0 | H | H | 0 | H | HCl |
| 261 | 3 | H | H | 0 | Et | H | 0 | $^n$Pr | HCl |
| 262 | 3 | H | H | 0 | H | H | 0 | $^i$Pr | HCl |
| 263 | 3 | $^n$Pr | H | 0 | H | H | 0 | H | HCl |
| 264 | 3 | H | H | 0 | $^n$Pr | H | 0 | H | HCl |
| 265 | 3 | H | H | 0 | H | H | 0 | Ac | HCl |
| 266 | 3 | —CH$_2$CH$_2$— | | 0 | H | H | 0 | H | HCl |
| 267 | 3 | H | H | 0 | —CH$_2$CH$_2$— | | 0 | H | HCl |
| 268 | 3 | H | H | 0 | H | H | 0 | Bz | HCl |
| 269 | 3 | CH$_2$CH$_2$F | H | 0 | H | H | 0 | H | 2HCl |
| 270 | 3 | H | H | 0 | CH$_2$CH$_2$F | H | 0 | CHO | 2HCl |

[*1]Numerals represent substitution positions in the structural formulas of (2)–(7) employed.
[*2]Numerals represent substitution positions on the benzene ring.

TABLE 19

| Ex. No. | A | T | R$_6$ | Substitution position of A | R$_7$[*1] | R$_8$[*1] | R$_9$[*1] | X$_1$[*2] | X$_2$[*2] | X$_3$[*2] | X$_4$[*2] |
|---|---|---|---|---|---|---|---|---|---|---|---|
| 271 | (5) | CR$_6$ | H | 4 | 2-CHO | 5-H | H | 2-F | 3-H | 5-H | 6-H |
| 272 | (5) | CR$_6$ | H | 4 | 2-CHO | 5-H | H | 2-Cl | 3-H | 5-H | 6-H |
| 273 | (5) | CR$_6$ | H | 4 | 2-H | 5-NHAc | Ac | 2-Br | 3-H | 5-H | 6-H |
| 274 | (5) | CR$_6$ | H | 4 | 2-H | 5-NHBz | H | 2-H | 3-H | 5-H | 6-H |
| 275 | (5) | CR$_6$ | H | 4 | 2-CONH$_2$ | 5-H | H | 2-H | 3-H | 5-H | 6-H |
| 276 | (5) | CR$_6$ | H | 4 | 2-CONHMe | 5-H | Bz | 2-H | 3-H | 5-H | 6-H |
| 277 | (5) | CR$_6$ | H | 4 | 2-H | 5-CONHEt | H | 2-H | 3-H | 4-H | 5-H |
| 278 | (5) | CR$_6$ | H | 4 | 2-H | 5-CONH$^n$Pr | H | 2-H | 3-H | 4-H | 5-H |
| 279 | (5) | CR$_6$ | H | 4 | 2-F | 5-H | CO$_2$Me | 2-H | 3-NHAc | 4-H | 5-H |
| 280 | (5) | CR$_6$ | H | 4 | 2-Cl | 5-H | H | 2-H | 3-NHBz | 4-H | 5-H |
| 281 | (5) | CR$_6$ | H | 4 | 2-Br | 5-H | H | 2-H | 2-CONHMe | 4-H | 5-H |
| 282 | (5) | CR$_6$ | NHMe | 4 | 2-H | 5-H | CO$_2$Et | 2-H | 3-H | 4-H | 5-H |
| 283 | (5) | CR$_6$ | NHEt | 4 | 2-H | 5-H | H | 2-H | 3-H | 4-H | 5-H |
| 284 | (5) | CR$_6$ | NH$^n$Pr | 4 | 2-H | 5-H | H | 2-H | 3-H | 4-H | 5-H |
| 285 | (5) | CR$_6$ | H | 4 | 2-OH | 5-H | CO$_2^t$Bu | 2-H | 3-H | 4-H | 5-H |

| Ex. No. | Substitution position of W* | R$_1$ | R$_2$ | n | R$_3$ | R$_4$ | m | R$_5$ | salt |
|---|---|---|---|---|---|---|---|---|---|
| 271 | 4 | H | H | 1 | H | H | 0 | CO$_2$Me | HCl |
| 272 | 4 | H | H | 1 | H | H | 0 | CO$_2$Et | HCl |
| 273 | 4 | Ac | H | 1 | H | H | 0 | H | |
| 274 | 4 | Bz | H | 1 | H | H | 0 | H | |
| 275 | 4 | Me | Me | 1 | H | H | 0 | H | 2HCl |
| 276 | 4 | H | H | 1 | Me | Me | 0 | H | 2HCl |
| 277 | 6 | CO$_2$Et | H | 0 | H | H | 1 | H | |
| 278 | 6 | H | H | 0 | H | H | 1 | H | 2HCl |
| 279 | 6 | CO$_2^t$Bu | H | 0 | H | H | 1 | H | |
| 280 | 6 | H | H | 0 | H | H | 1 | H | 2HCl |
| 281 | 6 | H | H | 0 | H | H | 1 | H | 2HCl |
| 282 | 6 | CH$_2$CH$_2$Cl | CH$_2$CH$_2$Cl | 0 | H | H | 1 | H | HCl |
| 283 | 6 | H | H | 0 | CH$_2$CH$_2$Br | CH$_2$CH$_2$Br | 1 | H | 2HCl |
| 284 | 6 | H | H | 0 | H | H | 1 | H | 2HCl |
| 285 | 6 | H | H | 0 | H | H | 1 | H | 2HCl |

[*1]Numerals represent substitution positions in the structural formulas of (2)–(7) employed.
[*2]Numerals represent substitution positions on the benzene ring.

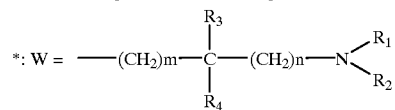

TABLE 20

[Structural formulas (1)–(7) shown with substituent definitions]

| Ex. No. | A | T | Substitution position of A | $R_7^{*1}$ | $R_8^{*1}$ | $R_9^{*1}$ | $X_1^{*2}$ | $X_2^{*2}$ | $X_3^{*2}$ | $X_4^{*2}$ |
|---|---|---|---|---|---|---|---|---|---|---|
| 286 | (5) | N | 2 | 4-NO$_2$ | 5-H | Me | 2-Me | 4-H | 5-H | 6-H |
| 287 | (5) | N | 2 | 4-NO$_2$ | 5-H | H | 2-Et | 4-H | 5-H | 6-H |
| 288 | (5) | N | 2 | 4-CO$_2$H | 5-H | H | 2-H | 4-$^n$Pr | 5-H | 6-H |
| 289 | (5) | N | 2 | 4-CO$_2$H | 5-H | Et | 2-H | 4-$^i$Pr | 5-H | 6-H |
| 290 | (5) | N | 2 | 4-CF$_3$ | 5-H | H | 2-H | 4-H | 5-OMe | 6-H |
| 291 | (5) | N | 2 | 4-CF$_3$ | 5-H | H | 2-H | 4-H | 5-OEt | 6-H |
| 292 | (5) | N | 2 | 4-CO$_2$Me | 5-H | $^n$Pr | 2-H | 4-H | 5-H | 6-NHMe |
| 293 | (5) | N | 2 | 4-CO$_2$Me | 5-H | H | 2-H | 4-H | 5-H | 6-NHEt |
| 294 | (5) | N | 2 | 4-CO$_2$Et | 5-H | H | 2-SMe | 4-H | 5-H | 6-H |
| 295 | (5) | N | 2 | 4-CO$_2$Et | 5-H | $^i$Pr | 2-SEt | 4-H | 5-H | 6-H |
| 296 | (5) | N | 2 | 4-CN | 5-H | H | 2-H | 4-OH | 5-H | 6-H |
| 297 | (5) | N | 2 | 4-CN | 5-H | H | 2-H | 4-F | 5-H | 6-H |
| 298 | (5) | N | 2 | 4-NH$_2$ | 5-H | Ac | 2-H | 4-H | 5-Cl | 6-H |
| 299 | (5) | N | 2 | 4-NHAc | 5-H | H | 2-H | 4-H | 5-Br | 6-H |
| 300 | (5) | N | 2 | 4-NHMe | 5-H | H | 2-H | 4-H | 5-H | 6-H |

| Ex. No. | Substitution position of W* | $R_1$ | $R_2$ | n | $R_3$ | $R_4$ | m | $R_5$ | salt |
|---|---|---|---|---|---|---|---|---|---|
| 286 | 3 | H | H | 0 | Me | H | 0 | H | HCl |
| 287 | 3 | Me | H | 0 | H | H | 0 | Me | HCl |
| 288 | 3 | H | H | 0 | Et | H | 0 | H | HCl |
| 289 | 3 | Et | H | 0 | H | H | 0 | Et | HCl |
| 290 | 3 | H | H | 0 | $^n$Pr | H | 0 | H | 2HCl |
| 291 | 3 | $^n$Pr | H | 0 | H | H | 0 | Ac | HCl |
| 292 | 3 | H | H | 0 | H | H | 0 | H | 2HCl |
| 293 | 3 | —CH$_2$CH$_2$— | | 0 | H | H | 0 | Bz | HCl |
| 294 | 3 | H | H | 0 | —CH$_2$CH$_2$— | | 0 | H | HCl |
| 295 | 3 | Ac | H | 0 | H | H | 0 | H | |
| 296 | 3 | H | Bz | 0 | CH$_2$CH$_2$F | H | 0 | H | HCl |
| 297 | 3 | Bz | H | 0 | H | H | 0 | H | |
| 298 | 3 | H | H | 0 | H | H | 0 | H | 2HCl |
| 299 | 3 | CO$_2^t$Bu | H | 0 | H | H | 0 | H | |
| 300 | 3 | H | H | 0 | CH$_2$CH$_2$Cl | H | 0 | H | 2HCl |

*1 Numerals represent substitution positions in the structural formulas of (2)–(7) employed.
*2 Numerals represent substitution positions on the benzene ring.

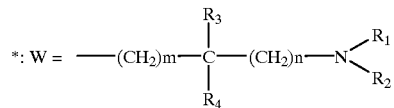

*: W = —(CH$_2$)m—C(R$_3$)(R$_4$)—(CH$_2$)n—N(R$_1$)(R$_2$)

TABLE 21

(Structures 1-7 with general formula and A group definitions)

| Ex. No. | A | T | Substitution position of A | R₇[*1] | R₈[*1] | R₉[*1] | X₁[*2] | X₂[*2] | X₃[*2] | X₄[*2] |
|---|---|---|---|---|---|---|---|---|---|---|
| 301 | (5) | N | 2 | 4-H | 5-NMe₂ | Bz | 2-H | 4-H | 5-H | 6-NO₂ |
| 302 | (5) | N | 2 | 4-H | 5-NHEt | H | 2-H | 4-H | 5-H | 6-NO₂ |
| 303 | (5) | N | 2 | 4-H | 5-NHⁿPr | H | 2-H | 4-H | 5-CO₂H | 6-H |
| 304 | (5) | N | 2 | 4-H | 5-OH | H | 2-H | 3-CO₂Me | 5-H | 6-H |
| 305 | (5) | N | 2 | 4-H | 5-OMe | H | 2-H | 3-CO₂Et | 5-H | 6-H |
| 306 | (5) | N | 2 | 4-H | 5-OEt | CO₂Me | 2-H | 3-H | 5-CN | 6-H |
| 307 | (5) | N | 2 | 4-H | 5-Me | H | 2-H | 3-H | 5-H | 6-CHO |
| 308 | (5) | N | 4 | 2-Me | 5-H | H | 3-CONH₂ | 4-H | 5-H | 6-H |
| 309 | (5) | N | 4 | 2-Et | 5-H | H | 3-H | 4-CONHMe | 5-H | 6-H |
| 310 | (5) | N | 4 | 2-ⁿPr | 5-H | CO₂Et | 3-CH₂OH | 4-H | 5-H | 6-H |
| 311 | (5) | N | 4 | 2-H | 5-SMe | H | 3-H | 4-CH₂Cl | 5-H | 6-H |
| 312 | (5) | N | 4 | 2-H | 5-SEt | H | 3-H | 4-H | 5-H | 6-H |
| 313 | (5) | N→O | 2 | 4-Me | 5-H | H | 2-H | 4-H | 5-H | 6-NO₂ |
| 314 | (5) | N→O | 2 | 4-Et | 5-H | CO₂ᵗBu | 2-H | 4-H | 5-H | 6-CHO |
| 315 | (5) | N→O | 2 | 4-ⁿPt | 5-H | H | 2-H | 4-H | 5-H | 6-H |

| Ex. No. | Substitution position of W* | R₁ | R₂ | n | R₃ | R₄ | m | R₅ | salt |
|---|---|---|---|---|---|---|---|---|---|
| 301 | 3 | CH₂CH₂Cl | CH₂CH₂Cl | 0 | H | H | 0 | H | 2HCl |
| 302 | 3 | H | H | 0 | H | H | 0 | H | 2HCl |
| 303 | 3 | CH₂CH₂Br | CH₂CH₂Br | 0 | H | H | 0 | H | 2HCl |
| 304 | 4 | H | H | 1 | Me | Me | 0 | CHO | HCl |
| 305 | 4 | H | H | 1 | Et | Et | 0 | CO₂Me | HCl |
| 306 | 4 | H | H | 0 | H | H | 1 | CO₂Et | HCl |
| 307 | 4 | H | H | 0 | H | H | 1 | H | 2HCl |
| 308 | 2 | CO₂ᵗBu | CO₂ᵗBu | 1 | H | H | 0 | H | |
| 309 | 2 | H | H | 1 | H | H | 0 | H | 2HCl |
| 310 | 2 | Me | Me | 0 | H | H | 1 | H | 2HCl |
| 311 | 2 | H | H | 0 | CH₂CH₂OH | CH₂CH₂OH | 1 | H | 2HCl |
| 312 | 2 | H | H | 0 | H | H | 1 | H | 2HCl |
| 313 | 3 | H | H | 0 | H | H | 0 | H | HCl |
| 314 | 3 | H | H | 0 | H | H | 0 | H | HCl |
| 315 | 3 | H | H | 0 | H | H | 0 | H | HCl |

[*1]Numerals represent substitution positions in the structural formulas of (2)–(7) employed.
[*2]Numerals represent substitution positions on the benzene ring.

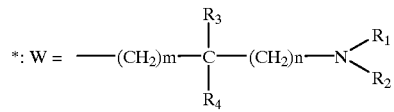

*: W = —(CH₂)m—C(R₃)(R₄)—(CH₂)n—N(R₁)(R₂)

TABLE 22

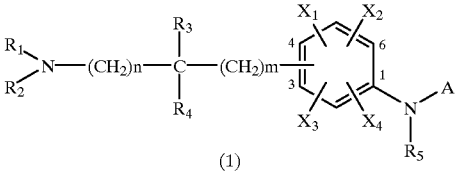

| Ex. No. | A | U | W | Substitution position of A | $R_7$[*1] | $R_8$[*1] | $R_9$[*1] | $X_1$[*2] | $X_2$[*2] | $X_3$[*2] | $X_4$[*2] |
|---|---|---|---|---|---|---|---|---|---|---|---|
| 316 | (4) | N | N | 3 | 2-$NO_2$ | 5-H | 6-Me | 2-H | 4-H | 5-H | 6-H |
| 317 | (4) | N | N | 3 | 2-$NO_2$ | 5-H | 6-H | 2-Me | 4-H | 5-H | 6-H |
| 318 | (4) | N | N | 3 | 2-$CO_2H$ | 5-H | 6-Et | 2-H | 4-OMe | 5-H | 6-H |
| 319 | (4) | N | N | 3 | 2-$CO_2H$ | 5-H | 6-H | 2-Et | 4-H | 5-H | 6-H |
| 320 | (4) | N | N | 3 | 2-$CO_2Me$ | 5-H | 6-$^nPr$ | 2-H | 4-OEt | 5-H | 6-H |
| 321 | (4) | N | N | 3 | 2-$CO_2Et$ | 5-H | 6-H | 2-$^nPr$ | 4-H | 5-H | 6-H |
| 322 | (4) | N | N | 3 | 2-$CO_2^nPr$ | 5-H | 6-$^nBu$ | 2-H | 4-$O^nPr$ | 5-H | 6-H |
| 323 | (4) | N | N | 3 | 2-CN | 5-H | 6-OH | 2-H | 4-H | 5-H | 6-H |
| 324 | (4) | N | N | 3 | 2-CN | 5-H | 6-H | 2-H | 4-H | 5-$NH_2$ | 6-H |
| 325 | (4) | N | N | 3 | 2-H | 5-$NH_2$ | 6-H | 2-H | 4-H | 5-NHMe | 6-H |
| 326 | (4) | N | N | 3 | 2-H | 5-NHAc | 6-H | 2-H | 4-H | 5-NHEt | 6-H |
| 327 | (4) | N | N | 3 | 2-H | 5-NHBz | 6-H | 2-H | 4-SMe | 5-H | 6-H |
| 328 | (4) | N | N | 3 | 2-$CONH_2$ | 5-H | 6-H | 2-H | 4-SEt | 5-H | 6-H |
| 329 | (4) | N | N | 3 | 2-CONHMe | 5-H | 6-H | 2-H | 4-H | 5-H | 6-H |
| 330 | (4) | N | N | 3 | 2-H | 5-H | 6-Me | 2-H | 4-H | 5-H | 6-$NO_2$ |

| Ex. No. | Substitution position of W* | $R_1$ | $R_2$ | n | $R_3$ | $R_4$ | m | $R_5$ | salt |
|---|---|---|---|---|---|---|---|---|---|
| 316 | 3 | $CO_2^tBu$ | H | 0 | H | H | 0 | H | |
| 317 | 3 | H | Me | 0 | H | H | 0 | H | HCl |
| 318 | 3 | Ac | H | 0 | H | H | 0 | H | |
| 319 | 3 | H | Et | 0 | H | H | 0 | H | HCl |
| 320 | 3 | Bz | H | 0 | H | H | 0 | H | |
| 321 | 3 | H | $^nPr$ | 0 | H | H | 0 | H | HCl |
| 322 | 3 | H | H | 0 | Me | H | 0 | H | HCl |
| 323 | 3 | H | H | 0 | H | H | 0 | H | HCl |
| 324 | 3 | H | H | 0 | Et | H | 0 | H | 2HCl |
| 325 | 3 | H | H | 0 | H | H | 0 | H | 2HCl |
| 326 | 3 | H | H | 0 | $CH_2CH_2Cl$ | $CH_2CH_2Cl$ | 0 | H | 2HCl |
| 327 | 3 | H | H | 0 | H | H | 0 | H | 2HCl |
| 328 | 3 | $CO_2Me$ | H | 0 | H | H | 0 | H | |
| 329 | 3 | $CH_2CH_2Br$ | $CH_2CH_2Br$ | 0 | H | H | 0 | H | 2HCl |
| 330 | 3 | H | H | 0 | $CH_2OH$ | H | 0 | H | 2HCl |

[*1]Numerals represent substitution positions in the structural formulas of (2)–(7) employed.
[*2]Numerals represent substitution positions on the benzene ring.

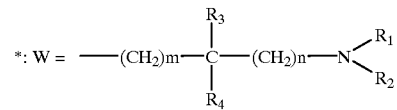

TABLE 23

[Structures (1)–(7) of formula variants shown]

| Ex. No. | A | U | W | Substitution position of A | $R_7^{*1}$ | $R_8^{*1}$ | $R_9^{*1}$ | $X_1^{*2}$ | $X_2^{*2}$ | $X_3^{*2}$ | $X_4^{*2}$ |
|---|---|---|---|---|---|---|---|---|---|---|---|
| 331 | (4) | N | N | 3 | 2-H | 5-H | 6-Et | 2-H | 3-H | 5-H | 6-CO$_2$H |
| 332 | (4) | N | N | 3 | 2-H | 5-H | 6-$^n$Pr | 2-H | 3-H | 5-H | 6-CO$_2$Me |
| 333 | (4) | N | N | 3 | 2-H | 5-H | 6-$^n$Bu | 2-H | 3-H | 5-H | 6-CO$_2$Et |
| 334 | (4) | N | N | 3 | 2-H | 5-OH | 6-H | 2-H | 3-H | 5-CN | 6-H |
| 335 | (4) | N | N | 3 | 2-H | 5-OMe | 6-H | 2-H | 3-H | 5-F | 6-H |
| 336 | (4) | N | N | 3 | 2-H | 5-OEt | 6-H | 2-H | 3-H | 5-H | 6-CO$_2$NH$_2$ |
| 337 | (4) | N | N | 3 | 2-SMe | 5-H | 6-H | 2-Cl | 3-H | 4-H | 5-H |
| 338 | (4) | N | N | 3 | 2-Et | 5-H | 6-H | 2-CH$_2$OH | 3-H | 4-H | 5-H |
| 339 | (4) | N | N | 3 | 2-CF$_3$ | 5-H | 6-H | 2-H | 3-H | 4-H | 5-CO$_2$NHMe |
| 340 | (4) | N | N | 3 | 2-CF$_3$ | 5-H | 6-H | 2-H | 3-H | 4-H | 5-cyclopentyl |
| 341 | (4) | N | N | 3 | 2-H | 5-H | 6-pyrrolidin-1-yl | 2-H | 3-H | 4-H | 5-H |
| 342 | (4) | N | N | 3 | 2-H | 5-H | 6-piparidino | 2-H | 3-H | 4-H | 5-H |
| 343 | (4) | N→I | N→I | 3 | 2-H | 5-H | 6-cyclobutyl | 2-H | 4-H | 5-H | 6-H |
| 344 | (4) | N→I | N→I | 3 | 2-H | 5-H | 6-H | 2-H | 3-H | 5-H | 6-cyclohexylthio |
| 345 | (4) | N→I | N→I | 3 | 2-H | 5-H | 6-H | 2-H | 3-H | 4-Bn | 5-H |

| Ex. No. | Substitution position of W* | $R_1$ | $R_2$ | n | $R_3$ | $R_4$ | m | $R_5$ | salt |
|---|---|---|---|---|---|---|---|---|---|
| 331 | 4 | Me | Me | 1 | H | H | 0 | Me | 2HCl |
| 332 | 4 | H | H | 1 | H | H | 0 | H | 2HCl |
| 333 | 4 | H | H | 1 | H | H | 0 | Et | 2HCl |
| 334 | 4 | H | H | 0 | Me | Me | 1 | H | 2HCl |
| 335 | 4 | H | H | 0 | H | H | 1 | $^n$Pr | 2HCl |
| 336 | 4 | H | H | 0 | H | H | 1 | H | 2HCl |
| 337 | 6 | H | H | 0 | H | H | 1 | Ac | HCl |
| 338 | 6 | H | H | 0 | H | H | 1 | H | 2HCl |
| 339 | 6 | H | H | 0 | H | H | 1 | Bz | HCl |
| 340 | 6 | H | H | 1 | H | H | 0 | H | 2HCl |
| 341 | 6 | H | H | 1 | H | H | 0 | CO$_2^i$Bu | — |
| 342 | 6 | H | H | 1 | H | H | 0 | H | 2HCl |
| 343 | 3 | H | H | 0 | H | H | 0 | H | 2HCl |
| 344 | 4 | H | H | 1 | H | H | 0 | H | 2HCl |
| 345 | 6 | H | H | 0 | H | H | 1 | H | 2HCl |

*1 Numerals represent substitution positions in the structural formulas of (2)–(7) employed.
*2 Numerals represent substitution positions on the benzene ring.

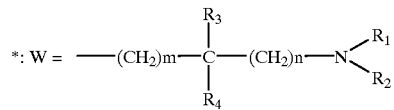

*: W =

TABLE 24

Structural formulas (1)–(7) with substituents $R_1$–$R_9$, $X_1$–$X_4$, A, U, W, Y, Z, T.

| Ex. No. | A | U | W | Substitution position of A | $R_7$[*1] | $R_8$[*1] | $R_9$[*1] | $X_1$[*2] | $X_2$[*2] | $X_3$[*2] | $X_4$[*2] |
|---|---|---|---|---|---|---|---|---|---|---|---|
| 346 | (3) | N | N | 3 | 4-$NO_2$ | 5-H | 6-H | 2-Me | 4-H | 5-H | 6-H |
| 347 | (3) | N | N | 3 | 4-$NO_2$ | 5-H | 6-H | 2-Et | 4-H | 5-H | 6-H |
| 348 | (3) | N | N | 3 | 4-H | 5-$CO_2$H | 6-H | 2-H | 4-$^n$Bu | 5-H | 6-H |
| 349 | (3) | N | N | 3 | 4-H | 5-$CO_2$Me | 6-H | 2-H | 4-Bn | 5-H | 6-H |
| 350 | (3) | N | N | 3 | 4-H | 5-H | 6-$CONH_2$ | 2-H | 4-H | 5-$NH_2$ | 6-H |
| 351 | (3) | N | N | 3 | 4-H | 5-H | 6-CONHMe | 2-H | 4-H | 5-NHMe | 6-H |
| 352 | (3) | N | N | 3 | 4-$CF_3$ | 5-H | 6-H | 2-F | 4-H | 5-H | 6-H |
| 353 | (3) | N | N | 3 | 4-$CF_3$ | 5-H | 6-H | 2-H | 4-Br | 5-H | 6-H |
| 354 | (3) | N | N | 3 | 4-H | 5-CN | 6-H | 2-Cl | 4-H | 5-H | 6-H |
| 355 | (3) | N | N | 3 | 4-H | 5-CN | 6-H | 2-H | 4-NHBn | 5-H | 6-H |
| 356 | (3) | N | N | 3 | 4-$NH_2$ | 5-H | 6-H | 2-H | 4-OMe | 5-H | 6-H |
| 357 | (3) | N | N | 3 | 4-H | 5-NHMe | 6-H | 2-H | 4-H | 5-OEt | 6-H |
| 358 | (3) | N | N | 3 | 4-H | 5-H | 6-NHBn | 2-$^n$Pr | 4-H | 5-H | 6-H |
| 359 | (3) | N | N | 3 | 4-$^n$Pr | 5-H | 6-H | 2-H | 4-H | 5-H | 6-$NO_2$ |
| 360 | (3) | N | N | 3 | 4-H | 5-Et | 6-H | 2-H | 4-H | 5-H | 6-CHO |

| Ex. No. | Substitution position of W* | $R_1$ | $R_2$ | n | $R_3$ | $R_4$ | m | $R_5$ | salt |
|---|---|---|---|---|---|---|---|---|---|
| 346 | 3 | Me | H | 0 | H | H | 0 | H | HCl |
| 347 | 3 | H | H | 0 | H | H | 0 | Me | HCl |
| 348 | 3 | Et | H | 0 | H | H | 0 | H | HCl |
| 349 | 3 | H | H | 0 | H | H | 0 | Et | HCl |
| 350 | 3 | Bn | H | 0 | H | H | 0 | H | |
| 351 | 3 | H | H | 0 | H | H | 0 | Ac | HCl |
| 352 | 3 | H | H | 0 | Me | Me | 0 | H | 2HCl |
| 353 | 3 | H | H | 0 | H | H | 0 | H | 2HCl |
| 354 | 3 | H | H | 0 | Me | H | 0 | H | HCl |
| 355 | 3 | H | H | 0 | H | H | 0 | H | HCl |
| 356 | 3 | Ac | H | 0 | H | H | 0 | H | — |
| 357 | 3 | H | H | 0 | H | H | 0 | Bz | 2HCl |
| 358 | 3 | $CO_2$Me | H | 0 | H | H | 0 | H | |
| 359 | 3 | H | H | 0 | H | H | 0 | H | 2HCl |
| 360 | 3 | $CO_2{}^t$Bu | H | 0 | H | H | 0 | H | |

[*1]Numerals represent substitution positions in the structural formulas of (2)–(7) employed.
[*2]Numerals represent substitution positions on the benzene ring.

*: W = 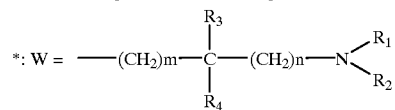

TABLE 25

[Chemical structures (1)-(7) with formula variables]

| Ex. No. | A | U | W | Substitution position of A | R₇*¹ | R₈*¹ | R₉*¹ | X₁*² | X₂*² | X₃*² | X₄*² |
|---|---|---|---|---|---|---|---|---|---|---|---|
| 361 | (3) | N | N | 3 | 4-Me | 5-H | 6-H | 2-H | 4-$CO_2H$ | 5-H | 6-H |
| 362 | (3) | N | N | 3 | 4-SMe | 5-H | 6-H | 2-H | 4-H | 5-$CO_2Et$ | 6-H |
| 363 | (3) | N | N | 3 | 4-H | 5-SEt | 6-H | 2-H | 4-H | 5-H | 6-$CONH_2$ |
| 364 | (3) | N | N | 3 | 4-H | 5-H | 6-S$^n$Pr | 2-H | 4-H | 5-CONHMe | 6-H |
| 365 | (3) | N | N | 3 | 4-F | 5-H | 6-H | 2-CN | 3-H | 5-pyrrolidin-1-yl | 6-H |
| 366 | (3) | N | N | 3 | 4-H | 5-Br | 6-H | 2-H | 3-H | 5-piperidino | 6-H |
| 367 | (3) | N→O | N→O | 3 | 4-H | 5-H | 6-Me | 2-H | 3-H | 5-H | 6-H |
| 368 | (3) | N→O | N→O | 3 | 4-H | 5-H | 6-H | 2-H | 4-H | 5-H | 6-H |
| 369 | (3) | N | N | 4 | 3-OMe | 5-H | 6-H | 2-F | 4-H | 5-H | 6-H |
| 370 | (3) | N | N | 4 | 3-H | 5-OEt | 6-H | 2-H | 3-Cl | 5-H | 6-H |
| 371 | (3) | N | N | 4 | 3-H | 5-H | 5-O$^n$Pr | 2-H | 3-H | 5-Br | 6-H |
| 372 | (3) | N | N | 4 | 3-$NO_2$ | 5-H | 6-OMe | 2-H | 3-H | 4-$CH_2CH_2Ph$ | 5-H |
| 373 | (3) | N | N | 4 | 3-H | 5-H | 6-H | 2-H | 3-H | 4-$CH_2(CH_2)_2Ph$ | 5-H |
| 374 | (3) | N→O | N→O | 4 | 3-H | 5-H | 6-NHMe | 2-H | 3-H | 4-H | 5-H |
| 375 | (3) | N→O | N→O | 4 | 3-H | 5-H | 6-NHEt | 2-H | 3-H | 5-H | 6-H |

| Ex. No. | Substitution position of W* | R₁ | R₂ | n | R₃ | R₄ | m | R₅ | salt |
|---|---|---|---|---|---|---|---|---|---|
| 361 | 3 | H | H | 0 | H | H | 0 | H | HCl |
| 362 | 3 | $CO_2^tBu$ | $CO_2^tBu$ | 0 | H | H | 0 | $CO_2^tBu$ | |
| 363 | 3 | H | H | 0 | H | H | 0 | H | 2HCl |
| 364 | 3 | H | H | 0 | H | H | 0 | H | 2HCl |
| 365 | 4 | H | H | 1 | H | H | 0 | Me | 2HCl |
| 366 | 4 | H | H | 0 | H | H | 1 | H | 2HCl |
| 367 | 4 | H | H | 1 | H | H | 0 | H | HCl |
| 368 | 3 | H | H | 0 | H | H | 0 | H | HCl |
| 369 | 3 | Et | H | 0 | H | H | 0 | H | 2HCl |
| 370 | 3 | H | H | 0 | Et | H | 0 | H | 2HCl |
| 371 | 3 | H | H | 0 | H | H | 0 | H | 2HCl |
| 372 | 6 | H | H | 1 | H | H | 0 | H | HCl |
| 373 | 6 | H | H | 1 | $CH_2OH$ | H | 0 | H | 2HCl |
| 374 | 6 | H | H | 0 | H | H | 1 | $CO_2Et$ | 2HCl |
| 375 | 3 | H | H | 0 | H | H | 1 | H | 2HCl |

*¹Numerals represent substitution positions in the structural formulas of (2)–(7) employed.
*²Numerals represent substitution positions on the benzene ring.

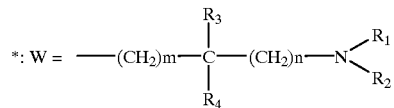

TABLE 26

[Structure (1): $R_1R_2N-(CH_2)_n-C(R_3)(R_4)-(CH_2)_m-$ phenyl ring with $X_1, X_2, X_3, X_4$ substituents and $-N(A)(R_5)$ group]

A = (2): 6-membered ring with Y at position 3, Z at position 1, $R_7$, $R_8$, $R_9$ substituents
A = (3): 6-membered ring with W at position 2, U at position 1
A = (4): 6-membered ring with W at position 3, U at position 1
A = (5): 5-membered ring with N at position 1, $R_9$ on N
A = (6): 5-membered ring with T at position 2, N at position 1, $R_9$ on N
A = (7): 5-membered ring with N at position 3, T at position 1

| Ex. No. | A | T | Substitution position of A | $R_7$ [*1] | $R_8$ [*1] | $R_9$ [*1] | $X_1$ [*2] | $X_2$ [*2] | $X_3$ [*2] | $X_4$ [*2] |
|---|---|---|---|---|---|---|---|---|---|---|
| 376 | (6) | N | 3 | 4-$NO_2$ | 5-H | H | 2-H | 4-Me | 5-H | 6-H |
| 377 | (6) | N | 3 | 4-$NO_2$ | 5-H | Me | 2-H | 4-Et | 5-H | 6-H |
| 378 | (6) | N | 3 | 4-$CF_3$ | 5-H | H | 2-H | 4-$^n$Pr | 5-H | 6-H |
| 379 | (6) | N | 3 | 4-$CF_3$ | 5-H | Et | 2-$CH_2OH$ | 4-H | 5-H | 6-H |
| 380 | (6) | N | 3 | 4-H | 5-$CO_2H$ | H | 2-$CH_2CH_2OH$ | 4-H | 5-H | 6-H |
| 381 | (6) | N | 3 | 4-H | 5-$CO_2Me$ | $^n$Pr | 2-H | 4-H | 5-H | 6-H |
| 382 | (6) | N | 3 | 4-H | 5-$CO_2Et$ | H | 2-H | 4-H | 5-$NH_2$ | 6-H |
| 383 | (6) | N | 3 | 4-CN | 5-H | H | 2-H | 4-H | 5-H | 6-NHMe |
| 384 | (6) | N | 3 | 4-$CONH_2$ | 5-H | H | 2-NHEt | 4-H | 5-H | 6-H |
| 385 | (6) | N | 3 | 4-CONHMe | 5-H | H | 2-H | 4-H | 5-H | 6-H |
| 386 | (6) | N | 3 | 4-H | 5-H | Ac | 2-Cl | 4-H | 5-H | 6-H |
| 387 | (6) | N | 3 | 4-H | 5-H | Bn | 2-Br | 4-H | 5-H | 6-H |
| 388 | (6) | N | 3 | 4-H | 5-H | $CO_2Me$ | 2-OMe | 4-H | 5-H | 6-H |
| 389 | (6) | N | 3 | 4-H | 5-H | $CO_2Et$ | 2-H | 4-OEt | 5-H | 6-H |
| 390 | (6) | N | 3 | 4-H | 5-H | $CO_2^nPr$ | 2-H | 4-OBn | 5-H | 6-H |

| Ex. No. | Substitution position of W* | $R_1$ | $R_2$ | n | $R_3$ | $R_4$ | m | $R_5$ | salt |
|---|---|---|---|---|---|---|---|---|---|
| 376 | 3 | Me | H | 0 | H | H | 0 | Me | 2HCl |
| 377 | 3 | H | H | 0 | Me | Me | 0 | H | 2HCl |
| 378 | 3 | H | H | 0 | Me | H | 0 | H | HCl |
| 379 | 3 | Et | H | 0 | H | H | 0 | H | HCl |
| 380 | 3 | H | H | 0 | H | H | 0 | Et | HCl |
| 381 | 3 | H | H | 0 | Et | H | 0 | H | HCl |
| 382 | 3 | $^n$Pr | H | 0 | H | H | 0 | H | 2HCl |
| 383 | 3 | H | H | 0 | H | H | 0 | Ac | 2HCl |
| 384 | 3 | H | H | 0 | $CH_2OH$ | H | 0 | H | 2HCl |
| 385 | 3 | Ac | H | 0 | H | H | 0 | H | |
| 386 | 3 | H | H | 0 | $CH_2CH_2OH$ | $CH_2CH_2OH$ | 0 | H | HCl |
| 387 | 3 | H | H | 0 | Et | Et | 0 | H | HCl |
| 388 | 3 | H | H | 0 | H | H | 0 | Bn | HCl |
| 389 | 3 | $CO_2^tBu$ | $CO_2^tBu$ | 0 | H | H | 0 | H | |
| 390 | 3 | H | H | 0 | Bn | H | 0 | Bz | HCl |

[*1] Numerals represent substitution positions in the structural formulas of (2)–(7) employed.
[*2] Numerals represent substitution positions on the benzene ring.

*: W = 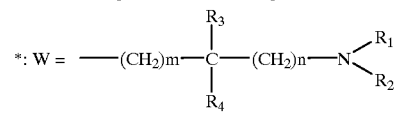

TABLE 27

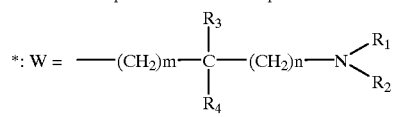

| Ex. No. | A | T | Substitution position of A | $R_7^{*1}$ | $R_8^{*1}$ | $R_9^{*1}$ | $X_1^{*2}$ | $X_2^{*2}$ | $X_3^{*2}$ | $X_4^{*2}$ |
|---|---|---|---|---|---|---|---|---|---|---|
| 391 | (6) | N | 3 | 4-OMe | 5-H | Bz | 2-H | 4-H | 5-H | 6-NO$_2$ |
| 392 | (6) | N | 3 | 4-OEt | 5-H | H | 2-H | 4-H | 5-H | 6-CO$_2$Me |
| 393 | (6) | N | 3 | 4-O$^n$Pr | 5-H | H | 2-H | 4-H | 5-H | 6-CO$_2$Et |
| 394 | (6) | N | 3 | 4-H | 5-SMe | H | 2-H | 3-H | 5-CONH$_2$ | 6-H |
| 395 | (6) | N | 3 | 4-H | 5-SEt | H | 2-H | 3-H | 5-CONHMe | 6-H |
| 396 | (6) | N | 4 | 3-H | 5-S$^n$Bu | H | 2-H | 3-H | 5-CONHEt | 6-H |
| 397 | (6) | N | 4 | 3-F | 5-H | H | 2-H | 3-H | 5-H | 6-H |
| 398 | (6) | N | 4 | 3-Cl | 5-H | H | 2-H | 4-SMe | 5-H | 6-H |
| 399 | (6) | N | 4 | 3-Br | 5-H | H | 2-H | 4-SEt | 5-H | 6-H |
| 400 | (6) | N | 4 | 3-NH$_2$ | 5-H | H | 2-H | 3-H | 4-H | 5-CHO |
| 401 | (6) | N | 4 | 3-NHMe | 5-H | H | 2-H | 3-H | 4-NHCO$_2$Me | 5-H |
| 402 | (6) | N→O | 4 | 3-H | 5-Me | H | 2-H | 3-OBn | 4-H | 5-H |
| 403 | (6) | N→O | 4 | 3-H | 5-Et | H | 2-H | 4-H | 5-H | 6-H |
| 404 | (6) | N→O | 3 | 4-H | 5-OMe | H | 2-H | 4-NHBn | 5-H | 6-H |
| 405 | (6) | N→O | 3 | 4-H | 5-OEt | H | 2-H | 3-H | 5-H | 6-H |

| Ex. No. | Substitution position of W* | $R_1$ | $R_2$ | n | $R_3$ | $R_4$ | m | $R_5$ | salt |
|---|---|---|---|---|---|---|---|---|---|
| 391 | 3 | H | H | 0 | H | H | 0 | H | HCl |
| 392 | 3 | Me | Me | 0 | H | H | 0 | H | 2HCl |
| 393 | 3 | H | H | 0 | H | H | 0 | CO$_2$Me | 2HCl |
| 394 | 4 | H | H | 1 | H | H | 0 | H | 2HCl |
| 395 | 4 | H | H | 1 | H | H | 0 | H | 2HCl |
| 396 | 4 | H | H | 0 | Me | H | 1 | H | 2HCl |
| 397 | 4 | CH$_2$CH$_2$Br | CH$_2$CH$_2$Br | 0 | H | H | 1 | H | 2HCl |
| 398 | 3 | H | H | 0 | H | H | 0 | H | 2HCl |
| 399 | 3 | H | H | 0 | H | H | 0 | H | 2HCl |
| 400 | 6 | H | H | 1 | H | H | 0 | H | 2HCl |
| 401 | 6 | H | H | 1 | H | H | 0 | H | 2HCl |
| 402 | 6 | —CH$_2$(CH$_2$)$_2$CH$_2$— | | 1 | H | H | 0 | H | HCl |
| 403 | 3 | H | H | 1 | —CH$_2$(CH$_2$)$_3$CH$_2$— | | 0 | H | HCl |
| 404 | 3 | H | H | 1 | H | H | 0 | H | 2HCl |
| 405 | 4 | H | H | 1 | H | H | 0 | H | HCl |

*1 Numerals represent substitution positions in the structural formulas of (2)–(7) employed.
*2 Numerals represent substitution positions on the benzene ring.

*: W = —(CH$_2$)m—C(R$_3$)(R$_4$)—(CH$_2$)n—N(R$_1$)(R$_2$)

TABLE 28

[Structural formulas (1)–(7) shown]

| Ex. No. | A | Y | Z | $R_6$ | Substitution position of A | $R_7$[*1] | $R_8$[*1] | $R_9$[*1] | $X_1$[*2] | $X_2$[*2] | $X_3$[*2] | $X_4$[*2] |
|---------|---|---|---|-------|---------------------------|-----------|-----------|-----------|-----------|-----------|-----------|-----------|
| 406 | (2) | $CR_6$ | N | $NO_2$ | 2 | 4-H | 5-H | 6-OMe | 2-Me | 4-H | 5-H | 6-H |
| 407 | (2) | $CR_6$ | N | $NO_2$ | 2 | 4-H | 5-H | 6-OMe | 2-H | 4-pyrrolidin-1-yl | 5-H | 6-H |
| 408 | (2) | $CR_6$ | N | $NO_2$ | 2 | 4-H | 5-H | 6-OMe | 2-H | 3-H | 5-H | 6-H |
| 409 | (2) | $CR_6$ | N | $NO_2$ | 2 | 4-H | 5-H | 6-OMe | 2-H | 4-H | 5-H | 6-OMe |
| 410 | (2) | $CR_6$ | N | $NO_2$ | 2 | 4-H | 5-H | 6-OMe | 2-H | 4-H | 5-H | 6-H |
| 411 | (2) | $CR_6$ | N | $NO_2$ | 2 | 4-H | 5-H | 6-OMe | 2-H | 4-H | 5-Me | 6-H |
| 412 | (2) | $CR_6$ | N | $NO_2$ | 2 | 4-H | 5-H | 6-OMe | 3-H | 4-H | 5-H | 6-H |
| 413 | (2) | $CR_6$ | N | $NO_2$ | 2 | 4-H | 5-H | 6-OMe | 2-OMe | 4-H | 5-H | 6-H |
| 414 | (2) | $CR_6$ | N | $NO_2$ | 2 | 4-H | 5-H | 6-OMe | 2-H | 4-Cl | 5-H | 6-H |
| 415 | (2) | $CR_6$ | N | $NO_2$ | 2 | 4-H | 5-H | 6-OMe | 2-H | 4-Me | 5-H | 6-H |
| 416 | (2) | $CR_6$ | N | $NO_2$ | 2 | 4-H | 5-H | 6-OMe | 2-H | 4-F | 5-H | 6-H |
| 417 | (2) | $CR_6$ | N | $NO_2$ | 2 | 4-H | 5-H | 6-OMe | 2-OEt | 4-H | 5-H | 6-H |
| 418 | (2) | $CR_6$ | CH | $NO_2$ | 2 | 4-H | 5-H | 6-Me | 2-H | 4-H | 5-H | 6-H |
| 419 | (2) | $CR_6$ | CH | $NO_2$ | 2 | 4-H | 5-H | 6-OMe | 2-H | 4-H | 5-H | 6-H |
| 420 | (2) | $CR_6$ | CH | $NO_2$ | 2 | 4-H | 5-H | 6-OMe | 2-H | 4-OMe | 5-H | 6-H |

| Ex. No. | Substitution position of W* | $R_1$ | $R_2$ | n | $R_3$ | $R_4$ | m | $R_5$ |
|---------|------------------------------|-------|-------|---|-------|-------|---|-------|
| 406 | 3 | $CO_2^tBu$ | $CO_2^tBu$ | 0 | H | H | 0 | H |
| 407 | 3 | $CO_2^tBu$ | $CO_2^tBu$ | 0 | H | H | 0 | H |
| 408 | 4 | $CO_2^tBu$ | H | 1 | H | H | 0 | H |
| 409 | 3 | $CO_2^tBu$ | H | 0 | H | H | 0 | H |
| 410 | 3 | $CO_2^tBu$ | H | 0 | Me | Me | 0 | H |
| 411 | 3 | $CO_2^tBu$ | $CO_2^tBu$ | 0 | H | H | 0 | H |
| 412 | 2 | $CO_2^tBu$ | H | 1 | H | H | 0 | H |
| 413 | 3 | $CO_2^tBu$ | $CO_2^tBu$ | 0 | H | H | 0 | H |
| 414 | 3 | $CO_2^tBu$ | $CO_2^tBu$ | 0 | H | H | 0 | H |
| 415 | 3 | $CO_2^tBu$ | H | 0 | H | H | 0 | H |
| 416 | 3 | $CO_2^tBu$ | H | 0 | H | H | 0 | H |
| 417 | 3 | $CO_2^tBu$ | $CO_2^tBu$ | 0 | H | H | 0 | H |
| 418 | 3 | $CO_2^tBu$ | $CO_2^tBu$ | 0 | H | H | 0 | H |
| 419 | 3 | $CO_2^tBu$ | $CO_2^tBu$ | 0 | H | H | 0 | H |
| 420 | 3 | $CO_2^tBu$ | $CO_2^tBu$ | 0 | H | H | 0 | H |

[*1] Numerals represent substitution positions in the structural formulas of (2)–(7) employed.
[*2] Numerals represent substitution positions on the benzene ring.

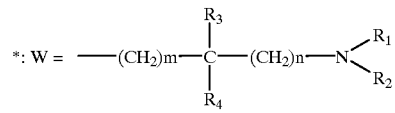

*: W =

TABLE 29

[Structural formulas (1)–(7) shown]

| Ex. No. | A | Y | Z | $R_6$ | Substitution position of A | $R_7^{*1}$ | $R_8^{*1}$ | $R_9^{*1}$ | $X_1^{*2}$ | $X_2^{*2}$ | $X_3^{*2}$ | $X_4^{*2}$ |
|---|---|---|---|---|---|---|---|---|---|---|---|---|
| 421 | (2) | $CR_6$ | N | H | 2 | 4-H | 5-$NO_2$ | 6-OMe | 2-H | 4-H | 5-H | 6-H |
| 422 | (2) | $CR_6$ | N | $NO_2$ | 2 | 4-H | 5-H | 6-OMe | 2-H | 4-H | 5-H | 6-H |
| 423 | (2) | $CR_6$ | N | H | 2 | 4-$CO_2$Me | 5-H | 6-H | 2-H | 4-H | 5-H | 6-H |
| 424 | (2) | $CR_6$ | N | — | 2 | 4-Me | 5-H | 6-H | 2-H | 4-H | 5-H | 6-H |
| 425 | (2) | $CR_6$ | N | $NO_2$ | 2 | 4-H | 5-H | 6-OEt | 2-H | 4-H | 5-H | 6-H |
| 426 | (2) | $CR_6$ | N | $CF_3$ | 2 | 4-H | 5-H | 6-OMe | 2-H | 4-H | 5-H | 6-H |
| 427 | (2) | $CR_6$ | CH | $NO_2$ | 2 | 4-H | 5-OMe | 6-H | 2-H | 4-H | 5-H | 6-H |
| 428 | (2) | $CR_6$ | CMe | $NO_2$ | 2 | 4-H | 5-H | 6-H | 2-H | 4-H | 5-H | 6-H |
| 429 | (2) | $CR_6$ | N | H | 2 | 4-Me | 5-H | 6-H | 2-H | 4-H | 5-H | 6-H |
| 430 | (2) | $CR_6$ | N | H | 2 | 4-Me | 5-H | 6-H | 2-H | 4-H | 5-H | 6-H |
| 431 | (2) | $CR_6$ | N | H | 2 | 4-Me | 5-H | 6-H | 2-Me | 4-H | 5-H | 6-H |
| 432 | (2) | $CR_6$ | N | H | 2 | 4-Me | 5-H | 6-H | 2-H | 4-Et | 5-H | 6-H |
| 433 | (2) | $CR_6$ | N | H | 2 | 4-Me | 5-H | 6-H | 2-H | 4-OEt | 5-H | 6-H |
| 434 | (2) | $CR_6$ | N | H | 2 | 4-Me | 5-H | 6-H | 3-H | 4-H | 5-H | 6-H |
| 435 | (2) | $CR_6$ | N | H | 2 | 4-Me | 5-H | 6-H | 2-Cl | 4-H | 5-H | 6-H |

| Ex. No. | Substitution position of W* | $R_1$ | $R_2$ | n | $R_3$ | $R_4$ | m | $R_5$ |
|---|---|---|---|---|---|---|---|---|
| 421 | 3 | $CO_2^tBu$ | $CO_2^tBu$ | 0 | H | H | 0 | H |
| 422 | 3 | $CO_2^tBu$ | $CO_2^tBu$ | 0 | H | H | 0 | H |
| 423 | 3 | $CO_2^tBu$ | H | 0 | H | H | 0 | H |
| 424 | 3 | $CO_2^tBu$ | H | 0 | H | H | 0 | H |
| 425 | 3 | $CO_2^tBu$ | $CO_2^tBu$ | 0 | H | H | 0 | H |
| 426 | 3 | $CO_2^tBu$ | $CO_2^tBu$ | 0 | H | H | 0 | H |
| 427 | 3 | $CO_2^tBu$ | H | 0 | H | H | 0 | H |
| 428 | 3 | $CO_2^tBu$ | H | 0 | H | H | 0 | H |
| 429 | 3 | $CO_2^tBu$ | H | 0 | Me | Me | 0 | H |
| 430 | 3 | $CO_2^tBu$ | H | 0 | Et | H | 0 | H |
| 431 | 3 | $CO_2^tBu$ | $CO_2^tBu$ | 0 | H | H | 0 | H |
| 432 | 3 | $CO_2^tBu$ | H | 0 | H | H | 0 | H |
| 433 | 3 | $CO_2^tBu$ | H | 0 | H | H | 0 | H |
| 434 | 2 | $CO_2^tBu$ | H | 1 | H | H | 0 | H |
| 435 | 3 | $CO_2^tBu$ | H | 0 | H | H | 0 | H |

*1 Numerals represent substitution positions in the structural formulas of (2)–(7) employed.
*2 Numerals represent substitution positions on the benzene ring.

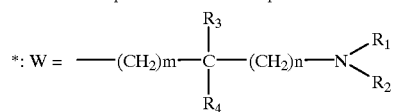

*: W =

TABLE 30

(Structures (1)–(7) shown)

| Ex. No. | A | Y | Z | $R_6$ | Substitution position of A | $R_7$[*1] | $R_8$[*1] | $R_9$[*1] | $X_1$[*2] | $X_2$[*2] | $X_3$[*2] | $X_4$[*2] |
|---|---|---|---|---|---|---|---|---|---|---|---|---|
| 436 | (2) | $CR_6$ | N | H | 2 | 4-Me | 5-H | 6-H | 2-H | 4-H | 5-H | 6-H |
| 437 | (2) | $CR_6$ | N | H | 2 | 4-Me | 5-H | 6-H | 2-H | 3-H | 5-H | 6-H |
| 438 | (2) | $CR_6$ | N | H | 2 | 4-Me | 5-H | 6-H | 2-OEt | 4-H | 5-H | 6-H |
| 439 | (2) | $CR_6$ | N | H | 2 | 4-Me | 5-H | 6-H | 2-H | 4-Cl | 5-H | 6-H |
| 440 | (2) | $CR_6$ | N | CN | 2 | 4-H | 5-H | 6-OMe | 2-H | 4-H | 5-H | 6-H |
| 441 | (2) | $CR_6$ | N | Cl | 2 | 4-H | 5-H | 6-H | 2-H | 4-H | 5-H | 6-H |
| 442 | (2) | $CR_6$ | N | $CO_2Me$ | 2 | 4-H | 5-H | 6-OMe | 2-H | 4-H | 5-H | 6-H |
| 443 | (2) | $CR_6$ | N | H | 2 | 4-$CO_2H$ | 5-H | 6-OMe | 2-H | 4-H | 5-H | 6-H |
| 444 | (2) | $CR_6$ | N | H | 2 | 4-$CH_2OH$ | 5-H | 6-OMe | 2-H | 4-H | 5-H | 6-H |
| 445 | (2) | $CR_6$ | N | H | 2 | 4-Me | 5-H | 6-OMe | 2-H | 4-H | 5-H | 6-H |
| 446 | (2) | $CR_6$ | N | $NO_2$ | 2 | 4-H | 5-H | 6-$CH(CO_2Me)_2$ | 2-H | 4-H | 5-H | 6-H |
| 447 | (2) | $CR_6$ | N | $NO_2$ | 2 | 4-H | 5-H | 6-$CMe(CO_2Et)_2$ | 2-H | 4-H | 5-H | 6-H |
| 448 | (2) | $CR_6$ | N | $NO_2$ | 2 | 4-H | 5-H | 6-SMe | 2-H | 4-H | 5-H | 6-H |
| 449 | (2) | $CR_6$ | N | H | 2 | 4-Me | 5-H | 6-H | 2-H | 4-H | 5-H | 6-H |
| 450 | (2) | $CR_6$ | N | H | 2 | 4-Me | 5-H | 6-Me | 2-H | 4-H | 5-H | 6-H |

| Ex. No. | Substitution position of W* | $R_1$ | $R_2$ | n | $R_3$ | $R_4$ | m | $R_5$ |
|---|---|---|---|---|---|---|---|---|
| 436 | 3 | $CO_2^tBu$ | H | 0 | —$CH_2CH_2CH_2$— | | 0 | H |
| 437 | 4 | $CO_2^tBu$ | H | 1 | H | H | 0 | H |
| 438 | 3 | $CO_2^tBu$ | $CO_2^tBu$ | 0 | H | H | 0 | H |
| 439 | 3 | $CO_2^tBu$ | $CO_2^tBu$ | 0 | H | H | 0 | H |
| 440 | 3 | $CO_2^tBu$ | $CO_2^tBu$ | 0 | H | H | 0 | H |
| 441 | 3 | $CO_2^tBu$ | H | 0 | H | H | 0 | H |
| 442 | 3 | $CO_2^tBu$ | H | 0 | H | H | 0 | H |
| 443 | 3 | $CO_2^tBu$ | H | 0 | H | H | 0 | H |
| 444 | 3 | $CO_2^tBu$ | H | 0 | H | H | 0 | H |
| 445 | 3 | $CO_2^tBu$ | H | 0 | H | H | 0 | H |
| 446 | 3 | $CO_2^tBu$ | $CO_2^tBu$ | 0 | H | H | 0 | H |
| 447 | 3 | $CO_2^tBu$ | $CO_2^tBu$ | 0 | H | H | 0 | H |
| 448 | 3 | $CO_2^tBu$ | H | 0 | H | H | 0 | H |
| 449 | 3 | $CO_2^tBu$ | H | 0 | H | H | 0 | H |
| 450 | 3 | $CO_2^tBu$ | H | 0 | H | H | 0 | H |

[*1]Numerals represent substitution positions in the structural formulas of (2)–(7) employed.
[*2]Numerals represent substitution positions on the benzene ring.

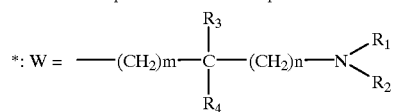

TABLE 31

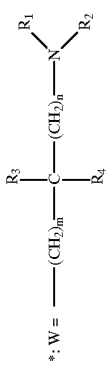

| Ex. No. | A | Y | Z | R6 | R7*1 Substitution position of A | R7*1 | R8*1 | R9*1 | X1*2 | X2*2 | X3*2 | X4*2 | Substitution position of W* | R1 | R2 | n | R3 | R4 | m | R5 | salt |
|---|---|---|---|---|---|---|---|---|---|---|---|---|---|---|---|---|---|---|---|---|---|
| 451 | (2) | CR6 | N | H | 2 | 4-Et | 5-H | 6-H | 2-H | 4-H | 5-H | 6-H | 3 | CO2tBu | H | 0 | H | H | 0 | H | |
| 452 | (2) | CR6 | N | CO2H | 2 | 4-H | 5-H | 6-OMe | 2-H | 4-H | 5-H | 6-H | 3 | CO2tBu | H | 0 | H | H | 0 | H | |
| 453 | (2) | CR6 | N | CONH2 | 2 | 4-H | 5-H | 6-OMe | 2-H | 4-H | 5-H | 6-H | 3 | CO2tBu | H | 0 | H | H | 0 | H | |
| 454 | (2) | CR6 | N | CH2OH | 2 | 4-H | 5-H | 6-OMe | 2-H | 4-H | 5-H | 6-H | 3 | CO2tBu | H | 0 | H | H | 0 | H | |
| 455 | (2) | CR6 | N | Me | 2 | 4-H | 5-H | 6-OMe | 2-H | 4-H | 5-H | 6-H | 3 | CO2tBu | H | 0 | H | H | 0 | H | |
| 456 | (2) | CR6 | N | CHO | 2 | 4-H | 5-H | 6-OMe | 2-H | 4-H | 5-H | 6-H | 3 | CO2tBu | H | 0 | H | H | 0 | H | |
| 457 | (2) | CR6 | N | H | 2 | 4-H | 5-NO2 | 6-OMe | 2-H | 4-H | 5-H | 6-H | 3 | H | H | 0 | H | H | 0 | H | HCl |
| 458 | (2) | CR6 | N | NO2 | 2 | 4-H | 5-H | 6-OMe | 2-Me | 4-H | 5-H | 6-H | 3 | H | H | 0 | H | H | 0 | H | HCl |
| 459 | (2) | CR6 | N | NO2 | 2 | 4-H | 5-H | 6-OMe | 2-H | 4-pyrrolidin-1-yl | 5-H | 6-H | 4 | H | H | 0 | H | H | 0 | H | 2HCl |
| 460 | (2) | CR6 | N | NO2 | 2 | 4-H | 5-H | 6-OMe | 2-H | 3-H | 5-H | 6-OMe | 3 | H | H | 1 | H | H | 0 | H | HCl |
| 461 | (2) | CR6 | N | NO2 | 2 | 4-H | 5-H | 6-OMe | 2-H | 4-H | 5-H | 6-H | 3 | H | H | 0 | H | H | 0 | H | HCl |
| 462 | (2) | CR6 | N | NO2 | 2 | 4-H | 5-H | 6-OMe | 2-H | 4-H | 5-Me | 6-H | 3 | H | H | 0 | Me | Me | 0 | H | HCl |
| 463 | (2) | CR6 | N | NO2 | 2 | 4-H | 5-H | 6-OMe | 3-H | 4-H | 5-H | 6-H | 2 | H | H | 1 | H | H | 0 | H | HCl |
| 464 | (2) | CR6 | N | NO2 | 2 | 4-H | 5-H | 6-OMe | 2-OMe | 4-H | 5-H | 6-H | 3 | H | H | 0 | H | H | 0 | H | HCl |
| 465 | (2) | CR6 | N | NO2 | 2 | A-H | 5-H | 6-OMe | 2-OMe | 4-H | 5-H | 6-H | 3 | H | H | 0 | H | H | 0 | H | HCl |

*1: Numerals represent substitution positions in the structural formulas of (2)-(7) employed.
*2: Numerals represent substitution positions on the benzene ring.

TABLE 32

| Ex. No. | A | Y | Z | R$_6$ | Substitution position of A R$_7$*1 | R$_8$*1 | R$_9$*1 | X$_1$*2 | X$_2$*2 | X$_3$*2 | X$_4$*2 | Substitution position of W* | R$_1$ | R$_2$ | n | R$_3$ | R$_4$ | m | R$_5$ | salt |
|---|---|---|---|---|---|---|---|---|---|---|---|---|---|---|---|---|---|---|---|---|
| 466 | (2) | CR$_6$ | N | NO$_2$ | 2 | 4-H | 5-H | 6-OMe | 2-H | 4-Cl | 5-H | 6-H | 3 | H | H | 0 | H | H | 0 | H | HCl |
| 467 | (2) | CR$_6$ | N | NO$_2$ | 2 | 4-H | 5-H | 6-OMe | 2-H | 4-F | 5-H | 6-H | 3 | H | H | 0 | H | H | 0 | H | HCl |
| 468 | (2) | CR$_6$ | N | NO$_2$ | 2 | 4-H | 5-H | 6-OMe | 2-OEt | 4-H | 5-H | 6-H | 3 | H | H | 0 | H | H | 0 | H | HCl |
| 469 | (2) | CR$_6$ | N | NO$_2$ | 2 | 4-H | 5-H | 6-OMe | 2-Cl | 4-H | 5-H | 6-H | 3 | H | H | 0 | H | H | 0 | H | HCl |
| 470 | (2) | CR$_6$ | N | H | 2 | 4-CO$_2$Me | 5-H | 6-OMe | 2-H | 4-H | 5-H | 6-H | 3 | H | H | 0 | H | H | 0 | H | HCl |
| 471 | (2) | CR$_6$ | N | H | 2 | 4-CO$_2$H | 5-H | 6-OMe | 2-H | 4-H | 5-H | 6-H | 3 | H | H | 0 | O | H | 0 | H | HCl |
| 472 | (2) | CR$_6$ | N | H | 2 | 4-CH$_2$OH | 5-H | 6-OMe | 2-H | 4-H | 5-H | 6-H | 3 | H | H | 0 | H | H | 0 | H | HCl |
| 473 | (2) | CR$_6$ | N | — | 2 | 4-Me | 5-H | 6-OMe | 2-H | 4-H | 5-H | 6-H | 3 | H | H | 0 | H | H | 0 | H | 2HCl |
| 474 | (2) | N | N | CF$_3$ | 2 | 4-Me | 5-H | 6-H | 2-H | 4-H | 5-H | 6-H | 3 | H | H | 0 | H | H | 0 | H | 2HCl |
| 475 | (2) | CR$_6$ | N | NO$_2$ | 2 | 4-H | 5-OMe | 6-OMe | 2-H | 4-H | 5-H | 6-H | 3 | H | H | 0 | H | H | 0 | H | 2HCl |
| 476 | (2) | CR$_6$ | CH | NO$_2$ | 2 | 4-H | 5-H | 6-H | 2-H | 4-H | 5-H | 6-H | 3 | H | H | 0 | H | H | 0 | H | HCl |
| 477 | (2) | CR$_6$ | CMe | H | 2 | 4-Me | 5-H | 6-OMe | 2-H | 4-H | 5-H | 6-H | 3 | H | H | 0 | H | H | 0 | H | 2HCl |
| 478 | (2) | CR$_6$ | N | H | 2 | 4-Me | 5-H | 6-H | 2-H | 4-H | 5-H | 6-H | 3 | H | H | 0 | Me | H | 0 | H | 2HCl |
| 479 | (2) | CR$_6$ | N | H | 2 | 4-Me | 5-H | 6-H | 2-H | 4-H | 5-H | 6-H | 3 | H | H | 0 | Et | Me | 6 | H | 2HCl |
| 480 | (2) | CR$_6$ | N | H | 2 | 4-Me | 5-H | 6-H | 2-H | 4-H | 5-H | 6-H | 3 | H | H | 0 | H | H | 0 | H | 2HCl |

*1: Numerals represent substitution positions in the structural formulas of (2)–(7) employed.
*2: Numerals represent substitution positions on the benzene ring.

*: W = 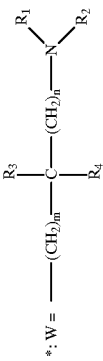

TABLE 33

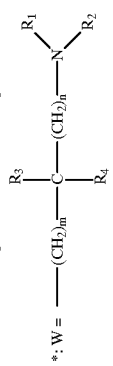

A =
(2) [pyridine with R7, R8, R9, Z]
(3) [ring with W, R7, R8, R9, U]
(4) [ring with W, R7, R8, R9, U]
(5) [pyrrole with T, R7, R8, R9]
(6) [pyrrole with R7, R8, R9]
(7) [pyrrole with T, R7, R8]

| Ex. No. | A | Y | Z | R₆ | Substitution position of A R₇*¹ | R₈*¹ | R₉*¹ | X₁*² | X₂*² | X₃*² | X₄*² | Substitution position of W* | R₁ | R₂ | n | R₃ | R₄ | m | R₅ | salt |
|---|---|---|---|---|---|---|---|---|---|---|---|---|---|---|---|---|---|---|---|---|
| 481 | (2) | CR₆ | N | H | 2 | 4-Me | 5-H | 6-H | 2-Me | 4-H | 5-H | 6-H | 3 | H | H | 0 | H | H | 0 | H | 2HCl |
| 482 | (2) | CR₆ | N | H | 2 | 4-Me | 5-H | 6-H | 2-H | 4-Et | 5-H | 6-H | 3 | H | H | 0 | H | H | 0 | H | 2HCl |
| 483 | (2) | CR₆ | N | H | 2 | 4-Me | 5-H | 6-H | 2-H | 4-OEt | 5-H | 6-H | 3 | H | H | 0 | H | H | 0 | H | 2HCl |
| 484 | (2) | CR₆ | N | H | 2 | 4-Me | 5-H | 6-H | 2-H | 4-H | 5-H | 6-H | 2 | H | H | 1 | H | H | 0 | H | 2HCl |
| 485 | (2) | CR₆ | N | H | 2 | 4-Me | 5-H | 6-Me | 3-Cl | 4-H | 5-H | 6-H | 3 | H | H | 0 | H | H | 0 | H | 2HCl |
| 486 | (2) | CR₆ | N | H | 2 | 4-Me | 5-H | 6-H | 2-H | 4-H | 5-H | 6-H | 3 | H | H | 0 | H | H | 0 | H | 2HCl |
| 487 | (2) | CR₆ | N | H | 2 | 4-Et | 5-H | 6-H | 2-H | 4-H | 5-H | 6-H | 3 | H | H | 0 | H | H | 0 | H | 2HCl |
| 488 | (2) | CR₆ | N | H | 2 | 4-Me | 5-H | 6-H | 2-H | 3-H | 5-H | 6-H | 3 | H | H | 0 | —CH₂CH₂CH₂— | H | 0 | H | 2HCl |
| 489 | (2) | CR₆ | N | H | 2 | 4-Me | 5-H | 6-H | 2-H | 4-H | 5-H | 6-H | 4 | H | H | 1 | H | H | 0 | H | 2HCl |
| 490 | (2) | CR₆ | N | H | 2 | 4-Me | 5-H | 6-H | 2-OEt | 4-H | 5-H | 6-H | 3 | H | H | 0 | H | H | 0 | H | 2HCl |
| 491 | (2) | CR₆ | N | H | 2 | 4-Me | 5-H | 6-H | 2-H | 4-Cl | 5-H | 6-H | 3 | H | H | 0 | H | H | 0 | H | 2HCl |
| 492 | (2) | CR₆ | N | CN | 2 | 4-H | 5-H | 6-OMe | 2-H | 4-H | 5-H | 6-H | 3 | H | H | 0 | H | H | 0 | H | HCl |
| 493 | (2) | CR₆ | N | Cl | 2 | 4-H | 5-H | 6-OMe | 2-H | 4-H | 5-H | 6-H | 3 | H | H | 0 | H | H | 0 | H | HCl |
| 494 | (2) | CR₆ | N | CONH₂ | 2 | 4-H | 5-H | 6-OMe | 2-H | 4-H | 5-H | 6-H | 3 | H | H | 0 | H | H | 0 | H | HCl |
| 495 | (2) | CR₆ | N | Me | 2 | 4-Me | 5-H | 6-OMe | 2-H | 4-H | 5-H | 6-H | 3 | H | H | 0 | H | H | 0 | H | 2HCl |

*¹:Numerals represent substitution positions in the structural formulas of (2)–(7) employed.
*²:Numerals represent substitution positions on the benzene ring.

*: W =

TABLE 34

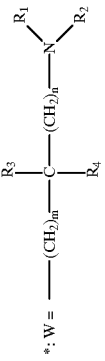

| Ex. No. | A | Y | Z | R$_6$ | Substitution position of A | R$_7$ *1 | R$_8$ *1 | R$_9$ *1 | X$_1$ *2 | X$_2$ *2 | X$_3$ *2 | X$_4$ *2 | Substitution position of W* | R$_1$ | R$_2$ | n | R$_3$ | R$_4$ | m | R$_5$ | salt |
|---|---|---|---|---|---|---|---|---|---|---|---|---|---|---|---|---|---|---|---|---|---|
| 496 | (2) | CR$_6$ | CH | NO$_2$ | 2 | 4-H | 5-H | 6-OMe | 2-H | 4-OMe | 5-H | 6-H | 3 | H | H | 0 | H | H | 0 | H | HCl |
| 497 | (2) | CR$_6$ | N | H | 2 | 4-H | 5-Me | 6-H | 2-H | 4-H | 5-H | 6-H | 3 | CO$_2^t$Bu | CO$_2^t$Bu | 0 | H | H | 0 | H | |
| 498 | (2) | CR$_6$ | N | Me | 2 | 4-H | 5-H | 6-H | 2-H | 4-H | 5-H | 6-H | 3 | H | CO$_2^t$Bu | 0 | H | H | 0 | H | |
| 499 | (2) | CR$_6$ | N | H | 2 | 4-Me | 5-H | 6-H | 2-H | 4-OMe | 5-H | 6-H | 3 | CO$_2^t$Bu | CO$_2^t$Bu | 0 | H | H | 0 | H | 2HCl |
| 500 | (2) | CR$_6$ | N | H | 2 | 4-H | 5-Me | 6-H | 2-H | 4-pyrazol-1-yl | 5-H | 6-H | 3 | CO$_2^t$Bu | H | 0 | H | H | 0 | H | 2HCl |
| 501 | (2) | CR$_6$ | N | H | 2 | 4-H | 5-H | 6-H | 2-H | 4-H | 5-H | 6-H | 3 | H | H | 0 | H | H | 0 | H | 2HCl |
| 502 | (2) | CR$_6$ | N | Me | 2 | 4-Me | 5-H | 6-H | 2-H | 4-OMe | 5-H | 6-H | 3 | H | H | 0 | H | H | 0 | H | 2HCl |
| 503 | (2) | CR$_6$ | N | H | 2 | 4-H | 5-H | 6-H | 2-H | 4-pyrazol-1-yl | 5-H | 6-H | 3 | H | H | 0 | H | H | 0 | H | 2HCl |
| 504 | (2) | CR$_6$ | N | H | 2 | 4-Me | 5-H | 6-H | 2-O$^n$Pr | 4-H | 5-H | 6-H | 3 | CO$_2^t$Bu | CO$_2^t$Bu | 0 | H | H | 0 | H | 2HCl |
| 505 | (2) | CR$_6$ | N | H | 2 | 4-Me | 5-H | 6-H | 2-O$^n$Pr | 4-H | 5-H | 6-H | 3 | H | H | 0 | H | H | 0 | H | 2HCl |
| 506 | (2) | CR$_6$ | N | H | 2 | 4-Me | 5-H | 6-H | 2-O$^n$Pr | 4-H | 5-H | 6-H | 3 | H | H | 0 | H | H | 0 | H | 2HCl |

| Ex. No. | A | T | Substitution position of A | R$_7$ *1 | R$_8$ *1 | R$_9$ *1 | X$_1$ *2 | X$_2$ *2 | X$_3$ *2 | X$_4$ *2 | Substitution position of W* | R$_1$ | R$_2$ | n | R$_3$ | R$_4$ | m | R$_5$ | salt |
|---|---|---|---|---|---|---|---|---|---|---|---|---|---|---|---|---|---|---|---|
| 507 | (7) | S | 2 | 4-H | 5-Me | — | 2-H | 4-H | 5-H | 6-H | 3 | CO$_2^t$Bu | H | 0 | H | H | 0 | H | |
| 508 | (7) | S | 2 | 4-H | 5-Me | — | 2-H | 4-H | 5-H | 6-H | 3 | H | H | 0 | H | H | 0 | H | |
| 509 | (7) | S | 2 | 4-Me | 5-H | — | 2-H | 4-H | 5-H | 6-H | 3 | CO$_2^t$Bu | H | 0 | H | H | 0 | H | |
| 510 | (7) | S | 2 | 4-Me | 5-H | — | 2-H | 4-H | 5-H | 6-H | 3 | H | H | 0 | H | H | 0 | H | |

*1: Numerals represent substitution positions in the structural formulas of (2)–(7) employed.
*2: Numerals represent substitution positions on the benzene ring.

TABLE 35

| Ex. No. | A | Y | Z | R$_6$ | Substitution position of A | R$_7$*1 | R$_8$*1 | R$_9$*1 | X$_1$*2 | X$_2$*2 | X$_3$*2 | X$_4$*2 | Substitution position of W* | R$_1$ | R$_2$ | n | R$_3$ | R$_4$ | m | R$_5$ | salt |
|---|---|---|---|---|---|---|---|---|---|---|---|---|---|---|---|---|---|---|---|---|---|
| 511 | (7) | O | — | — | 2 | 4-H | 5-Me | — | 2-H | 4-H | 5-H | 6-H | 3 | CO$_2^t$Bu | CO$_2^t$Bu | 0 | H | H | 0 | H | |
| 512 | (7) | O | — | — | 2 | 4-H | 5-Me | — | 2-OEt | 4-H | 5-H | 6-H | 3 | CO$_2^t$Bu | CO$_2^t$Bu | 0 | H | H | 0 | H | |
| 513 | (7) | O | — | — | 2 | 4-H | 5-Me | — | 2-Me | 4-H | 5-H | 6-H | 3 | CO$_2^t$Bu | CO$_2^t$Bu | 0 | H | H | 0 | H | |
| 514 | (7) | O | — | — | 2 | 4-H | 5-Me | — | 2-H | 4-OMe | 5-H | 6-H | 3 | CO$_2^t$Bu | CO$_2^t$Bu | 0 | H | H | 0 | H | |
| 515 | (7) | O | — | — | 2 | 4-H | 5-Me | — | 2-OEt | 4-H | 5-H | 6-H | 3 | H | H | 0 | H | H | 0 | H | CF$_3$CO$_2$H |
| 516 | (7) | O | — | — | 2 | 4-H | 5-Me | — | 2-Me | 4-H | 5-H | 6-H | 3 | H | H | 0 | H | H | 0 | H | CF$_3$CO$_2$H |
| 517 | (7) | O | — | — | 2 | 4-H | 5-Me | — | 2-H | 4-OMe | 5-H | 6-H | 3 | H | H | 0 | H | H | 0 | H | CF$_3$CO$_2$H |
| 518 | (7) | O | — | — | 2 | 4-CN | 5-Me | — | 2-H | 4-H | 5-H | 6-H | 3 | H | H | 0 | H | H | 0 | H | CF$_3$CO$_2$H |

| Ex. No. | A | Y | Z | R$_6$ | Substitution position of A | R$_7$*1 | R$_8$*1 | R$_9$*1 | X$_1$*2 | X$_2$*2 | X$_3$*2 | X$_4$*2 | Substitution position of W* | R$_1$ | R$_2$ | n | R$_3$ | R$_4$ | m | R$_5$ | salt |
|---|---|---|---|---|---|---|---|---|---|---|---|---|---|---|---|---|---|---|---|---|---|
| 519 | (2) | CR$_6$ | N | H | 2 | 4-Me | 5-H | 6-H | 2-OEt | 4-Cl | 5-H | 6-H | 3 | CO$_2^t$Bu | CO$_2^t$Bu | 0 | H | H | 0 | H | |
| 520 | (2) | CR$_6$ | N | H | 2 | 4-Me | 5-H | 6-H | 2-OEt | 4-Me | 5-H | 6-H | 3 | CO$_2^t$Bu | CO$_2^t$Bu | 0 | H | H | 0 | H | |
| 521 | (2) | CR$_6$ | N | H | 2 | 4-Me | 5-H | 6-H | 2-OEt | 4-Cl | 5-H | 6-H | 3 | H | H | 0 | H | H | 0 | H | 2HCl |
| 522 | (2) | CR$_6$ | N | H | 2 | 4-Me | 5-H | 6-H | 2-OEt | 4-Me | 5-H | 6-H | 3 | H | H | 0 | H | H | 0 | H | 2HCl |
| 523 | (2) | CR$_6$ | N | NO$_2$ | 2 | 4-H | 5-NO$_2$ | 6-H | 2-H | 4-H | 5-H | 6-H | 3 | H | H | 0 | H | H | 0 | H | |
| 524 | (2) | CR$_6$ | N | CN | 2 | 4-Me | 5-H | 6-Me | 2-H | 4-H | 5-H | 6-H | 3 | H | H | 0 | H | H | 0 | H | |
| 525 | (2) | CR$_6$ | N | H | 2 | 4-H | 5-H | 6-H | 2-H | 4-H | 5-H | 6-H | 3 | H | H | 0 | H | H | 0 | H | |

*1: Numerals represent substitution positions in the structural formulas of (2)–(7) employed.
*2: Numerals represent substitution positions on the benzene ring.

*: W = 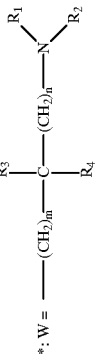

TABLE 36

| Ex. No. | A | Y | Z | R₆ | Substitution position of A | R₇*¹ | R₈*¹ | R₉*¹ | X₁*² | X₂*² | X₃*² | X₄*² | Substitution position of W* | R₁ | R₂ | n | R₃ | R₄ | m | R₅ | salt |
|---|---|---|---|---|---|---|---|---|---|---|---|---|---|---|---|---|---|---|---|---|---|
| 526 | (2) | CR₆ | N | H | 2 | 4-H | 4-H | 5-CN | 6-H | 2-H | 5-H | 6-H | 3 | H | H | 0 | H | H | H | 0 | H |
| 527 | (2) | CR₆ | N | CN | 2 | 4-H | 4-CO₂Et | 5-H | 6-Me | 2-H | 5-H | 6-H | 3 | H | H | 0 | H | H | H | 0 | H |
| 528 | (2) | CR₆ | N | H | 2 | 4-H | 4-CO₂H | 5-H | 6-H | 2-H | 5-H | 6-H | 3 | H | H | 0 | H | H | H | 0 | H |
| 529 | (2) | CR₆ | N | Cl | 2 | 4-H | 4-H | 5-CO₂H | 6-H | 2-H | 5-H | 6-H | 3 | H | H | 0 | H | H | H | 0 | H |
| 530 | (2) | CR₆ | N | H | 2 | 4-H | 4-CO₂H | 5-CO₂H | 6-Me | 2-H | 5-H | 6-H | 3 | H | H | 0 | H | H | H | 0 | H |
| 531 | (2) | CR₆ | N | H | 2 | 4-H | 4-H | 5-H | 6-CO₂H | 2-H | 5-H | 6-H | 3 | H | H | 0 | H | H | H | 0 | H |
| 532 | (2) | CR₆ | N | CONH₂ | 2 | 4-H | 4-H | 5-H | 6-Me | 2-H | 5-H | 6-H | 3 | H | H | 0 | H | H | H | 0 | H |
| 533 | (2) | CR₆ | N | CONH₂ | 2 | 4-H | 4-H | 5-Cl | 6-H | 2-H | 5-H | 6-H | 3 | H | H | 0 | H | H | H | 0 | H |
| 534 | (2) | CR₆ | N | H | 2 | 4-H | 4-CONH₂ | 5-H | 6-OMe | 2-H | 5-H | 6-H | 3 | H | H | 0 | H | H | H | 0 | H |
| 535 | (2) | CR₆ | N | CONH₂ | 2 | 4-H | 4-H | 5-Br | 6-H | 2-H | 5-H | 6-H | 3 | H | H | 0 | H | H | H | 0 | H |
| 536 | (2) | CR₆ | N | H | 2 | 4-H | 4-H | 5-Cl | 6-H | 2-H | 5-H | 6-H | 3 | H | H | 0 | H | H | H | 0 | H |
| 537 | (2) | CR₆ | N | Cl | 2 | 4-H | 4-H | 5-H | 6-H | 2-H | 5-H | 6-H | 3 | H | H | 0 | H | H | H | 0 | H |
| 538 | (2) | CR₆ | N | H | 2 | 4-H | 4-Me | 5-H | 6-H | 2-OMe | 5-H | 6-H | 3 | CO₂ᵗBu | CO₂ᵗBu | 0 | H | H | H | 0 | H |

*¹: Numerals represent substitution positions in the structural formulas of (2)–(7) employed.
*²: Numerals represent substitution positions on the benzene ring.

TABLE 37

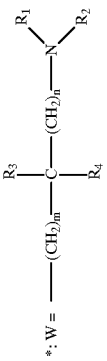

| Ex. No. | A | Y | Z | R₆ | Substitution position of A | R₇ *1 | R₈ *1 | R₉ *1 | X₁ *2 | X₂ *2 | X₃ *2 | X₄ *2 | Substitution position of W* | R₁ | R₂ | n | R₃ | R₄ | m | R₅ | salt |
|---|---|---|---|---|---|---|---|---|---|---|---|---|---|---|---|---|---|---|---|---|---|
| 541 | (2) | CR₆ | N | H | 2 | 4-Me | 5-H | 6-H | 2-OMe | 4-H | 5-H | 6-H | 3 | H | H | 0 | H | H | 0 | H | 2HCl |
| 542 | (2) | CR₆ | N | H | 2 | 4-Me | 5-H | 6-H | 2-OiPr | 4-H | 5-H | 6-H | 3 | CO₂tBu | CO₂tBu | 0 | H | H | 0 | H | 2HCl |
| 543 | (2) | CR₆ | N | H | 2 | 4-Me | 5-H | 6-H | 2-OiPr | 4-H | 5-H | 6-H | 3 | H | H | 0 | H | H | 0 | H | 2HCl |
| 544 | (2) | CR₆ | N | H | 2 | 4-Me | 5-H | 6-H | 2-OnBu | 4-H | 5-H | 6-H | 3 | CO₂tBu | H | 0 | H | H | 0 | H | 2HCl |
| 545 | (2) | CR₆ | N | H | 2 | 4-Me | 5-H | 6-H | 2-OnBu | 4-H | 5-H | 6-H | 3 | H | H | 0 | H | H | 0 | H | 2HCl |
| 546 | (2) | CR₆ | N | H | 2 | 4-Me | 5-H | 6-H | 2-OtBu | 4-H | 5-H | 6-H | 3 | CO₂tBu | H | 0 | H | H | 0 | H | 2HCl |
| 547 | (2) | CR₆ | N | H | 2 | 4-Me | 5-H | 6-H | 2-OtBu | 4-H | 5-H | 6-H | 3 | H | H | 0 | H | H | 0 | H | 2HCl |
| 548 | (2) | CR₆ | N | H | 2 | 4-Me | 5-H | 6-H | 2-OCH₂Ph | 4-H | 5-H | 6-H | 3 | H | H | 0 | H | H | 0 | H | 2HCl |
| 549 | (2) | CR₆ | N | H | 2 | 4-Me | 5-H | 6-H | 2-OCH₂CH₂Ph | 4-H | 5-H | 6-H | 3 | H | H | 0 | H | H | 0 | H | 2HCl |
| 550 | (2) | CR₆ | N | H | 2 | 4-Me | 5-H | 6-H | 2-Et | 4-H | 5-H | 6-H | 3 | H | H | 0 | H | H | 0 | H | 2HCl |
| 551 | (2) | CR₆ | N | H | 2 | 4-Me | 5-H | 6-H | 2-CH₂Ph | 4-H | 5-H | 6-H | 3 | H | H | 0 | H | H | 0 | H | 2HCl |
| 552 | (2) | CR₆ | N | H | 2 | 4-Me | 5-H | 6-H | 2-OMe | 4-Me | 5-H | 6-H | 3 | H | H | 0 | H | H | 0 | H | 2HCl |
| 553 | (2) | CR₆ | N | H | 2 | 4-Me | 5-H | 6-H | 2-OiPr | 4-Me | 5-H | 6-H | 3 | H | H | 0 | H | H | 0 | H | 2HCl |
| 554 | (2) | CR₆ | N | H | 2 | 4-Me | 5-H | 6-H | 2-OnBu | 4-Me | 5-H | 6-H | 3 | H | H | 0 | H | H | 0 | H | 2HCl |
| 555 | (2) | CR₆ | N | H | 2 | 4-Me | 5-H | 6-H | 2-OtBu | 4-Me | 5-H | 6-H | 3 | H | H | 0 | H | H | 0 | H | 2HCl |

*1: Numerals represent substitution positions in the structural formulas of (2)–(7) employed.
*2: Numerals represent substitution positions on the benzene ring.

*: W =

Example 1

Synthesis of 2-(3-(di-(t-butoxycarbonyl)aminomethyl)phenylamino)-3-nitropyridine A mixture of 3-(di-(t-butoxycarbonyl)aminomethyl) aniline (1.50 g), triethylamine (2.0 ml), 2-chloro-3-nitropyridine (1.10 g) and anhydrous dimethylformamide (15 ml) was stirred at 60° C. for 20 h and, thereafter, ethyl acetate and water were added. The organic layer was washed with a saturated aqueous sodium chloride solution, dried with anhydrous sodium sulfate and concentrated under reduced pressure. The resulting residue was purified by silica gel column chromatography (eluent, n-hexane:ethyl acetate=3:1) to give 1.42 g of the titled compound (yield, 69%).

$^1$H-NMR(CDCL$_3$) δ: 1.47(18H, s), 4.81(2H, s), 6.83(1H, dd, J=8.3, 4.3 Hz), 7.11(1H, d, J=7.9 Hz), 7.34(1H, dd, J=7.9, 7.9 Hz), 7.55–7.63 (2H, m), 8.47(1H, dd, J=4.3, 1.7 Hz), 8.53(1H, dd, J=8.3, 1.7 Hz), 10.11(1H, brs)

The procedure of Example 1 was repeated using corresponding aniline derivatives or corresponding halogenated derivatives to give the compounds shown in Tables 38–43 (under "Reaction condition" in the tables, base:(1) is triethylamine and base:(2) is diisopropylethylamine).

TABLE 38

| Example | Aniline derivative | Halogenated derivative | Product | Reaction condition | Spectral data |
|---|---|---|---|---|---|
| 9 | | | | base: (1) | ¹H—NMR(CDCl₃)δ1.47(18H, s), 4.80(2H, s), 6.77(1H, d, J=9.2Hz), 7.16(1H, d, J=7.3Hz), 7.26–7.39(3H, m), 8.23(1H, dd, J=9.2, 2.6Hz), 9.08(1H, d, J=2.6Hz) |
| 13 | | | | base: (1) | ¹H—NMR(CDCl₃)δ1.46(18H, s), 2.57(3H, s), 4.79(2H, s), 6.66(1H, d, J=5.0Hz), 7.06(1H, d, J=7.6Hz), 7.26–7.33(1H, m), 7.33(1H, dd, J=7.6, 7.6Hz), 7.46(1H, s), 8.18(1H, d, J=5.0Hz), 9.14(1H, brs) |
| 17 | | | | base: (1) | ¹H—NMR(CDCl₃)δ1.46(18H, s), 3.96(3H, s), 4.80(2H, s), 6.23(1H, d, J=9.2Hz), 7.10(1H, d, 8.6Hz), 7.32(1H, dd, J=7.6, 7.6Hz), 7.56(1H, d, J=7.6Hz), 7.60(1H, s), 8.42(1H, d, J=9.2Hz), 10.63(1H, brs) |
| 21 | | | | base: (1) | ¹H—NMR(CDCl₃)δ1.45(18H, s), 3.85(3H, s), 3.90(3H, s), 4.84(2H, s), 6.17(1H, d, J=9.2Hz), 6.85(1H, d, J=8.6Hz), 7.34(1H, d, J=2.3Hz), 7.46(1H, dd, J=8.6, 2.3Hz), 8.39(1H, d, J=9.2Hz), 10.50(1H, brs) |

TABLE 39

| Example | Aniline derivative | Halogenated derivative | Product | Reaction condition | Spectral data |
|---|---|---|---|---|---|
| 23 | | | | base: (1) | ¹H—NMR(CDCl₃)δ1.24(3H, t, J=7.3Hz), 1.45(18H, s), 2.69(2H, q, J=7.3Hz), 3.94(3H, s), 4.85(2H, s), 6.19(1H, d, J=8.9Hz), 7.18(1H, d, J=8.3Hz), 7.32(1H, d, J=2.0Hz), 7.54(1H, dd, J=8.3, 2.0Hz), 8.40(1H, d, J=8.9Hz) |
| 25 | | | | base: (1) | ¹H—NMR(CDCl₃)δ1.30(3H, t, J=7.3Hz), 1.30(9H, s), 2.85(2H, q, J=7.3Hz), 3.59(4H, s), 3.92(3H, s), 5.07(1h, brs), 6.18(1H, d, J=8.9Hz), 7.18–7.29(5H, m), 7.43(1H, s), 7.73(1H, dd, J=8.6, 2.0Hz), 8.40(1H, d, J=8.9Hz), 10.58(1H, brs) |
| 27 | | | | base: (1) | ¹H—NMR(CDCl₃)δ10.33(1H, brs), 8.40(1H, d, J=8.9Hz), 7.61 1.47(18H, s), 4.81(2H, s), 6.80(1H, d, J=8.6Hz), 7.13(1H, d, J=7.6Hz), 7.36(1H, dd, J=7.6, 7.6Hz), 7.49(1H, s), 7.65(1H, d, J=7.6Hz), 8.46(1H, d, J=8.6Hz), 10.24(1H, brs) |
| 406 | | | | base: (1) | ¹H—NMR(CDCl₃)δ10.33(1H, brs), 8.40(1H, d, J=8.9Hz), 7.61 (1H, d, J=7.9Hz), 7.21(1H, dd, J=7.9, 7.6Hz), 7.05(1H, d, J=7.6Hz), 6.18(1H, d, J=8.9Hz), 4.85(2H, s), 3.76(3H, s), 2.27(3H, s), 1.45(18H, s)<br>FAB—MS(m/z) 489(M\* + 1) |

TABLE 40

| Example | Aniline derivative | Halogenated derivative | Product | Reaction condition | Spectral data |
|---|---|---|---|---|---|
| 407 | | | | base: (1) | ¹H—NMR(CDCl₃)δ10.54(1H, brs), 8.39(1H, d, J=9.2Hz), 7.45 (1H, dd, J=8.6, 2.3Hz), 7.30–7.24(1H, m), 6.98(1H, d, J=8.6Hz), 6.16(1H, d, J=9.2Hz), 4.85(2H, s), 3.92(3H, s), 3.10(4H, t, J=5.4Hz), 1.94(4H, t, J=5.4Hz), 1.41(18H, s) FAB—MS(m/z) 544(M* + 1) |
| 408 | | | | base: (1) | ¹H—NMR(CDCl₃)δ10.62(1H, brs), 8.42(1H, d, J=8.9Hz), 7.60 (2H, d, J=8.6Hz), 7.21(2H, d, J=8.6Hz), 6.22(1H, d, J=8.9Hz), 4.57(1H, brs), 3.96(3H, s), 3.39(2H, dt, J=6.9, 6.9Hz), 2.81(2H, t, J=6.9Hz), 1.44(9H, s) FAB—MS(m/z) 389(M* + 1) |
| 409 | | | | base: (1) | ¹H—NMR(CDCl₃)δ11.20(1H, brs), 8.56(1H, d, J=2.0Hz), 8.44 (1H, d, J=9.2Hz), 7.00(1H, dd, J=8.3, 2.0Hz), 6.90(1H, d, J=8.3Hz), 6.23(1H, d, J=9.2Hz), 4.75(1H, brs), 4.29(2H, d, J=5.6Hz), 3.96(3H, s), 3.96(3H, s), 1.46(9H, s) FAB—MS(m/z) 405(M* + 1) |
| 410 | | | | base: (1) | ¹H—NMR(CDCl₃)δ10.68(1H, brs), 8.41(1H, d, J=8.9Hz), 7.65 (1H, s), 7.58(1H, t, J=7.9Hz), 7.33(1H, t, J=7.9Hz), 7.22(1 H, d, J=7.9Hz), 6.22(1H, d, J=8.9Hz), 4.97(1H, s), 3.98(3H, s), 1.65(9H, s), 1.38(6H, s) FAB—MS(m/z) 403(M* + 1) |

TABLE 41

| Example | Aniline derivative | Halogenated derivative | Product | Reaction condition | Spectral data |
|---|---|---|---|---|---|
| 411 | | | | base: (1) | $^1$H—NMR(CDCl$_3$)δ10.60(1H, br), 8.40(1H, d, J=8.9Hz), 7.44(1H, s), 7.37(1H, s), 6.92(1H, s), 6.21(1H, d, J=8.9Hz), 4.76(2H, s), 3.97(3H, s), 2.35(3H, s), 1.46(18H, s) FAB—MS(m/z) 489(M* + 1) |
| 412 | | | | base: (1) | $^1$H—NMR(CDCl$_3$)δ10.45(1H, brs), 8.41(1H, d, J=9.2Hz), 7.83(1H, d, J=7.3Hz), 7.31–7.25(2H, m), 7.21(1H, d, J=7.3Hz), 6.20(1H, d, J=9.2Hz), 4.67(1H, brs), 3.81(3H, s), 3.39(2H, dt, J=6.9, 6.9Hz), 2.89(2H, t, J=6.9Hz), 1.39(9H, s) FAB—MS(m/z) 389(M* + 1) |
| 413 | | | | base: (1) | $^1$H—NMR(CDCl$_3$)δ11.24(1H, brs), 8.45(1H, d, J=9.2Hz), 8.42(1H, d, J=7.9Hz), 7.12(1H, dd, J=7.9, 7.6Hz), 6.95(1H, d, J=7.6Hz), 6.26(1H, d, J=9.2Hz), 4.94(2H, s), 4.04(3H, s), 3.87(3H, s), 1.46(18H, s) FAB—MS(m/z) 505(M* + 1) |
| 414 | | | | base: (1) | $^1$H—NMR(CDCl$_3$)δ10.59(1H, brs), 8.41(1H, d, J=9.2Hz), 7.54(1H, dd, J=8.6, 2.3Hz), 7.39(1H, d, J=2.3Hz), 7.35(1H, d, J=8.6Hz), 6.24(1H, d, J=9.2Hz), 4.93(2H, s), 3.94(3H, s), 1.45(18H, s) |

TABLE 42

| Example | Aniline derivative | Halogenated derivative | Product | Reaction condition | Spectral data |
|---|---|---|---|---|---|
| 415 | Me-C6H3(CH2NHBoc)-NH2 | O2N-pyridine(Cl)-OMe | O2N-C6H3(OMe)-NH-C6H3(Me)(CH2NHBoc) | base: (1) | ¹H—NMR(CDCl₃)δ10.59(1H, brs), 8.40(1H, d, J=9.2Hz), 7.57 (1H, d, J=2.0Hz), 7.46(1H, dd, J=7.9, 2.0Hz), 7.11(1H, d, J=7.9Hz), 6.21(1H, d, J=9.2Hz), 4.75(1H, brs), 4.33(2H, s, J=5.6Hz), 3.96(3H, s), 2.32(3H, s), 1.47(9H, s) |
| 416 | F-C6H3(CH2NHBoc)-NH2 | O2N-pyridine(Cl)-OMe | O2N-C6H3(OMe)-NH-C6H3(F)(CH2NHBoc) | base: (1) | ¹H—NMR(CDCl₃)δ10.53(1H, brs), 8.44(1H, d, J=9.2Hz), 7.67 (1H, d, J=8.9Hz), 7.52–7.43(1H, m), 7.05(1H, dd, J=9.2, 8.9 Hz), 6.23(1H, d, J=9.2Hz), 4.92(1H, brs), 4.38(2H, d, J=6.3 Hz), 3.94(3H, s), 1.45(9H, s) |
| 417 | OEt-C6H3(CH2NBoc2)-NH2 | O2N-pyridine(Cl)-OMe | O2N-pyridine(OMe)-NH-C6H3(OEt)(CH2NBoc2) | base: (1) | ¹H—NMR(CDCl₃)δ11.24(1H, brs), 8.46(1H, d, J=8.9Hz), 8.43 (1H, d, J=7.9Hz), 7.11(1H, dd, J=8.3, 7.9Hz), 6.93(1H, d, J=8.3Hz), 6.25(1H, d, J=8.9Hz), 4.93(2H, s), 4.04(3H, s), 3.96(2H, q, J=6.9Hz), 1.52(3H, t, J=6.9Hz), 1.45(18H, s) |
| 418 | C6H4(CH2NBoc2)-NH2 | O2N-pyridine(Cl)-OMe | O2N-C6H3(OMe)-NH-C6H4(CH2NBoc2) | base: (1) | ¹H—NMR(CDCl₃)δ1.47(18H, s), 2.26(3H, s), 4.80(2H, s), 6.59(1H, d, J=8.6Hz), 6.97(1H, s), 7.14–7.21(3H, m), 7.36( 1H, dd, J=7.6, 7.6Hz), 8.10(1H, d, J=8.6Hz) |

TABLE 43

| Example | Aniline derivative | Halogenated derivative | Product | Reaction condition | Spectral data |
|---|---|---|---|---|---|
| 419 | Boc₂N-CH₂-C₆H₄-NH₂ | O₂N-C₆H₃(F)-OMe | O₂N-C₆H₃(OMe)-NH-C₆H₄-CH₂-NBoc₂ | base: (1) | ¹H—NMR(CDCl₃)δ1.46(18H, s), 3.74(3H, s), 4.79(2H, s), 6.34(1H, dd, J=9.6, 2.6Hz), 6.57(1H, dd, J=2.6Hz), 7.14–7.20(2H, m), 7.24(1H, s), 7.37(1H, dd, J=7.6, 7.6Hz), 8.18(1H, d, J=9.6Hz), 9.77(1H, brs) |
| 420 | MeO-C₆H₃(CH₂NBoc₂)-NH₂ | O₂N-C₆H₃(F)-OMe | O₂N-C₆H₃(OMe)-NH-C₆H₃(OMe)-CH₂NBoc₂ | base: (2) | ¹H—NMR(CDCl₃)δ1.44(18H, s), 3.70(3H, s), 3.86(3H, s), 4.81(2H, s), 6.27(1H, dd, J=9.6, 2.6Hz), 6.33(1H, d, J=2.6Hz), 6.89(1H, d, J=8.3Hz), 7.03(1H, d, J=2.0Hz), 7.11(1H, dd, J=8.3, 2.0Hz), 8.16(1H, d, J=9.6Hz), 9.66(1H, s) |

Example 2

Synthesis of 2-(3-aminomethylphenylamino)-3-nitropyridine hydrochloride

A mixture of the compound (95.2 mg) obtained in Example 1 and trifluoroacetic acid (2 ml) was stirred at room temperature for 1 h and concentrated under reduced pressure. The resulting residue was dissolved in methanol (3 ml) and a 1,4-dioxane solution (4 N, 0.5 ml) of hydrogen chloride was added at room temperature and the mixture was concentrated under reduced pressure. In addition, the resulting residue was recrystallized from ethanol-ethyl acetate to give 56.7 mg of the titled compound (yield, 94%)

$^1$H-NMR(DMSO-$d_6$) δ: 4.03(2H, q, J=5.6 Hz), 7.03(1H, dd, J=8.2, 4.3 Hz), 7.28(1H, d, J=7.6 Hz), 7.42(1H, dd, J=7.6, 7.6 Hz), 7.74(1H, s), 7.75(1H, d, J=7.6 Hz), 8.46(3H, brs), 8.50–8.60(2H, m), 10.00(1H, s)

The procedure of Example 2 was repeated using corresponding reagents to give the compounds shown in Tables 44–62.

TABLE 44

| Example | Reagent | Product | Spectral data |
|---|---|---|---|
| 4 | (structure) | (structure) 2HCl | ¹H—NMR(DMSO-d₆)δ3.52(3H, brs), 4.03(2H, q, J=5.6Hz), 6.95(1H, dd, J=7.0, 7.0Hz), 7.28(1H, d, J=7.9Hz), 7.33–7.40(3H, m), 7.48(1H, d, J=7.9Hz), 7.58(1H, s), 8.52(3H, brs), 10.22(1H, brs) |
| 8 | (structure) | (structure) 2HCl | ¹H—NMR(DMSO-d₆)δ1.30(3H, t, J=6.9Hz), 3.21(2H, q, J=6.9Hz), 4.04(2H, q, J=6.9Hz), 7.01(1H, dd, J=7.9, 5.9Hz), 7.10(1H, d, J=7.3Hz), 7.35(1H, d, J=5.9Hz), 7.39(1H, dd, J=7.3, 7.3Hz), 7.41(1H, d, J=7.3Hz), 7.50(1H, d, J=7.9Hz), 7.59(1H, s), 8.57(3H, brs), 10.55(1H, brs) |
| 10 | (structure) | (structure) HCl | ¹H—NMR(DMSO-d₆)δ4.01(2H, q, J=5.6Hz), 7.08(1H, d, J=9.6Hz), 7.23(1H, d, J=7.6Hz), 7.41(1H, dd, J=7.6, 7.6Hz), 7.74(1H, d, J=7.6Hz), 7.85(1H, s), 8.31(1H, dd, J=9.6, 2.6Hz), 8.47(3H, brs), 9.04(1H, d, J=2.6Hz), 10.52(1H, s) |
| 12 | (structure) | (structure) 2HCl | ¹H—NMR(DMSO-d₆)δ3.99(2H, q, J=5.3Hz), 7.14(1H, d, J=7.6Hz), 7.14(1H, d, J=8.9Hz), 7.36(1H, dd, J=7.6, 7.6Hz), 7.53(1H, d, J=7.6Hz), 7.67(1H, d, J=8.9Hz), 7.73(1H, s), 8.10(1H, s), 8.49(3H, brs), 9.87(1H, brs) |

TABLE 45

| Example | Reagent | Product | Spectral data |
|---|---|---|---|
| 14 | [structure: Me-pyridine with O2N, NH-phenyl-CH2-NBoc2] | [structure: Me-pyridine with O2N, NH-phenyl-CH2-NH2·HCl] | $^1$H—NMR(DMSO-d$_6$)δ2.36(3H, s), 3.97(2H, brs), 6.91(1H, d, J=5.0Hz), 7.19(1H, d, J=7.6Hz), 7.34(1H, q, J=5.6Hz), 7.55(1H, d, J=7.6Hz), 7.64(1H, s), 8.20(1H, d, J=5.0Hz), 8.48(3H, brs), 9.08(1H, s) |
| 16 | [structure: Me-pyridine with H2N, NH-phenyl-CH2-NBoc2] | [structure: Me-pyridine with H2N, NH-phenyl-CH2-NH2·2HCl] | $^1$H—NMR(DMSO-d$_6$)δ2.26(3H, s), 3.56(3H, brs), 4.03(2H, q, J=5.6Hz), 6.96(1H, d, J=5.9Hz), 7.30–7.38(3H, m), 7.48(1H, dd, J=7.9, 7.9Hz), 7.53(1H, s), 8.58(3H, brs), 10.23(1H, brs) |
| 18 | [structure: OMe-pyridine with O2N, NH-phenyl-CH2-NBoc2] | [structure: OMe-pyridine with O2N, NH-phenyl-CH2-NH2·HCl] | $^1$H—NMR(DMSO-d$_6$)δ3.92(3H, s), 4.03(2H, s), 6.41(1H, d, J=9.2Hz), 7.31(1H, d, J=7.9Hz), 7.45(1H, dd, J=7.9, 7.9Hz), 7.77–7.87(2H, m), 8.46(1H, d, J=9.2Hz), 8.48(3H, brs), 10.49(1H, brs) |
| 20 | [structure: OMe-pyridine with H2N, NH-phenyl-CH2-NBoc2] | [structure: OMe-pyridine with H2N, NH-phenyl-CH2-NH2·2HCl] | $^1$H—NMR(DMSO-d$_6$)δ3.83(3H, s), 3.98(2H, s), 6.33(1H, d, J=8.6Hz), 7.09(1H, d, J=7.3Hz), 7.36(1H, dd, J=7.3, 7.3Hz), 7.61(1H, d, J=7.3Hz), 7.63(1H, d, J=8.6Hz), 7.76(1H, s) |

TABLE 46

| Example | Reagent | Product | Spectral data |
|---|---|---|---|
| 22 | (structure) | (structure) | $^1$H—NMR(DMSO-d$_6$)δ3.86(3H, s), 3.89(3H, s), 3.98(2H, s), 6.36(1H, d, J=8.9Hz), 7.12(1H, d, J=8.9Hz), 7.71(1H, s), 7.77(1H, d, J=8.9Hz), 8.31(3H, brs), 8.43(1H, d, J=8.9Hz), 10.42(1H, s) |
| 24 | (structure) | (structure) | $^1$H—NMR(DMSO-d$_6$)δ1.19(3H, t, J=7.6Hz), 2.70(2H, q, J=7.6Hz), 3.94(3H, s), 4.04(2H, s), 6.40(1H, d, J=9.2Hz), 7.31(1H, s, J=8.6Hz), 7.71(1H, d, J=1.3Hz), 7.84(1H, dd, J=8.6, 1.3Hz), 8.40(3H, brs), 8.46(1H, d, J=9.2Hz), 10.50(1H, s) |
| 26 | (structure) | (structure) | $^1$H—NMR(DMSO-d$_6$)δ1.22(3H, t, J=7.3Hz), 2.59(2H, q, J=7.3Hz), 3.63(4H, s), 3.94(3H, s), 6.42(1H, d, J=9.2Hz), 7.29–7.44(5H, m), 7.52(1H, s), 8.05(1H, d, J=8.6Hz), 8.47(1H, d, J=9.2Hz), 8.68(3H, bs), 10.55(1H, s) |
| 28 | (structure) | (structure) | $^1$H—NMR(DMSO-d$_6$)δ4.03(2H, s), 7.05(1H, d, J=8.6Hz), 7.35(1H, d, J=7.6Hz), 7.47(1H, dd, J=7.6, 7.6Hz), 7.62(1H, s), 7.73(1H, d, J=7.6Hz), 8.48(3H, brs), 8.57(1H, d, J=8.6Hz), 10.15(1H, s) |

TABLE 47

| Example | Reagent | Product | Spectral data |
|---|---|---|---|
| 30 | [3-(Boc₂N-CH₂)-C₆H₄-NH-pyridine-3-NO₂-6-NHMe] | [3-(H₂N-CH₂)-C₆H₄-NH-pyridine-3-NO₂-6-NHMe · HCl] | ¹H—NMR(DMSO-d₆)δ2.93(3H, s), 4.04(2H, s), 6.19(1H, d, J=9.2Hz), 7.24(1H, q, J=7.6Hz), 7.44(1H, dd, J=7.6, 7.6Hz), 7.80(1H, s), 7.98(1H, d, J=7.6Hz), 8.10(1H, d, J=9.2Hz) |
| 32 | [3-(Boc₂N-CH₂)-C₆H₄-NH-pyridine-3-NO₂-6-NHEt] | [3-(H₂N-CH₂)-C₆H₄-NH-pyridine-3-NO₂-6-NHEt · HCl] | ¹H—NMR(DMSO-d₆)δ1.17(3H, t, J=7.3Hz), 3.40(2H, q, J=7.3Hz), 4.01(2H, q, J=5.3Hz), 6.06(1H, brs), 6.19(1H, d, J=9.2Hz), 7.26(1H, d, J=7.3Hz), 7.42(1H, dd, J=7.3, 7.3Hz), 7.77(1H, s), 7.93(1H, d, J=7.3Hz), 8.09(1H, d, J=9.2Hz), 8.52(3H, brs), 10.98(1H, s) |
| 34 | [3-(Boc₂N-CH₂)-C₆H₄-NH-pyridine-3-NO₂-6-NHⁿPr] | [3-(H₂N-CH₂)-C₆H₄-NH-pyridine-3-NO₂-6-NHⁿPr · HCl] | ¹H—NMR(DMSO-d₆)δ0.92(3H, t, J=7.3Hz), 1.55–1.63(2H, m), 3.29–3.40(2H, m), 4.01(2H, q, J=5.3Hz), 6.10(1H, brs), 6.21(1H, d, J=9.2Hz), 7.27(1H, d, J=7.6Hz), 7.41(1H, dd, J=7.6, 7.6Hz), 7.73(1H, s), 7.97(1H, d, J=9.2Hz), 8.09(1H, d, J=7.6Hz), 8.53(3H, brs), 10.98(1H, s) |
| 36 | [3-(Boc₂N-CH₂)-C₆H₄-NH-pyridine-3-NO₂-6-NMe₂] | [3-(H₂N-CH₂)-C₆H₄-NH-pyridine-3-NO₂-6-NMe₂ · HCl] | ¹H—NMR(DMSO-d₆)δ3.19(6H, s), 4.01(2H, s), 6.40(1H, d, J=9.6Hz), 7.26(1H, d, J=7.6Hz), 7.42(1H, dd, J=7.6, 7.6Hz), 7.75(1H, s), 7.88(1H, d, J=7.6Hz), 8.21(1H, d, J=9.6Hz), 8.46(3H, brs), 10.78(1H, s) |

TABLE 48

| Example | Reagent | Product | Spectral data |
|---|---|---|---|
| 38 | (BocHN-CH2-C6H4-NH-pyridine(Cl)-CO2H) | (H2N-CH2-C6H4-NH-pyridine(Cl)-CO2H · HCl) | $^1$H—NMR(DMSO-d$_6$)δ4.01(2H, s), 6.93(1H, s), 7.21(1H, d, J=8.1Hz), 7.42(1H, dd, J=7.6, 7.6Hz), 7.55(1H, s), 7.93(1H, d, J=7.6Hz), 8.25(1H, d, J=8.1Hz), 8.46(3H, brs), 10.66(1H, s) |
| 40 | (Boc$_2$N-CH2-C6H4-NH-pyridine(OMe)) | (H2N-CH2-C6H4-NH-pyridine(OMe) · 2HCl) | $^1$H—NMR(DMSO-d$_6$)δ3.88(3H, s), 3.94(2H, s), 6.16(1H, d, J=7.9Hz), 6.49(1H, d, J=7.9Hz), 6.62(2H, brs), 7.05(1H, d, J=7.6Hz), 7.30(1H, dd, J=7.6, 7.6Hz), 7.49(1H, dd, J=7.9, 7.9Hz), 7.63(1H, d, J=7.6Hz), 7.80(1H, s), 8.50(3H, brs) |
| 42 | (Boc$_2$N-CH2-C6H4-NH-pyridine(CF3)) | (H2N-CH2-C6H4-NH-pyridine(CF3) · 2HCl) | $^1$H—NMR(DMSO-d$_6$)δ3.41(2H, s), 6.39(1H, dd, J=7.3, 5.9Hz), 6.68—6.89(4H, m), 7.35(1H, d, J=5.9Hz), 7.67(1H, d, J=7.3Hz) |
| 44 | (Boc$_2$N-CH2-C6H4-NH-pyridine(OMe)-CO2Me) | (H2N-CH2-C6H4-NH-pyridine(OMe)-CO2Me · HCl) | $^1$H—NMR(DMSO-d$_6$)δ3.87(3H, s), 3.95(3H, s), 4.01(2H, brs), 6.29(1H, d, J=8.6Hz), 7.15(1H, d, J=7.6Hz), 7.40(1H, dd, J=7.9, 7.6Hz), 7.74(1H, s), 7.88(1H, d, J=7.9Hz), 8.16(1H, d, J=8.6Hz), 8.30(3H, brs), 10.47(1H, s) |

TABLE 49
| Example | Reagent | Product | Spectral data |
|---|---|---|---|
| 57 | 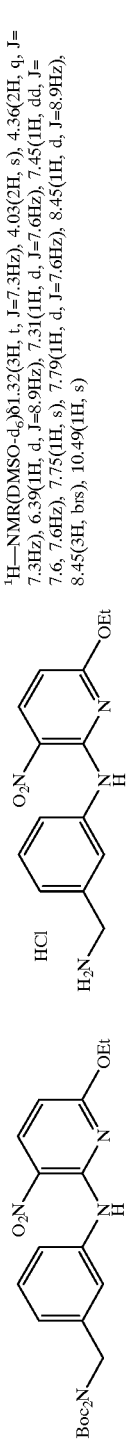 | 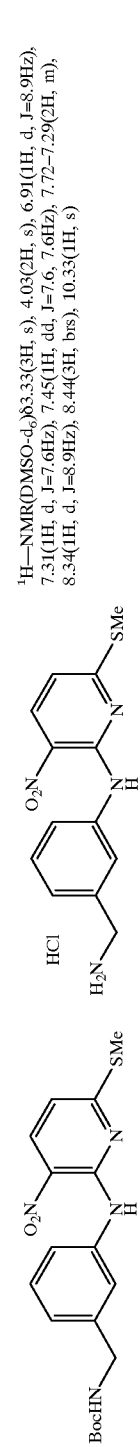 | $^{1}$H—NMR(DMSO-$d_6$)δ1.32(3H, t, J=7.3Hz), 4.03(2H, s), 4.36(2H, q, J=7.3Hz), 6.39(1H, d, J=8.9Hz), 7.31(1H, d, J=7.6Hz), 7.45(1H, dd, J=7.6, 7.6Hz), 7.75(1H, s), 7.79(1H, d, J=7.6Hz), 8.45(1H, d, J=8.9Hz), 8.45(3H, brs), 10.49(1H, s) |
| 61 | 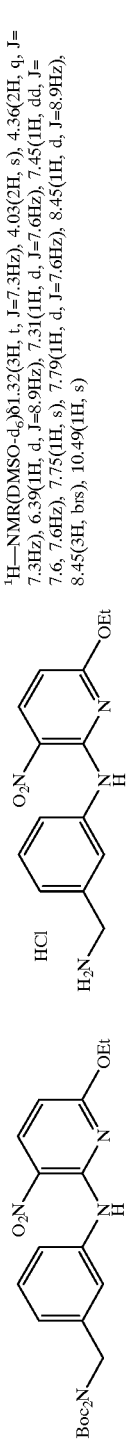 | 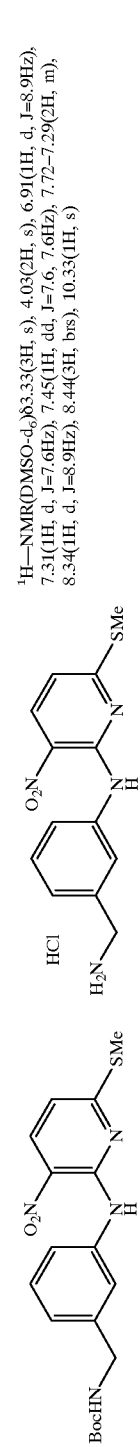 | $^{1}$H—NMR(DMSO-$d_6$)δ3.33(3H, s), 4.03(2H, s), 6.91(1H, d, J=8.9Hz), 7.31(1H, d, J=7.6Hz), 7.45(1H, dd, J=7.6, 7.6Hz), 7.72–7.29(2H, m), 8.34(1H, d, J=8.9Hz), 8.44(3H, brs), 10.33(1H, s) |
| 77 | 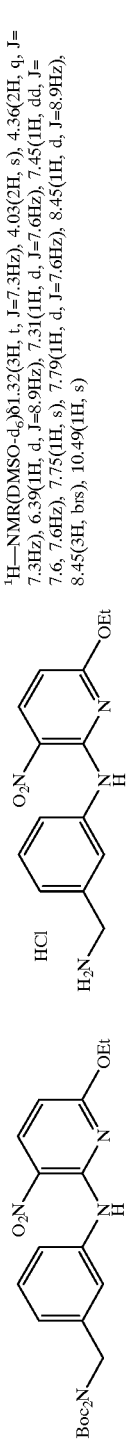 | 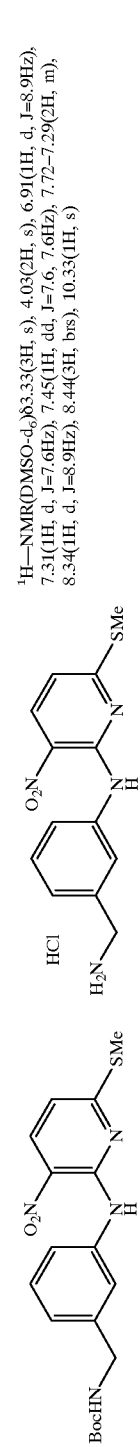 | $^{1}$H—NMR(DMSO-$d_6$)δ10.50(1H, brs), 8.45(1H, d, J=9.2Hz), 8.30(3H, brs), 7.78(1H, dd, J=8.3, 2.0Hz), 7.67(1H, d, J=2.0Hz), 7.28(1H, d, J=8.3Hz), 6.38(1H, d, J=9.2Hz), 4.03(2H, s), 3.93(3H, s), 2.37(3H, s) |
| 108 | 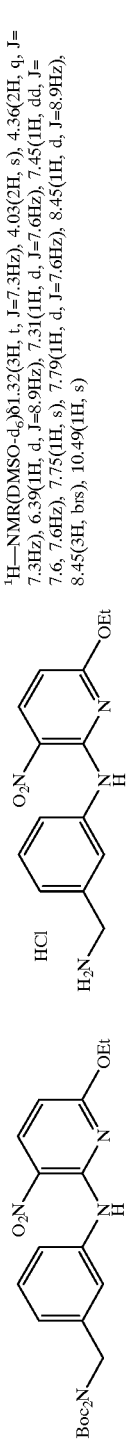 | 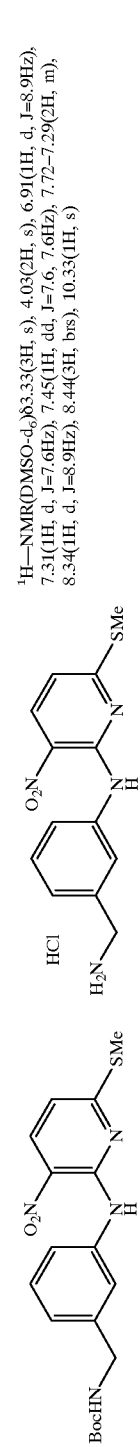 | $^{1}$H—NMR(DMSO-$d_6$)δ3.99(3H, s), 4.04(2H, q, J=5.6Hz), 6.40(1H, d, J=8.6Hz), 7.19(1H, d, J=7.9Hz), 7.43(1H, dd, J=7.9, 7.9Hz), 7.74(1H, s), 7.97(1H, d, J=7.9Hz), 8.09(1H, d, J=8.6Hz), 8.27(3H, brs), 9.78(1H, s), 10.96(1H, s) |

TABLE 50
| Example | Reagent | Product | Spectral data |
|---|---|---|---|
| 151 | 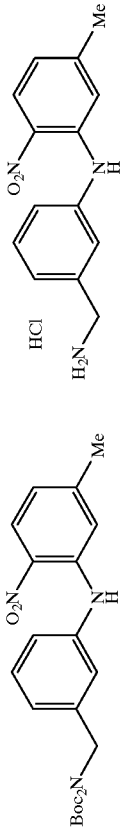 |  | $^1$H—NMR(DMSO-d$_6$)δ2.28(3H, s), 4.03(2H, s), 6.75(1H, d, J=8.9Hz), 7.08(1H, s), 7.27–7.36(2H, m), 7.42–7.49(2H, m), 8.04(1H, d, J=8.9 Hz), 8.30(3H, brs), 9.40(1H, s) |
| 153 | 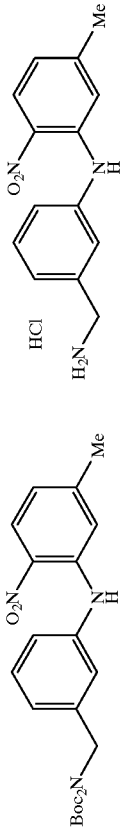 |  | $^1$H—NMR(DMSO-d$_6$)δ3.77(3H, s), 4.05(2H, q, J=4.6Hz), 6.53(1H, dd, J= 9.2, 2.3Hz), 6.60(1H, d, J=2.3Hz), 7.34(1H, d, J=7.6Hz), 7.39(1H, d, J=7.6Hz), 7.48(1H, dd, J=7.6, 7.6Hz), 7.54(1H, s), 8.15(1H, d, J=9.2 Hz), 8.46(3H, brs), 9.65(1H, s) |
| 457 | 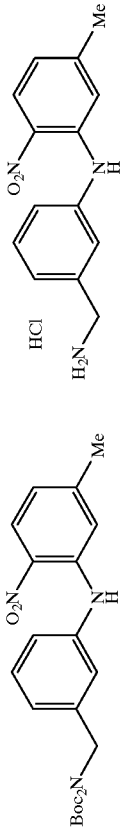 |  | $^1$H—NMR(DMSO-d$_6$)δ10.43(1H, brs), 8.40(3H, brs), 8.28(1H, d, J=8.9 Hz), 7.87(1H, s), 7.62–7.54(1H, m), 7.41(1H, dd, J=7.9, 7.6Hz), 7.22 (1H, d, J=7.6Hz), 6.61(1H, d, J=8.9Hz), 4.06(3H, s), 4.01(2H, brs) FAB—MX(m/z) 275(M* + 1) |
| 458 | 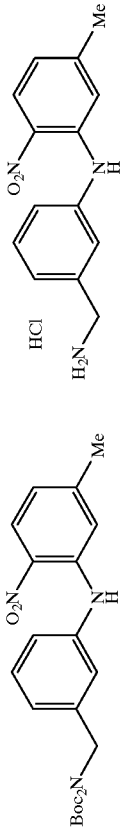 |  | $^1$H—NMR(DMSO-d$_6$)δ10.34(1H, brs), 8.43(1H, d, J=8.9Hz), 8.42–8.20 (4H, m), 7.77(1H, dd, J=5.0, 4.6Hz), 7.32(1H, d, J=4.6Hz), 6.33(1H, d, J=8.9Hz), 4.11(2H, s), 3.72(3H, s), 2.29(3H, s) FAB—MS(m/z) 289(M* + 1) |

TABLE 51
| Example | Reagent | Product | Spectral data |
|---|---|---|---|
| 459 | 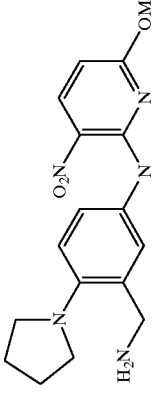 | 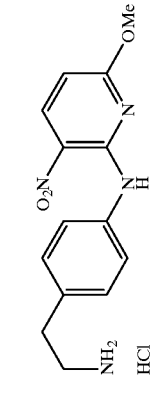 | $^1$H—NMR(DMSO-$d_6$,)δ10.52(1H, brs), 8.45(1H, d, J=9.2Hz), 8.45–8.28(4H, m), 8.02–7.73(2H, m), 7.40(1H, brs), 6.40(1H, d, J=9.2Hz), 4.23(2H, s), 3.94(3H, s), 3.50–3.20(4H, m), 2.21–1.95(4H, m) FAB—MS(m/z) 344(M* + 1) |
| 460 | | | $^1$H—NMR(DMSO-$d_6$)δ10.50(1H, s), 8.44(1H, d, J=8.9Hz), 7.98(3H, brs), 7.69(2H, d, J=7.9Hz), 7.28(2H, d, J=7.9Hz), 6.26(1H, d, J=8.9Hz), 3.92(3H, s), 3.15–2.97(2H, m), 2.93(2H, t, J=7.6Hz) FAB—MS(m/z) 289(M* + 1) |
| 461 | | | $^1$H—NMR(DMSO-$d_6$)δ11.06(1H, s), 8.63(1H, s), 8.46(1H, d, J=8.9Hz), 8.33(3H, brs), 7.57(1H, d, J=7.3Hz), 7.15–7.10(1H, m), 6.38(1H, d, J=8.9Hz), 4.08(2H, s), 3.98(6H, s) FAB—MS(m/z) 305(M* + 1) |
| 462 | | | $^1$H—NMR(DMSO-$d_6$)δ10.52(1H, s), 8.57(3H, brs), 8.46(1H, d, J=9.2Hz), 7.84(1H, d, J=7.9Hz), 7.75(1H, s), 7.47(1H, dd, J=8.2, 7.9Hz), 7.42–7.35(1H, m), 6.41–6.37(1H, m), 3.91(3H, s), 1.67(6H, s) FAB—MS(m/z) 303(M* + 1) |

TABLE 52
| Example | Reagent | Product | Spectral data |
|---|---|---|---|
| 463 |  | 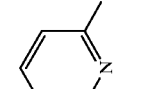 | ¹H—NMR(DMSO-d₆)δ10.49(1H, s), 8.45(1H, d, J=8.9Hz), 8.35(3H, brs), 7.68(1H, s), 7.61(1H, s), 7.12(1H, s), 6.40(1H, d, J=8.9Hz), 3.99(2H, s), 3.95(3H, s), 2.36(3H, s) FAB—MS(m/z) 289(M* + 1) |
| 464 | | | ¹H—NMR(DMSO-d₆)δ10.20(1H, brs), 8.43(1H, d, J=9.2Hz), 7.95(3H, brs), 7.50(1H, dd, J=7.9, 1.7Hz), 7.40–7.25(3H, m), 6.30(1H, d, J=9.2 Hz), 3.58(3H, s), 3.03–2.88(4H, m) FAB—MS(m/z) 289(M* + 1) |
| 465 | 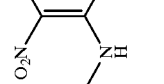 | | ¹H—NMR(DMSO-d₆)δ11.09(1H, s), 8.58–8.53(1H, m), 8.51(1H, d, J=9.2 Hz), 8.40(3H, brs), 7.32–7.28(2H, m), 6.46(1H, d, J=9.2Hz), 4.11(2H, s), 4.01(3H, s), 3.84(3H, s) FAB—MS(m/z) 305(M* + 1) |
| 466 | 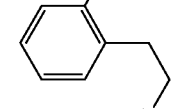 | | ¹H—NMR(DMSO-d₆)δ10.51(1H, brs), 8.50(3H, brs), 8.47(1H, d, J=9.2Hz ), 7.93–7.89(2H, m), 7.55(1H, d, J=9.2Hz), 6.43(1H, d, J=9.2Hz), 4.14 (2H, s), 3.93(3H, s) FAB—M(m/z) 309(M* + 1) |

TABLE 53

| Example | Reagent | Product | Spectral data |
|---|---|---|---|
| 467 | (structure) | (structure) | $^1$H—NMR(DMSO-d$_6$)δ10.45(1H, brs), 8.58–8.37(4H, m), 7.87–7.79(2H, m), 7.31(1H, dd, J=9.2, 8.9Hz), 6.39(1H, d, J=8.9Hz), 4.07(2H, s), 3.89 (3H, s) |
| 468 | (structure) | (structure) | $^1$H—NMR(DMSO-d$_6$)δ11.10(1H, s), 8.57–8.53(1H, m), 8.50(1H, d, J=9.2 Hz), 8.37(3H, brs), 7.35–7.24(2H, m), 6.46(1H, d, J=9.2Hz), 4.10(2H, s), 4.01(3H, s), 3.96(2H, q, J=6.9Hz), 1.45(3H, t, J=6.9Hz) |
| 469 | (structure) | (structure) | $^1$H—NMR(DMSO-d$_6$)δ10.85(1H, brs), 8.50(1H, d, J=9.2Hz), 8.49(3H, brs), 8.39(1H, d, J=7.9Hz), 7.51(1H, dd, J=7.9, 7.6Hz), 7.42(1H, d, J=7.6Hz), 6.47(1H, d, J=9.2Hz), 4.22(2H, s), 3.90(3H, s) |
| 470 | (structure) | (structure) | $^1$H—NMR(DMSO-d$_6$)δ9.52(1H, s), 8.35(3H, brs), 7.79(1H, s), 7.70–7.64 (1H, m), 7.35–7.27(1H, m), 7.06(1H, d, J=7.6Hz), 6.98(1H, s), 6.87 (1H, s), 4.02(2H, s), 3.93(3H, s), 3.87(3H, s) |

TABLE 54
| Example | Reagent | Product | Spectral data |
|---|---|---|---|
| 471 | 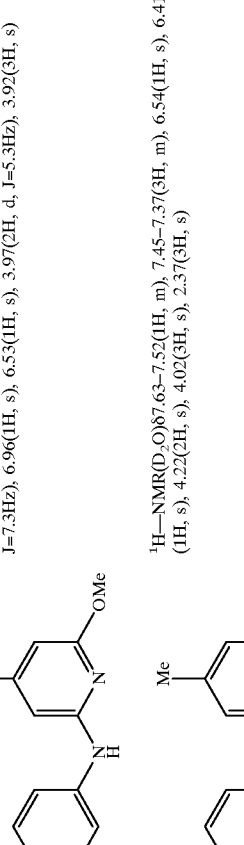 | | $^1$H—NMR(DMSO-d$_6$)δ13.28(1H, brs), 9.47(1H, s), 8.34(3H, brs), 7.79 (1H, s), 7.65(1H, d, J=8.6Hz), 7.33(1H, dd, J=8.6, 7.3Hz), 7.06(1H, d, J=7.3Hz), 6.96(1H, s), 6.53(1H, s), 3.97(2H, d, J=5.3Hz), 3.92(3H, s) |
| 473 | 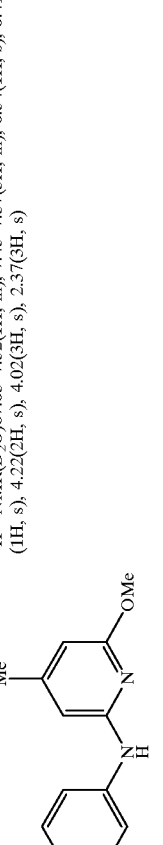 | | $^1$H—NMR(D$_2$O)δ7.63–7.52(1H, m), 7.45–7.37(3H, m), 6.54(1H, s), 6.41 (1H, s), 4.22(2H, s), 4.02(3H, s), 2.37(3H, s) |
| 474 | 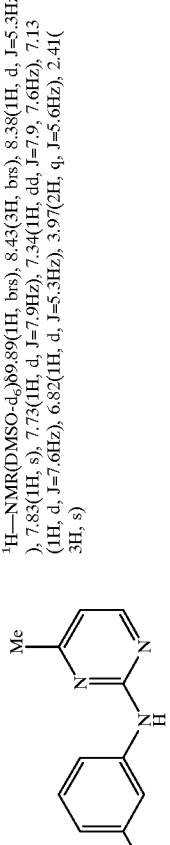 | | $^1$H—NMR(DMSO-d$_6$)δ9.89(1H, brs), 8.43(3H, brs), 8.38(1H, d, J=5.3Hz ), 7.83(1H, s), 7.73(1H, d, J=7.9Hz), 7.34(1H, dd, J=7.9, 7.6Hz), 7.13 (1H, d, J=7.6Hz), 6.82(1H, d, J=5.3Hz), 3.97(2H, q, J=5.6Hz), 2.41( 3H, s) |

TABLE 55

| Example | Reagent | Product | Spectral data |
|---|---|---|---|
| 475 | F₃C-pyridine-OMe with NH-phenyl-CH₂-NHBoc | F₃C-pyridine-OMe with NH-phenyl-CH₂-NH₂·2HCl | ¹H—NMR(DMSO-d₆)δ3.78(3H, s), 3.98(2H, s), 6.33(1H, d, J=8.2Hz), 7.18(1H, d, J=7.6Hz), 7.35(1H, dd, J=7.6, 7.6Hz), 7.57(1H, d, J=7.6Hz), 7.69(1H, s), 7.84(1H, d, J=8.2Hz), 8.16(1H, s), 8.37(3H, brs) |
| 476 | O₂N-phenyl-OMe with NH-phenyl-CH₂-NHBoc | O₂N-phenyl-OMe with NH-phenyl-CH₂-NH₂·HCl | ¹H—NMR(DMSO-d₆)δ3.81(3H, s), 3.98(2H, s), 7.17(1H, d, J=7.6Hz), 7.21(1H, dd, J=9.2, 3.0Hz), 7.25(1H, dd, J=7.6, 7.6Hz), 7.39(1H, d, J=9.2Hz), 7.57(1H, d, J=3.0Hz), 7.38 (1H, s), 8.36(3H, brs), 9.02(1H, s) |
| 477 | O₂N-phenyl-Me with NH-phenyl-CH₂-NHBoc | O₂N-phenyl-Me with NH-phenyl-CH₂-NH₂·HCl | ¹H—NMR(DMSO-d₆)δ2.18(3H, s), 3.87(2H, s), 6.58(1H, d, J=7.9Hz), 6.63(1H, s), 6.87(1H, d, J=7.6Hz), 7.18(1H, dd, J=7.6, 7.6Hz), 7.32 (1H, dd, J=7.9, 7.9Hz), 7.62(1H, d, J=7.6Hz), 7.80(1H, d, J=7.9Hz), 8.12(1H, s), 8.28(3H, brs) |
| 478 | Me-pyridine with NH-phenyl-CH₂-NHBoc | Me-pyridine with NH-phenyl-CH₂-NH₂·2HCl | ¹H—NMR(DMSO-d₆)δ2.40(3H, s), 4.05(2H, q, J=5.3Hz), 6.93(1H, d, J=6.3Hz), 7.14(1H, s), 7.34–7.39(2H, m), 7.49(1H, dd, J=7.6, 7.6Hz), 7.62(1H, s), 8.02(1H, d, J=6.3Hz), 8.59(3H, brs), 10.83(1H, brs) |

TABLE 56

| Example | Reagent | Product | Spectral data |
|---|---|---|---|
| 479 | (BocHN-C(Me)2-phenyl)-NH-(4-Me-pyridin-2-yl) | (H2N-C(Me)2-phenyl)-NH-(4-Me-pyridin-2-yl) · 2HCl | ¹H—NMR(DMSO-d₆)δ1.66(6H, s), 2.38(3H, s), 6.90(1H, d, J=6.3Hz), 7.04(1H, s), 7.40–7.53(3H, m), 7.62(1H, s), 8.00(1H, d, J=6.3Hz), 8.76(3H, brs), 10.52(1H, brs) |
| 480 | (BocHN-CH(Et)-phenyl)-NH-(4-Me-pyridin-2-yl) | (H2N-CH(Et)-phenyl)-NH-(4-Me-pyridin-2-yl) · 2HCl | ¹H—NMR(DMSO-d₆)δ0.81(3H, t, J=7.3Hz), 1.83–2.06(2H, m), 2.39(3H, s), 4.10–4.25(1H, m), 6.92(1H, d, J=6.3Hz), 7.11(1H, s), 7.37(1H, d, J=7.6Hz), 7.39(1H, d, J=7.6Hz), 7.50(1H, dd, J=7.6, 7.6Hz), 7.60(1H, s), 8.02(1H, d, J=6.3Hz), 8.69(3H, brs), 10.76(1H, brs) |
| 481 | (Boc2N-CH2-(2-Me-phenyl))-NH-(4-Me-pyridin-2-yl) | (H2N-CH2-(2-Me-phenyl))-NH-(4-Me-pyridin-2-yl) · 2HCl | ¹H—NMR(DMSO-d₆)δ2.26(3H, s), 2.38(3H, s), 4.11(2H, q, J=5.3Hz), 6.87(1H, d, J=6.9Hz), 6.87(1H, s), 7.33–7.52(3H, m), 7.92(1H, d, J=6.9Hz), 8.58(3H, brs), 10.67(1H, brs) |
| 482 | (BocHN-CH2-(Et-phenyl))-NH-(4-Me-pyridin-2-yl) | (H2N-CH2-(Et-phenyl))-NH-(4-Me-pyridin-2-yl) · 2HCl | ¹H—NMR(DMSO-d₆)δ1.20(3H, t, J=7.6Hz), 2.41(3H, s), 2.72(2H, q, J=7.6Hz), 4.07(2H, q, J=5.6Hz), 6.92(1H, d, J=6.3Hz), 7.12(1H, s), 7.30(1H, d, J=8.3Hz), 7.35(1H, d, J=8.3Hz), 7.57(1H, s), 8.00(1H, d, J=6.3Hz), 8.61(3H, brs), 10.79(1H, brs) |

TABLE 57

| Example | Reagent | Product | Spectral data |
|---|---|---|---|
| 483 | [structure with EtO, BocHN, Me-pyridine-NH-phenyl] | [structure with EtO, H₂N, Me-pyridine-NH-phenyl, 2HCl] | $^1$H—NMR(DMSO-d$_6$)δ1.40(3H, t, J=6.9Hz), 2.38(3H, s), 3.99(2H, q, J=5.3Hz), 4.13(2H, q, J=6.9Hz), 6.87(1H, d, J=6.3Hz), 7.03(1H, s), 7.15(1H, d, J=8.9Hz), 7.33(1H, dd, J=8.9, 1.7Hz), 7.51(1H, d, J=1.7Hz), 7.94(1H, d, J=6.3Hz), 8.48(3H, brs), 10.72(1H, brs) |
| 484 | [structure with BocHN, Me-pyridine-NH-phenyl] | [structure with H₂N, Me-pyridine-NH-phenyl, 2HCl] | $^1$H—NMR(DMSO-d$_6$)δ2.37(3H, s), 2.88–3.10(4H, m), 6.88(1H, d, J=6.6Hz), 6.95(1H, s), 7.39–7.50(4H, m), 7.89(1H, d, J=6.6Hz), 8.12(3H, brs), 10.69(1H, brs) |
| 485 | [structure with BocHN, Cl, Me-pyridine-NH-phenyl] | [structure with H₂N, Cl, Me-pyridine-NH-phenyl, 2HCl] | $^1$H—NMR(DMSO-d$_6$)δ2.39(3H, s), 4.19(2H, q, J=5.0Hz), 6.93(1H, d, J=6.3Hz), 6.98(1H, s), 7.48–7.68(3H, m), 7.97(1H, d, J=6.3Hz), 8.71(3H, brs), 10.56(1H, brs) |
| 486 | [structure with BocHN, Me, Me-pyridine-NH-phenyl] | [structure with H₂N, Me, Me-pyridine-NH-phenyl, 2HCl] | $^1$H—NMR(DMSO-d$_6$)δ2.35(3H, s), 2.49(3H, s), 4.05(2H, q, J=5.3Hz), 6.82(1H, s), 7.00(1H, s), 7.33–7.38(2H, m), 7.48(1H, dd, J=7.6, 7.6Hz), 7.56(1H, s), 8.58(3H, brs), 10.30(1H, brs) |

TABLE 58

| Example | Reagent | Product | Spectral data |
|---|---|---|---|
| 487 | (structure with BocHN, Et-pyridine, NH-phenyl) | (structure with H₂N, 2HCl, Et-pyridine, NH-phenyl) | ¹H—NMR(DMSO-d₆)δ1.20(3H, t, J=7.3Hz), 2.71(2H, q, J=7.3Hz), 4.05(2H, q, J=5.3Hz), 6.98(1H, d, J=6.3Hz), 7.18(1H, s), 7.34–7.42(2H, m), 7.49(1H, dd, J=7.6, 7.6Hz), 7.64(1H, s), 8.03(1H, d, J=6.3Hz), 8.66(3H, brs), 11.00(1H, brs) |
| 488 | (structure with BocHN, cyclobutyl, Me-pyridine) | (structure with H₂N, 2HCl, cyclobutyl, Me-pyridine) | ¹H—NMR(DMSO-d₆)δ1.73–1.85(1H, m), 2.15–2.27(1H, m), 2.40(3H, s), 2.56–2.66(4H, m), 6.92(1H, d, J=6.3Hz), 7.13(1H, s), 7.35–7.42(2H, m), 7.53(1H, dd, J=7.6, 7.6Hz), 7.63(1H, s), 8.00(1H, d, J=6.3Hz), 8.94(3H, brs), 10.84(1H, brs) |
| 489 | (structure with BocHN, Me-pyridine) | (structure with NH₂, 2HCl, Me-pyridine) | ¹H—NMR(DMSO-d₆)δ2.37(3H, s), 2.87–3.15(4H, m), 6.87(1H, d, J=6.3Hz), 7.01(1H, s), 7.37(4H, s), 7.92(1H, d, J=6.3Hz), 8.16(3H, brs), 10.65(1H, brs) |
| 490 | (structure with Boc₂N, OEt, Me-pyridine) | (structure with H₂N, 2HCl, OEt, Me-pyridine) | ¹H—NMR(DMSO-d₆)δ1.13(3H, t, J=6.9Hz), 2.40(3H, s), 3.86(2H, q, J=6.9Hz), 4.06(2H, q, J=5.3Hz), 6.93(1H, d, J=5.9Hz), 7.07(1H, s), 7.28(1H, dd, J=7.6, 7.6Hz), 7.45(1H, d, J=7.6Hz), 7.51(1H, d, J=7.6Hz), 7.96(1H, d, J=5.9Hz), 8.54(3H, brs), 10.71(1H, brs) |

TABLE 59

| Example | Reagent | Product | Spectral data |
|---|---|---|---|
| 491 | (structure with Me-pyridine, Cl, Boc₂N-CH₂-phenyl) | (structure with Me-pyridine, Cl, H₂N-CH₂-phenyl) · 2HCl | $^1$H—NMR(DMSO-d$_6$)δ2.41(3H, s), 4.14(2H, q, J=5.3Hz), 6.95(1H, d, J=6.3Hz), 7.18(1H, s), 7.44(1H, dd, J=8.6, 2.0Hz), 7.58(1H, d, J=8.6Hz), 7.79(1H, d, J=2.0Hz), 8.04(1H, d, J=6.3Hz), 8.76(3H, brs), 10.89(1H, brs) |
| 492 | (structure with OMe-pyridine-CN, Boc₂N-CH₂-phenyl) | (structure with OMe-pyridine-CN, H₂N-CH₂-phenyl) · HCl | $^1$H—NMR(DMSO-d$_6$)δ3.86(3H, s), 4.01(2H, q, J=5.9Hz), 6.36(1H, d, J=8.5Hz), 7.19(1H, d, J=7.8Hz), 7.38(1H, dd, J=7.8, 7.8Hz), 7.63(1H, d, J=7.8Hz), 7.77(1H, s), 7.95(1H, d, J=8.5Hz), 8.41(3H, brs), 9.28(1H, s) |
| 493 | (structure with Cl-pyridine, BocHN-CH₂-phenyl) | (structure with Cl-pyridine, H₂N-CH₂-phenyl) · HCl | $^1$H—NMR(DMSO-d$_6$)δ3.98(2H, q, J=5.3Hz), 6.86(1H, d, J=7.9, 5.0Hz), 7.14(1H, d, J=7.6Hz), 7.34(1H, dd, J=7.6, 7.6Hz), 7.66(1H, d, J=7.6Hz), 7.76–7.86(2H, m), 8.10(1H, dd, J=5.0, 1.3Hz), 8.38(3H, brs), 8.47(1H, s) |
| 494 | (structure with OMe-pyridine-CONH₂, Boc₂N-CH₂-phenyl) | (structure with OMe-pyridine-CONH₂, H₂N-CH₂-phenyl) · HCl | $^1$H—NMR(DMSO-d$_6$)δ3.93(3H, s), 4.01(2H, q, J=5.9Hz), 6.24(1H, d, J=8.6Hz), 7.08(1H, d, J=7.9Hz), 7.37(1H, dd, J=7.9, 7.9Hz), 7.42(1H, brs), 7.65(1H, s), 7.88(1H, d, J=7.9Hz), 8.04(1H, brs), 8.14(1H, d, J=8.6Hz), 8.22(3H, brs), 11.76(1H, s) |

TABLE 60
| Example | Reagent | Product | Spectral data |
|---|---|---|---|
| 495 | 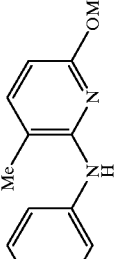 | 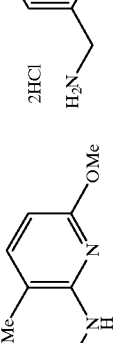 | ¹H—NMR(DMSO-d₆)δ2.19(3H, s), 3.79(3H, s), 3.94(2H, q, J=5.6Hz), 6.16(1H, d, J=7.6Hz), 7.03(1H, d, J=7.9Hz), 7.29(1H, dd, J=7.9, 7.9Hz), 7.36(1H, d, J=7.6Hz), 7.64(1H, d, J=7.9Hz), 7.82(1H, s), 7.95(1H, brs), 8.35(3H, brs) |
| 496 | 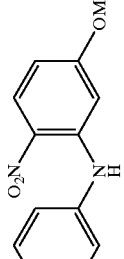 | 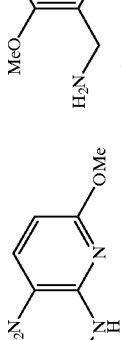 | ¹H—NMR(DMSO-d₆)δ3.74(3H, s), 3.88(3H, s), 4.00(2H, q, J=5.3Hz), 6.35(1H, d, J=2.3Hz), 6.46(1H, dd, J=9.6, 2.3Hz), 7.15(1H, d, J=8.6Hz), 7.40(1H, d, J=8.6Hz), 7.43(1H, s), 8.13(1H, d, J=9.6Hz), 8.18(3H, brs), 9.60(1H, s) |
| 501 | 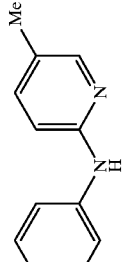 | 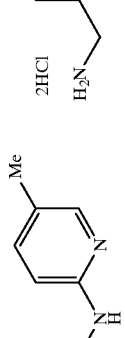 | ¹H—NMR(DMSO-d₆)δ2.25(3H, s), 4.21(2H, q, J=5.6Hz), 7.26–7.50(4H, m), 7.62(1H, s), 7.88(1H, d, J=10.2Hz), 7.95(1H, s), 8.57(3H, brs), 10.77(1H, brs) |
| 502 | 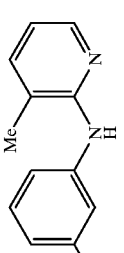 | 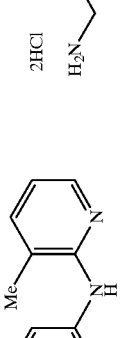 | ¹H—NMR(DMSO-d₆)δ2.40(3H, s), 4.04(2H, q, J=5.6Hz), 7.42(1H, dd, J=6.6, 6.6Hz), 7.40–7.57(3H, m), 7.66(1H, s), 7.90–7.99(2H, m), 8.65(3H, brs), 9.77(1H, brs) |

TABLE 61

| Example | Reagent | Product | Spectral data |
|---|---|---|---|
| 503 | (structure: MeO-phenyl-CH2-NBoc2, NH-pyridine-Me) | (structure: MeO-phenyl-CH2-NH2·2HCl, NH-pyridine-Me) | 1H-NMR(CDCl3)δ2.38(3H, s), 3.88(3H, s), 3.99(2H, q, J=5.6Hz), 6.87(1H, d, J=6.3Hz), 7.02(1H, s), 7.17(1H, d, J=8.6Hz), 7.36(1H, dd, J=8.6, 2.0Hz), 7.51(1H, d, J=2.0Hz), 7.94(1H, d, J=6.3Hz), 8.46(3H, brs), 10.70(1H, brs) |
| 504 | (structure: pyrazolyl-phenyl-CH2-NHBoc, NH-pyridine-Me) | (structure: pyrazolyl-phenyl-CH2-NH2·2HCl, NH-pyridine-Me) | 1H-NMR(CDCl3)δ2.43(3H, s), 3.99(2H, q, J=5.3Hz), 6.61(1H, s), 6.97(1H, d, J=5.9Hz), 7.23(1H, s), 7.53–7.64(2H, m), 7.83(1H, s), 7.88(1H, s), 8.07(1H, d, J=5.9Hz), 8.24–8.28(1H, m), 8.66(3H, brs), 11.01(1H, brs) |
| 506 | (structure: OnPr-phenyl-CH2-NBoc2, NH-pyridine-Me) | (structure: OnPr-phenyl-CH2-NH2·2HCl, NH-pyridine-Me) | 1H-NMR(DMSO-d6)δ8.46(3H, brs), 7.95(1H, d, J=6.3Hz), 7.55–7.36(2H, m), 7.28(1H, dd, J=7.9, 7.6Hz), 7.01(1H, s), 6.91(1H, d, J=6.3Hz), 4.06(2H, q, J=5.3Hz), 3.75(2H, t, J=6.0Hz), 2.40(3H, s), 1.60–1.51(2H, m), 0.76(3H, t, J=7.3Hz) |
| 521 | (structure: Cl-phenyl-OEt-CH2-NHBoc, NH-pyridine-Me) | (structure: Cl-phenyl-OEt-CH2-NH2·2HCl, NH-pyridine-Me) | 1H-NMR(DMSO-d6)δ1.13(3H, t, J=6.9Hz), 2.42(3H, s), 3.91(2H, q, J=6.9Hz), 4.16(2H, q, J=5.0Hz), 6.95(1H, d, J=6.3Hz), 7.13(1H, s), 7.42(1H, d, J=8.6Hz), 7.51(1H, d, J=8.6Hz), 7.95(1H, d, J=6.3Hz), 8.54(3H, brs), 10.96(1H, brs) |

TABLE 62
| Example | Reagent | Product | Spectral data |
|---|---|---|---|
| 522 | 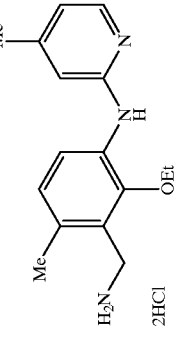 | 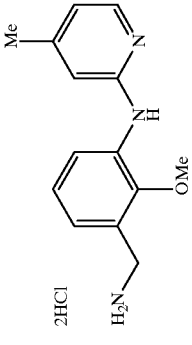 | ¹H-NMR(DMSO-d₆)δ1.10(3H, t, J=6.9Hz), 2.41(3H, s), 2.46(3H, s), 3.84(2H, q, J=6.9Hz), 3.96–4.19(2H, m), 6.91(1H, d, J=6.3Hz), 7.04–7.19(2H, m), 7.30(1H, d, J=7.9Hz), 7.94(1H, d, J=6.3Hz), 8.47(3H, brs), 10.95(1H, brs) |
| 541 | 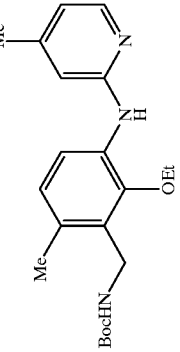 | 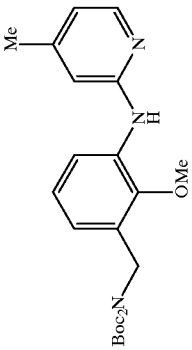 | ¹H-NMR(DMSO-d₆)δ10.68(1H, brs), 8.46(3H, brs), 7.94(1H, d, J=5.9 Hz), 7.55–7.36(2H, m), 7.32–7.22(1H, m), 7.06(1H, s), 6.90(1H, d, J=5.9Hz), 4.06(2H, s), 3.67(3H, s), 2.40(3H, s) |
| 543 |  |  | ¹H-NMR(DMSO-d₆)δ10.66(1H, brs), 8.48(3H, brs), 7.95(1H, d, J=6.3Hz), 7.50(1H, d, J=8.3Hz), 7.44(1H, d, J=7.6Hz), 7.27(1H, dd, J=8.3, 7.6 Hz), 7.06(1H, s), 6.92(1H, d, J=6.3Hz), 4.27–4.12(1H, m), 4.07(2H, q, J=5.3Hz), 2.41(3H, s), 1.07(6H, d, J=5.9Hz) |

Example 3

Synthesis of 3-amino-2-(3-(di(t-butoxycarbonyl)aminomethyl)phenyl-amino)pyridine A mixture of the compound (1.41 g) obtained in Example 1, 10% palladium-carbon (170 mg), methanol (60 ml) and ethyl acetate (30 ml) was stirred in a hydrogen atmosphere at room temperature for one day. The reaction mixture was filtered and the filtrate was concentrated under reduced pressure. The resulting residue was purified by silica gel column chromatography (eluent, n-hexane:ethyl acetate= 2:1) to give 1.15 g of the titled compound (yield, 88%).

$^1$H-NMR (CDCl$_3$) δ: 1.45(18H, s), 3.40(2H, brs), 4.75 (2H, s), 6.20(1H, brs), 6.77(1H, dd, J=7.6, 5.0 Hz), 6.84–6.90(1H, m), 7.00(1H, dd, J=7.6, 1.3 Hz), 7.13(1H, s), 7.19–7.23(2H, m), 7.82 (1H, dd, J=5.0, 1.3 Hz)

The procedure of Example 3 was repeated using corresponding reagents to give the compounds shown in Table 63.

TABLE 63

| Example | Reagent | Product | Spectral data |
|---|---|---|---|
| 11 | 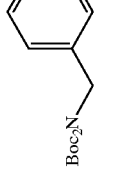 | 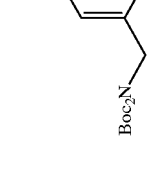 | $^1$H-NMR(CDCl$_3$)δ1.45(18H, s), 3.38(2H, brs), 4.74(2H, s), 6.35(1H, brs), 6.83(1H, d, J=8.9Hz), 6.86(1H, d, J=7.6Hz), 6.98(1H, dd, J=8.9, 2.6Hz), 7.10(1H, s), 7.12(1H, d, J=7.6Hz), 7.20(1H, dd, J=7.6, 7.6Hz), 7.79(1H, d, J=2.6Hz) |
| 15 | 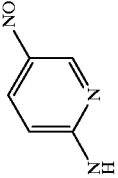 | 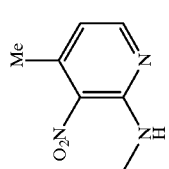 | $^1$H-NMR(CDCl$_3$)δ1.44(18H, s), 2.22(3H, s), 3.41(2H, brs), 4.73(2H, s), 6.11(1H, brs), 6.72(1H, d, J=5.0Hz), 6.85(1H, d, J=7.6Hz), 7.01(1H, s), 7.07(1H, d, J=7.6Hz), 7.20(1H, dd, J=7.6, 7.6Hz), 7.72(1H, d, J=5.0Hz) |
| 19 | 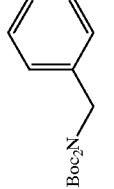 | 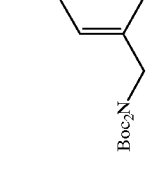 | $^1$H-NMR(CDCl$_3$)δ1.44(18H, s), 3.88(3H, s), 4.76(2H, s), 6.15(1H, d, J=8.3Hz), 6.74(1H, brs), 6.86(1H, d, J=7.8Hz), 7.06(1H, d, J=8.3Hz), 7.23(1H, dd, J=7.8, 7.8Hz), 7.36(1H, s), 7.49(1H, d, J=7.8Hz) |
| 445 |  |  | $^1$H-NMR(CDCl$_3$)δ7.35(1H, s), 7.30−7.23(2H, m), 6.92−6.87(1H, m), 6.31(1H, brs), 6.12(1H, s), 6.05(1H, s), 4.81(1H, brs), 4.30(2H, d, J=5.6Hz), 3.89(3H, s), 2.22(3H, s), 1.46(9H, s) |
| 455 |  |  | $^1$H-NMR(CDCl$_3$)δ1.46(9H, s), 2.17(3H, s), 3.91(3H, s), 4.31(2H, d, J=5.6Hz), 4.80(1H, brt), 6.13(1H, s), 6.18(1H, d, J=7.9Hz), 6.89(1H, d, J=7.3Hz), 7.21−7.30(2H, m), 7.49(1H, d, J=7.3Hz), 7.62(1H, s) |

Example 5

Synthesis of 3-methylamino-2-(3-(di-(t-butoxycarbonyl)aminomethyl)phenylamino)pyridine To a mixture of the compound (88.5 mg) obtained in Example 3, methyl iodide (15 μl) and dimethylformamide (2 ml), sodium hydride (content=60%; 10 mg) was added and the resulting mixture was stirred at room temperature for 4 days. To the reaction mixture, ethyl acetate and a saturated aqueous sodium hydrogencarbonate solution were added. The organic layer was washed with a saturated aqueous sodium chloride solution, dried with anhydrous sodium sulfate and concentrated under reduced pressure. The resulting residue was purified by silica gel column chromatography (eluent, n-hexane:ethyl acetate=2:3) to give 19.3 mg of the titled compound (yield, 21%).

$^1$H-NMR (CDCl$_3$) δ: 1.44(18H, s), 2.85(3H, s), 3.48(1H, brs), 4.74(2H, s), 6.02(1H, s), 6.82–6.95(3H, m), 7.03(1H, s), 7.09(1H, d, J=8.0 Hz), 7.20(1H, dd, J=8.0, 8.0 Hz), 7.75 (1H, dd, J=4.3, 1.7 Hz)

Example 6

Synthesis of 3-methylamino-2-(3-aminomethylphenylamino)pyridine

Using the compound obtained in Example 5 as a starting material, reaction was performed as in Example 2 and thereafter the liquid reaction mixture was concentrated under reduced pressure. The resulting residue was purified by basic silica gel column chromatography (eluent, chloroform: methanol=10:1) to give the titled compound quantitatively.

$^1$H-NMR (CDCl$_3$) δ: 1.69(2H, brs), 2.85(3H, s), 3.53(1H, brs), 3.81(2H, s), 6.08(1H, brs), 6.84–6.94(3H, m), 7.05(1H, d, J=7.6 Hz), 7.12(1H, s), 7.22(1H, dd, J=7.6, 7.6 Hz), 7.76 (1H, dd, J=4.6, 2.0 Hz)

Example 7

Synthesis of 3-ethylamino-2-(3-(di-(t-butoxycarbonyl)aminomethyl)phenylamino)pyridine Using the compound obtained in Example 3 as a starting material and also using ethyl iodide as a reagent, the procedure of Example 5 was repeated to give the titled compound (yield, 54%).

$^1$H-NMR (CDCl$_3$)

δ: 1.28(3H, t, J=7.3 Hz), 1.45(18H, s), 3.15(2H, q, J=7.3 Hz), 3.30(1H, brs), 4.74(2H, s), 6.05(1H, s), 6.82–6.96(3H, m), 7.07(1H, s), 7.12–7.18(1H, m), 7.18 (1H, dd, J=7.3, 7.3 Hz), 7.75(1H, dd, J=4.6, 1.3 Hz)

Example 29

Synthesis of 2-(3-(di-(t-butoxycarbonyl)aminomethyl)phenylamino)-6-methylamino-3-nitropyridine A mixture of the compound (77.0 mg) obtained in Example 27, potassium carbonate (89 mg), methylamine hydrochloride (22.0 mg) and acetonitrile (2 ml) was stirred at 60° C. for 6 h and the reaction mixture was concentrated under reduced pressure. Ethyl acetate and water were added to the resulting residue. The organic layer was washed with a saturated aqueous sodium chloride solution, dried with anhydrous sodium sulfate and concentrated under reduced pressure. The resulting residue was purified by silica gel column chromatography (eluent, n-hexane:ethyl acetate= 2:1) to give 71.0 mg of the titled compound (yield, 93%).

$^1$H-NMR (CDCl$_3$) δ: 1.43(18H, s), 3.03(3H, d, J=4.3 Hz), 4.81(2H, s), 5.93(1H, d, J=8.9 Hz), 6.98–7.80(5H, m), 8.20–8.42(1H, m), 10.81(1H, brs)

The procedure of Example 29 was repeated using corresponding amine derivatives to give the compounds shown in Table 64.

TABLE 64

| Example | Amine derivative | Product | Spectral data |
|---|---|---|---|
| 31 | NH$_2$EtHCl | 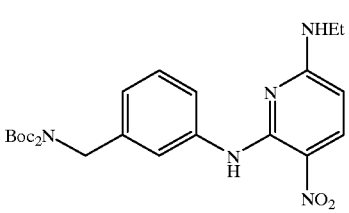 | $^1$H-NMR(CDCl$_3$)δ1.32(3H, t, J=6.9Hz), 1.43(18H, s), 3.38–3.52(2H, m), 4.81(2H, s), 5.92(1H, d, J=9.2Hz), 6.97–7.78(5H, m), 8.26(1H, d, J=9.2Hz), 10.79(1H, brs) |
| 33 | NH$_2$$^a$Pr.HCl | 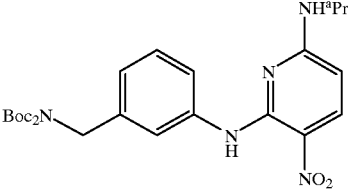 | $^1$H-NMR(CDCl$_3$)δ1.00(3H, t, J=7.3Hz), 1.43(18H, s), 1.62–1.80(2H, m), 3.22–3.44(2H, m), 4.81(2H, s), 5.92(1H, d, J=6.5Hz), 6.95–7.83(5H, m), 8.20–8.37(1H, m), 10.80(1H, brs) |

TABLE 64-continued

| Example | Amine derivative | Product | Spectral data |
|---|---|---|---|
| 35 | NHMe$_2$.HCl | Boc$_2$N-CH$_2$-C$_6$H$_4$-NH-(pyridine with NMe$_2$ and NO$_2$) | $^1$H-NMR(CDCl$_3$)δ1.46(18H, s), 3.19(6H, s), 4.78(2H, s), 6.08(1H, d, J=9.6Hz), 7.04(1H, d, J=7.6Hz), 7.29(1H, dd, J=7.6, 7.6Hz), 7.58(1H, s), 7.59(1H, d, J=7.6Hz), 8.28(1H, d, J=9.6 Hz), 10.81(1H, brs) |

Example 37

Synthesis of 6-chloro-2-(3-(t-butoxycarbonylaminomethyl)phenylamino)nicotinic acid A mixture of 3-(di-(t-butoxycarbonyl)aminomethyl)aniline (81 mg), 2,6-dichloronicotinic acid (90%, 53 mg), di-i-propylethylamine (64 mg) and 1,4-dioxane (1 ml) was heated under reflux for 3 days and then concentrated under reduced pressure. The resulting residue was purified by silica gel column chromatography (eluent, methylene chloride:methanol=20:1) to give 24 mg of the titled compound (yield, 25%).

$^1$H-NMR (DMSO-d$_6$) δ: 1.44(9H, s), 4.14–4.26(2H, m), 6.72(1H, d, J=7.9 Hz), 6.89(1H, d, J=7.6 Hz), 7.09(1H, brt), 7.26(1H, dd, J=7.6, 7.6 Hz), 7.51(1H, s), 7.71 (1H, d, J=7.6 Hz), 8.22(1H, d, J=7.9 Hz)

Example 39

Synthesis of 2-(3-(di-(t-butoxycarbonyl)aminomethyl)phenylamino)-6-methoxypyridine A mixture of 3-(di-(t-butoxycarbonyl)aminomethyl)aniline (50 mg), tetrakistriphenylphosphine palladium (18 mg), potassium carbonate (24 mg), 2-chloro-6-methoxypyridine (25 mg) and toluene (3 ml) was heated under reflux under nitrogen atmosphere for 16 h and, thereafter, ethyl acetate and water were added. The organic layer was washed with a saturated aqueous sodium chloride solution, dried with anhydrous sodium sulfate and concentrated under reduced pressure. The resulting residue was purified by silica gel column chromatography (eluent, ethyl acetate:hexane=1:4) to give 54.5 mg of the titled compound (yield, 82%).

$^1$H-NMR (CDCl$_3$) δ: 1.45(18H, s), 3.91(3H, s), 4.77(2H, s), 6.19(1H, d, J=7.9 Hz), 6.36(1H, brs), 6.39(1H, d, J=7.9 Hz), 6.93(1H, d, J=6.9 Hz) 7.23–7.30(3H, m), 7.39(1H, dd, J=7.9, 7.9 Hz)

The procedure of Example 39 was repeated using corresponding aniline derivatives and corresponding halogenated derivatives to give the compounds shown in Tables 65–73 (under "Reaction conditions" in the tables: palladium Pd:(1) is tetrakistriphenylphosphine palladium, Pd:(2) is tris(dibenzylideneacetone)dipalladium, base:(1) is potassium t-butoxide, base:(2) is sodium t-butoxide, base:(3) is potassium carbonate; ligand:(1) is diphenylphosphino-ferrocene and ligand:(2) is 2,2'-bis(diphenylphosphino)-1,1'-binaphthyl.

TABLE 65

| Example | Aniline derivative | Halogentaed derivative | Product | Reaction conditions | Spectral data |
|---|---|---|---|---|---|
| 41 | 3-(Boc$_2$NCH$_2$)-aniline | 2-chloro-3-(trifluoromethyl)pyridine | F$_3$C-pyridine-NH-C$_6$H$_4$-CH$_2$NBoc$_2$ | Pd: (1) base: (3) | $^1$H-NMR(CDCl$_3$)1.47(18H, s), 4.78(2H, s), 6.71(1H, brs), 6.81(1H, dd, J=7.6, 4.3Hz), 7.02(1H, d, J=7.6Hz), 7.29(1H, dd, J=7.6, 7.6Hz), 7.43(1H, s), 7.49(1H, d, J=7.6Hz), 7.79(1H, d, J=7.6Hz), 8.33(1H, d, J=4.3Hz) |
| 43 | 3-(Boc$_2$NCH$_2$)-aniline | 2-chloro-6-methoxy-3-(methoxycarbonyl)pyridine | MeO-pyridine(CO$_2$Me)-NH-C$_6$H$_4$-CH$_2$NBoc$_2$ | Pd: (1) base: (3) | $^1$H-NMR(CDCl$_3$)δ1.45(18H, s), 3.88(3H, s), 3.97(3H, s), 4.78(2H, s), 6.14(1H, d, J=8.8Hz), 6.95(1H, d, J=7.6Hz), 7.26(1H, dd, J=7.6, 7.6Hz), 7.59(1H, d, J=7.6Hz), 7.66(1H, s), 8.10(1H, d, J=8.8Hz), 10.42(1H, brs) |
| 421 | 3-(Boc$_2$NCH$_2$)-aniline | 2-chloro-6-methoxy-3-nitropyridine | O$_2$N-pyridine(OMe)-NH-C$_6$H$_4$-CH$_2$NBoc$_2$ | Pd: (1) base: (3) | $^1$H-NMR(CDCl$_3$)δ8.27(1H, d, J=8.9Hz), 7.45–7.30(3H, m), 7.16–7.06(2H, m), 6.32(1H, d, J=8.9Hz), 4.79(2H, s), 4.09(3H, s), 1.46(18H, s) |
| 422 | 3-(Boc$_2$NCH$_2$)-aniline | 2-chloro-3-nitro-6-methoxypyridine (Cl-substituted) | O$_2$N-pyridine(OMe)-NH-C$_6$H$_3$(Cl)-CH$_2$NBoc$_2$ | Pd: (1) base: (3) | $^1$H-NMR(CDCl$_3$)δ11.00(1H, brs), 8.46(1H, d, J=9.2Hz), 8.28(1H, d, J=8.3Hz), 7.28(1H, dd, J=8.3, 7.9Hz), 6.99(1H, d, J=7.9Hz), 6.28(1H, d, J=9.2Hz), 4.95(2H, s), 3.95(3H, s), 1.46(18H, s) |

TABLE 66

| Example | Aniline derivative | Halogenated derivative | Product | Reaction conditions | Spectral data |
|---|---|---|---|---|---|
| 423 | Boc₂N-CH₂-C₆H₄-NH₂ | 4-CO₂Me, 6-OMe, 2-Cl pyridine | BocHN-CH₂-C₆H₄-NH-pyridine(CO₂Me, OMe) | Pd: (2) base: (2) ligand: (2) | ¹H-NMR(CDCl₃)δ7.38(1H, brs), 7.34–7.27(2H, m), 6.96(1H, d, J=6.6Hz), 6.89(1H, s), 6.74(1H, s), 6.51(1H, s), 4.83(1H, brs), 4.31(2H, d, J=5.6Hz), 3.94(3H, s), 3.90(3H, s), 1.46 (9H, s) |
| 424 | Boc₂N-CH₂-C₆H₄-NH₂ | 4-Me, 2-Cl pyrimidine | BocHN-CH₂-C₆H₄-NH-pyrimidine(Me) | Pd: (2) base: (1) ligand: (1) | ¹H-NMR(CDCl₃)δ8.27(1H, d, J=5.6Hz), 7.58(1H, s), 7.55(1H, d, J=7.9Hz), 7.28(1H, dd, J=7.9, 7.3Hz), 7.10(1H, brs), 6.94(1H, d, J=7.3Hz), 6.61(1H, d, J=5.6Hz), 4.83(1H, brs), 4.32(2H, d, J=5.6Hz), 2.42(3H, s), 1.47(9H, s) |
| 425 | Boc₂N-CH₂-C₆H₄-NH₂ | 3-NO₂, 6-OEt, 2-Cl pyridine | Boc₂N-CH₂-C₆H₄-NH-pyridine(NO₂, OEt) | Pd: (1) base: (3) | ¹H-NMR(CDCl₃)δ1.39(3H, t, J=6.9Hz), 1.47(18H, s), 4.39(2H, q, J=6.9Hz), 4.79(2H, s), 6.20(1H, d, J=8.9Hz), 7.11(1H, d, J=7.6Hz), 7.32(1H, dd, J=7.6, 7.6Hz), 7.53(1H, s), 7.57(1H, d, J=7.6Hz), 8.41(1H, d, J=8.9Hz), 10.61(1H, brs) |
| 426 | Boc₂N-CH₂-C₆H₄-NH₂ | 3-CF₃, 6-OMe, 2-Cl pyridine | Boc₂N-CH₂-C₆H₄-NH-pyridine(CF₃, OMe) | Pd: (1) base: (3) | ¹H-NMR(CDCl₃)δ1.46(18H, s), 3.90(3H, s), 4.77(2H, s), 6.22(1H, d, J=8.6Hz), 6.73(1H, brs), 6.99(1H, d, J=7.6Hz), 7.26(1H, dd, J=7.6, 7.6Hz), 7.44(1H, s), 7.49(1H, d, J=7.6Hz), 7.66(1H, d, J=8.6Hz) |

TABLE 67

| Example | Aniline derivative | Halogenated derivative | Product | Reaction conditions | Spectral data |
|---|---|---|---|---|---|
| 427 | 3-(Boc₂N-CH₂)-aniline | 2-Br-3-NO₂-4-OMe-benzene | BocHN-CH₂-C₆H₄-NH-(2-pyridyl with 3-NO₂, 5-OMe) | Pd: (1) base: (1) | ¹H-NMR(CDCl₃)δ1.46(9H, s), 3.83(3H, s), 4.32(2H, d, J=5.9 Hz), 4.88(1H, brt), 7.03–7.12(3H, m), 7.15(1H, s), 7.23 (1H, s), 7.34(1H, dd, J=7.6, 7.6Hz), 7.63(1H, d, J=3.0Hz), 9.30(1H, brs) |
| 428 | 3-(Boc₂N-CH₂)-aniline | 2-Br-3-Me-nitrobenzene | BocHN-CH₂-C₆H₄-NH-(2-Me-6-NO₂-phenyl) | Pd: (2) base: (1) ligand: (1) | ¹H-NMR(CDCl₃)δ1.44(9H, s), 2.09(3H, s), 4.24(2H, d, J=5.9 Hz), 4.80(1H, brt), 6.64(1H, d, J=7.9Hz), 6.66(1H, s), 6.87 (1H, d, J=7.6), 7.08(1H, dd, J=7.9, 7.9Hz), 7.19(1H, dd, J= 7.6, 7.6Hz), 7.43(1H, d, J=7.6Hz), 7.97(1H, d, J=7.9Hz), 8.24(1H, brs) |
| 429 | 3-(BocHN-C(Me)₂)-aniline | 2-Br-4-Me-pyridine | BocHN-C(Me)₂-C₆H₄-NH-(4-Me-2-pyridyl) | Pd: (2) base: (1) ligand: (1) | ¹H-NMR(CDCl₃)δ1.37(9H, s), 1.63(6H, s), 2.24(3H, s), 4.99 (1H, brs), 6.56(1H, d, J=5.0Hz), 6.70(1H, s), 6.74(1H, brs ), 7.09(1H, d, J=7.3Hz), 7.20–7.31(3H, m), 8.05(1H, d, J= 5.0Hz) |
| 430 | 3-(BocHN-CH(Et))-aniline | 2-Br-4-Me-pyridine | BocHN-CH(Et)-C₆H₄-NH-(4-Me-2-pyridyl) | Pd: (2) base: (1) ligand: (1) | ¹H-NMR(CDCl₃)δ0.92(3H, t, J=7.3Hz), 1.42(9H, s), 1.66– 1.82(2H, m), 2.26(3H, s), 4.43–4.60(1H, m), 4.77–4.87(1H, m), 6.52(1H, brs), 6.58(1H, d, J=5.0Hz), 6.68(1H, s), 6.94 (1H, d, J=6.6Hz), 7.17(1H, s), 7.23–7.32(2H, m), 8.06(1H, d, J=5.0Hz) |

TABLE 68

| Example | Aniline derivative | Halogenated derivative | Product | Reaction conditions | Spectral data |
|---|---|---|---|---|---|
| 431 | 3-(Boc₂NCH₂)-2-Me-aniline | 2-Br-4-Me-pyridine | N-(3-(Boc₂NCH₂)-2-Me-phenyl)-4-Me-pyridin-2-amine | Pd: (2) base: (1) ligand: (1) | ¹H-NMR(CDCl₃)δ1.46(18H, s), 2.19(3H, s), 2.20(3H, s), 4.83(2H, s), 6.21(1H, brs), 6.27(1H, s), 6.52(1H, d, J=5.0 Hz), 6.60(1H, d, J=7.6Hz), 6.99(1H, d, J=7.6Hz), 7.18(1H, dd, J=7.6, 7.6Hz), 7.24(1H, s), 8.02(1H, d, J=5.0Hz) |
| 432 | 3-(BocHNCH₂)-4-Et-aniline | 2-Br-4-Me-pyridine | N-(3-(BocHNCH₂)-4-Et-phenyl)-4-Me-pyridin-2-amine | Pd: (2) base: (1) ligand: (1) | ¹H-NMR(CDCl₃)δ1.23(3H, t, J=7.3Hz), 1.46(9H, s), 2.25(3H, s), 2.64(2H, q, J=7.3Hz), 4.33(2H, q, J=5.3Hz), 4.71(1H, brt), 6.44(1H, brs), 6.56(1H, d, J=5.3Hz), 6.64(1H, s), 7.14–7.26(3H, m), 8.04(1H, d, J=5.3Hz) |
| 433 | 3-(BocHNCH₂)-4-EtO-aniline | 2-Br-4-Me-pyridine | N-(3-(BocHNCH₂)-4-EtO-phenyl)-4-Me-pyridin-2-amine | Pd: (2) base: (1) ligand: (1) | ¹H-NMR(CDCl₃)δ1.44(3H, t, J=6.9Hz), 1.44(9H, s), 2.22(3H, s), 4.06(2H, q, J=6.9Hz), 4.31(2H, d, J=5.6Hz), 5.02(1H, brt), 6.31(1H, brs), 6.50(1H, s), 6.51(1H, d, J=5.3Hz), 6.83(1H, d, J=8.6Hz), 7.16–7.23(2H, m), 8.01(1H, d, J=5.3 Hz) |
| 434 | 2-(BocHNCH₂CH₂)-aniline | 2-Br-4-Me-pyridine | N-(2-(BocHNCH₂CH₂)-phenyl)-4-Me-pyridin-2-amine | Pd: (2) base: (1) ligand: (1) | ¹H-NMR(CDCl₃)δ1.44(9H, s), 2.22(3H, s), 2.78–2.86(2H, m), 3.25–3.34(2H, m), 4.78(1H, brt), 6.54(1H, d, J=5.3Hz), 6.58(1H, s), 6.86(1H, brs), 7.01–7.13(1H, m), 7.17–7.28(2H, m), 7.66–7.75(1H, m), 8.03(1H, d, J=5.3Hz) |

TABLE 69

| Example | Aniline derivative | Halogenated derivative | Product | Reaction conditions | Spectral data |
|---|---|---|---|---|---|
| 435 | (structure) | (structure) | (structure) | Pd: (2) base: (1) ligand: (1) | ¹H-NMR(CDCl₃)δ1.46(9H, s), 2.29(3H, s), 4.42(2H, d, J=5.6 Hz), 4.96(1H, brt), 6.66(1H, d, J=5.0Hz), 6.69(1H, s), 6.81 (1H, brs), 7.02(1H, d, J=7.3Hz), 7.23(1H, dd, J=7.3, 7.3Hz ), 7.96(1H, d, J=7.3Hz), 8.12(1H, d, J=5.0Hz) |
| 436 | (structure) | (structure) | (structure) | Pd: (2) base: (1) ligand: (1) | ¹H-NMR(CDCl₃)δ1.36(9H, brs), 1.80–1.95(1H, m), 2.01– 2.17(1H, m), 2.45–2.60(4H, m), 5.09(1H, brs), 6.56(1H, brs), 6.57(1H, d, J=5.3Hz), 6.70(1H, s), 7.11(1H, d, J=7.3 Hz), 7.22–7.31(3H, m), 8.05(1H, d, J=5.3Hz) |
| 437 | (structure) | (structure) | (structure) | Pd: (2) base: (1) ligand: (1) | ¹H-NMR(CDCl₃)δ1.44(9H, s), 2.25(3H, s), 2.72–2.79(2H, m), 3.32–3.42(2H, m), 4.56(1H, s), 6.47(1H, brs), 6.56( 1H, d, J=4.9Hz), 6.65(1H, s), 7.10–7.19(2H, m), 7.22–7.30( 2H, m), 8.05(1H, d, J=4.9Hz) |
| 438 | (structure) | (structure) | (structure) | Pd: (2) base: (1) ligand: (1) | ¹H-NMR(CDCl₃)δ1.40(3H, t, J=6.9Hz), 1.44(18H, s), 2.28( 3H, s), 3.91(2H, q, J=6.9Hz), 4.89(2H, s), 6.60(1H, d, J=5.0 Hz), 6.68(1H, s), 6.77(1H, s), 6.79(1H, d, J=7.9Hz), 7.05( 1H, dd, J=7.9, 7.9Hz), 7.77(1H, d, J=7.9Hz), 8.09(1H, d, J= 5.0Hz) |

TABLE 70

| Example | Aniline derivative | Halogenated derivative | Product | Reaction conditions | Spectral data |
|---|---|---|---|---|---|
| 439 | | | | Pd: (2) base: (1) ligand: (1) | $^1$H-NMR(CDCl$_3$)δ1.44(18H, s), 2.26(3H, s), 4.88(2H, s), 6.45(1H, brs), 6.59(1H, d, J=5.3Hz), 6.62(1H, s), 7.08(1H, s), 7.25–7.29(2H, m), 8.05(1H, d, J=5.3Hz) |
| 440 | | | | Pd: (1) base: (3) | $^1$H-NMR(CDCl$_3$)δ1.45(18H, s), 3.93(3H, s), 4.78(2H, s), 6.22(1H, d, J=8.6Hz), 7.00(1H, s), 7.03(1H, d, J=7.6Hz), 7.29(1H, dd, J=7.6, 7.6Hz), 7.46(1H, d, J=7.6Hz), 7.54(1H, s), 7.62(1H, d, J=8.6Hz) |
| 441 | | | | Pd: (2) base: (2) ligand: (1) | $^1$H-NMR(CDCl$_3$)δ1.47(9H, s), 4.32(2H, d, J=5.6Hz), 4.86(1H, brs), 6.71(1H, dd, J=7.6, 5.0Hz), 6.97(1H, d, J=7.6Hz), 6.98(1H, s), 7.30(1H, dd, J=7.6, 7.6Hz), 7.52–7.50(3H, m), 8.12(1H, dd, J=5.0, 1.7Hz) |
| 442 | | | | Pd: (1) base: (3) | $^1$H-NMR(CDCl$_3$)δ1.47(9H, s), 3.89(3H, s), 3.98(3H, s), 4.32(2H, d, J=5.4Hz), 4.81(1H, brt), 6.15(1H, d, J=8.5Hz), 6.96(1H, d, J=8.3Hz), 7.28(1H, dd, J=8.3, 8.3Hz), 7.57(1H, d, J=8.3Hz), 7.77(1H, s), 8.11(1H, d, J=8.5Hz), 10.47(1H, s) |

TABLE 71

| Example | Aniline derivative | Halogenated derivative | Product | Reaction conditions | Spectral data |
|---|---|---|---|---|---|
| 497 | | | | Pd: (2) base: (1) ligand: (1) | 1H-NMR(CDCl3)δ1.46(18H, s), 2.23(3H, s), 4.76(2H, s), 6.50(1H, brs), 6.83(1H, d, J=6.9Hz), 6.93(1H, d, J=6.9Hz), 7.15–7.36(4H, m), 8.02(1H, s) |
| 498 | | | | Pd: (2) base: (1) ligand: (1) | 1H-NMR(CDCl3)δ1.46(9H, s), 2.24(3H, s), 4.30(2H, d, J=5.6 Hz), 4.83(1H, brt), 6.13(1H, brs), 6.72(1H, dd, J=7.3, 5.0 Hz), 6.91(1H, d, J=7.3Hz), 7.27(1H, dd, J=7.6, 7.6Hz), 7.36 (1H, d, J=7.6Hz), 7.46(1H, s), 7.48(1H, d, J=7.6Hz), 8.11( 1H, dd, J=5.0Hz) |
| 499 | | | | Pd: (2) base: (1) ligand: (1) | 1H-NMR(CDCl3)δ1.43(18H, s), 2.20(3H, s), 3.82(3H, s), 4.81(2H, s), 6.27(1H, brs), 6.46(1H, s), 6.50(1H, d, J=5.3 Hz), 6.84(1H, d, J=8.9Hz), 7.00(1H, d, J=2.3Hz), 7.18(1H, dd, J=8.9, 2.3Hz), 8.00(1H, d, J=5.3Hz) |
| 500 | | | | Pd: (2) base: (1) ligand: (1) | 1H-NMR(CDCl3)δ1.44(9H, s), 2.29(3H, s), 4.11(2H, d, J=6.6 Hz), 5.72(1H, brt), 6.43–6.46(1H, m), 6.60–6.73(3H, m), 7.24(1H, d, J=8.6Hz), 7.39–7.45(1H, m), 7.41(1H, s), 7.50–7.58(1H, m), 7.64(1H, d, J=2.0Hz), 7.72(1H, d, J=1.3Hz), 8.09(1H, d, J=5.3Hz) |

TABLE 72

| Example | Aniline derivative | Halogenated derivative | Product | Reaction conditions | Spectral data |
|---|---|---|---|---|---|
| 505 | 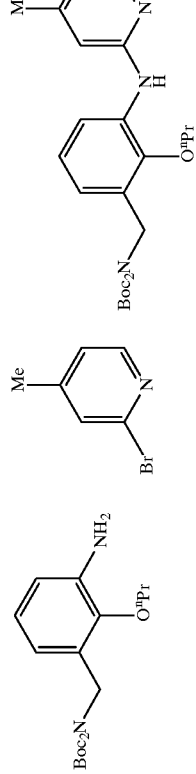 | 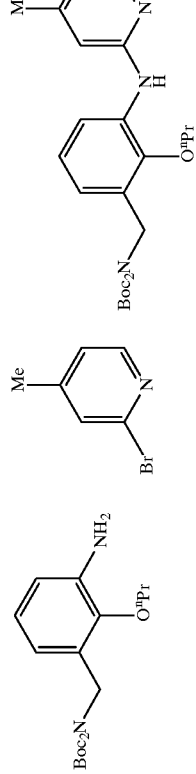 | 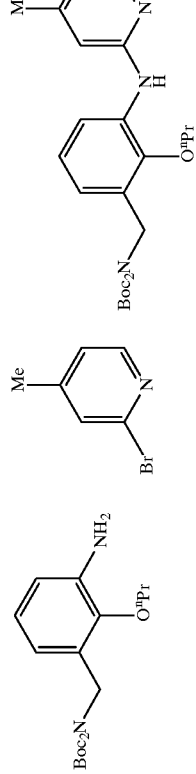 | Pd: (2) base: (1) ligand: (1) | $^1$H-NMR(CDCl$_3$)δ8.09(1H, d, J=5.3Hz), 7.80(1H, d, J=7.9Hz), 7.05(1H, dd, J=7.9, 7.9Hz), 6.83–6.72(2H, m), 6.66(1H, s), 6.59(1H, d, J=5.3Hz), 4.90(2H, s), 3.78(2H, t, J=6.6Hz), 2.28(3H, s), 1.90–1.75(2H, m), 1.44(18H, s), 1.06(3H, t, J=7.4Hz) |
| 519 | 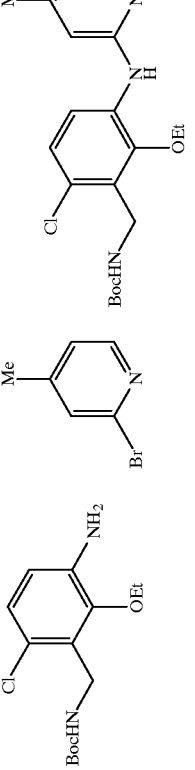 | 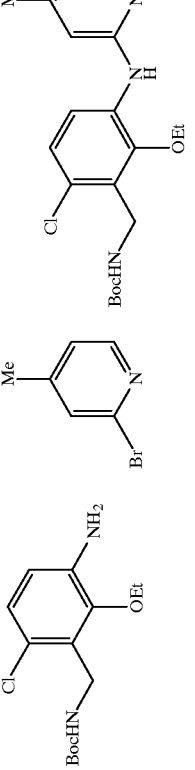 | 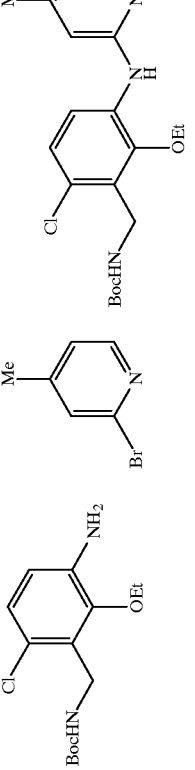 | Pd: (2) base: (1) ligand: (1) | $^1$H-NMR(CDCl$_3$)δ1.45(3H, t, J=6.9Hz), 1.45(9H, s), 2.29(3H, s), 3.94(2H, q, J=6.9Hz), 4.52(1H, d, J=5.6Hz), 4.94(1H, brt), 6.58(1H, s), 6.62(1H, d, J=5.0Hz), 6.74(1H, brs), 7.12(1H, d, J=8.9Hz), 8.00(1H, d, J=8.9Hz), 8.10(1H, d, J=5.0Hz) |
| 520 | 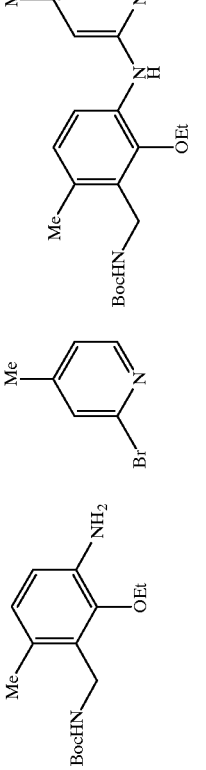 | 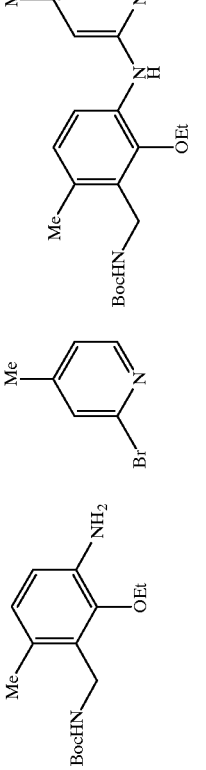 | 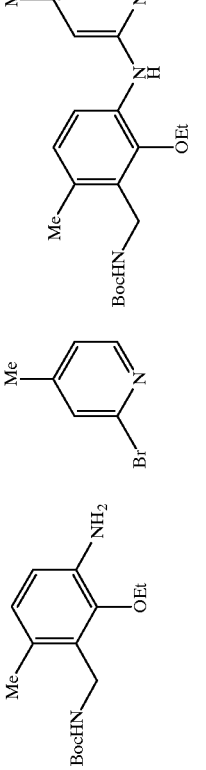 | Pd: (2) base: (1) ligand: (1) | $^1$H-NMR(CDCl$_3$)δ1.40(3H, t, J=6.9Hz), 1.45(9H, s), 2.26(3H, s), 2.35(3H, s), 3.88(2H, q, J=6.9Hz), 4.39(2H, d, J=5.0Hz), 4.76(1H, brs), 6.58(1H, d, J=5.3Hz), 6.61(1H, s), 6.93(1H, d, J=8.2Hz), 7.65(1H, d, J=8.2Hz), 8.07(1H, d, J=5.3Hz) |

TABLE 73

| Example | Aniline derivative | Halogenated derivative | Product | Reaction conditions | Spectral data |
|---|---|---|---|---|---|
| 540 | BocHN-CH2-C6H3(OMe)-NH2 | 2-Br-4-Me-pyridine | BocHN-CH2-C6H3(OMe)-NH-(4-Me-pyridin-2-yl) | Pd: (2) base: (1) ligand: (1) | $^1$H-NMR(CDCl$_3$)δ8.10(1H, d, J=5.3Hz), 7.80(1H, d, J=7.3 Hz), 7.06(1H, dd, J=8.6, 7.3Hz), 6.81(1H, s), 6.77(1H, d, J=8.6Hz), 6.69(1H, s), 6.60(1H, d, J=5.3Hz), 4.89(2H, s), 3.75(3H, s), 2.28(3H, s), 1.45(18H, s) |
| 542 | Boc$_2$N-CH2-C6H3(OiPr)-NH2 | 2-Br-4-Me-pyridine | Boc$_2$N-CH2-C6H3(OiPr)-NH-(4-Me-pyridin-2-yl) | Pd: (2) base: (1) ligand: (1) | $^1$H-NMR(CDCl$_3$)δ8.09(1H, d, J=5.3Hz), 7.74(1H, d, J=7.6Hz), 7.04(1H, dd, J=8.6, 7.6Hz), 6.80(1H, d, J=8.6Hz), 6.74(1H, s), 6.67(1H, s), 6.58(1H, d, J=5.3Hz), 4.88(2H, s), 4.19–4.07(1H, m), 2.27(3H, s), 1.43(18H, s), 1.29(6H, d, J=6.3 Hz) |

Example 45

Synthesis of 2-(3-aminomethylphenylamino)-6-methoxynicotinic acid hydrochloride

A mixture of the compound (37 mg) obtained in Example 43, potassium hydroxide (96 mg), water (2 ml) and 1,4-dioxane (2 ml) was heated at 60° C. for 2 h. The reaction mixture was cooled, then rendered acidic with 2 N HCl and subjected to extraction with methylene chloride. The organic layer was dried with anhydrous sodium sulfate and concentrated under reduced pressure. The resulting residue was worked up as in Example 2 to give the titled compound quantitatively.

$^1$H-NMR (DMSO-d$_6$) δ: 3.95(3H, s), 4.01(2H, brs), 6.27 (1H, d, J=8.6 Hz), 7.14(1H, d, J=7.6 Hz), 7.39(1H, dd, J=8.3, 7.6 Hz), 7.71(1H, s), 7.90(1H, d, J=8.3 Hz), 8.14(1H, d, J=8.6 Hz), 8.30(3H, brs), 10.75 (1H, s), 13.06(1H, brs)

Example 52

Synthesis of 2-(3-aminomethylphenylamino)-6-methyl-3-nitropyridine hydrochloride A mixture of the compound (118 mg) obtained in Example 446, concentrated sulfuric acid (1 ml) and water (2 ml) was heated at 120° C. for 4 h. The reaction mixture was put into ice water, adjusted to pH 8 with saturated sodium hydrogencarbonate and subjected to extraction with ethyl acetate. The organic layer was washed with a saturated aqueous sodium chloride solution, dried with anhydrous sodium sulfate and dried under reduced pressure. The resulting residue was dissolved in methanol (2 ml) and, after addition of a 1,4-dioxane solution (4 N, 0.5 ml) of hydrogen chloride at room temperature, the reaction mixture was concentrated under reduced pressure. The residue was recrystallized from methanol-ethyl acetate to give 37.1 mg of the titled compound (61%).

$^1$H-NMR (DMSO-d$_6$) δ: 2.49(3H, s), 4.03(2H, q, J=5.6 Hz), 6.90(1H, d, J=8.6 Hz), 7.27(1H, d, J=7.9 Hz), 7.42(1H, dd, J=7.9, 7.9 Hz), 7.77 (1H, s), 7.86(1H, d, J=7.9 Hz), 8.31(3H, brs), 8.45 (1H, d, J=8.6 Hz), 10.09(1H, s)

Example 53

Synthesis of 2-(3-aminomethylphenylamino)-6-ethyl-3-nitropyridine hydrochloride

Using the compound obtained in Example 447 as a starting material, the procedure of Example 52 was repeated to give the titled compound (yield, 85%).

$^1$H-NMR (DMSO-d$_6$) δ: 1.24(3H, t, J=7.3 Hz), 2.79(2H, q, J=7.3 Hz), 4.02(2H, q, J=5.0 Hz), 6.92(1H, d, J=8.6 Hz), 7.26(1H, d, J=7.6 Hz), 7.43 (1H, dd, J=7.6, 7.6 Hz), 7.75 (1H, s), 7.90(1H, d, J=7.6 Hz), 8.41(3H, brs), 8.48(1H, d, J=8.6 Hz), 10.10(1H, s)

Example 443

Synthesis of 2-(3-(t-butoxycarbonylaminomethyl)phenylamino)- 6-methoxy-isonicotinic acid To a mixture of the compound (53.8 mg) obtained in Example 423 and methanol (3 ml), a 2N aqueous sodium hydroxide solution (1 ml) was added. The reaction mixture was stirred at room temperature for 4 h and concentrated under reduced pressure. To the resulting residue, ethyl acetate was added and mixture was subjected to extraction with water. The aqueous layer was adjusted to pH 1 with 2N HCl and subjected to extraction with ethyl acetate. The organic layer was washed with a saturated aqueous sodium chloride solution, dried with anhydrous sodium sulfate and concentrated under reduced pressure to give 47.3 mg of the titled compound (yield, 90%).

$^1$H-NMR(CDCl$_3$) δ: 7.49(1H, d, J=7.9 Hz), 7.45(1H, s), 7.28(1H, dd, J=7.9, 7.3 Hz), 6.98(1H, s), 6.93(1H, d, J=7.3 Hz), 6.76(1H, s), 4.92(1H, brs), 4.31(2H, d, J=5.6 Hz), 3.95(3H, s), 1.46(9H, s)

Example 444

Synthesis of 2-(3-(t-butoxycarbonylaminomethyl)phenylamino)-4-hydroxymethyl-6-methoxypyridine To a mixture of the compound (155.3 mg) obtained in Example 423, tetrahydrofuran (4 ml) and methanol (2 ml), lithium borohydride (13 mg) was added. The reaction mixture was stirred at room temperature for one week and, after addition of water, the mixture was concentrated under reduced pressure. Water was added to the resulting residue and the mixture was subjected to extraction with ethyl acetate. The organic layer was washed with a saturated aqueous sodium chloride solution, dried with anhydrous sodium sulfate and concentrated under reduced pressure. The resulting residue was purified by silica gel column chromatography (eluent, ethyl acetate:n-hexane=1:1) to give 86.1 mg of the titled compound (yield, 60%).

$^1$H-NMR(CDCl$_3$) δ: 7.37(1H, s), 7.18–7.12(2H, m), 6.93–6.88(1H, m), 6.42(1H, s), 6.42(1H, s), 6.18(1H, s), 4.88(1H, brs), 4.59(2H, s), 4.29(2H, d, J=5.6 Hz), 3.90(3H, s), 1.45(9H, s)

Example 446

Synthesis of 2-(2-(3-(di-(t-butoxycarbonyl)aminomethyl)phenylamino)-3-nitropyridine-6-yl) malonic acid dimethyl ester To a mixture of the compound (150 mg) obtained in Example 27, dimethyl malonate (50 mg) and dimethylformamide (3 ml), sodium hydride (content, 60%; 15 mg) was added. The reaction mixture was stirred at room temperature for 3 h and then ethyl acetate and water were added. The organic layer was washed with a saturated aqueous sodium chloride solution, dried with anhydrous sodium sulfate and concentrated under reduced pressure. The resulting residue was purified by silica gel column chromatography (eluent, n-hexane:ethyl acetate=2:1) to give 123 mg of the titled compound (yield, 68%).

$^1$H-NMR(CDCl$_3$) δ: 1.47(18H, s), 3.76(6H, s), 4.81(2H, s), 4.91(1H, s), 6.95(1H, d, J=8.6 Hz), 7.08(1H, d, J=7.9 Hz), 7.32(1H, dd, J=7.9, 7.9 Hz), 7.44(1H, s), 7.68(1H, d, J=7.9 Hz), 8.54(1H, d, J=8.6 Hz), 10.18(1H, brs)

The procedure of Example 446 was repeated using corresponding chlorinated derivatives forms and corresponding reagents to give the compounds listed in Table 74.

TABLE 74

| Example | Chlorinated derivative | Reagent | Product | Spectral data |
|---|---|---|---|---|
| 447 | (structure: 6-chloro-3-nitro-N-[3-(Boc₂N-CH₂)phenyl]pyridin-2-amine) | CH₃CH(CO₂Et)₂ | (structure: 6-[Me-C(CO₂Et)₂]-3-nitro-N-[3-(Boc₂N-CH₂)phenyl]pyridin-2-amine) | $^1$H-NMR(CDCl$_3$)δ1.15–1.23(6H, m), 1.47(18H, s), 1.85(3H, s), 4.10–4.40(4H, m), 4.81(2H, s), 6.97(1H, d, J=8.9Hz), 7.07(1H, d, J=7.6Hz), 7.31(1H, dd, J=7.6, 7.6Hz), 7.34(1H, d, J=2.0Hz), 7.62–7.69(1H, m), 8.51(1H, d, J=8.9Hz), 10.17(1H, brs) |
| 448 | (structure: 6-chloro-3-nitro-N-[3-(BocHN-CH₂)phenyl]pyridin-2-amine) | MeSH | (structure: 6-SMe-3-nitro-N-[3-(BocHN-CH₂)phenyl]pyridin-2-amine) | $^1$H-NMR(CDCl$_3$)δ1.47(9H, s), 2.53(3H, s), 4.35(2H, d, J=5.6Hz), 4.85(1H, brt), 6.68(1H, d, J=8.9Hz), 7.10(2H, d, J=7.6Hz), 7.34(1H, dd, J=7.6, 7.6Hz), 7.52(1H, d, J=7.6Hz), 7.60(1H, s), 8.27(1H, d, J=8.9Hz), 10.45(1H, brs) |

Example 449

Synthesis of 2-(3-(t-butoxycarbonylaminomethyl)phenylamino)-4-methylpyridine

A mixture of 3-(di-(t-butoxycarbonyl)aminomethyl)bromobenzene (260 mg), tris(dibenzylideneacetone)dipalladium (42 mg), diphenylphosphinoferrocene (50 mg), potassium t-butoxide (102 mg), 2-amino-4-methylpyridine (108 mg) and toluene (10 ml) was heated under a nitrogen atmosphere at 80° C. for 22 h. Ethyl acetate and water were added to the reaction mixture. The organic layer was washed with a saturated aqueous sodium chloride solution, dried with anhydrous sodium sulfate and concentrated under reduced pressure. The resulting residue was purified by silica gel column chromatography (eluent, ethyl acetate:n-hexane=1:1) to give 29.2 mg of the titled compound (yield, 10%).

$^1$H-NMR(CDCl$_3$) δ: 1.46(9H, s), 2.26(3H, s), 4.30(2H, d, J=5.9 Hz), 4.90(1H, brt), 6.59(1H, d, J=5.0 Hz), 6.60(1H, s), 6.68(1H, s), 6.94(1H, d, J=6.3 Hz), 7.21–7.31(3H, m), 8.06(1H, d, J=5.0 Hz)

The procedure of Example 449 was repeated using corresponding amine derivatives to give the compounds listed in Table 75.

Example 452

Synthesis of 2-(3-(t-butoxycarbonylaminomethyl)phenylamino)-6-methoxynicotinic acid obtained in Example 442 as a starting material, the procedure of Example 45 was repeated to give the titled compound (yield, 92%).

$^1$H-NMR(CDCl$_3$—CD$_3$OD) δ: 1.46(9H, s), 3.99(3H, s), 4.30(2H, s), 6.16(1H, d, J=8.6 Hz), 6.94(1H, d, J=7.8 Hz), 7.28(1H, dd, J=7.8, 7.8 Hz), 7.58(1H, d, J=7.8 Hz), 7.73(1H, s), 8.16(1H, d, J=8.6 Hz)

Example 453

Synthesis of 2-(3-t-butoxycarbonylaminomethyl)phenylamino)-6-methoxynicotinamide To a mixture of the compound (44 mg) obtained in Example 452, triethylamine (18 mg) and tetrahydrofuran (2 ml), ethyl chlorocarbonate (14.3 mg) was added and the resulting mixture was stirred at room temperature for 15 min. Ammonia gas was blown through the reaction mixture at room temperature and after stirring at room temperature for 5 min, the mixture was concentrated under reduced pressure. To the resulting residue, a saturated aqueous sodium hydrogencarbonate solution was added and the mixture was subjected to extraction with methylene chloride. The organic layer was washed with a saturated aqueous sodium chloride solution, dried with anhydrous magnesium sulfate and concentrated under reduced pressure. The resulting residue was purified by preparative thin-layer chromatography (eluent, methanol:methylene chloride=1:20) to give 10 mg of the titled compound (yield, 11%).

$^1$H-NMR(DMSO-d$_6$) δ: 1.39 (9H, s), 3.92(3H, s), 4.12 (2H, d, J=5.9 Hz), 6.20(1H, d, J=8.6 Hz), 6.85(1H, d, J=7.6 Hz), 7.24(1H, dd, J=7.6, 7.6 Hz), 7.32–7.40(2H, m), 7.51 (1H, d, J=7.6 Hz), 7.61(1H, s), 8.01(1H, brs), 8.10(1H, d, J=8.6 Hz)

Example 454

Synthesis of 2-(3-(t-butoxycarbonylaminomethyl)phenylamino)-3-hydroxymethyl-6-methoxypyridine To a mixture of the compound (300 mg) obtained in Example 452, triethylamine (101 mg) and tetrahydrofuran (8 ml), a tetrahydrofuran solution (1 ml) of ethyl chlorocarbonate (109 mg) was added under ice cooling and the resulting mixture was stirred at 0° C. for 15 min. The reaction mixture was filtered and a tetrahydrofuran solution (2 M, 0.8 ml) of lithium borohydride was added to the filtrate under ice cooling. The reaction mixture was stirred at 0° C. for 30 min and thereafter a 1 N aqueous sodium hydroxide solution was added under ice cooling. Further, the reaction mixture was stirred at 0° C. for 5 min and then ether and water were added. The organic layer was washed with a saturated aqueous sodium chloride solution, dried with anhydrous magnesium sulfate and concentrated under reduced pressure. The resulting residue was purified by silica gel column chromatography (eluent, ethyl acetate:methylene chloride=1:10) to give 199 mg of the titled compound (yield, 69%).

$^1$H-NMR(CDCl$_3$) δ: 1.46(9H, s), 3.93(3H, s), 4.31(2H, d, J=5.6 Hz), 4.67(2H, d, J=5.6 Hz), 4.79(1H, brt), 6.15(1H, d, J=7.9 Hz), 6.89(1H, d, J=7.6 Hz), 7.21–7.31(3H, m), 7.48 (1H, d, J=7.6 Hz), 7.64(1H, brs), 7.70(1H, brs)

TABLE 75

| Example | Amine derivative | Product | Spectral data |
|---|---|---|---|
| 450 | (structure) | (structure) | $^1$H-NMR(CDCl$_3$)δ1.46(9H, s), 2.22(3H, s), 2.40(3H, s), 4.30(2H, d, J=5.6 Hz), 4.83(1H, brt), 6.43(1H, brs), 6.47(1H, s), 6.53(1H, s), 6.93(1H, d, J=7.3Hz), 7.19–7.29(3H, m) |
| 451 | (structure) | (structure) | $^1$H-NMR(CDCl$_3$)δ1.21(3H, t, J=7.6Hz), 1.46(9H, s), 2.56(2H, q, J=7.6Hz), 4.30(2H, d, J=5.6Hz), 4.83(1H, brt), 6.54(1H, brs), 6.61(1H, d, J=5.0Hz), 6.69(1H, s), 6.91–6.95(1H, m), 7.18–7.31(3H, m), 8.09(1H, d, J=5.0Hz) |

Example 456

Synthesis of 2-(3-(t-butoxycarbonylaminomethyl) phenylamino)-6-methoxypyridine-3-carboaldehyde A mixture of the compound (24 mg) obtained in Example 454, manganese tetraoxide (40 mg) and benzene (8 ml) was stirred at room temperature for 2 days.

The reaction mixture was filtered and the filtrate was concentrated under reduced pressure. The resulting residue was purified by silica gel column chromatography (eluent, ethyl acetate:methylene chloride=1:20) to give 14 mg of the titled compound (yield, 59%).

$^1$H-NMR(CDCl$_3$) δ: 1.47(9H, s), 4.01(3H, s), 4.33(2H, d, J=5.6 Hz), 4.82(1H, brt), 6.24(1H, d, J=8.3 Hz), 7.00(1H, d, J=7.6 Hz), 7.30(1H, dd, J=7.6, 7.6 Hz), 7.61(1H, d, J=7.6 Hz), 7.71(1H, d, J=8.3 Hz), 7.72(1H, s), 9.67(1H, s), 10.95 (1H, s)

Example 472

Synthesis of 2-(3-aminomethylphenylamino)-4-hydroxymethyl-6-methoxypyridine dihydrochloride To a mixture of the compound (109.5 mg) obtained in Example 423, tetrahydrofuran (4 ml) and methanol (1 ml), lithium borohydride (19 mg) was added. The reaction mixture was stirred at room temperature for 44 h and after addition of 2 N HCl, the resulting mixture was concentrated under reduced pressure. The resulting residue was subjected to basic silica gel column chromatography (eluent, methanol:methylene chloride=1:19). To a mixture of the purified product and methanol (3 ml), a 1,4-dioxane solution (4 N, 0.3 ml) of hydrogen chloride was added and the resulting mixture was concentrated under reduced pressure. The resulting residue was recrystallized from methanol-ethyl acetate to give 48 mg of the titled compound (yield, 58%).

$^1$H-NMR(DMSO-d$_6$) δ: 9.18(1H, brs), 8.39(3H, brs), 7.78 (1H, s), 7.61(1H, d, J=7.9 Hz), 7.29(1H, dd, J=7.9, 7.3 Hz), 7.08(1H, brs), 7.02(1H, d, J=7.3 Hz), 6.47(1H, s), 6.11(1H, s), 4.42(2H, s), 3.94(2H, q, J=5.6 Hz), 3.87(3H, s)

Example 507

Synthesis of 2-(3-(t-butoxycarbonylaminomethyl) phenylamino)-5-methylthiazole

To a mixture of propionaldehyde (72 μl), chloroform (1 ml) and 1,4-dioxane (1 ml), bromine (52 μl) was added. The reaction mixture was stirred at room temperature for 30 min and then N-(3-(t-butoxycarbonylaminomethyl)phenyl) thiourea (262 mg), acetone (2 ml) and triethylamine (0.14 ml) were added. The reaction mixture was heated under reflux for 3.5 h and concentrated under reduced pressure. To the resulting residue, water was added and the resulting mixture was subjected to extraction with ethyl acetate. The organic layer was washed with a saturated aqueous sodium chloride solution, dried with anhydrous sodium sulfate and concentrated under reduced pressure. The resulting residue was purified by basic silica gel column chromatography (eluent, methylene chloride:methanol=99:1) to give 79.2 mg of the titled compound (yield, 27%).

$^1$H-NMR(CDCl$_3$) δ: 7.30–7.22(4H, m), 7.17(1H, d, J=7.6 Hz), 6.91(1H, d, J=1.0 Hz), 4.94(1H, brs), 4.30(2H, d, J=5.6 Hz), 2.34(3H, d, J=1.0 Hz), 1.47(9H, s)

Example 508

Synthesis of 2-(3-aminomethylphenylamino)-5-methylthiazole

A mixture of the compound (73 mg) obtained in Example 507 and trifluoroacetic acid (5 ml) was stirred at room temperature for 1 h and concentrated under reduced pressure. The resulting residue was purified by basic silica gel column chromatography (eluent, methylene chloride:methanol=95:5) to give 34.5 mg of the titled compound (yield, 67%).

$^1$H-NMR(CDCl$_3$) δ: 7.32–7.28(3H, m), 7.19(1H, d, J=7.3 Hz), 6.97(1H, d, J=7.3 Hz), 6.92(1H, d, J=1.0 Hz), 3.87(2H, s), 2.35(3H, d, J=1.0 Hz), 1.76(2H, brs)

Example 509

Synthesis of 2-(3-(t-butoxycarbonylaminomethyl) phenylamino)-4-methylthiazole

Example 511

Synthesis of 2-(3-(di-(t-butoxycarbonyl) aminomethyl)phenylamino)-5-methyloxazole To a mixture of 3-(di-(t-butoxycarbonyl)aminomethyl) aniline (200 mg), dimethylaminopyridine (166 mg) and methylene chloride (10 ml), thiophosgene (45 μl) was added under ice cooling and the resulting mixture was stirred at room temperature for 5 h. The reaction mixture was concentrated under reduced pressure and the resulting residue was purified by silica gel column chromatography (eluent, ethyl acetate:n-hexane=1:3) to give N-(3-(di-(t-butoxycarbonyl)aminomethyl)phenyl)isothiocyanate.

A mixture of the thus obtained compound (193 mg), 1-azido-propane-2-one (81 mg), triphenylphosphine (217 mg) and methylene chloride (5 ml) was stirred at room temperature for 15 h and then oxalic acid (115 mg) was added at room temperature. The reaction mixture was heated under stirring at 60° C. for 30 min and concentrated under reduced pressure. To the resulting residue, ethyl acetate and a 2 N aqueous sodium hydroxide solution were added. The organic layer was washed with a saturated aqueous sodium chloride solution, dried with anhydrous sodium sulfate and concentrated under reduced pressure. The resulting residue was purified by silica gel column chromatography (eluent, ethyl acetate:n-hexane=1:10) to give 78 mg of the titled compound (yield, 33%).

$^1$H-NMR(CDCl$_3$) δ: 1.45(18H, s), 2.25(3H, d, J=1.0 Hz), 4.77(2H, s), 6.51(1H, d, J=1.0 Hz), 6.91(1H, d, J=7.6 Hz), 7.15(1H, brs), 7.22–7.26(1H, m), 7.25(1H, dd, J=7.6, 7.6 Hz), 7.40(1H, d, J=7.6 Hz)

The procedure of Example 511 was repeated using corresponding reagents to give the compounds shown in Table 76.

TABLE 76

| Example | Aniline derivative | Product | Spectral data |
|---|---|---|---|
| 512 | Boc₂N—⟨benzene with OEt, NH₂⟩ | Boc₂N—⟨benzene-OEt⟩-NH-oxazole-Me | ¹H—NMR(CDCl₃)δ1.43(18H, s), 1.46(3H, t, J=6.9Hz), 2.27(3H, d, J=1.0Hz), 3.93(2H, q, J=6.9Hz), 4.88(2H, s), 6.52(1H, d, J=1.0Hz), 6.77(1H, d, J=7.6Hz), 7.08(1H, dd, J=7.6, 7.6Hz), 7.19(1H, s), 8.02(1H, d, J=7.6Hz) |
| 513 | Boc₂N—⟨benzene with Me, NH₂⟩ | Boc₂N—⟨benzene-Me⟩-NH-oxazole-Me | ¹H—NMR(CDCl₃)δ1.44(18H, s), 2.21(3H, s), 2.24(3H, s), 4.82(2H, s), 6.48(1H, s), 6.88(1H, d, J=7.9Hz), 7.19(1H, dd, J=7.9, 7.9Hz), 7.77(1H, d, J=7.9Hz) |
| 514 | MeO—⟨benzene with Boc₂N, NH₂⟩ | MeO—⟨benzene-Boc₂N⟩-NH-oxazole-Me | ¹H—NMR(CDCl₃)δ1.44(18H, s), 2.23(3H, s), 3.79(3H, s), 4.80(2H, s), 6.46(1H, s), 6.81(1H, d, J=8.9Hz), 6.97(1H, d, J=2.3Hz), 7.45(1H, dd, J=8.9, 2.3Hz) |

Example 515

Synthesis of 2-(3-aminomethyl)phenylamino)-5-methyloxazole trifluoroacetic acid salt A mixture of the compound (292 mg) obtained in Example 511 and trifluoroacetic acid (2 ml) was stirred at room temperature for 2 h and concentrated under reduced pressure. The resulting residue was recrystallized from ethanol/ethyl acetate/n-hexane to give 119 mg of the titled compound (38%).

¹H-NMR(DMSO-d₆) δ: 2.24(3H, s), 3.98(2H, q, J=5.6 Hz), 6.59(1H, s), 7.00(1H, d, J=7.3 Hz), 7.32(1H, dd, J=7.3, 7.3 Hz), 7.53(1H, d, J=7.3 Hz), 7.67(1H, s), 8.16(3H, brs), 10.08(1H, s)

The procedure of Example 515 was repeated using corresponding reagents to give the compounds listed in Table 77.

TABLE 77

| Example | Reagent | Product | Spectral data |
|---|---|---|---|
| 516 | Boc₂N—⟨benzene-OEt⟩-NH-oxazole-Me | H₂N—⟨benzene-OEt⟩-NH-oxazole-Me · CF₃CO₂H | ¹H—NMR(DMSO-d₆)δ1.37(3H, t, J=6.9 Hz), 2.24(3H, s), 3.89(2H, q, J=6.9 Hz), 4.05(2H, q, J=5.6Hz), 6.63(1H, s), 7.08(1H, d, J=7.9Hz), 7.15(1H, dd, J=7.9, 7.9Hz), 8.13(1H, d, J=7.9 Hz), 8.18(3H, brs), 9.33(1H, brs) |
| 517 | Boc₂N—⟨benzene-Me⟩-NH-oxazole-Me | H₂N—⟨benzene-Me⟩-NH-oxazole-Me · CF₃CO₂H | ¹H—NMR(DMSO-d₆)δ2.22(3H, s), 2.33(3H, s), 4.05(2H, q, J=5,6Hz), 6.60(1H, s), 7.12(1H, d, J=7.9Hz), 7.24(1H, dd, J=7.9, 7.9Hz), 7.75(1H, d, J=7.9Hz), 8.18(3H, brs), 9.40(1H, brs) |

TABLE 77-continued

| Example | Reagent | Product | Spectral data |
|---|---|---|---|
| 518 | 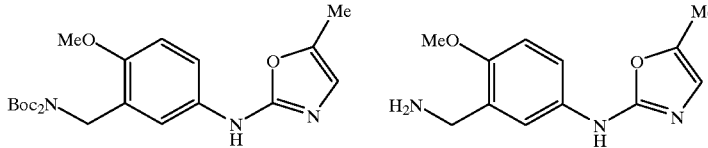 | 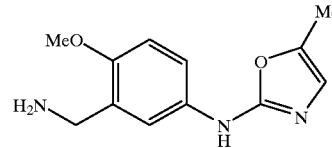 CF₃CO₂H | $^1$H—NMR(DMSO-$d_6$)δ2.22(3H, s), 3.80 (3H, s), 3.94(2H, q, J=5.6Hz), 6.55( 1H, s), 7.02(1H, d, J=8.9Hz), 7.54( 1H, dd, J=8.9, 2.3Hz), 7.59(1H, d, J= 2.3Hz), 8.00(3H, brs), 9.87(1H, s) |

Example 523

Synthesis of 2-(3-aminomethylphenylamino)-3,5-dinitropyridine

A mixture of 3-aminobenzylamine (696 mg), dimethylaminopyridine (674 mg), 3-nitrophenyloxycarbonyl-Wang resin (2.85 g; Tetrahedron Lett., Vol, 37, 937 (1996)) and tetrahydrofuran (60 ml) was stirred at room temperature for 24 h and then filtered. The resulting resin was washed sequentially with dimethylformamide, water, methanol and methylene chloride and then dried under reduced pressure to give 3-aminobenzylaminocarbonyl-Wang resin.

A mixture of the thus obtained resin (100 mg, 0.071 mol), potassium carbonate (100 mg), 2-chloro-3,5-dinitropyridine (72 mg), palladium (II) acetate (16 mg), diphenylphosphinoferrocene (79 mg) and acetonitrile (9 ml) was stirred under a nitrogen atmosphere at 80° C. and then filtered. The resulting resin was washed sequentially with dimethylformamide, water, methanol and methylene chloride, dried under reduced pressure and, after adding trifluoroacetic acid, the mixture was stirred at room temperature for 1 h. The reaction mixture was filtered and the filtrate was concentrated under reduced pressure. To the resulting residue, water and ethyl acetate were added. The aqueous layer was washed with ethyl acetate and concentrated under reduced pressure. The resulting residue was purified with Sep-PaK® Plus C18 Cartridges (Waters) to give 1.7 mg of the titled compound (8%).

$^1$H-NMR(CD$_3$OD) δ: 4.16(2H, s), 7.35(1H, d, J=7.9 Hz), 7.53(1H, dd, J=7.9, 7.9 Hz), 7.75(1H, d, J=7.9 Hz), 7.80(1H, s), 9.25(1H, d, J=2.4 Hz), 9.30(1H, d, J=2.4 Hz)

The procedure of Example 523 was repeated using corresponding chlorinated derivatives to give the compounds listed in Tables 78–80.

TABLE 78

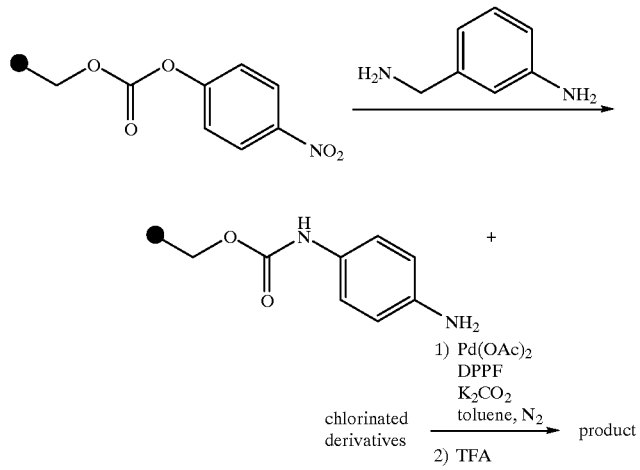

| Example | Chlorinated derivative | Product | Spectral data |
|---|---|---|---|
| 524 | 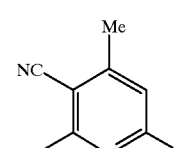 | 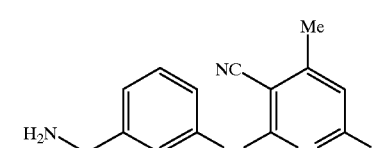 | $^1$H—NMR(CD$_3$OD)2.35(3H, s), 2.44(3H, s), 4.13(2H, s), 6.78(1H, s), 7.19–7.50(3H, m), 7.72(1H, d, J=2.0Hz) |

TABLE 78-continued
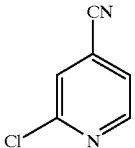
| Example | Chlorinated derivative | Product | Spectral data |
|---|---|---|---|
| 525 | 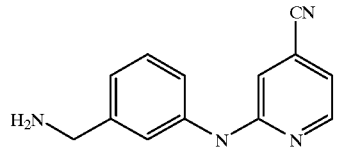 | 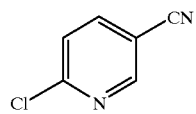 | ¹H—NMR(CD₃OD)4.18(2H, s), 7.33–7.46(4 H, m), 7.51(1H, d, J=7.6Hz), 7.64(1H, dd, J=7.6, 7.6Hz), 8.45(1H, d, J=5.0Hz) |
| 526 | 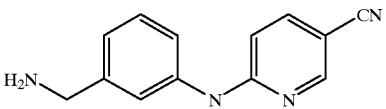 | 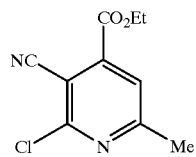 | ¹H—NMR(CD₃OD)4.17(2H, s), 7.29(1H, d, J=8.7Hz), 7.34(1H, d, J=7.6Hz), 7.39(1H, s), 7.53(1H, d, J=7.6Hz), 7.64(1H, dd, J=7.6, 7.6Hz), 8.04(1H, dd, J=8.7, 2.0Hz), 8.61(1H, d, J=2.0Hz) |
| 527 | 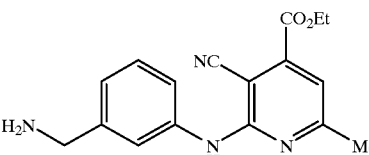 | 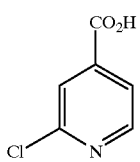 | ¹H—NMR(CD₃OD)1.47(3H, t, J=7.3Hz), 2.56 (3H, s), 4.14(2H, s), 4.48(2H, q, J=7.3 Hz), 7.27(1H, d, J=7.9Hz), 7.30(1H, s), 7.46(1H, dd, J=7.9, 7.9Hz), 7.74(1H, s), 7.75(1H, d, J=7.9Hz) |
| 528 | 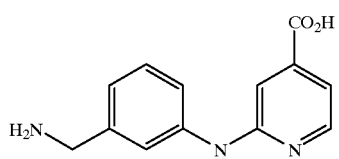 |  | ¹H—NMR(CD₃OD)4.12(2H, s), 7.02–7.12( 2H, m), 7.26(1H, d, J=5.2Hz), 7.37–7.42 (2H, m), 7.81(1H, s), 8.18(1H, d, J=5.2 Hz) |

TABLE 79

| Example | Chlorinated derivative | Product | Spectral data |
|---|---|---|---|
| 529 | 6-chloropyridine-3-CO2H | H2NCH2-C6H4-NH-(pyridine)-CO2H | ¹H—NMR(CD₃OD)4.15(2H, s), 6.87(1H, d, J=8.7Hz), 7.14(1H, d, J=7.4Hz), 7.43(1H, dd, J=7.4, 6.9Hz), 7.53(1H, d, J=6.9Hz), 7.98(1H, s), 8.11(1H, J=8.7, 2.1Hz), 8.81(1H, d, J=2.1Hz) |
| 530 | 5,6-dichloropyridine-3-CO2H | 3-chloro-6-(3-aminomethylanilino)pyridine-5-CO2H | ¹H—NMR(CD₃OD)4.16(2H, s), 7.22(1H, d, J=7.9Hz), 7.47(1H, dd, J=7.9, 7.9Hz), 7.65(1H, d, J=7.9Hz), 7.92(1H, s), 8.22(1H, d, J=2.0Hz), 8.69(1H, d, J=2.0Hz) |
| 531 | 6-chloro-2-methylpyridine-4-CO2H | 6-(3-aminomethylanilino)-2-methylpyridine-4-CO2H | ¹H—NMR(CD₃OD)2.49(3H, s), 4.12(2H, s), 7.05(1H, d, J=6.2Hz), 7.15(1H, s), 7.25(1H, s), 7.38–7.42(2H, m), 7.72(1H, s) |
| 532 | 6-chloropyridine-2-CO2H | 6-(3-aminomethylanilino)pyridine-2-CO2H | ¹H—NMR(CD₃OD)4.14(2H, s), 6.82(1H, d, J=8.9Hz), 7.10(1H, d, J=6.6Hz), 7.41–7.45(2H, m), 8.02(1H, s), 8.11(1H, dd, J=8.9, 2.0Hz), 8.78(1H, d, J=2.0Hz) |
| 533 | 2-chloro-6-methylpyridine-3-CONH2 | 2-(3-aminomethylanilino)-6-methylpyridine-3-CONH2 | ¹H—NMR(CD₃OD)2.50(3H, s), 4.12(2H, s), 6.84(1H, d, J=7.6Hz), 7.20(1H, d, J=7.0Hz), 7.40(1H, dd, J=7.0, 7.0Hz), 7.74–7.80(2H, m), 7.87(1H, d, J=7.6Hz) |
| 534 | 2,5-dichloropyridine-3-CONH2 | 5-chloro-2-(3-aminomethylanilino)pyridine-3-CONH2 | ¹H—NMR(CD₃OD)4.15(2H, s), 7.21(1H, d, J=7.6Hz), 7.46(1H, dd, J=7.6, 7.6Hz), 7.61(1H, d, J=7.6Hz), 7.75(1H, s), 8.11(1H, d, J=2.6Hz), 8.35(1H, d, J=2.6Hz) |

TABLE 80

| Example | Chlorinated derivative | Product | Spectral data |
|---|---|---|---|
| 535 | 6-chloro-2-methoxypyridine-4-CONH2 | 6-(3-aminomethylanilino)-2-methoxypyridine-4-CONH2 | ¹H—NMR(CD₃OD)4.00(3H, s), 4.12(2H, s), 6.58(1H, d, J=1.0Hz), 6.81(1H, d, J=1.0Hz), 7.09(1H, d, J=6.9Hz), 7.37–7.43(1H, m), 7.53(1H, d, J=6.9Hz), 7.83(1H, s) |

TABLE 80-continued

| Example | Chlorinated derivative | Product | Spectral data |
|---|---|---|---|
| 536 | H₂NOC-pyridine-Cl | H₂N-CH₂-phenyl-NH-pyridine-CONH₂ | ¹H—NMR(CD₃OD)4.15(2H, s), 6.83–6.89(1H, m), 6.96(1H, dd, J=7.6, 3.9Hz), 7.21 (1H, d, J=7.6Hz), 7.46(1H, dd, J=7.6, 7.6 Hz), 7.62(1H, d, J=7.6Hz), 7.76(1H, s), 8.02(1H, dd, J=7.6, 1.6Hz), 8.37(1H, dd, J=3.9, 1.6Hz) |
| 537 | Br-pyridine-Cl | H₂N-CH₂-phenyl-NH-pyridine-Br | ¹H—NMR(CD₃OD)4.12(2H, s), 6.82(1H, d, J=9.0Hz), 7.08(1H, d, J=7.6Hz), 7.38(1H, dd, J=7.6, 7.6Hz), 7.50(1H, d, J=7.6Hz), 7.71(1H, dd, J=9.0, 2.3Hz), 7.90(1H, s), 8.22(1H, d, J=2.3Hz) |
| 538 | Cl-pyridine(Cl,Cl) | H₂N-CH₂-phenyl-NH-pyridine(Cl,Cl) | ¹H—NMR(CD₃OD)4.13(2H, s), 7.16(1H, d, J=7.6Hz), 7.43(1H, dd, J=7.6, 7.6Hz), 7.64 (1H, d, J=7.6Hz), 7.84(1H, s), 7.87(1H, d, J=2.3Hz), 7.84(1H, s), 7.87(1H, d, J=2.3Hz), 8.10(1H, d, J=2.3Hz) |
| 539 | Cl-pyridine-Me | H₂N-CH₂-phenyl-NH-pyridine-Me | ¹H—NMR(CD₃OD)2.48(3H, s), 4.13(2H, s), 6.72–6.80(2H, m), 7.35–7.42(1H, m), 7.44(1h, s), 7.51–7.60(1H, m), 7.68(1H, dd, J=7.9, 7.9Hz), 7.74(1H, s) |

Several compounds used in the reactions described above are novel and the methods of synthesizing these compounds are described below as Examples 25e, 417e, 500b, 519e, 520d, 538e and 542a.

Example 25e

Synthesis of 2-(5-amino-2-ethylphenyl)-2-(t-butoxycarbonylamino)indane

Example 25a

Synthesis of 3-cyanomethyl-4-ethylnitrobenzene

To a mixture of 3-chloromethyl-4-ethylnitrobenzene (4.0 g) and dimethyl sulfoxide (50 ml), sodium cyanide (982 mg) was added. The reaction mixture was stirred at room temperature for 3 h and then ethyl acetate, n-hexane and water were added. The organic layer was washed with a saturated aqueous sodium chloride solution, dried with anhydrous sodium sulfate and concentrated under reduced pressure to give the titled compound quantitatively.

¹H-NMR(CDCl₃) δ: 1.33(3H, t, J=7.6 Hz), 2.78(2H, q, J=7.6 Hz), 3.80(2H, s), 7.44(1H, d, J=8.6 Hz), 8.18(1H, dd, J=8.6, 2.3 Hz), 8.35(1H, d, J=2.3 Hz)

Example 25b

Synthesis of 2-cyano-2-(2-ethyl-5-nitrophenyl)indane

To a mixture of the compound (3.0 g) obtained in Example 25a, α,α'-dichloro-o-xylene (4.15 g) and dimethyl sulfoxide (200 ml), potassium t-butoxide (3.55 g) was added and after stirring the resulting mixture at room temperature for 3 h, ethyl acetate and water were added. The organic layer was washed with a saturated aqueous sodium chloride solution, dried with anhydrous sodium sulfate and concentrated under reduced pressure to give the titled compound (1.36 g) (yield, 29%).

¹H-NMR(CDCl₃) δ: 1.45(3H, t. J=7.6 Hz), 3.11(2H, q, J=7.6 Hz), 3.61(2H, d, J=15.5 Hz), 3.91(2H, d, J=15.5 Hz), 7.25–7.33(4H, m), 7.53(1H, d, J=9.2 Hz), 8.12–8.16(2H, m)

Example 25c

Synthesis of 2-(2-ethyl-5-nitrophenyl)-2-indaneamide

To a mixture of the compound (1.16 g) obtained in Example 25b and acetic acid (10 ml), water (2 ml) and concentrated sulfuric acid (20 ml) were added sequentially. The reaction mixture was heated under reflux for 13 h, cooled, put into ice water and subjected to extraction with ethyl acetate. The organic layer was washed with a saturated aqueous sodium chloride solution, dried with anhydrous sodium sulfate and concentrated under reduced pressure to give the titled compound (870 mg) (yield, 71%).

¹H-NMR(CDCl₃) δ: 1.35(3H, t, J=7.6 Hz), 2.82(2H, q, J=7.6 Hz), 3.36(2H, d, J=15.9 Hz), 3.95(2H, d, J=15.9 Hz), 5.13(1H, brs), 5.43(1H, brs), 7.15–7.25(4H, m), 7.49(1H, d, J=8.3 Hz), 8.08(1H, dd, J=8.3, 2.3 Hz), 8.17(1H, d, J=2.3 Hz)

Example 25d

Synthesis of 2-(t-butoxycarbonylamino)-2-(2-ethyl-5-nitrophenyl)indane

To a mixture of the compound (815 mg) obtained in Example 25c and t-butanol (12 ml), lead tetracetate (1.40 g) was added. The reaction mixture was heated under reflux for 3 h, cooled and, after adding water, subjected to extraction with ethyl acetate-ethylene glycol. The organic layer was washed with water, dried with anhydrous sodium sulfate and concentrated under reduced pressure. The resulting residue was purified by silica gel column chromatography (eluent, chloroform) to give the titled compound (620 mg) (yield, 62%).

$^1$H-NMR(CDCl$_3$) δ: 1.30(3H, t, J=7.6 Hz), 1.31(9H, s), 2.93(2H, q, J=7.6 Hz), 3.55(2H, d, J=15.9 Hz), 3.63(2H, d, J=15.9 Hz), 5.18(1H, s), 7.20–7.29(4H, m), 7.40(1H, d, J=8.6 Hz), 8.05(1H, dd, J=8.6, 2.3 Hz), 8.32(2H, d, J=2.3 Hz)

Example 25e

Synthesis of 2-(5-amino-2-ethylphenyl)-2-(t-butoxycarbonylamino)indane

Using the compound obtained in Example 25d as a starting material, the procedure of Example 3 was repeated to give the titled compound (yield, 97%).

$^1$H-NMR(CDCl$_3$) δ: 1.23(3H, t, J=7.6 Hz), 1.30(9H, s), 2.74(2H, q, J=7.6 Hz), 3.48–3.67(6H, m), 5.02(1H, s), 6.56(1H, dd, J=8.3, 2.3 Hz), 6.74(1H, d, J=2.3 Hz), 7.03(1H, d, J=8.3 Hz), 7.15–7.24(4H, m)

Example 417e

Synthesis of N-(3-amino-2-ethoxyphenylmethyl)iminodicarboxylic acid di-t-butyl ester

Example 417a

Synthesis of 2-ethoxy-3-nitrobenzoic acid ethyl ester

To a mixture of 3-nitrosalicylic acid (5.0 g), ethyl iodide (11 ml) and dimethylformamide (200 ml), potassium carbonate (9.4 g) was added. The reaction mixture was stirred at 60° C. for 4.5 h and, after adding water, subjected to extraction with ethyl acetate. The organic layer was washed with a saturated aqueous sodium chloride solution, dried with anhydrous sulfate and concentrated under reduced pressure. The resulting residue was purified by silica gel column chromatography (eluent, ethyl acetate:n-hexane=1:1) to give 5.66 g of the titled compound (yield, 87%).

$^1$H-NMR(CDCl$_3$) δ: 8.01(1H, dd, J=7.9, 1.7 Hz), 7.89 (1H, dd, J=7.9, 1.7 Hz), 7.26(1H, dd, J=7.9, 7.9 Hz), 4.42(2H, q, J=7.3 Hz), 4.18(2H, q, J=6.9 Hz), 1.43(3H, t, J=6.9 Hz), 1.42(3H, t, J=7.3 Hz)

Example 417b

Synthesis of 2-ethyoxy-3-nitrobenzyl alcohol

To a mixture of the compound (117 mg) obtained in Example 417a, tetrahydrofuran (5 ml) and methanol (2 ml), lithium borohydride (10.7 mg) was added. The reaction mixture was stirred at room temperature for 15 h, and, after addition of water, concentrated under reduced pressure. To the resulting residue, 2 N HCl was added and the mixture was subjected to extraction with ethyl acetate. The organic layer was washed with a saturated aqueous sodium chloride solution, dried with anhydrous sodium sulfate and concentrated under reduced pressure. The resulting residue was purified by silica gel column chromatography (eluent, ethyl acetate:n-hexane=1:2) to give the titled compound quantitatively.

$^1$H-NMR(CDCl$_3$) δ: 7.77(1H, d, J=7.9 Hz), 7.67(1H, d, J=7.3 Hz), 7.22(1H, dd, J=7.9, 7.3 Hz), 4.80(2H, s), 4.08 (2H, q, J=6.8 Hz), 2.10(1H, brs), 1.44(3H, t, J=6.8 Hz)

Example 417c

Synthesis of 2-ethoxy-3-nitrobenzyl bromide

To a mixture of the compound (3.13 g) obtained in Example 417b, carbon tetrabromide (5.26 g) and methylene chloride (100 ml), triphenylphosphine (4.16 g) was added under ice cooling. The reaction mixture was stirred under ice cooling for 30 min and concentrated under reduced pressure. The resulting residue was purified by silica gel column chromatography (eluent, ethyl acetate: n-hexane=1:9) to give 3.59 g of the titled compound (yield, 87%).

$^1$H-NMR(CDCl$_3$) δ: 7.78(1H, dd, J=7.9, 1.7 Hz), 7.65 (1H, dd, J=7.6, 1.7 Hz), 7.20(1H, dd, J=7.9, 7.6 Hz), 4.57(2H, s), 4.17(2H, q, J=6.9 Hz), 1.49(3H, t, J=6.9 Hz)

Example 417d

Synthesis of N-(2-ethoxy-3-nitrophenylmethyl)iminodicarboxylic acid di-t-butyl ester A mixture of iminodicarboxylic acid di-t-butyl ester (3.23 g), dimethylformamide (50 ml) and sodium hydride (0.57 g) was stirred under ice cooling for 1 h and then a mixture of the compound (3.51 g) obtained in Example 417c and dimethylformamide (20 ml) was added under ice cooling. The reaction mixture was stirred at room temperature for 14 h and, after addition of 2 N HCl, subjected to extraction with ethyl acetate. The organic layer was washed with a saturated aqueous sodium chloride solution, dried with anhydrous sodium sulfate and concentrated under reduced pressure. The resulting residue was purified by silica gel column chromatography (eluent, ethyl acetate:n-hexane=1:9) to give 5.09 g of the titled compound (yield, 95%).

$^1$H-NMR(CDCl$_3$) δ: 7.72(1H, dd, J=7.9, 1.3 Hz), 7.38 (1H, dd, J=7.3, 1.3 Hz), 7.17(1H, dd, J=7.9, 7.3 Hz), 4.91(2H, s), 4.06(2H, q, J=6.9 Hz), 1.45(18H, s), 1.44(3H, t, J=6.9 Hz)

Example 417e

Synthesis of N-(3-amino-2-ethoxyphenylmethyl)iminodicarboxylic acid di-t-butyl ester To a mixture of the compound (5.09 g) obtained in Example 417d, nickel (II) chloride hexahydrate (61 mg) and methanol (130 ml), sodium borohydride (1.46 g) was added. The reaction mixture was stirred at room temperature for 20 min and, after addition of 2 N HCl, adjusted to pH 8 with a saturated aqueous sodium hydrogencarbonate solution and then concentrated under reduced pressure. To the resulting residue, water was added and the mixture was subjected to extraction with ethyl acetate. The organic layer was washed with a saturated aqueous sodium chloride solution, dried with anhydrous sodium sulfate and concentrated under reduced pressure. The resulting residue was purified by silica gel column chromatography (eluent, ethyl acetate:n-hexane=1:4) to give the titled compound (yield, 85%).

$^1$H-NMR(CDCl$_3$) δ: 6.86(1H, dd, J=7.9, 7.6 Hz), 6.63 (1H, dd, J=7.6, 1.0 Hz), 6.53(1H, dd, J=7.9, 1.0 Hz), 4.85(2H, s), 3.90(2H, q, J=6.9 Hz), 3.74(2H, brs), 1.43(18H, s), 1.41(3H, t, J=6.9 Hz)

Example 500b

Synthesis of N-(5-amino-2-(pyrazole-1-yl)phenylmethyl)carbamic acid t-butyl ester

Example 500a

Synthesis of N-(5-nitro-2-(pyrazole-1-yl)phenylmethyl)iminodicarboxylic acid di-t-butyl ester To a mixture of pyrazole (1.0 g) and dimethylsulfoxide (50 ml), sodium hydride (0.54 g) was added under ice cooling. The reaction mixture was stirred under ice cooling for 1 h and then a solution of N-(2-fluoro-5-nitrophenylmethyl)iminodicarboxylic acid di-t-butyl ester (5.0 g) in dimethyl sulfoxide (50 ml) was added. The reaction mixture was stirred at room temperature for 15 h and, after addition of water, subjected to extraction with ethyl acetate. The organic layer was washed with a saturated aqueous sodium chloride solution, dried with anhydrous sodium sulfate and concentrated under reduced pressure. The resulting residue was purified by silica gel column chromatography (eluent, ethyl acetate:n-hexane=1:4) to give the titled compound (yield, 73%).

$^1$H-NMR(CDCl$_3$) δ: 8.22–8.19(2H, m), 7.79–7.78(2H, m), 7.50(1H, d, J=9.6 Hz), 6.53(1H, dd, J=2.3, 2.0 Hz), 4.95(2H, s), 1.46(18H, s)

Example 500b

Synthesis of N-(5-amino-2-(pyrazole-1-yl) phenylmethyl)carbamic acid t-butyl ester To a mixture of the compound (4.15 g) obtained in Example 500a, nickel (II) chloride hexahydrate (0.183 g) and methanol (300 ml), sodium borohydride (2.43 g) was added. The reaction mixture was stirred at room temperature for 55 min; thereafter, 2 N HCl was added to render the reaction solution acidic and then a saturated aqueous sodium hydrogencarbonate solution was added to render the reaction solution basic; subsequently, the reaction mixture was concentrated under reduced pressure. To the resulting residue, water was added and the resulting mixture was subjected to extraction with ethyl acetate. The organic layer was washed with a saturated aqueous sodium chloride solution, dried with anhydrous sodium sulfate and concentrated under reduced pressure. The resulting residue was recrystallized from ethyl acetate/n-hexane to give the titled compound (yield, 89%).

$^1$H-NMR(CDCl$_3$) δ: 7.69(1H, d, J=1.3 Hz), 7.57(1H, d, J=2.0 Hz), 7.06(1H, d, J=8.3 Hz), 6.86–6.83(1H, m), 6.60 (1H, dd, J=8.3, 2.3 Hz), 6.41(1H, dd, J=2.0, 1.3 Hz), 5.62(1H, brs), 4.01(2H, d, J=6.6 Hz), 3.82(2H, brs), 1.43 (9H, s)

Example 519e

Synthesis of 3-(t-butoxycarbonylaminomethyl)-4-chloro-2-ethoxyaniline

Example 519a

Synthesis of 5-bromo-4-chloro-2-fluoronitrobenzene

To a mixture of 4-chloro-2-fluoronitrobenzene (1.00 g), silver sulfate (1.95 g) and concentrated sulfuric acid (5 ml), bromine (0.32 ml) was added under ice cooling and the resulting mixture was stirred at 0° C. for 30 min, then at room temperature for 1 h. The reaction mixture was put into ice water and subjected to extraction with ether. The organic layer was washed with water, a saturated aqueous sodium hydrogencarbonate solution and a saturated aqueous sodium chloride solution sequentially, dried with anhydrous sodium sulfate and concentrated under reduced pressure to give 1.38 g of the titled compound (yield, 95%).

$^1$H-NMR(CDCl$_3$) δ: 7.47(1H, d, J=9.9 Hz), 8.37(1H, d, J=7.3 Hz)

Example 519b

Synthesis of 5-bromo-4-chloro-2-fluoro-3-(trifluoromethylcarbonylaminomethyl)nitrobenzene A mixture of the compound (204 mg) obtained in Example 519a, N-hydroxymethyl-2,2,2-trifluoroacetamide (115 mg) and 10% fuming sulfuric acid (1.6 ml) was stirred at 80° C. for 10 h. The reaction mixture was cooled, put into ice water and subjected to extraction with ether. The organic layer was washed with water and a saturated aqueous sodium chloride solution sequentially, then dried with anhydrous sodium sulfate and concentrated under reduced pressure.

The resulting residue was purified by silica gel column chromatography (eluent, ethyl acetate:n-hexane=1:3) to give 85.1 mg of the titled compound (yield, 28%).

$^1$H-NMR(CDCl$_3$) δ: 4.86(2H, d, J=4.0 Hz), 6.73(1H, brt), 8.39(1H, d, J=7.3 Hz)

Example 519c

Synthesis of 5-bromo-3-(t-butoxycarbonylaminomethyl)-4-chloro-2-fluoronitrobenzene A mixture of the compound (601 mg) obtained in Example 519b, concentrated sulfuric acid (3 ml) and methanol (12 ml) was heated under reflux for 1 h. The reaction mixture was concentrated under reduced pressure and, after being rendered basic by addition of a 2 N aqueous sodium hydroxide solution, it was subjected to extraction with methylene chloride (20 ml). To the organic layer, di-t-butyl dicarbonate (414 mg) and a 2 N aqueous sodium hydroxide solution (10 ml) were added at room temperature and the resulting mixture was stirred at room temperature for 2 h. The organic layer was washed with water and a saturated aqueous sodium chloride solution sequentially, then dried with anhydrous sodium sulfate and concentrated under reduced pressure. The resulting residue was purified by silica gel column chromatography (eluent, chloroform) to give 402 mg of the titled compound (yield, 66%).

$^1$H-NMR(CDCl$_3$) δ: 1.44(9H, s), 4.57–4.66(2H, m), 5.01 (1H, brt), 8.31(1H, d, J=7.6 Hz)

Example 519d

Synthesis of 5-bromo-3-(t-butoxycarbonylaminomethyl)-4-chloro-2-ethoxynitrobenzene To a mixture of the compound (200 mg) obtained in Example 519c, ethanol (36 μl) and tetrahydrofuran (5 ml), sodium hydride (content, 60%; 25 mg) was added under ice cooling. The reaction mixture was stirred at 0° C. for 2 h and then water and ether were added. The organic layer was washed with water and a saturated aqueous sodium chloride solution sequentially, then dried with anhydrous sodium sulfate and concentrated under reduced pressure. The resulting residue was purified by silica gel column chromatography (eluent, ethyl acetate:n-hexane=1:4) to give 197 mg of the titled compound (yield, 92%).

$^1$H-NMR(CDCl$_3$) δ: 1.45(9H, s), 1.47(3H, t, J=6.9 Hz), 4.08(2H, q, J=6.9 Hz), 4.62(2H, d, J=5.9 Hz), 4.93(1H, brt), 8.10(1H, s)

Example 519e

Synthesis of 3-(t-butoxycarbonylaminomethyl)-4-chloro-2-ethoxyaniline

Using the compound obtained in Example 519d as a starting material, the procedure of Example 3 was repeated to give the titled compound (86%).

$^1$H-NMR(DCDl$_3$) δ: 1.44(3H, t, J=7.3 Hz), 1.45(9H, s), 3.78(2H, brs), 3.92(2H, q, J=7.3 Hz), 4.47(2H, d, J=5.3 Hz), 4.91(1H, brt), 6.63(1H, d, J=8.3 Hz), 6.94(1H, d, J=8.3 Hz)

Example 520d

Synthesis of 3-(t-butoxycarbonylaminomethyl)-2-ethoxy-6-methylaniline

Example 520a

Synthesis of 3-methyl-6-nitro-2-(trifluoromethylcarbonylaminomethyl)phenol

Using 5-methyl-2-nitrophenol as a starting material, the procedure of Example 545b was repeated to give the titled compound (16%).

$^1$H-NMR(CDCl$_3$) δ: 2.57(3H, s), 4.67(2H, d, J=6.3 Hz), 6.89(1H, d, J=8.6 Hz), 7.00(1H, brs), 8.00(1H, d, J=8.6 Hz), 11.23(1H, s)

Example 520b

Synthesis of 2-(t-butoxycarbonylaminomethyl)-4-methyl-6-nitrophenol

A mixture of the compound (100 mg) obtained in Example 520a, potassium carbonate (99.4 mg), water (1.0 ml) and methanol (6.0 ml) was stirred at room temperature for 3 h and then di-t-butyl dicarbonate (157 mg) was added. The reaction mixture was stirred at room temperature for 30 min and concentrated under reduced pressure. To the resulting residue, a saturated aqueous sodium chloride solution was added and the mixture was subjected to extraction with ethyl acetate. The organic layer was dried with anhydrous sodium sulfate and concentrated under reduced pressure. The resulting residue was purified by silica gel column chromatography (eluent, ethyl acetate:n-hexane=3:17) to give the titled compound (yield, 70%).

$^1$H-NMR(CDCl$_3$) δ: 1.43(9H,s), 2.55(3H, s), 4.44(2H, d, J=6.3 Hz), 5.17(1H, brs), 6.82(1H, d, J=8.6 Hz), 7.94(1H, d, J=8.6 Hz), 11.11(1H, s)

Example 520c

Synthesis of 3-(t-butoxycarbonylaminomethyl)-2-ethoxy-4-methylnitrobenzene

A mixture of the compound (350 mg) obtained in Example 520b, cesium carbonate (404 mg), dimethylformamide (15 ml) and ethyl iodide (0.4 ml) was stirred at 60° C. for 2 h. To the reaction mixture, ethyl acetate and water were added. The organic layer was washed with a saturated aqueous sodium chloride solution, dried with anhydrous sodium sulfate and concentrated under reduced pressure. The resulting residue was purified by silica gel column chromatography (eluent, ethyl acetate:n-hexane=2:8) to give the titled compound quantitatively.

$^1$H-NMR(CDCl$_3$) δ: 1.44(9H, s), 1.48(3H, t, J=6.9 Hz), 2.49(3H, s), 4.03(2H, q, J=6.9 Hz), 4.41(2H, d, J=5.6 Hz), 4.86(1H, brs), 7.03(1H, d, J=8.6 Hz), 7.72(1H, d, J=8.6 Hz)

Example 520d

Synthesis of 3-(t-butoxycarbonylaminomethyl)-2-ethoxy-4-methylaniline

Using the compound obtained in Example 520c as a starting material, the procedure of Example 3 was repeated to give the titled compound (92%).

$^1$H-NMR(CDCl$_3$) δ: 1.43(3H, t, J=6.9 Hz), 1.44(9H, s), 2.26(3H, s), 3.61(2H, brs), 3.89(2H, q, J=6.9 Hz), 4.34(2H, d, J=5.3 Hz), 4.70(1H, brs), 6.61(1H, d, J=7.9 Hz), 6.75(1H, d, J=7.9 Hz)

Example 538e

Synthesis of N-(3-amino-2-(n-propoxy)phenylmethyl)iminodicarboxylic acid di-t-butyl ester

Example 538a

Synthesis of 3-nitro-2-(n-propoxy)benzoic acid n-propyl ester

Using 3-nitrosalicylic acid as a starting material and also using n-propyl iodide as a reagent, the procedure of Example 417a was repeated to give the titled compound (yield, 29%).

$^1$H-NMR(CDCl$_3$) δ: 7.98(1H, dd, J=7.6, 1.7 Hz), 7,87 (1H, dd, J=7.9, 1.7 Hz), 7.24(1H, dd, J=7.9, 7.6 Hz), 4.31(2H, t, J=6.9 Hz), 4.05(2H, t, J=6.9 Hz), 1.90–1.71(4H, m), 1.08–0.97(6H, m)

Example 538b

Synthesis of 3-nitro-2-(n-propoxy)benzyl alcohol

Using the compound obtained in Example 538a as a starting material, the procedure of Example 417b was repeated to give the titled compound (yield, 70%).

$^1$H-NMR(CDCl$_3$) δ: 7.76(1H, dd, J=8.3, 1.3 Hz), 7.68 (1H, dd, J=7.3, 1.3 Hz), 7.21(1H, dd, J=8.3, 7.3 Hz), 4.80(2H, s), 3.96(2H, t, J=6.9 Hz), 2.13(1H, brs), 1.91–1.77 (2H, m), 1.04(3H, t, J=7.3 Hz)

Example 538c

Synthesis of 3-nitro-2-(n-propoxy)benzyl bromide

Using the compound obtained in Example 538b as a starting material, the procedure of Example 417c was repeated to give the titled compound (yield, 95%).

$^1$H-NMR(CDCl$_3$) δ: 7.77(1H, dd, J=7.9, 1.3 Hz), 7.64 (1H, dd, J=7.9, 1.3 Hz), 7.19(1H, dd, J=7.9, 7.9 Hz), 4.57(2H, s), 4.05(2H, t, J=6.6 Hz), 1.96–1.83(2H, m), 1.07 (3H, t, J=7.3 Hz)

Example 538d

Synthesis of N-(3-nitro-2-(n-propoxy)phenylmethyl)iminodicarboxylic acid di-t-butyl ester Using the compound obtained in Example 538c as a starting material, the procedure of Example 417d was repeated to give the titled compound (yield, 62%).

$^1$H-NMR(CDCl$_3$) δ: 7.70(1H, dd, J=7.9, 1.3 Hz), 7.37 (1H, dd, J=7.9, 1.3 Hz), 7.16(1H, dd, J=7.9, 7.9 Hz), 4.91(2H, s), 3.94(2H, t, J=6.6 Hz), 1.91–1,80(2H, m), 1.45 (18H, s), 1.05(3H, t, J=7.3 Hz)

Example 538e

Synthesis of N-(3-amino-2-(n-propoxy)phenylmethyl)iminodicarboxylic acid di-t-butyl ester Using the compound obtained in Example 538d as a starting material, the procedure of Example 417e was repeated to give the titled compound quantitatively.

$^1$H-NMR(CDCl$_3$) δ: 6.86(1H, dd, J=7.9, 7.6 Hz), 6.63 (1H, d, J=7.9 Hz), 6.52(1H, d, J=7.6 Hz), 4.85(2H, s), 3.78(2H, t, J=6.6 Hz), 3.74(2H, brs), 1.89–1.75(2H, m), 1.43(18H, s), 1.07(3H, t, J=7.3 Hz)

Example 542a

Synthesis of N-(3-amino-2-(i-propoxy)phenylmethyl)iminodicarboxylic acid di-t-butyl ester Using 3-nitrosalicylic acid as a staring material and also using i-propyl iodide as a reagent, the procedures of Examples 417a–417e were repeated to give the titled compound.

$^1$H-NMR(CDCl$_3$) δ: 6.85(1H, dd, J=7.9, 7.6 Hz), 6.62 (1H, d, J=7.6 Hz), 6.53(1H, d, J=7.9 Hz), 4.83(2H, s), 4.26–4.15(1H, m), 3.69(2H, brs), 1.42 (18H, s), 1.31(6H, d, J=6.3 Hz)

Test Examples

Test Example 1

Compounds of the invention were evaluated for their inhibitory effect on the presently known three NOS isoforms.

Crude enzymes of the respective NOS isoforms were prepared by the following procedures (Nagafuji et al., Neuroreport 6, 1541–1545, 1995).

The crude enzyme of nNOS was prepared by the following procedure. Normal untreated male Sprague Dawley (SD) rats (body weight, 300–400 g) were decapitated; the whole brain was immediately taken out from each animal and the cerebral cortex was separated on ice. Then, 5 volumes of 50 mM Tris-HCl containing 1 mM DTT (pH 7.4) was added and the mixture was homogenized for 3 min and centrifuged at 1,000×g for 10 min. The resulting supernatant was further centrifuged at 100,000×g for 60 min and a soluble cytosolic fraction of the finally obtained supernatant was used as the crude enzyme of nNOS.

The crude enzyme of iNOS was prepared by the following procedure. Rats were administered LPS (10 mg/kg) intraperitoneally and, 6 h later, perfused in a transcardiac manner with physiological saline containing 10 U/ml of heparin; thereafter, lungs were taken out. Subsequently, 5 volumes of 50 mM Tris-HCl containing 1 mM DTT (pH 7.4) was added and the mixture was homogenized for 3 min, followed by centrifugation of the homogenate at 1,000×g for 10 min. The resulting supernatant was centrifuged at 100,000×g for 60 min and a soluble cytosolic fraction of the finally obtained supernatant was used as the crude enzyme of iNOS.

The crude enzyme of eNOS was prepared by the following procedure. Cow pulmonary arterial endothelium cells (CPAE) were cultured in a MEM medium containing 20% FBS. Several days later, the cells were detached from the flask using a 0.25% trypsin solution containing 1 mM EDTA and, after addition of a suitable amount of FBS, centrifuged at 1,000 rpm for 10 min. A suitable amount of Ca- and Mg-free phosphate buffer (pH 7.4) was added to the precipitating cells and they were centrifuged at 1,000 rpm for 10 min. The same step was repeated to wash the cells which, upon addition of 50 mM Tris-HCl (pH 7.4) containing 1% Triton X-100 and 1 mM DTT, were left to stand in ice for 1 h. Subsequently, the mixture was homogenized for 3 min and kept in ice for 30 min with occasional stirring. Finally, the mixture was centrifuged at 100,000×g for 60 min and the resulting supernatant was used as the crude enzyme of eNOS.

The method of measuring NOS activity was basically the same as already reported by the present inventors and consisted of determining quantitatively the conversion of a substrate L-[$^3$H]arginine to a reaction product L-[$^3$H] citrulline (Nagafuji et al., in Brain Edema IX (Ito et al, eds.) 60, pp. 285–288, 1994; Nagafuji et al., Neuroreport 6, 1541–1545, 1995)

The reaction solution consisted of 100 nM L-[$^3$H] arginine, a prepared crude NOS enzyme sample (10–30 μg/ml protein), 1.25 mM CaCl$_2$, 1 mM EDTA, 10 μg/ml calmodulin, 1 mM NADPH, 100 μM tetrahydrobiopterine, 10 μM FAD, 10 μM FMN and 50 mM Tris-HCl (pH 7.4), to which one of the compounds of the invention or one of the control compounds was added.

The reaction was started by addition of L-[$^3$H] arginine. After incubation at 37° C. for 10 min, the reaction was terminated by addition of 2 ml of 50 mM Tris-HCl (pH 5.5) containing 1 mM EDTA and placing the mixture on ice. The reaction solution was passed through a cation-exchange resin column (Dowex AG50WX-8, Na$^+$ form, 3.2 ml) to separate the reaction product L-[$^3$H] citrulline from the unreacted residual substrate L-[$^3$H] arginine. The eluate was combined with another eluate resulting from the passage of a given amount of distilled water through the column and put into a minivial for recovery of L-[$^3$H] citrulline. Thereafter, a scintillation fluid was added and the contained radioactivity was measured with a liquid scintillation counter to determine the amount of L-[$^3$H] citrulline.

The activity of nNOS or eNOS was determined by subtracting the activity detected in the absence of CaCl$_2$ and calmodulin from the activity detected in the presence of CaCl$_2$ and calmodulin. The activity of iNOS was detected in the absence of CaCl$_2$ and calmodulin. The protein concentration of each crude enzyme sample was determined with a micro-assay kit of Bio Rad Co. Each Experiment was conducted in a duplicate.

Table 81 lists the mean values of IC$_{50}$ (the concentration necessary to inhibit 50% activity) of all test compounds against each NOS isoform. The table also lists the ratios of IC$_{50}$ values to each other as an index of selectivity.

TABLE 81

Inhibitory Action and Selectivity of Test Compounds against Three NOS Isoforms

| Example No. or Control Compound | Inhibitory action IC$_{50}$ (nM) | | | Selectivity | | |
|---|---|---|---|---|---|---|
| | nNOS | iNOS | eNOS | iNOS/ nNOS | eNOS/ nNOS | eNOS/ iNOS |
| 18 | 22.6 | 916.7 | 322.4 | 41 | 14 | 0.14 |
| 52 | 79.8 | N.D. | 1476.7 | — | 19 | — |
| 53 | 86.1 | N.D. | 6624.3 | — | 77 | — |
| 57 | 70.8 | N.D. | 947.4 | — | 13 | — |
| 61 | 126.0 | N.D. | 1614.9 | — | 13 | |
| 151 | 126.2 | N.D. | 679.3 | — | 5 | — |
| 153 | 29.8 | N.D. | 586.1 | — | 20 | — |
| 458 | 20.8 | N.D. | 403.1 | — | 19 | — |
| 460 | 111.7 | N.D. | 1244.3 | — | 11 | — |
| 462 | 16.4 | N.D. | 257.2 | — | 16 | — |
| 465 | 31.2 | N.D. | 1000.0 | — | 32 | — |
| 466 | 35.5 | N.D. | 421.0 | — | 12 | — |
| 467 | 19.6 | N.D. | 274.6 | — | 14 | — |
| 468 | 56.3 | N.D. | 2481.0 | — | 44 | — |
| 469 | 40.0 | N.D. | 994.0 | — | 25 | — |
| 478 | 61.6 | N.D. | 447.5 | — | 7 | — |
| 479 | 66.9 | N.D. | 802.0 | — | 12 | — |
| 481 | 78.1 | N.D. | 1984.5 | — | 25 | — |
| 482 | 50.5 | N.D. | 1348.6 | — | 27 | — |
| 483 | 65.4 | N.D. | 711.0 | — | 11 | — |
| 484 | 69.2 | N.D. | 1264.2 | — | 18 | — |
| 485 | 54.4 | 1774.9 | 2882.4 | 32 | 53 | 1.6 |
| 488 | 39.9 | N.D. | 297.9 | — | 8 | — |
| 489 | 22.1 | N.D. | N.D. | — | — | — |
| 490 | 18.1 | N.D. | 347.5 | — | 19 | — |
| 491 | 45.8 | N.D. | 1768.0 | — | 39 | — |
| 506 | 29.1 | N.D. | 1292.7 | — | 45 | — |
| 521 | 19.5 | N.D. | 485.2 | — | 25 | — |
| 522 | 19.7 | N.D. | 398.4 | — | 20 | — |
| 541 | 25.9 | N.D. | 712.6 | — | 28 | — |
| 543 | 12.5 | N.D. | 249.8 | — | 20 | — |
| L-NA | 16.9 | 3464.3 | 68.2 | 205.0 | 4.0 | 0.02 |

Notes:
Symbol "N.D." means "not determined", and
"—" means "uncalculable"

INDUSTRIAL APPLICABILITY

The compounds of the present invention exhibit an outstanding nNOS or iNOS inhibiting activity and are useful as therapeutics of cerebrovascular diseases [cerebral hemorrhage, subarachnoid hemorrhage, cerebral infarction (atherothrombotic infarction, lacunar infarction and cardiogenic embolism), transient ischemic attack and cerebral edema], traumatic brain injury, spinal injury, pains [headache (migraine, tension headache, cluster headache and chronic paroxysmal headache)], Parkinson's disease, Alzheimer's disease, seizure, morphine tolerance or dependence, septic shock, chronic rheumatoid arthritis, osteoarthritis, viral or nonviral infections and diabetes mellitus.

What is claimed is:

1. A compound represented by formula (1), or a tautomer, stereoisomer or optically active form of the compound or a pharmaceutically acceptable salt thereof

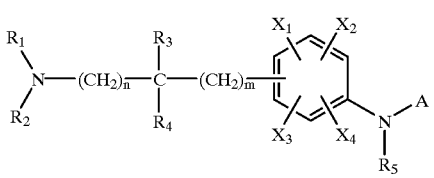

(1)

where $R_1$ and $R_2$, which may be the same or different, are each a hydrogen atom, an optionally substituted lower alkyl group, an acyl group or a lower alkoxycarbonyl group, or $R_1$ and $R_2$ may combine together to form a 3- to 8-membered ring;

$R_3$ and $R_4$, which may be the same or different, are each a hydrogen atom, an optionally substituted lower alkyl group, or $R_3$ and $R_4$ may combine together to form a monocyclic or fused ring having 3–10 carbon atoms;

$R_5$ is a hydrogen atom, a lower alkyl group, an acyl group or a lower alkoxycarbonyl group;

$X_1$, $X_2$, $X_3$, and $X_4$ which may be the same or different are each a hydrogen atom, a halogen atom, a nitro group, a cyano group, a hydroxyl, group, an optionally substituted lower alkyl group, a lower alkenyl group, a lower alkynyl group, an optionally substituted lower alkoxy group, an optionally substituted lower alkylthio group, a phenyl group optionally substituted by a halogen atom and/or a lower alkyl group, $NX_5X_6$ or $C(=O)X_7$;

where $X_5$ and $X_6$, which may be the same or different, are each a hydrogen atom, an optionally substituted lower alkyl group, an acyl group, an optionally substituted lower alkoxycarbonyl group, or $X_5$ and $X_6$ may combine together to form a 3- to 8-membered ring;

$X_7$ is a hydrogen atom, a hydroxyl group, an optionally substituted lower alkyl group, an optionally substituted lower alkoxy group, or $NX_8X_9$;

where $X_8$ and $X_9$, which may be the same or different, are each a hydrogen atom, an optionally substituted lower alkyl group, or $X_8$ and $X_9$ may combine together to form a 3- to 8-membered ring;

A is a substituted benzene ring or a 5- or 6-membered aromatic hetero ring which is optionally substituted and which contains at least one nitrogen atom as a hetero atom;

n and m are each an integer of 0 or 1, with the proviso that when A is a substituted benzene ring the substituent(s) of which is (are) a nitro group, an amino group or a carboxyl group, either of $R_1$ or $R_2$ is a hydrogen atom, and that when A is a substituted benzene, the substituent is not a di-(3-chloroethyl)amino group, and that when A is a pyridine ring substituted by a nitro group, none of $X_1$, $X_2$, $X_3$ and $X_4$ are a hydroxyl group.

2. The compound according to claim 1 wherein $X_1$, $X_2$, $X_3$ and $X_4$, which may be the same or different, are each a hydrogen atom, a halogen atom, a nitro group, a cyano group, an optionally substituted lower alkyl group, a lower alkenyl group, a lower alkynyl group, an optionally substituted lower alkoxy group, an optionally substituted lower alkylthio group, a phenyl group optionally substituted by a halogen atom and/or a lower alkyl group, $NX_5X_6$ or $C(=O)X_7$; and A is a substituted benzene or pyridine ring.

3. The compound of claim 1 wherein:

A is a 5- or 6-membered aromatic hetero ring which is optionally substituted and which contains at least one nitrogen atom as a hetero atom (exclusive of an optionally substituted pyridine ring).

4. The compound of claim 1 wherein:

$R_1$ is a hydrogen atom;

$R_2$ is a hydrogen atom, a lower alkyl group, an acyl group or a lower alkoxycarbonyl group; and A is a substituted benzene ring.

5. The compound of claim 2 wherein:

A is an optionally substituted pyridine ring.

6. The compound claim 1 wherein:

$R_1$ and $R_2$ are each a hydrogen atom;

$R_5$ is a hydrogen atom;

$X_1$, $X_2$, $X_3$ and $X_4$ which may be the same or different are each a hydrogen atom, a halogen atom, an optionally substituted lower alkyl group, an optionally substituted lower alkoxy group or $NX_5X_6$; and A is a substituted benzene ring, an optionally substituted pyridine ring, an optionally substituted pyrimidine ring, an optionally substituted oxazole ring, or an optionally substituted thiazole ring.

7. The compound of claim 6 wherein:

A is a substituted benzene ring or an optionally substituted pyridine ring.

8. The compound of claim 1 wherein:

$R_3$ and $R_4$ which may be the same or different are each a hydrogen atom or a lower alkyl group, or $R_3$ and $R_4$ may combine together to form a monocyclic ring having 3–10 carbon atoms.

9. The compound of claim 1 wherein:

$X_1$, $X_2$, $X_3$, and $X_4$ which may be the same or different are each a hydrogen atom, a halogen atom, a lower alkyl group, a lower alkoxy group optionally substituted by a phenyl group or $NX_5X_6$;

where $X_5$ and $X_6$ which may be the same or different are each a hydrogen atom, a lower alkyl group optionally substituted by a phenyl group or an acyl group, or $X_5$ and $X_6$ may combine together to form a 3- to 8-membered ring.

10. The compound of claim 6 wherein:

A is a substituted benzene ring or a substituted pyridine ring, with the optional substituent being a nitro group, a lower alkoxy group, a lower alkyl group or a lower alkylthio group.

11. The compound of claim 1 wherein:

$X_1$, $X_2$, $X_3$, or $X_4$ which may be the same or different are each a hydrogen atom, a halogen atom, a lower alkyl group, a lower alkoxy group or $NX_5X_6$;

where $X_5$ and $X_6$, which may be the same or different, are each a hydrogen atom, a lower alkyl group or an acyl group, or $X_5$ and $X_6$ may combine together to form a 3- to 8-membered ring.

12. The compound of claim 1 wherein:
m and n are each 0; and
the substituents other than $X_1$, $X_2$, $X_3$ and $X_4$ are meta-substituted on the benzene ring.

13. The compound of claim 1 wherein:
m+n=1; and
the substituents other than $X_1$, $X_2$, $X_3$ and $X_4$ are ortho- or para-substituted on the benzene ring.

14. The compound of claim 1 selected from the group consisting of: 2-(3-aminomethylphenylamino)-6-methoxy-3-nitropyridine, 2-(3-aminomethylphenylamino)-6-methyl-3-nitropyridine, 2-(3-aminomethylphenylamino)-6-ethyl-3-nitropyridine, 2-(3-aminomethylphenylamino)-6-ethoxy-3-nitropyridine, 2-(3-aminomethylphenylamino)-6-methylthio-3-nitropyridine, 2-(3-aminomethylphenylamino)-6-methyl-3-nitrobenzene, 2-(3-aminomethylphenylamino)-6-methoxy-3-nitrobenzene, 2-(3-aminomethyl-2-methylphenylamino)-6-methoxy-3-nitropyridine, 2-(4-aminoethylphenylamino)-6-methoxy-3-nitropyridine, 2-(3-(1-amino-1-methylethyl)phenylamino)-6-methoxy-3-nitropyridine, 2-(3-aminomethyl-2-methoxyphenylamino)-6-methoxy-3-nitropyridine, 2-(3-aminomethyl-4-chlorophenylamino)-6-methoxy-3-nitropyridine, 2-(3-aminomethyl-4-fluorophenylamino)-6-methoxy-3-nitropyridine, 2-(3-aminomethyl-2-ethoxyphenylamino)-6-methoxy-3-nitropyridine, 2-(3-aminomethyl-2-chlorophenylamino)-6-methoxy-3-nitropyridine, 2-(3-aminomethylphenylamino)-4-methylpyridine, 2-(3-(1-amino-1-methylethyl)-phenylamino)-4-methylpyridine, 2-(3-aminomethyl-2-methylphenylamino)-4-methylpyridine, 2-(3-aminomethyl-4-ethylphenylamino)-4-methylpyridine, 2-(3-aminomethyl-4-ethoxyphenylamino)-4-methylpyridine, 2-(2aminoethylphenylamino)-4-methylpyridine, 2-(3-aminomethyl-2-chlorophenylamino)-4-methylpyridine, 2-(3-(1-amino-cyclobutyl)phenylamino)-4-methylpyridine, 2-(4-aminoethylphenylamino)-4-methylpyridine, 2-(3-aminomethyl-2-ethoxyphenylamino)-4-methylpyridine, 2-(3-aminomethyl-4-chlorophenylamino)-4-methylpyridine, 2-(3-aminomethyl-2-(n-propoxy)phenylamino)-4-methylpyridine, 2-(3-aminomethyl-4-chloro-2-ethoxyphenylamino)-4-methylpyridine, 2-(3-aminomethyl-2-ethoxy-4-methylphenylamino)-4-methylpyridine, 2-(3-aminomethyl-2-methoxyphenylamino)-4-methylpyridine, and 2-(3-aminomethyl-2-(i-propoxy)phenylamino)-4-methylpyridine.

15. A nNOS inhibitor composition comprising as an active ingredient the compound of claim 1 in a pharmaceutically effective amount, and a pharmaceutically acceptable adjuvant.

16. A method for the treatment of a cerebrovascular disease comprising administering to a patient in need thereof an amount sufficient for said therapy of the compound of claim 1.

17. The method of claim 16, wherein said patient is one suffering from cerebral hemorrhage.

18. The method according to claim 16, wherein the type of cerebrovascular disease is subarachnoid hemorrhage.

19. The method according to claim 16, wherein the type of cerebrovascular disease is cerebral infarction.

20. The method according to claim 19, wherein the subtype of cerebral infarction is atherothrombotic infarction.

21. The method according to claim 19, wherein the subtype of cerebral infarction is lacunar infarction.

22. The method according to claim 19, wherein the subtype of cerebral infarction is cardiogenic embolism.

23. The method according to claim 19, wherein the type of cerebrovascular disease is transient ischemic attack.

24. The method according to claim 16, wherein the type of cerebrovascular disease is cerebral edema.

25. A method for the treatment of a traumatic brain injury comprising administering to a patient in need thereof an amount sufficient for said therapy of the compound of claim 1.

26. A method for the treatment of a spinal injury comprising administering to a patient in need thereof an amount sufficient for said therapy of the compound of claim 1.

27. A method for the treatment of pain in a patient in need of said therapy, comprising administering to said patient an analgesic-effective amount of the compound of claim 1.

28. The method according to 27 wherein said patient is suffering from headache.

29. The method according to claim 28, wherein said headache is a migraine headache.

30. The method according to claim 28, wherein said headache is a tension headache.

31. The therapeutic according to claim 28, wherein said headache is a cluster headache or chronic paroxysmal headache.

32. A method for the treatment of Parkinson's disease comprising administering to a patient suffering from Parkinson's disease an amount sufficient for said treatment of the compound of claim 1.

33. A method for the treatment of Alzheimer's disease comprising administering to a patient suffering from Parkinson's disease an amount sufficient for said treatment of the compound of claim 1.

34. A method for the treatment of seizure disorder, comprising administering to a patient in need thereof an effective amount for seizure control or seizure diminution of the compound of claim 1.

35. A method for the treatment of morphine tolerance or dependents, comprising administering to a patient in need thereof an amount sufficient for said therapy of the compound of claim 1.

36. A method for the treatment of septic shock comprising administering to a patient in need thereof an amount effective for said treatment of the compound of claim 1.

37. A method for the treatment of chronic rheumatoid arthritis comprising administering to a patient in need of said therapy an amount sufficient for said treatment of the compound of claim 1.

38. A method for the treatment of osteoarthritis comprising administering to a patient in need of said therapy an effective amount for said treatment of the compound of claim 1.

39. A method for the treatment of an infection comprising administering to a patient in need of said therapy an amount sufficient for said therapy of the compound of claim 1.

40. The method of claim 39 wherein said patient is suffering from a viral infection.

41. A method for the treatment of diabetes mellitus comprising administering to a patient in need of said therapy an amount effective for said treatment of the compound of claim 1.

42. A process for producing a compound according to claim 1 by the reaction pathway (A):

Reaction pathway (A)
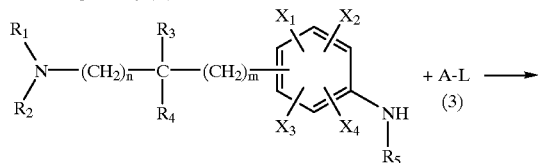
(2)       + A-L ⟶
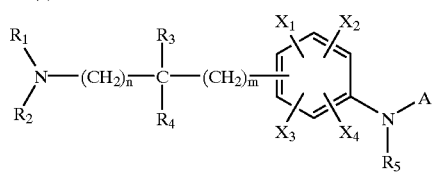
(1)
wherein;
$R_5$ is a hydrogen atom or an optionally substituted lower alkyl group; and
L is a leaving group.
43. A process for producing a compound according to claim 1 by the reaction pathway (B):
Reaction pathway (B)
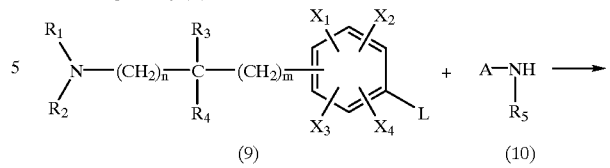
(9)    +   A—NH—$R_5$    ⟶
(10)
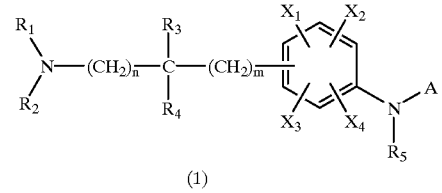
(1)
wherein
$R_5$ is a hydrogen atom or an optionally substituted lower alkyl group; and
L is a leaving group.
* * * * *